US010961300B2

(12) United States Patent
Kim et al.

(10) Patent No.: US 10,961,300 B2
(45) Date of Patent: Mar. 30, 2021

(54) ANTIBODY SPECIFICALLY BINDING TO AN ISOLATED PEPTIDE DERIVED FROM VIMENTIN OR A FRAGMENT BINDING TO THE PEPTIDE

(71) Applicant: IMMUNEMED INC., Gangwon-do (KR)

(72) Inventors: Yoon Won Kim, Gangwon-do (KR); Young Jin Kim, Gangwon-do (KR); Hyo Jeong Hong, Seoul (KR); Sang Jin Park, Ulsan (KR); Min Woo Kim, Gangwon-do (KR); Sung Man Park, Gangwon-do (KR)

(73) Assignee: IMMUNEMED INC., Gangwon-do (KR)

( * ) Notice: Subject to any disclaimer, the term of this patent is extended or adjusted under 35 U.S.C. 154(b) by 107 days.

(21) Appl. No.: 15/570,734

(22) PCT Filed: Jun. 10, 2016

(86) PCT No.: PCT/KR2016/006215
§ 371 (c)(1),
(2) Date: Oct. 30, 2017

(87) PCT Pub. No.: WO2016/200220
PCT Pub. Date: Dec. 15, 2016

(65) Prior Publication Data

US 2019/0256585 A1 Aug. 22, 2019

(30) Foreign Application Priority Data

Jun. 10, 2015 (KR) ........................ 10-2015-0082132

(51) Int. Cl.
*A61K 39/00* (2006.01)
*C07K 16/18* (2006.01)
(Continued)

(52) U.S. Cl.
CPC .............. *C07K 16/18* (2013.01); *A61P 29/00* (2018.01); *A61P 31/12* (2018.01); *A61P 31/16* (2018.01);
(Continued)

(58) Field of Classification Search
None
See application file for complete search history.

(56) References Cited

U.S. PATENT DOCUMENTS

2013/0130971 A1 5/2013 Fernandez Ortega et al.

FOREIGN PATENT DOCUMENTS

EP 1067142 A1 1/2001
EP 1593691 A1 11/2005
(Continued)

OTHER PUBLICATIONS

Rudikoff et al., "Single amino acid substitution altering antigen-binding specificity," Proc Natl Acad Sci USA 79:1979-1983 (Year: 1982).*
(Continued)

*Primary Examiner* — M Franco G Salvoza
(74) *Attorney, Agent, or Firm* — Knobbe Martens Olson & Bear LLP

(57) ABSTRACT

The present invention relates to an antibody specifically binding to the peptide of SEQ ID NO: 1, and specifically, to an antibody specifically binding to an isolated peptide of SEQ ID NO: 1 or a fragment binding to the peptide specifically binding to the peptide, a polynucleotide encoding the antibody or the fragment binding to the peptide, a vector containing the polynucleotide, a cell introduced with the vector, a method of producing the antibody or the fragment binding to the peptide using the cell, an antibody or a fragment binding to the peptide produced by the method, an antiviral composition containing the antibody or
(Continued)

pCAGGS.Ck.mVL.IRES.Cγ2.mVH.neo chVSF HC and LC
(simultaneous expression vectors)

the fragment binding to the peptide, a composition for preventing or treating inflammatory diseases containing the antibody or the fragment binding to the peptide, and a method of treating infectious viral diseases or inflammatory diseases using the composition.

21 Claims, 52 Drawing Sheets

Specification includes a Sequence Listing.

(51) Int. Cl.

| | |
|---|---|
| ***A61P 31/12*** | (2006.01) |
| ***A61P 31/20*** | (2006.01) |
| ***A61P 29/00*** | (2006.01) |
| ***A61P 31/16*** | (2006.01) |

(52) U.S. Cl.

CPC ........ *A61P 31/20* (2018.01); *A61K 2039/505* (2013.01); *C07K 2317/20* (2013.01); *C07K 2317/24* (2013.01); *C07K 2317/565* (2013.01); *C07K 2317/567* (2013.01); *C07K 2317/622* (2013.01); *C07K 2317/76* (2013.01); *C07K 2317/92* (2013.01)

(56) References Cited

FOREIGN PATENT DOCUMENTS

| | | | | |
|---|---|---|---|---|
| EP | 2784510 | A1 * | 10/2014 | ........... C12Q 1/6886 |
| JP | 2007-515924 | | 6/2007 | |
| JP | 2013-523662 | | 6/2013 | |
| KR | 10-2003-0066419 | A | 3/2005 | |
| KR | 10-2013-0027016 | A | 3/2013 | |
| WO | WO 03/064461 | A1 | 8/2003 | |
| WO | WO 2006/053061 | | 5/2006 | |
| WO | WO 2013/158333 | A1 | 10/2013 | |
| WO | WO 2014/138183 | A1 | 9/2014 | |
| WO | WO 2015/010791 | A2 | 1/2015 | |

OTHER PUBLICATIONS

Goel et al., "Plasticity within the Antigen-Combining Site May Manifest as Molecular Mimicry in the Humoral Immune Response," J. Immunol. 173: 7358-7367 (Year: 2004).*

Lloyd et al., "Modelling the human immune response: performance of a 1011 human antibody repertoire against a broad panel of therapeutically relevant antigens," Protein Engineering, Design & Selection, vol. 22, No. 3: 159-168 (Year: 2009).*

Edwards et al., "The Remarkable Flexibility of the Human Antibody Repertoire; Isolation of Over One Thousand Different Antibodies to a Single Protein, BLys," J. Mol. Biol. 334: 103-118 (Year: 2003).*

Cassell, "Infectious Causes of Chronic Inflammatory Diseases and Cancer," Emerging Infectious Diseases, vol. 4, No. 3: 475-487 (Year: 1998).*

Pelegrin et al., "Antiviral Monoclonal Antibodies: Can They Be More than Simple Neutralizing Agents?", Cell Press: Trends in Microbiology, vol. 23, No. 10 (Year: 2015).*

Office Action issued in Australian Patent Application No. 2016277027, dated Jun. 29, 2018.

Alcaro et al, Biocatalysed synthesis of β-O-glucosides from 9-fluorenon-2-carbohydroxyesters. Part 3: IFN-inducing and anti-HSV-2 properties, Bioorganic & Medicinal Chemistry, 2005, pp. 3371-3378, vol. 13.

Cha et al, Nonstereotyped Lymphoma B Cell Receptors Recognize Vimentin as a Shared Autoantigen, Journal of Immunology, 2013, pp. 4887-4898, vol. 190.

Du et al, Cell Surface Vimentin is an Attachment Receptor for Enterovirus 71, Journal of Virology, 2014, pp. 5816-5833, vol. 33, No. 10.

Liang et al, Vimentin binding is critical for infection by the virulent strain of Japanese encephalitis virus, Cellular Microbiology, 2011, pp. 1358-1370, vol. 13, No. 9.

International Search Report, dated Sep. 27, 2016, in International Patent Application No. PCK/KR2016/006215.

International Search Report, dated Nov. 10, 2015, in International Patent Application No. PCK/KR2015/005917.

Das et al., "Japanese encephalitis virus interacts with vimentin to facilitate its entry into porcine kidney cell line", *Vir. Res.*, 2011, vol. 160, p. 404-408.

Office Action issued in JP application No. 2018-517109, dated Nov. 6, 2018.

Supplementary Search Report issued in European Patent Application No. EP16807860, dated Nov. 3, 2018.

* cited by examiner

[FIG. 1]
pCAGGS.Ck.mVL.IRES.$C\gamma_2$.mVH.neo
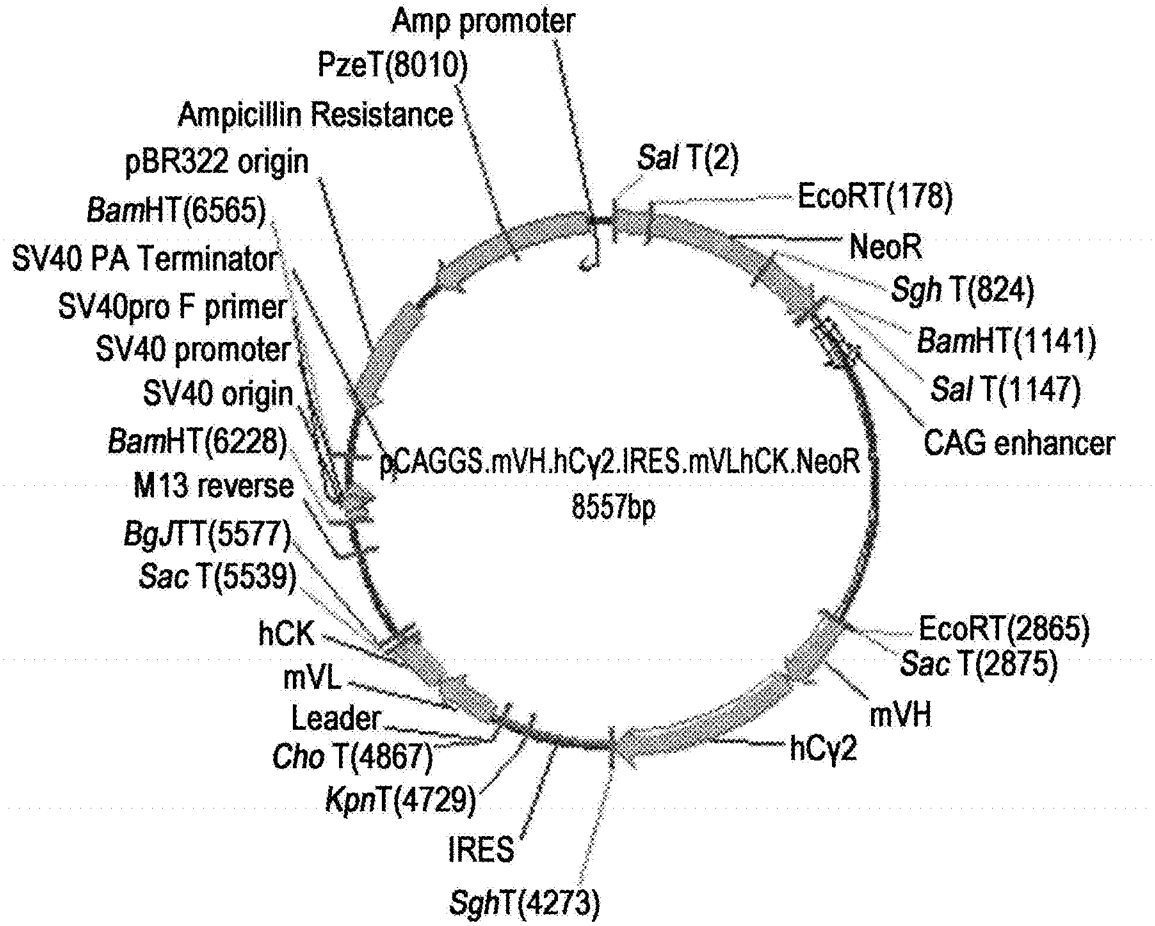
chVSF HC and LC
(simultaneous expression vectors)

[FIG. 2]
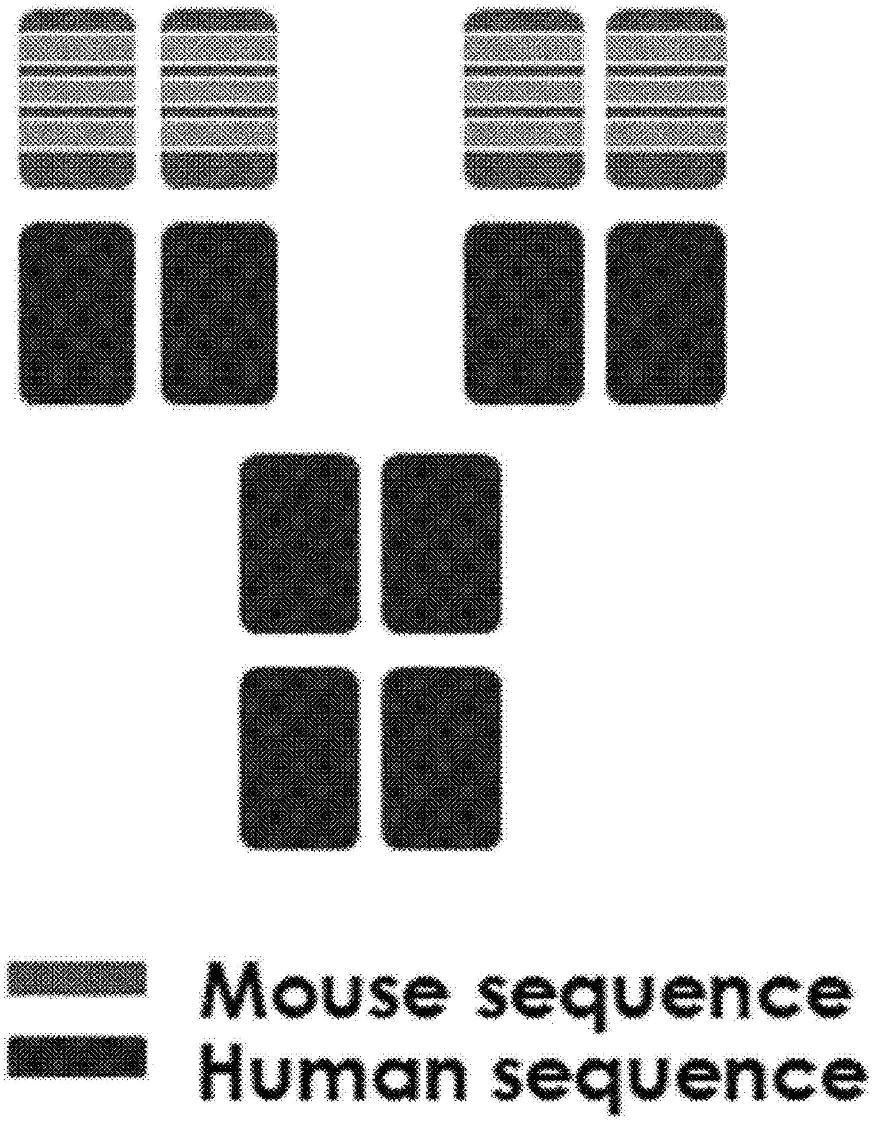

[FIG. 3]
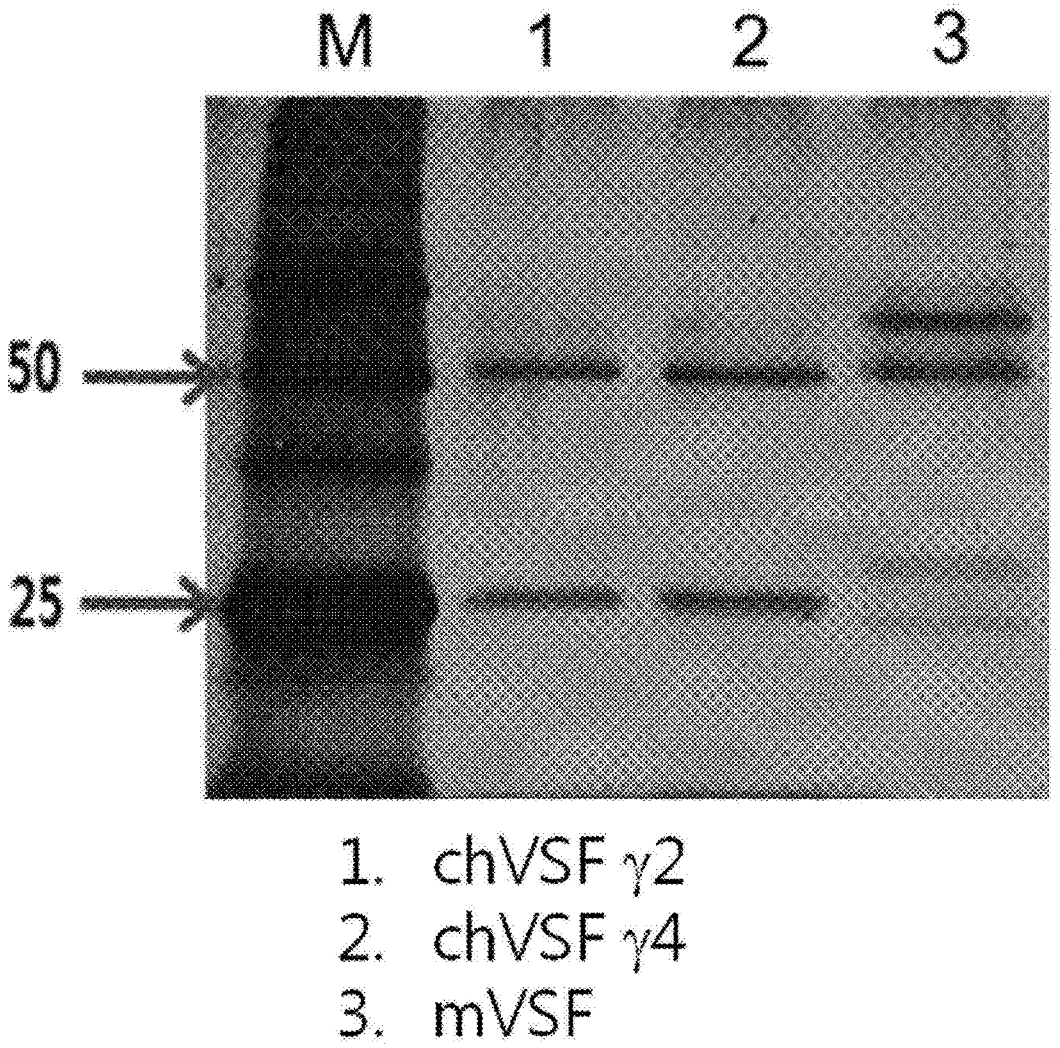

[FIG. 4] SEQ ID NO: 150

CGTCGACGAGATCCAGCTGCAGCAGTCT

GAGATCCAGCTGCAGCAGTCT

GGAGCTGAGCTGGTGAAGCCTGGGGCTTCAGTGAAGATATCCTGCAAGGCTTCTGGTTACT

CATTCACTGGCTACAACATGAACTGGGTGAAGCAGAGCCATGGAAAGAGCCTTGAGTGGATT

GGAAATATTGATCCTTACTATGGTAGTACTACCTACAATCAGAAGTTCAAGGGCAAGGCCACA

TTGACTGTAGACAAATCTTCCAGCACAGCCTACATGCAGCTCAACAGCCTGACATCTGAGGA

CTCTGCAGTCTATTACTGTGCAAGAGAGACTGGGACGAGGGCTATGGACTACTGGGGTCAA

GGAACCTCAGTCACCGTCTCCTCA

CCTTGGAGTCAGTGGCAGAGGAGTCCACCTCCACCGAGACCACCTCCTCCTAGGCCACCT

CAGGAGGATCCGGTGGA

GGTGGCTCTGGTGGAGGTGGCTCTGACATCCAGATGACTCAGTC

GACATCCAGATGACTCAGTCTCCAGCCTCCCTATCTG

CATCTGTGGGAGAAACTGTCACCATGACATGTCGAGCAAGTGAGAATATTTACAGTAATTTAG

CATGGTATCAGCAGAAACAGGGAAAATCTCCTCAGCTCCTGGTCTATGTTGCAACAAACTTAG

CAGATGGTGTGCCATCAAGGTTCAGTGGCAGTGGATCAGGCACACAGTTTTCTCTGAAGATC

AACAGCCTGCAGCCTGAAGATTTTGGGAGTTATTACTGTCAACATTTTTATGGTTCTCCTCGG

ACGTTCGGTGGAGGCACCAAGCTGGAAATCAAAC

CCGTGGTTCGACCTTTAGTTTGGAGCTCC

[FIG. 5]
(A)
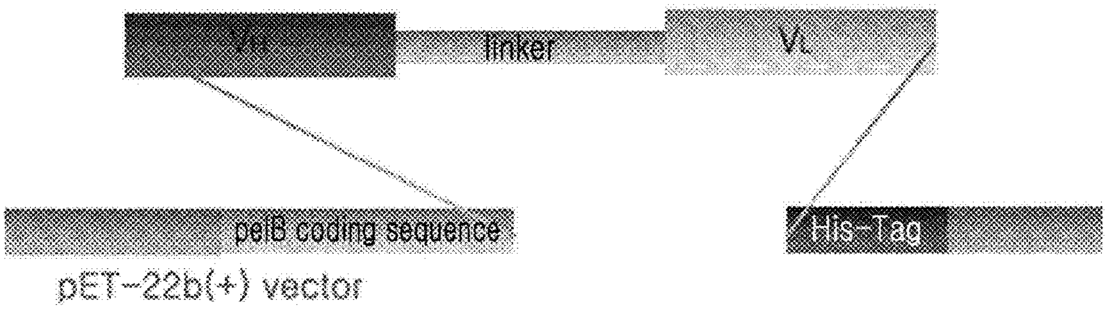
(B)
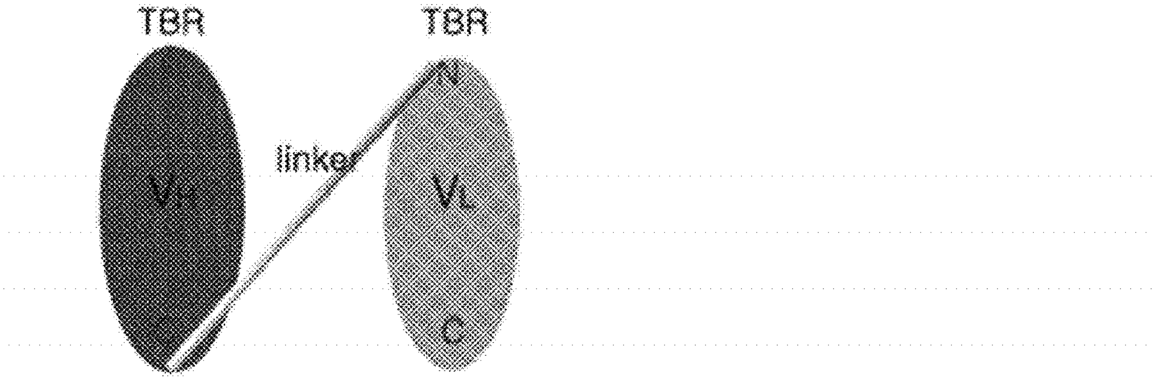

[FIG. 6]
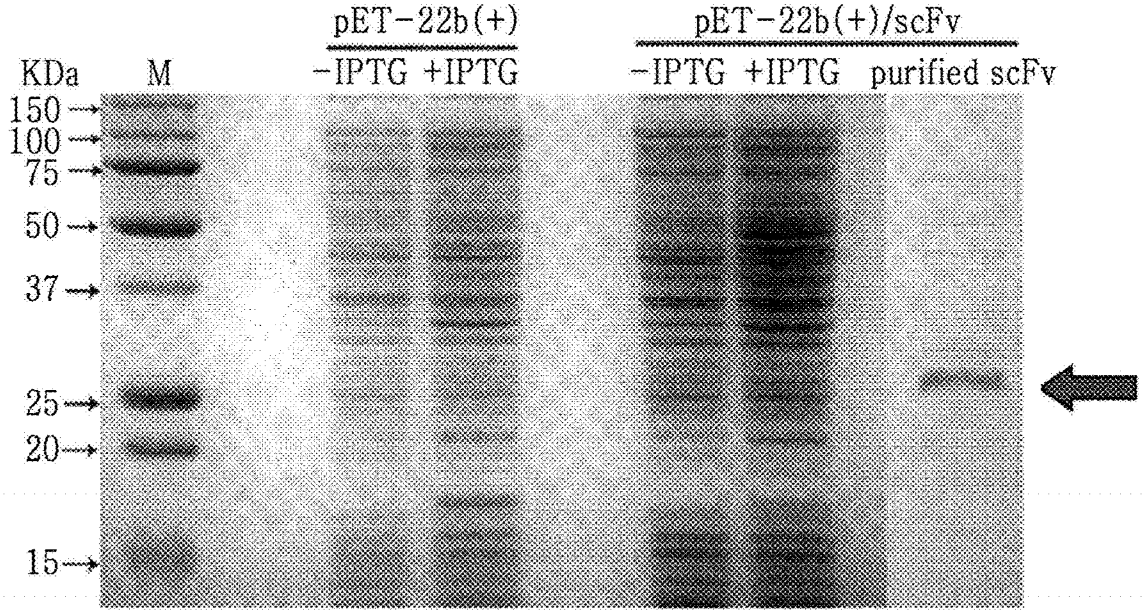
Lane 1: molecular weight marker.
Lane 2: pET-22b (+) (no induction).
Lane 3: pET-22b (+) (IPTG induction)
Lane 4: pET-22b (+)/scFv (no induction)
Lane 5: pET-22b (+)/scFv (IPTG induction)
Lane 6: purified scFv by Ni-NTA column (IPTG induction)

[FIG. 7]
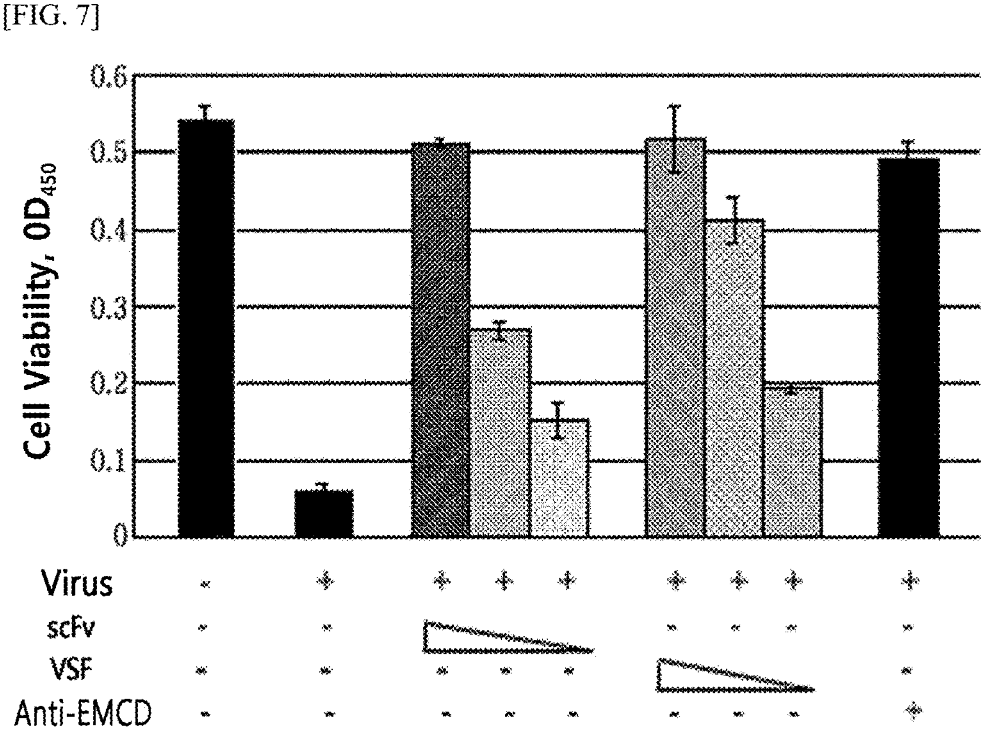
[FIG. 8]
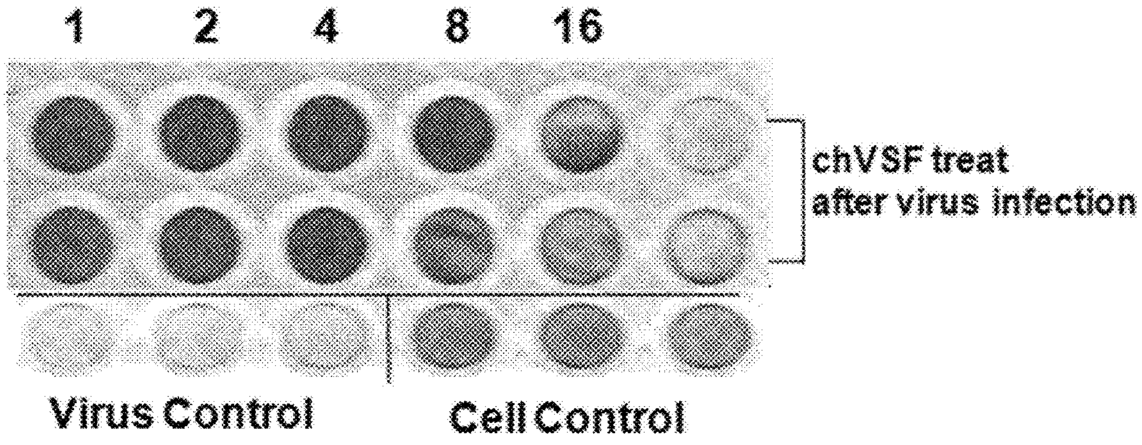

[FIG. 9]
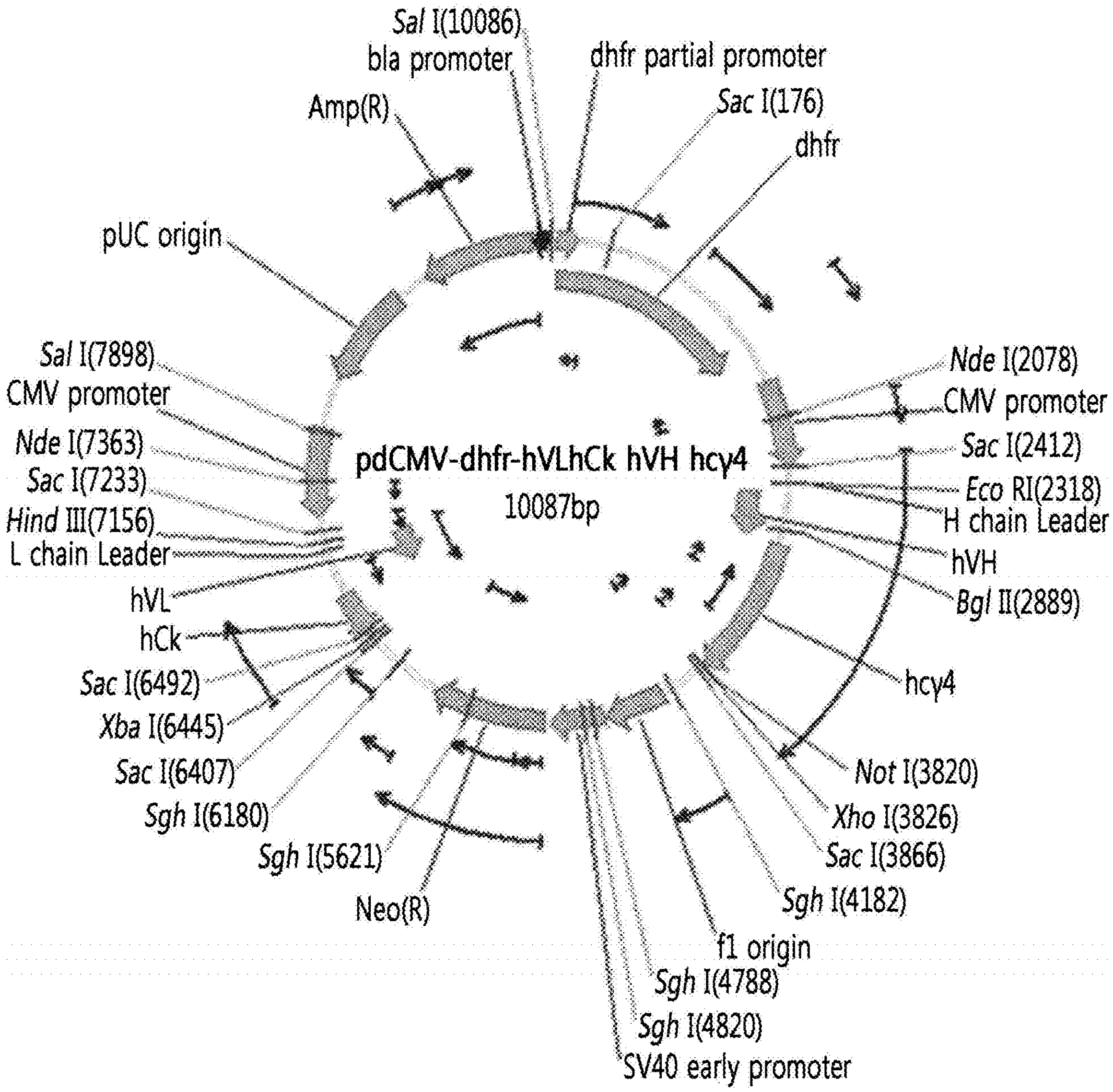

[FIG. 10]
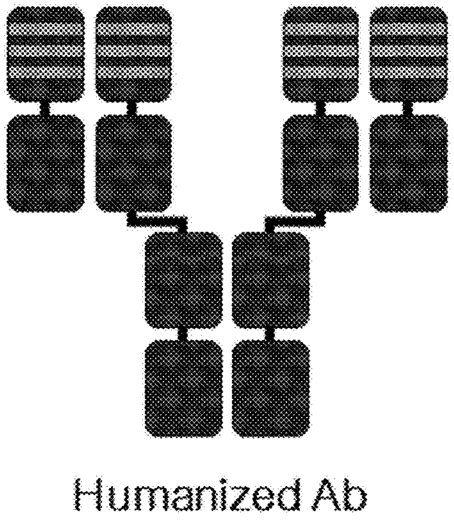
[FIG. 11]
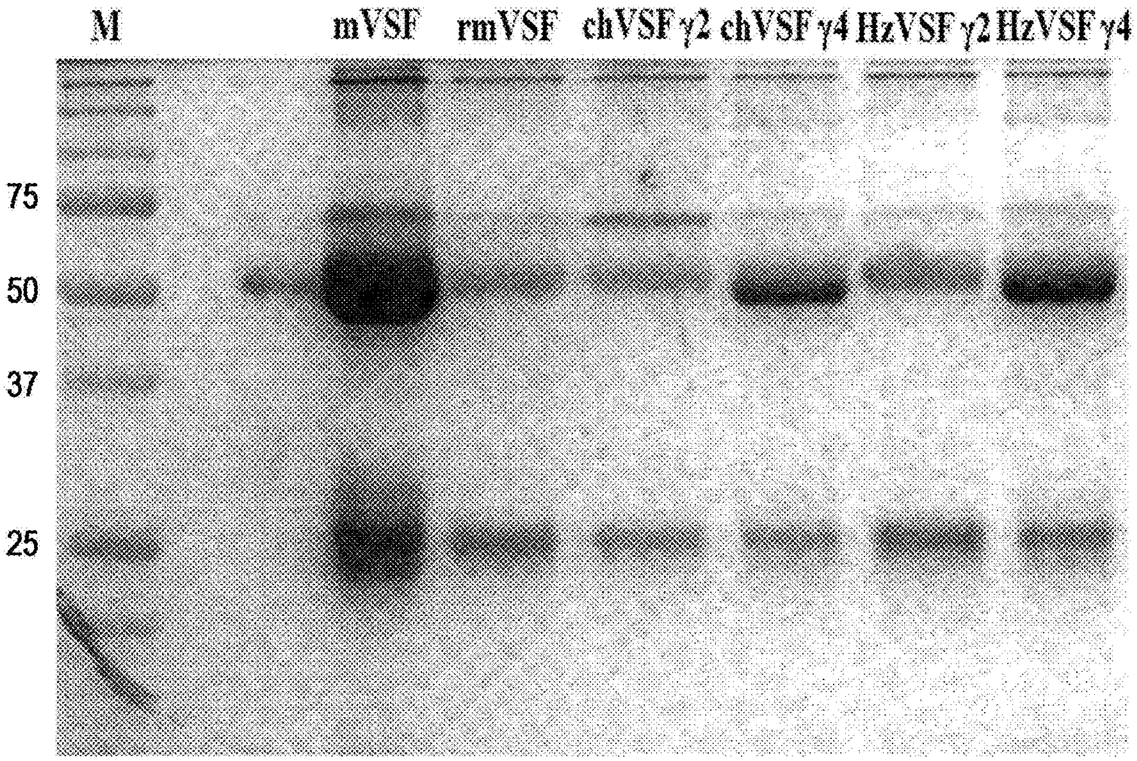

[FIG. 12]
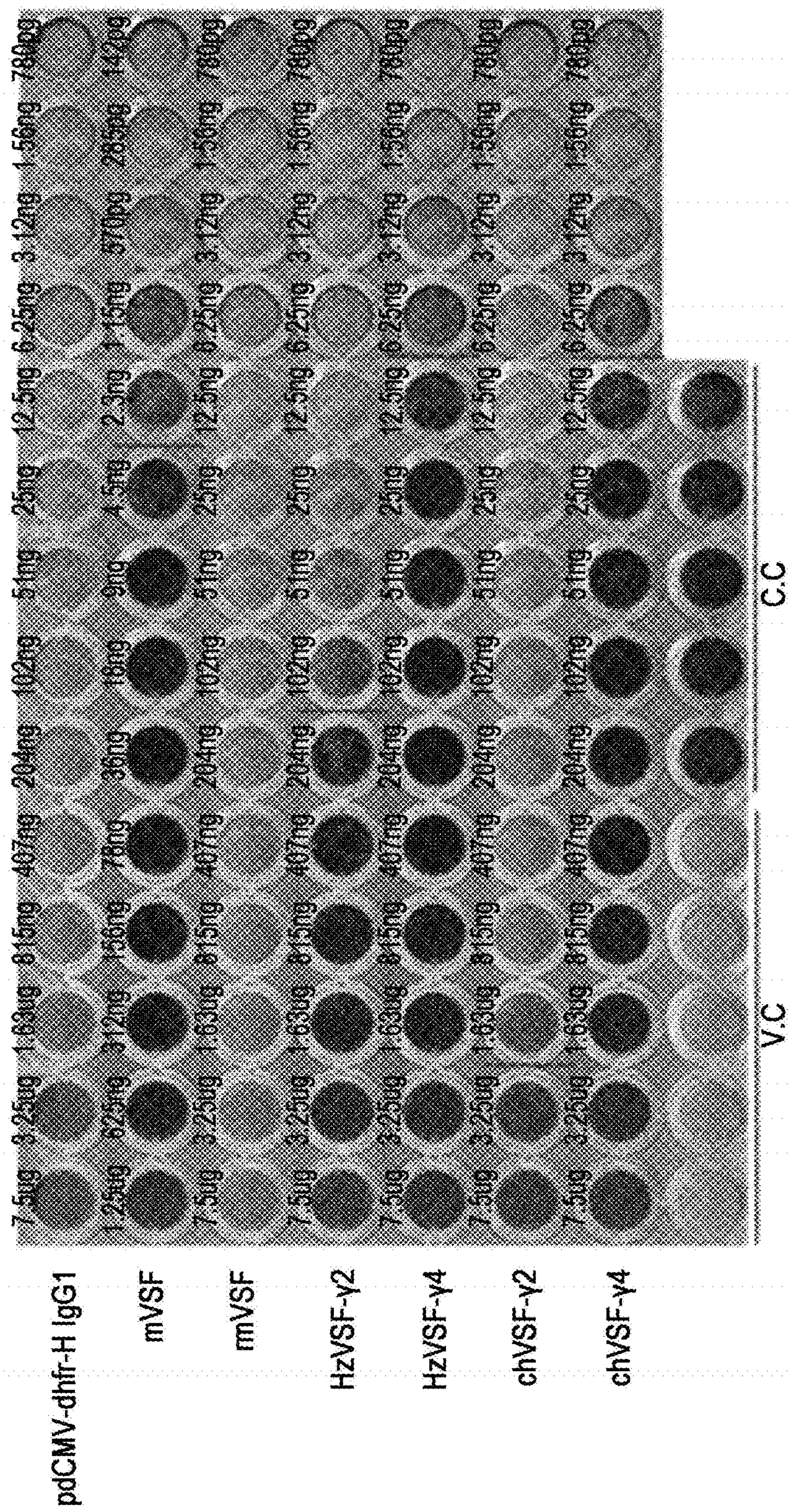

[FIG. 13]
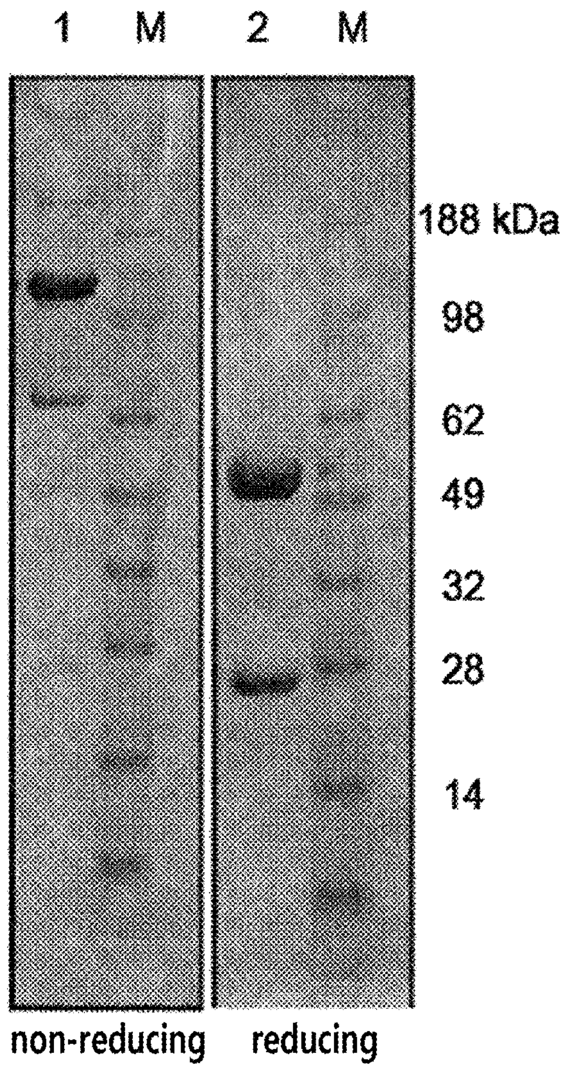

[FIG. 14A]
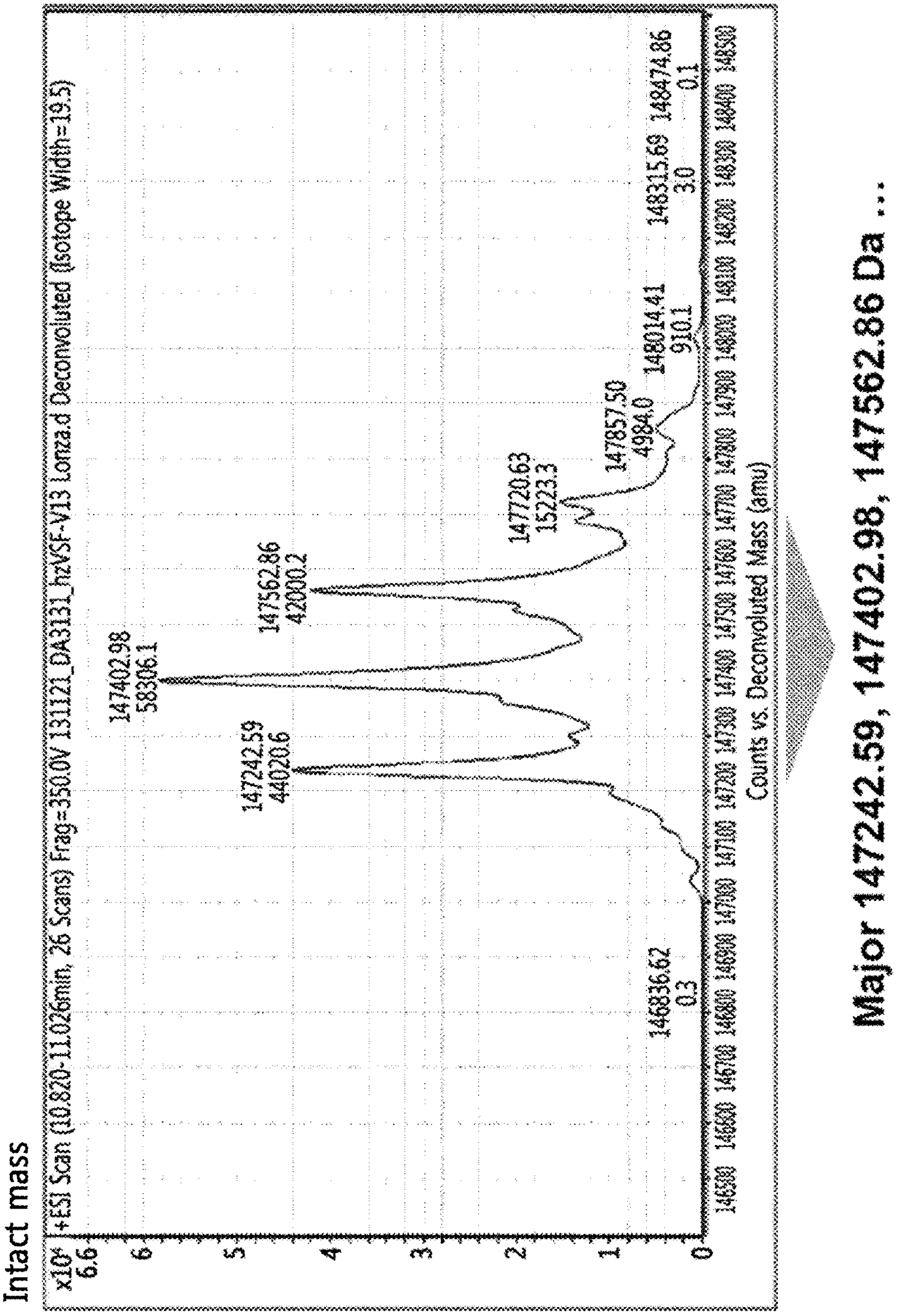

[FIG. 14B]
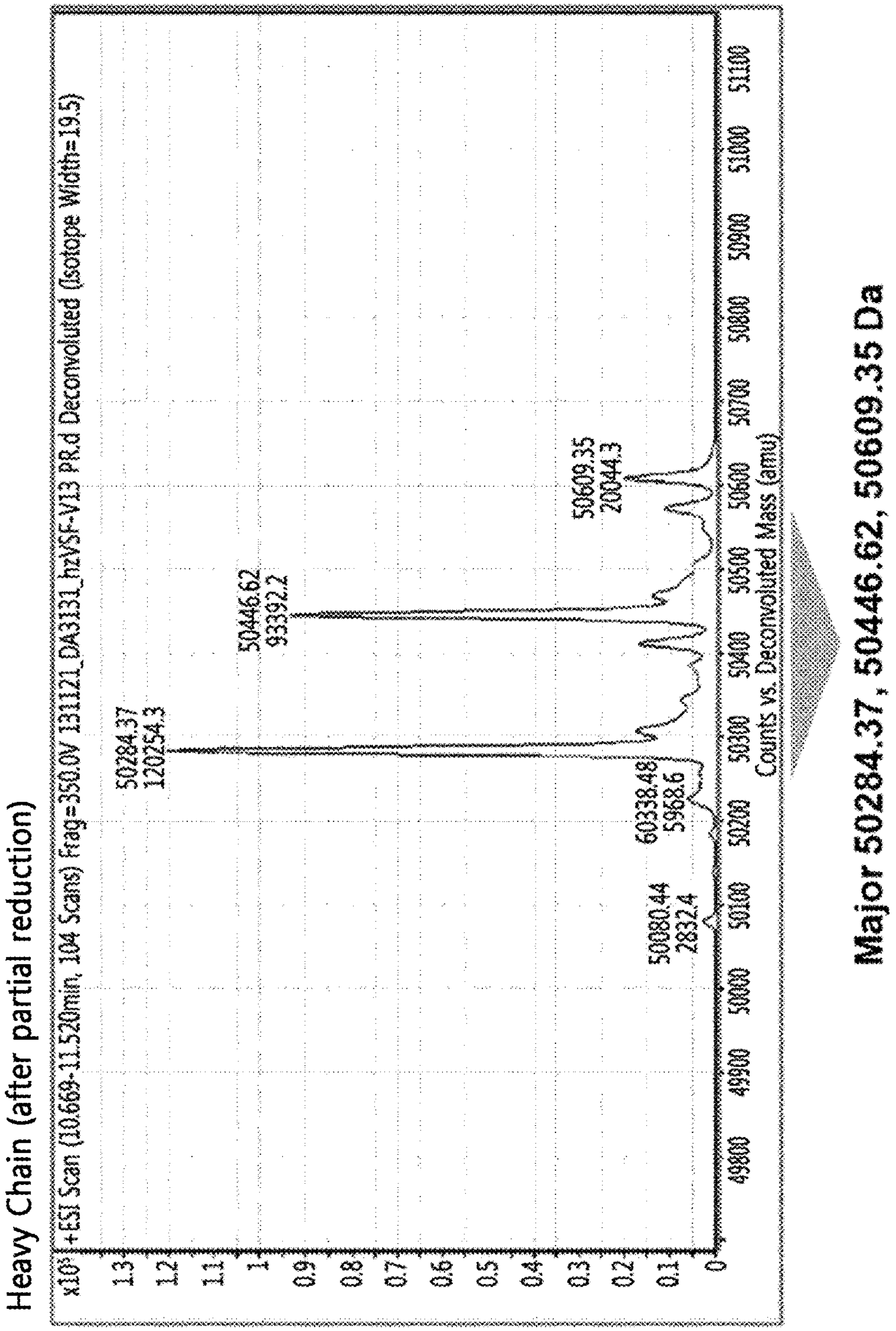

[FIG. 14C]
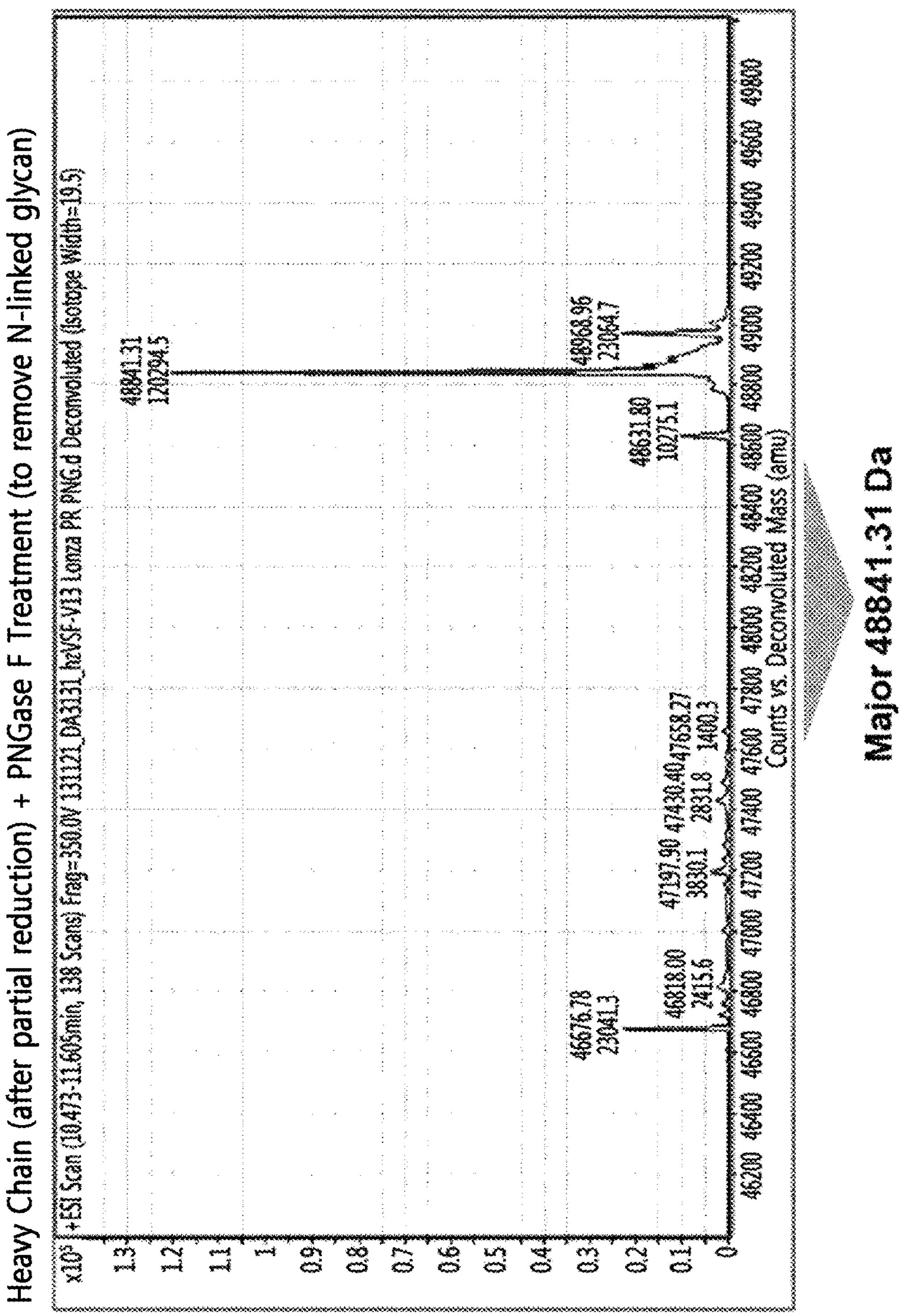

[FIG. 14D]
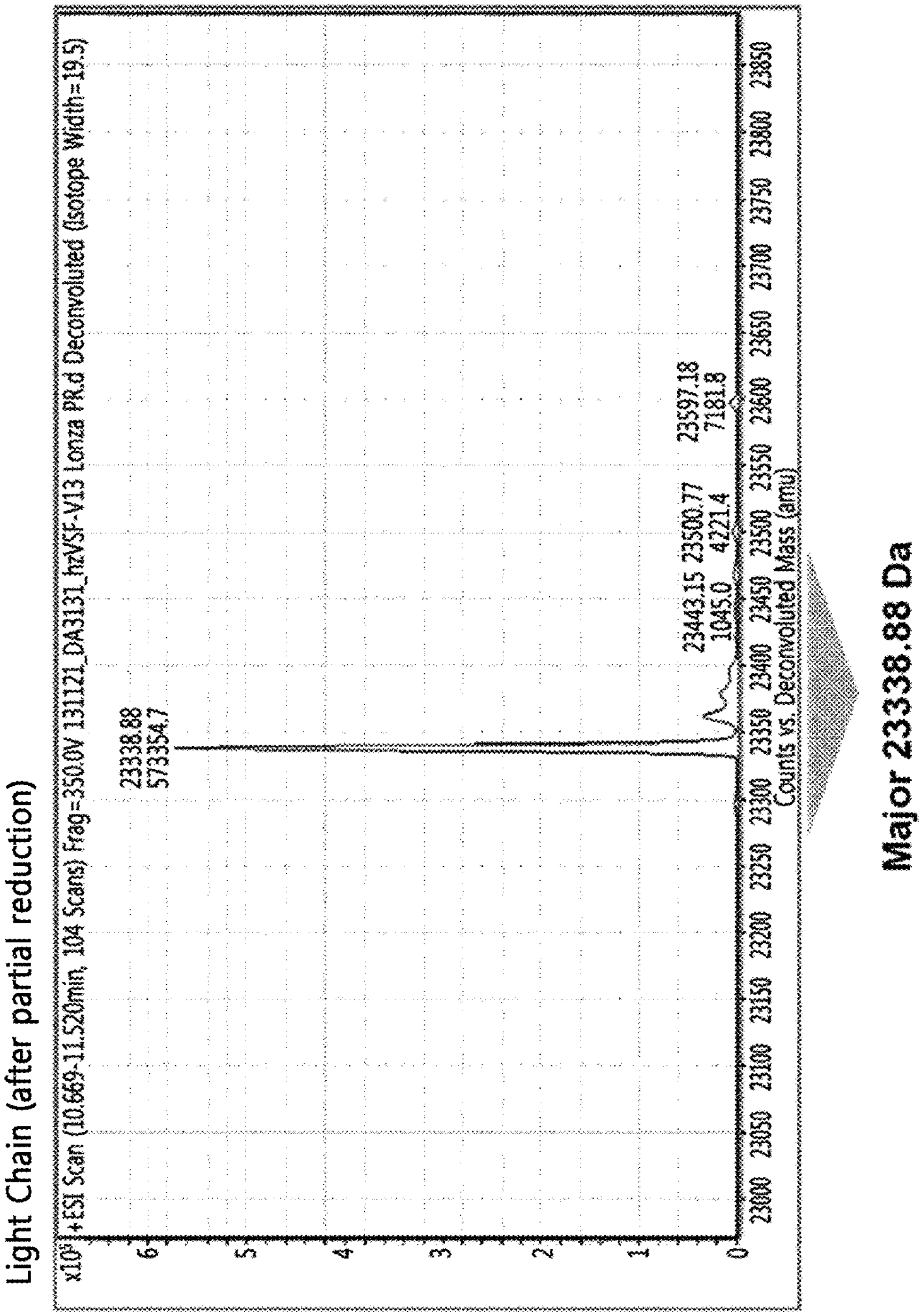

[FIG. 15]
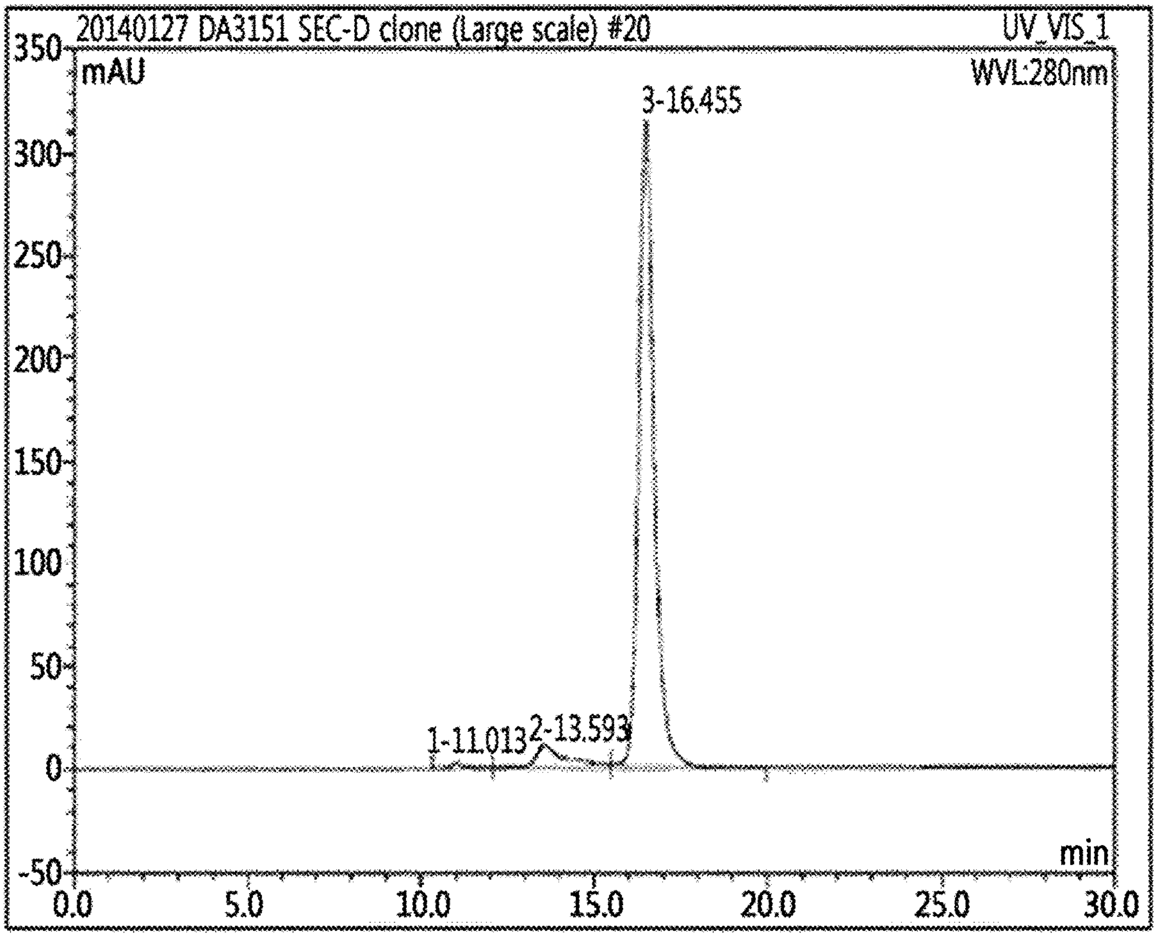
| No. | Ret.Time min | Peak Name | Height mAU | Area mAU*min | Rel. Area % | Amount | Type |
|---|---|---|---|---|---|---|---|
| 1 | 11.01 | n.a. | 2.262 | 1.304 | 0.72 | n.a. | BM |
| 2 | 13.59 | n.a. | 11.330 | 12.308 | 6.84 | n.a. | M |
| 3 | 16.49 | n.a. | 316.673 | 116.343 | 92.44 | n.a. | MB |
| Total: | | | 330.265 | 179.955 | 100.00 | 0.000 | |

[FIG. 16]
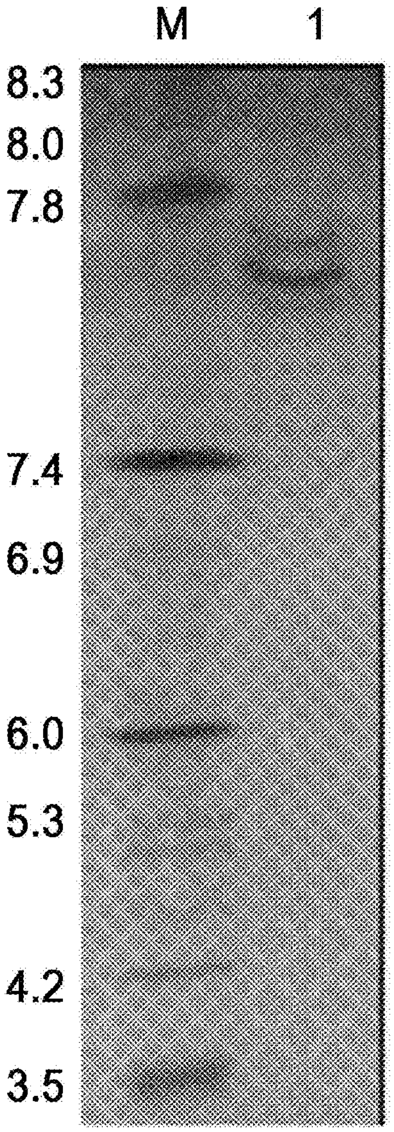

[FIG. 17]
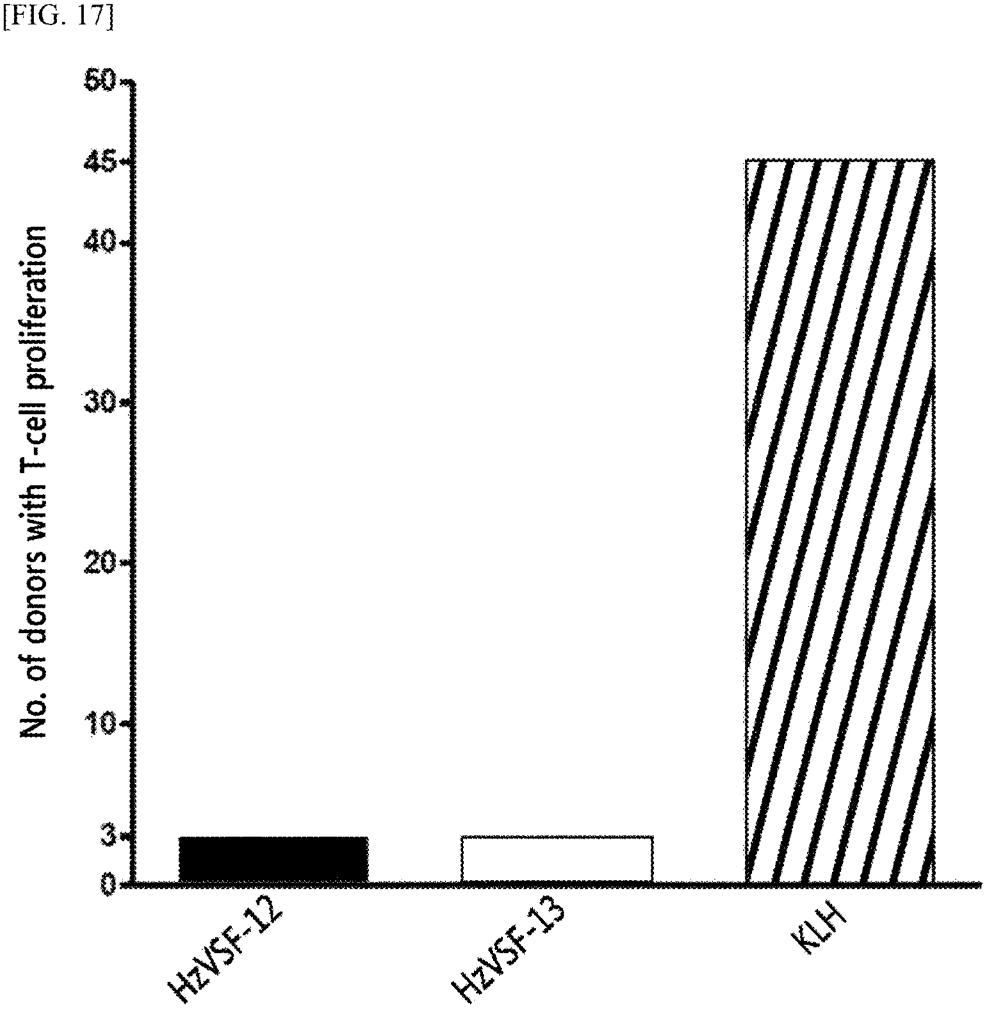

[FIG. 18]
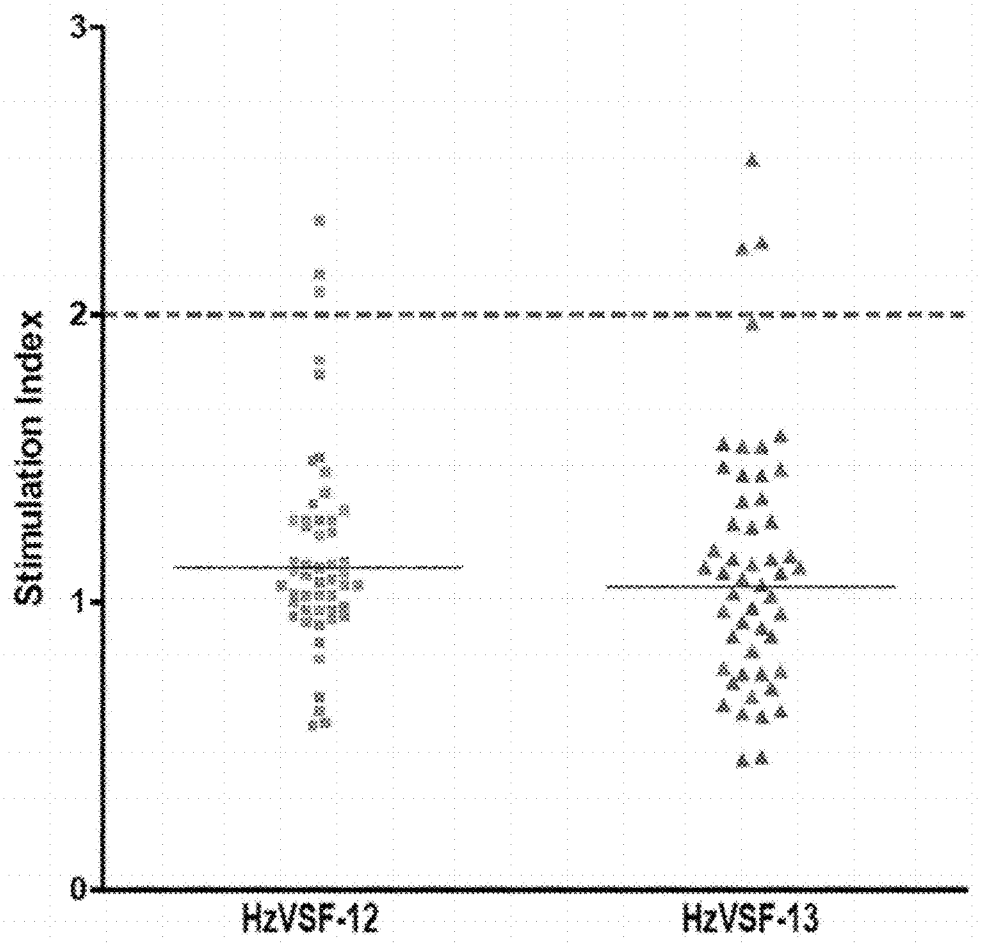

[FIG. 19]
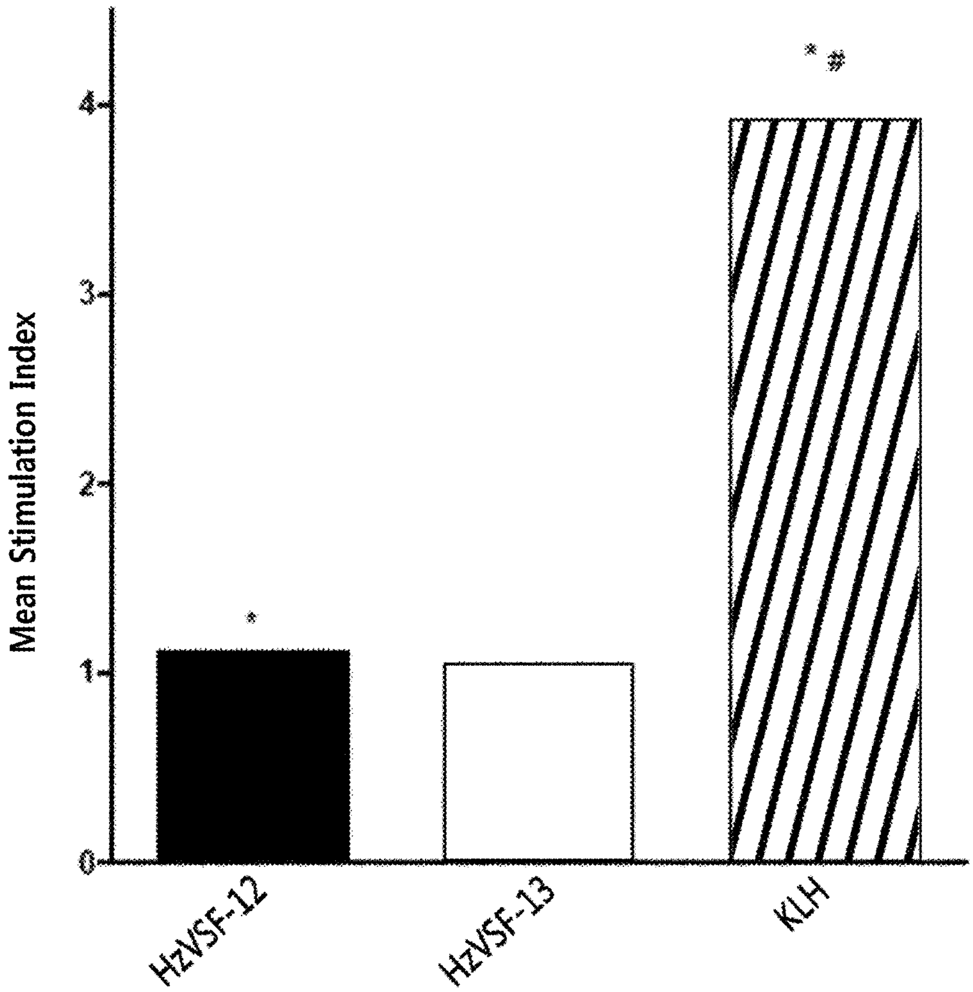
* Significantly different from the blank
Significantly different from HzVSF-12 and HzVSF-13

[FIG. 20]
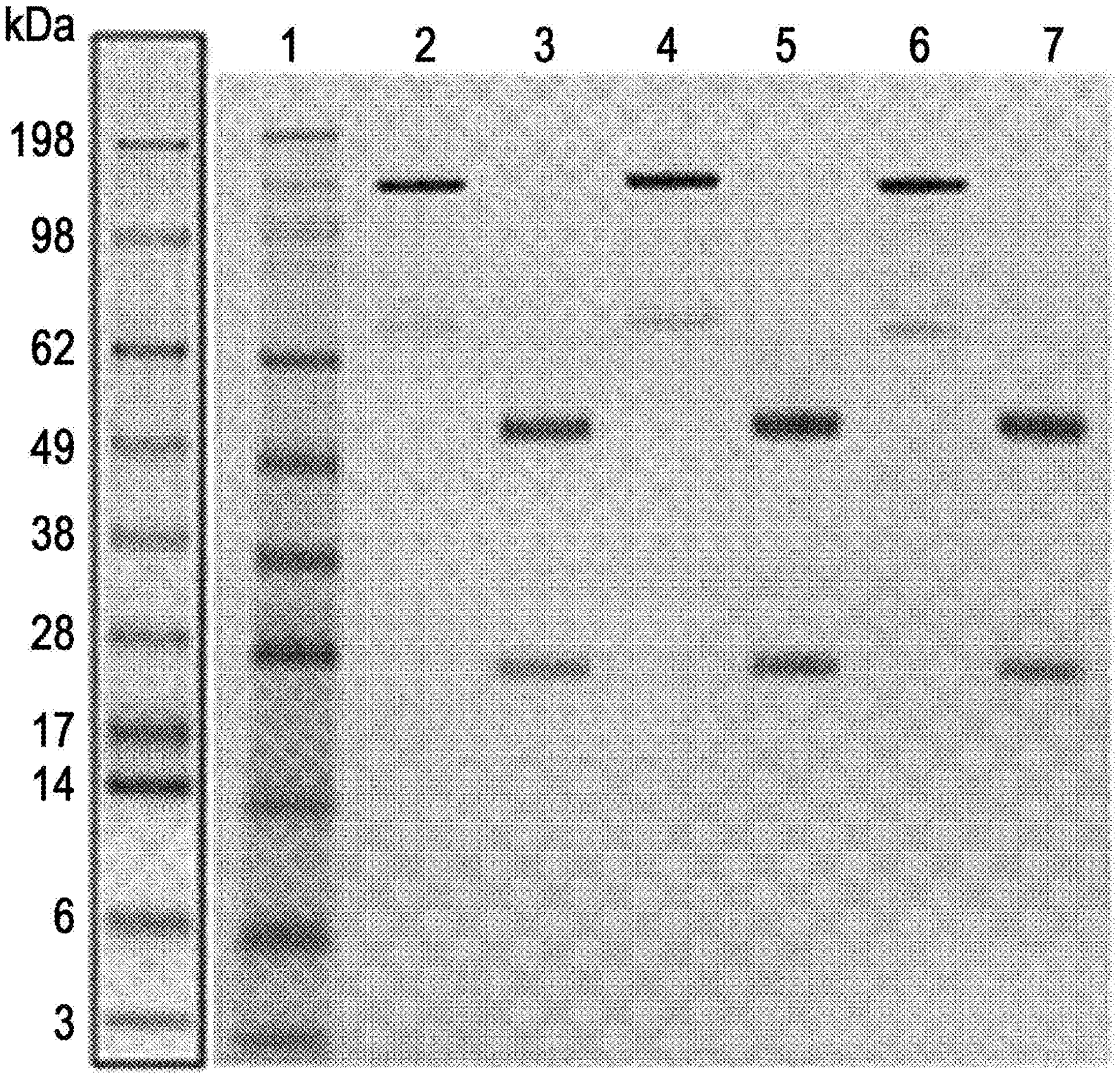

[FIG. 21]
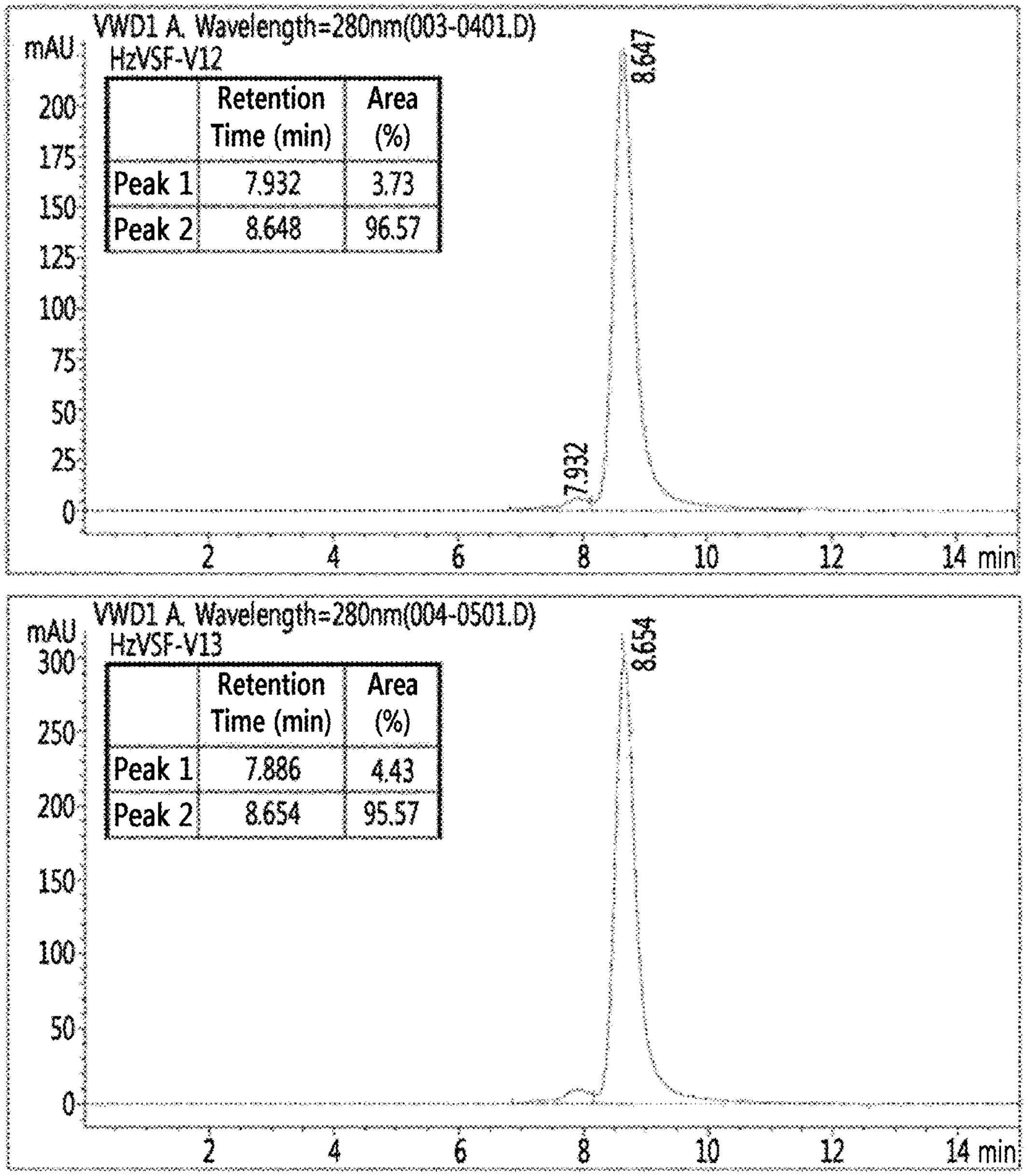

[FIG. 22]
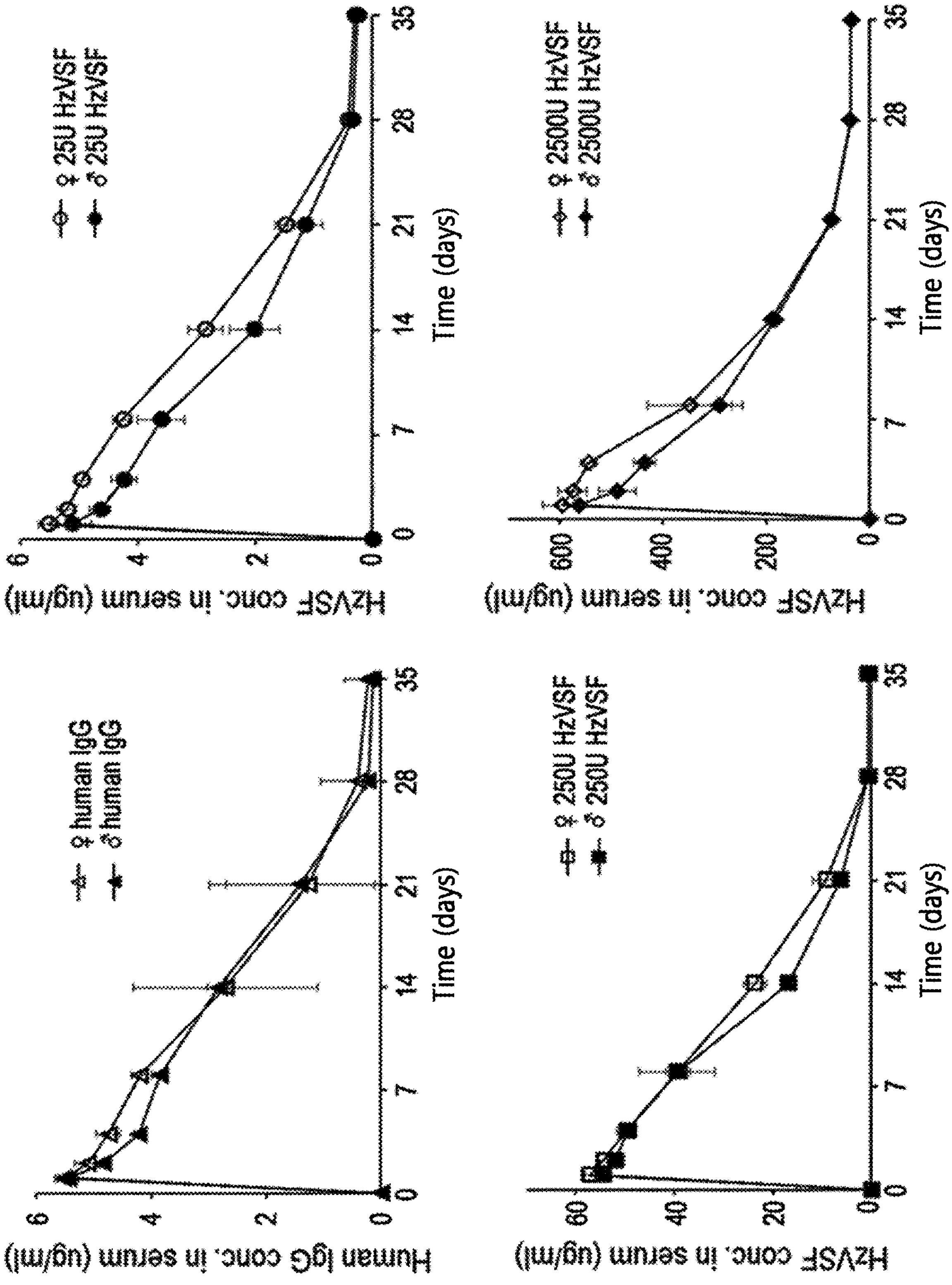

[FIG. 23]
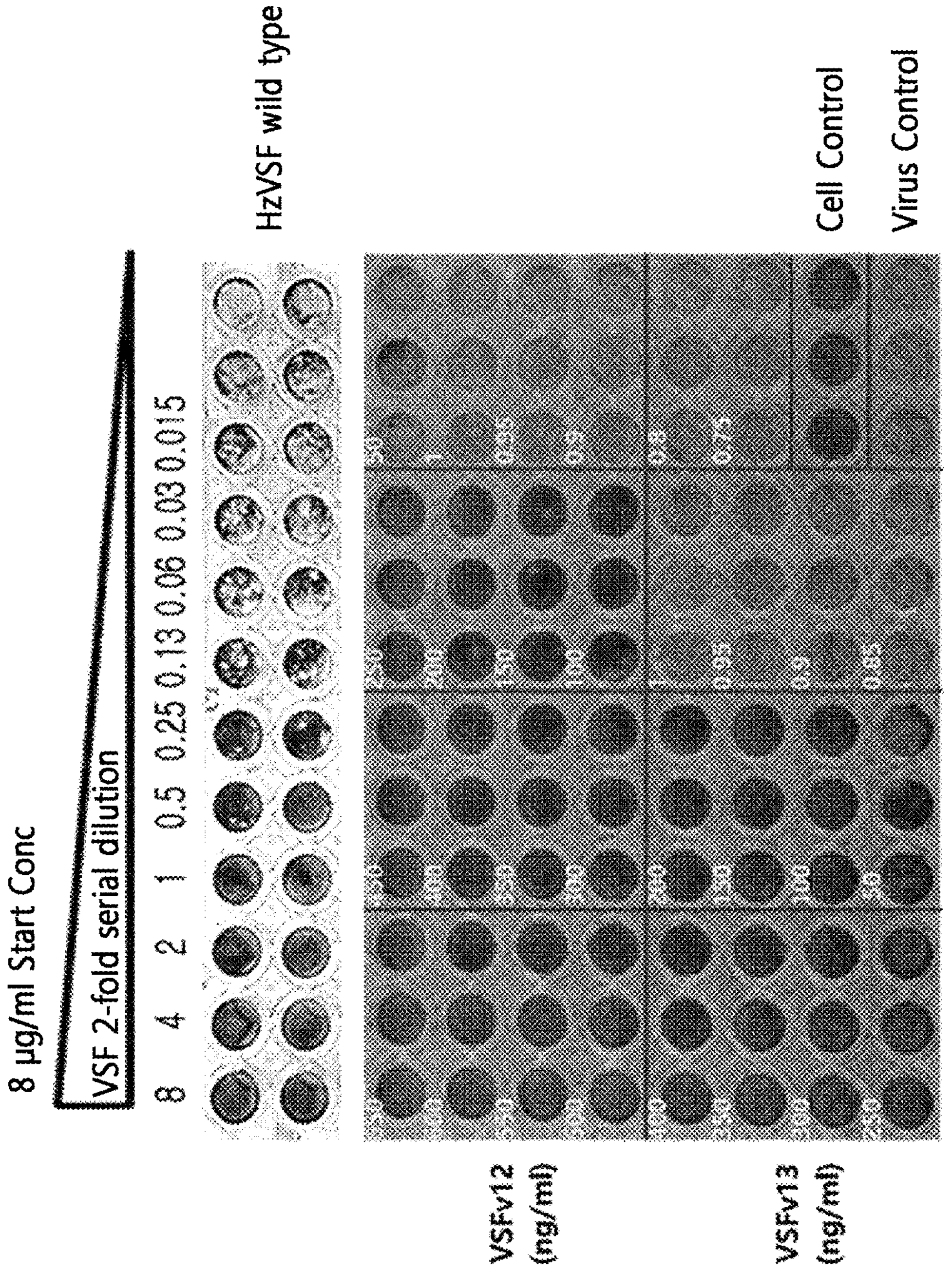

[FIG. 24]
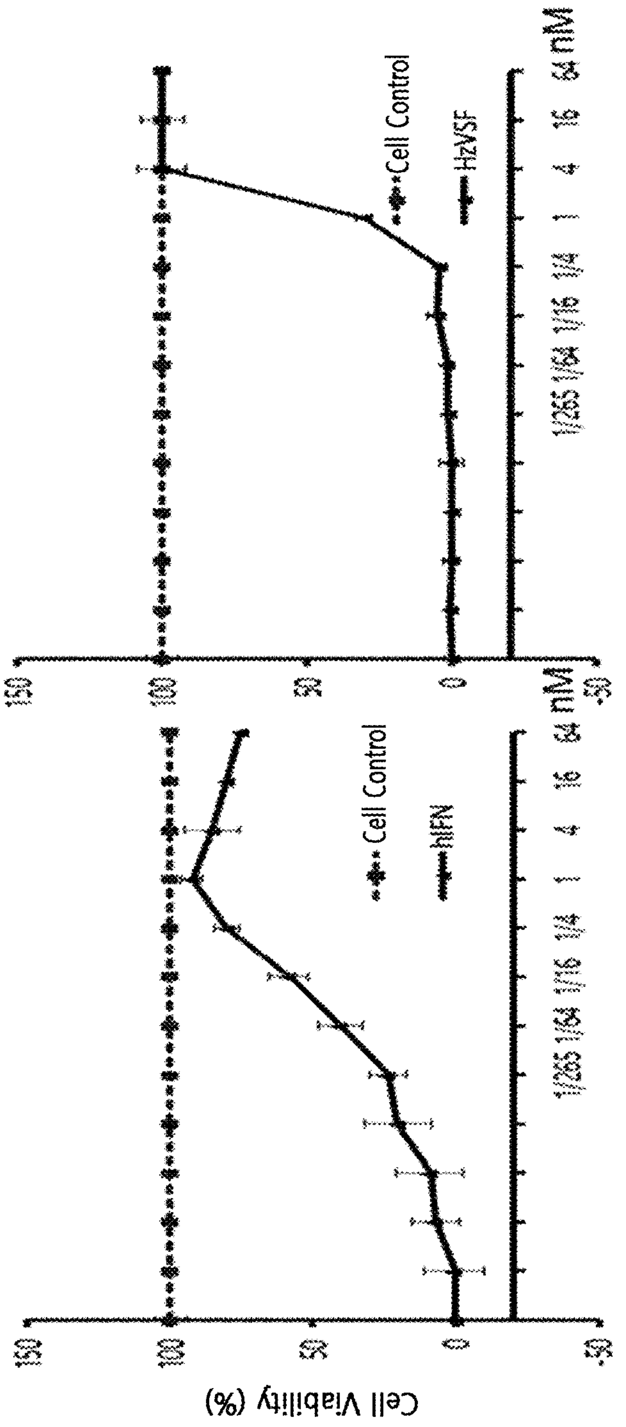

[FIG. 25]
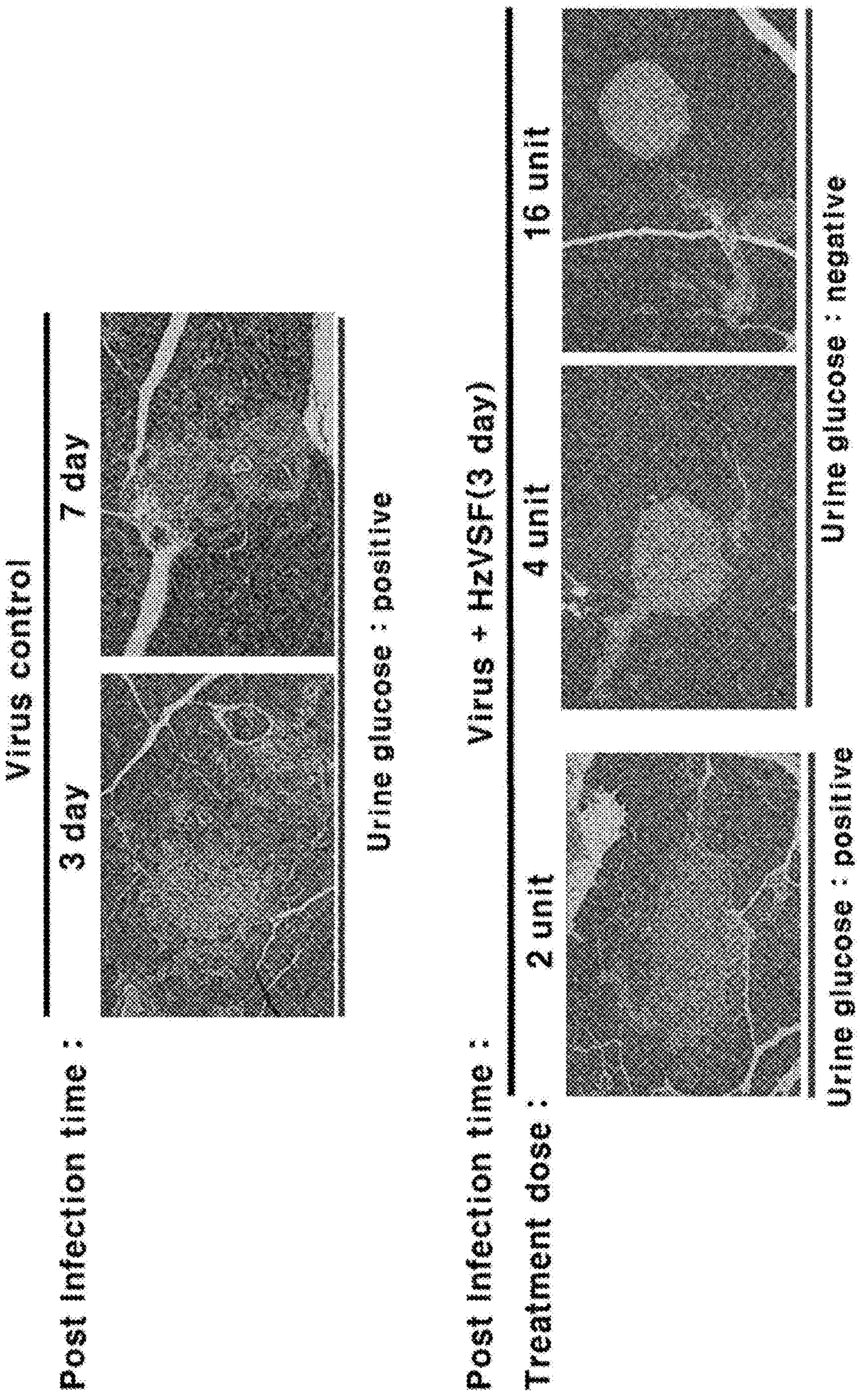

[FIG. 26]
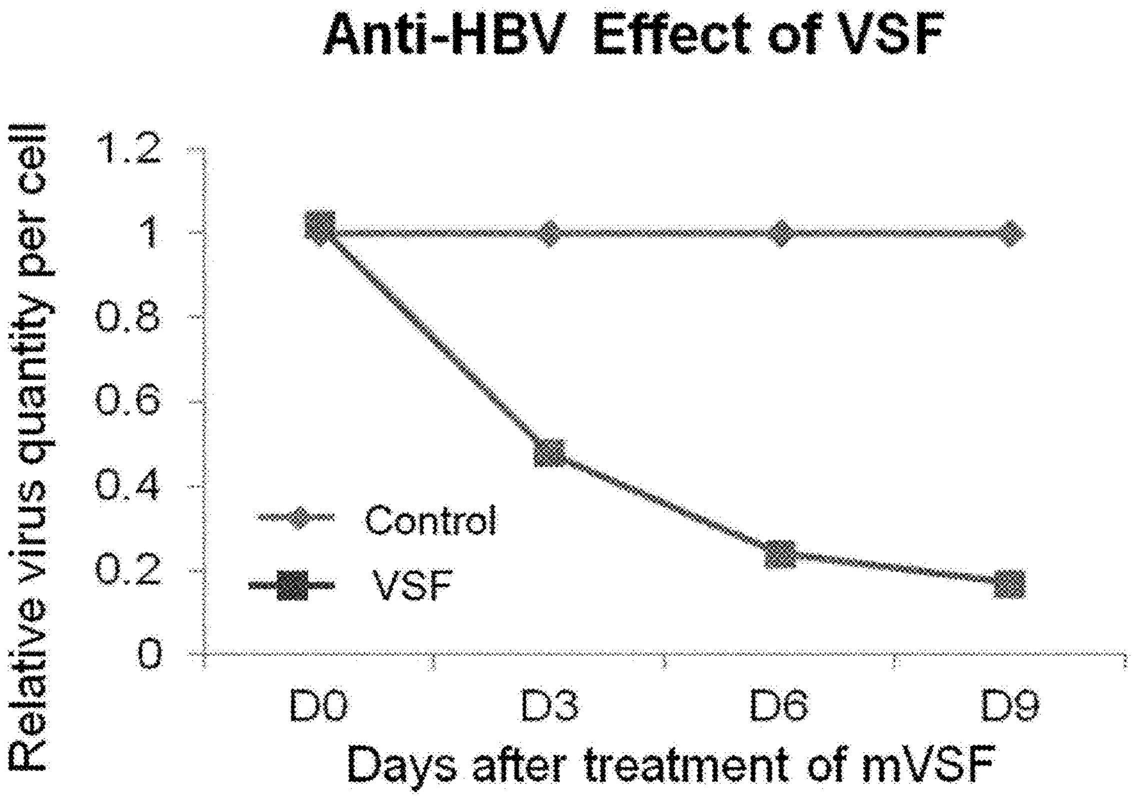

[FIG. 27]
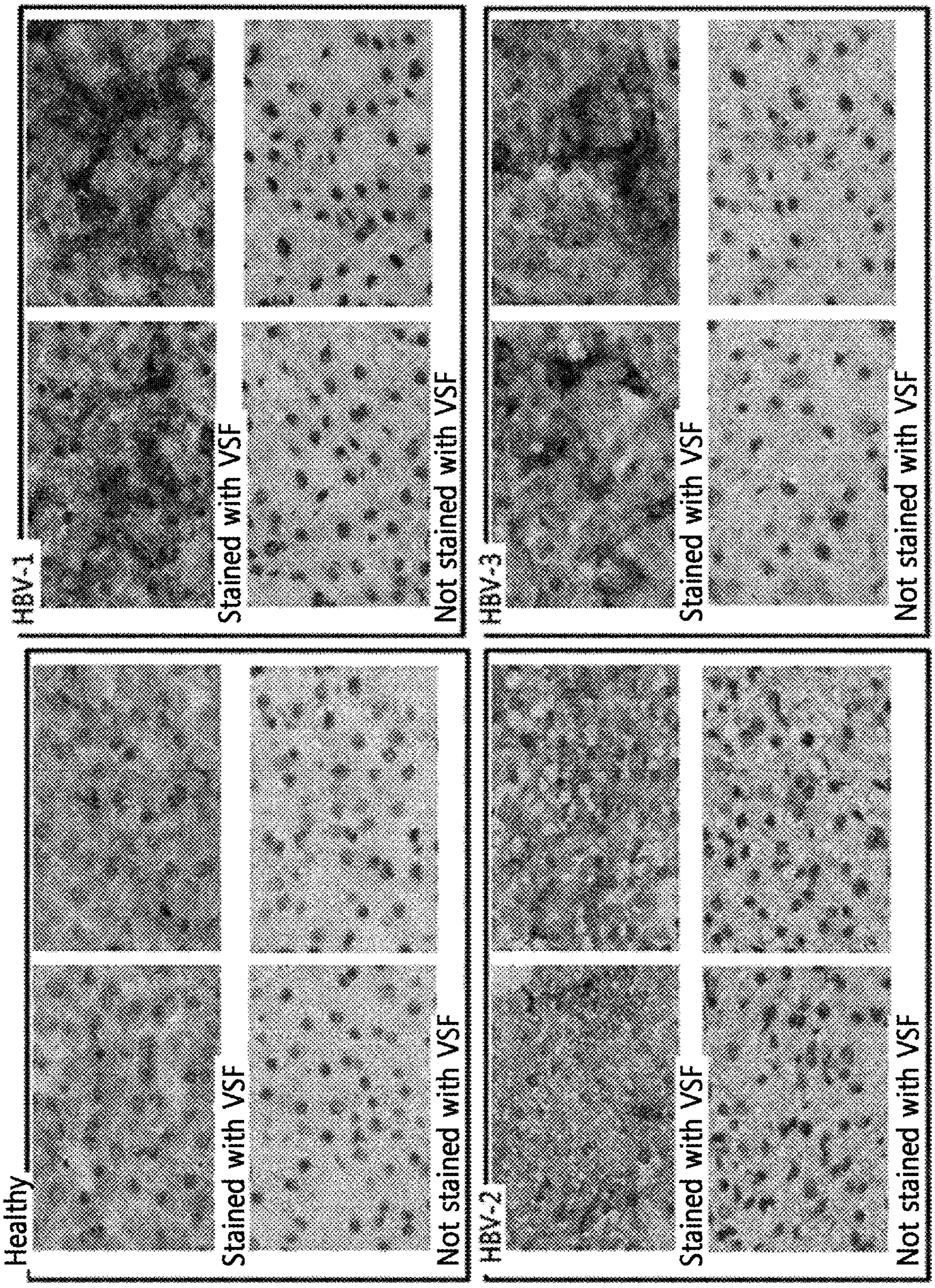

[FIG. 28]
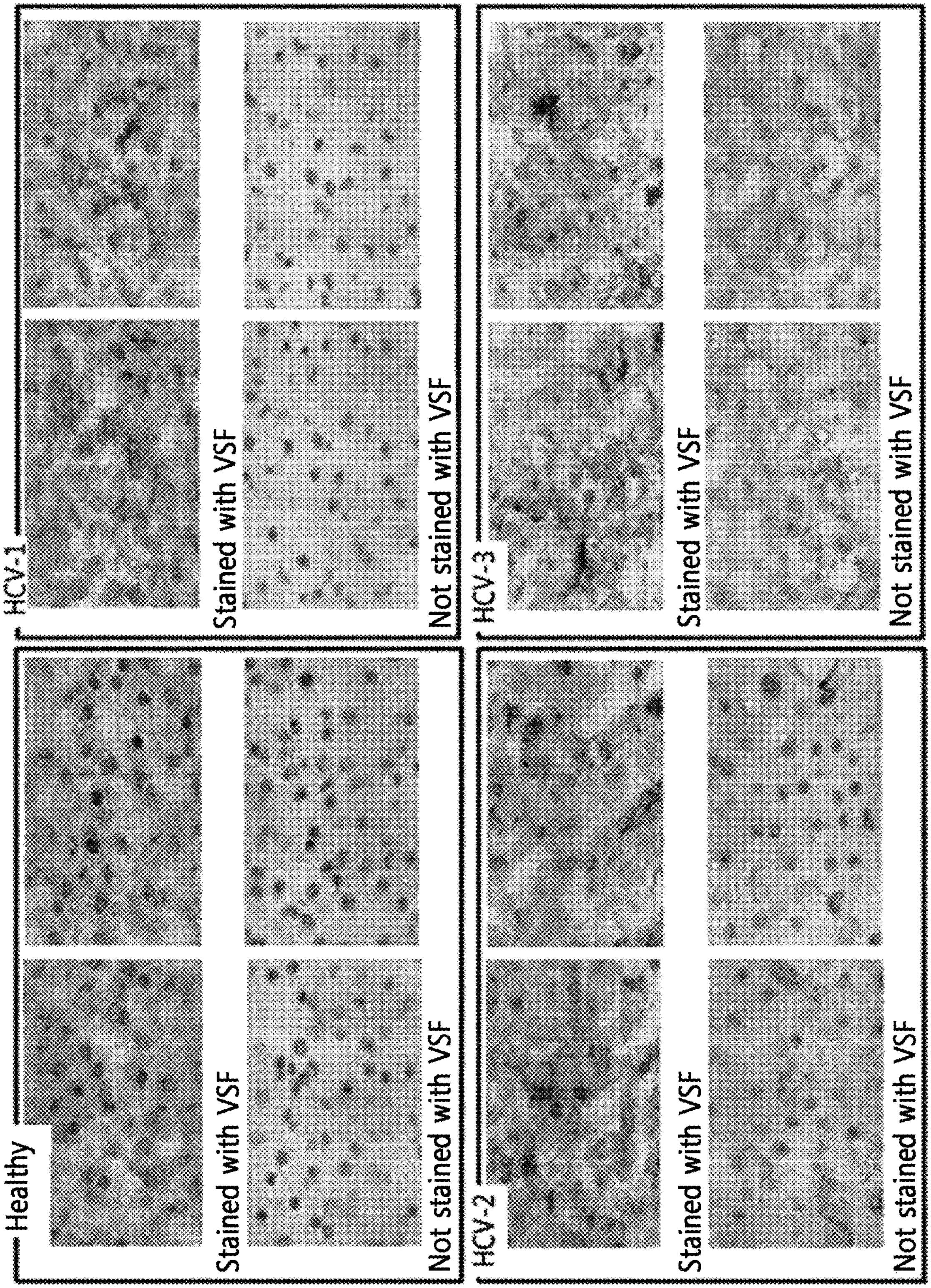

[FIG. 29]
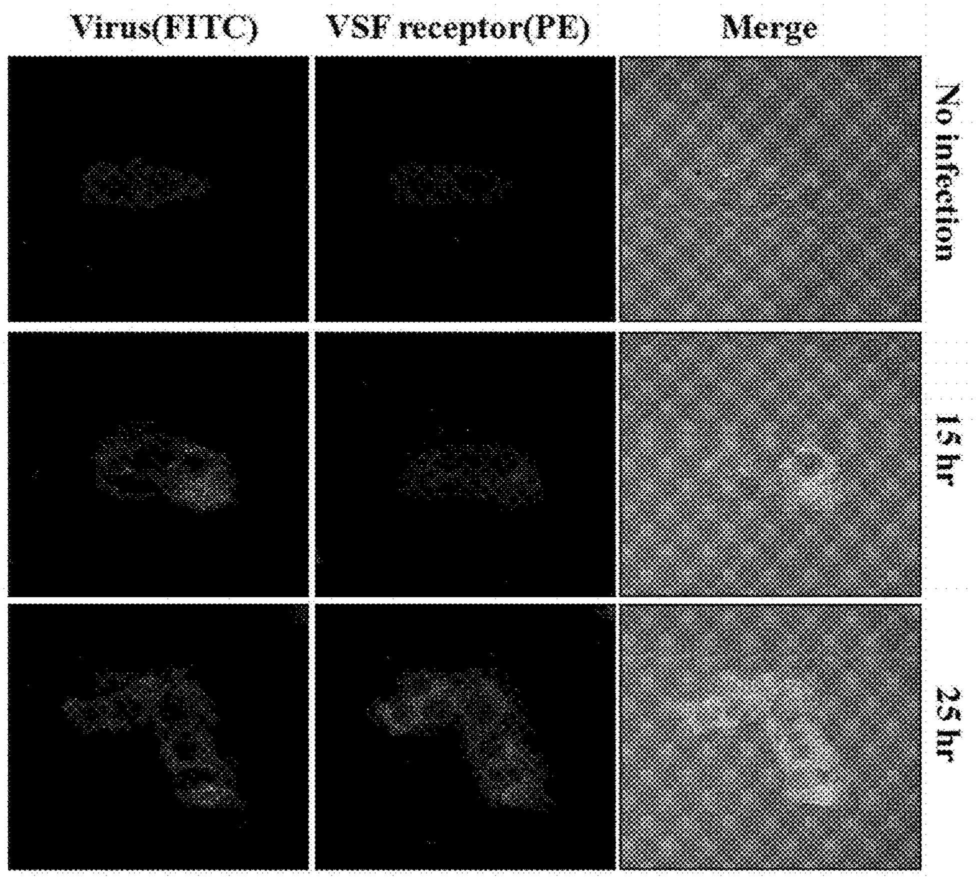
[FIG. 30]
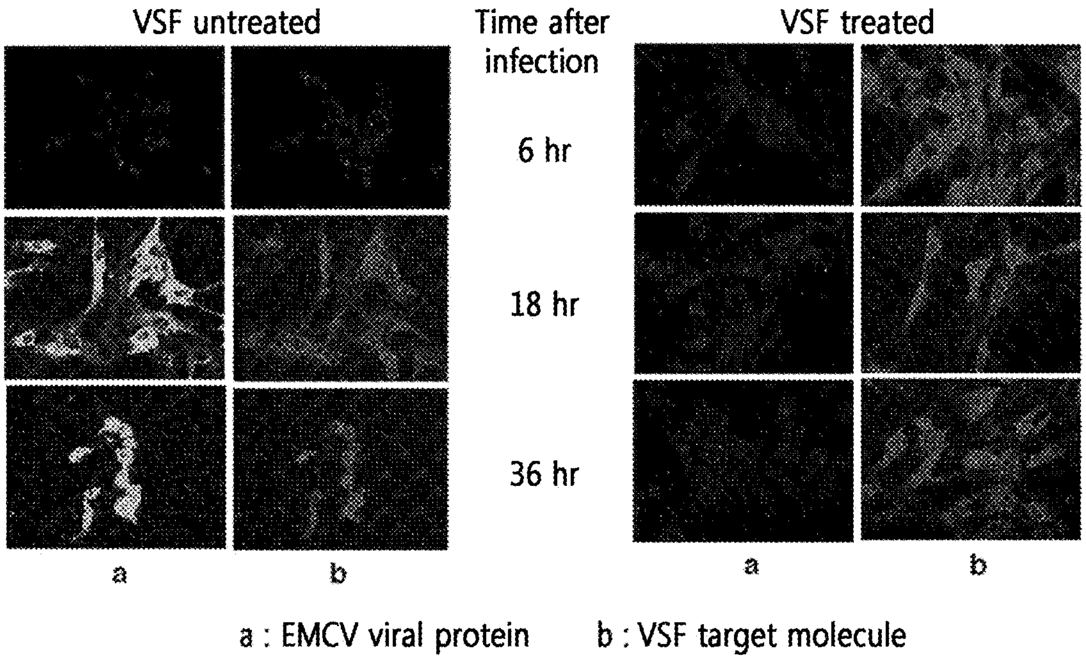

[FIG. 31]
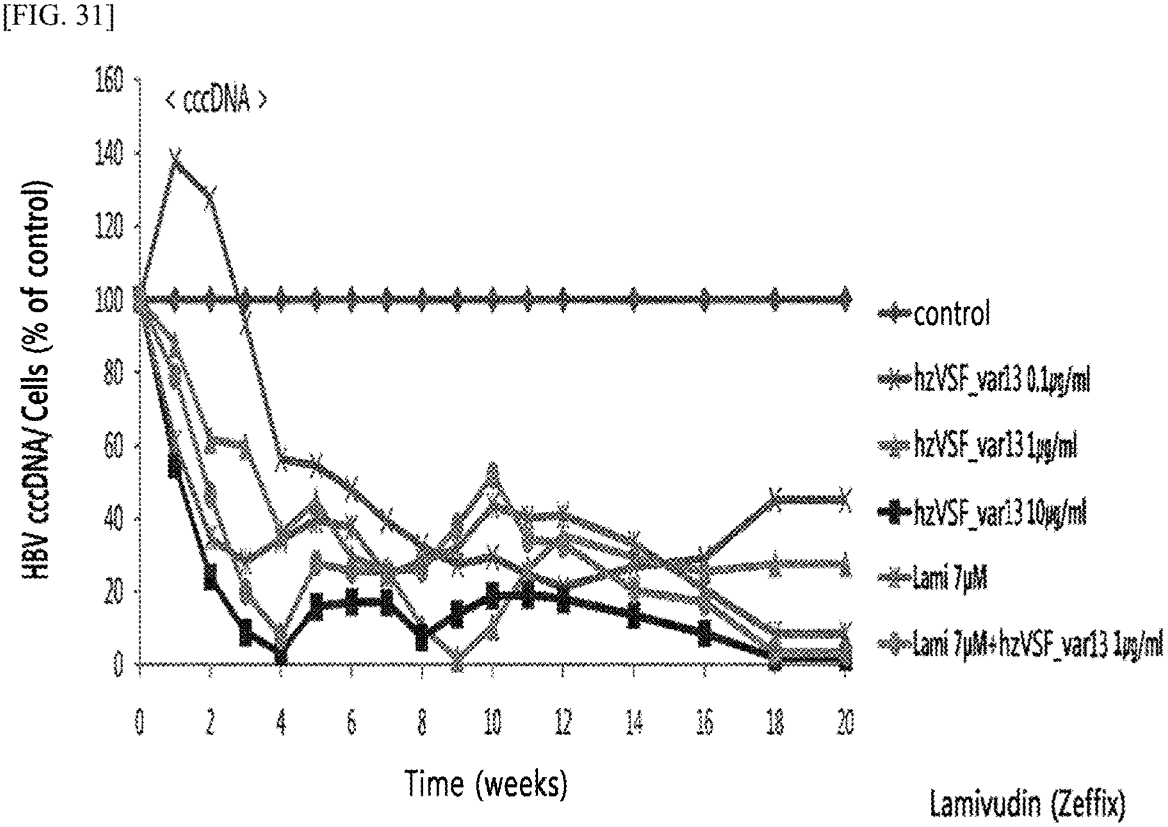
[FIG. 32]
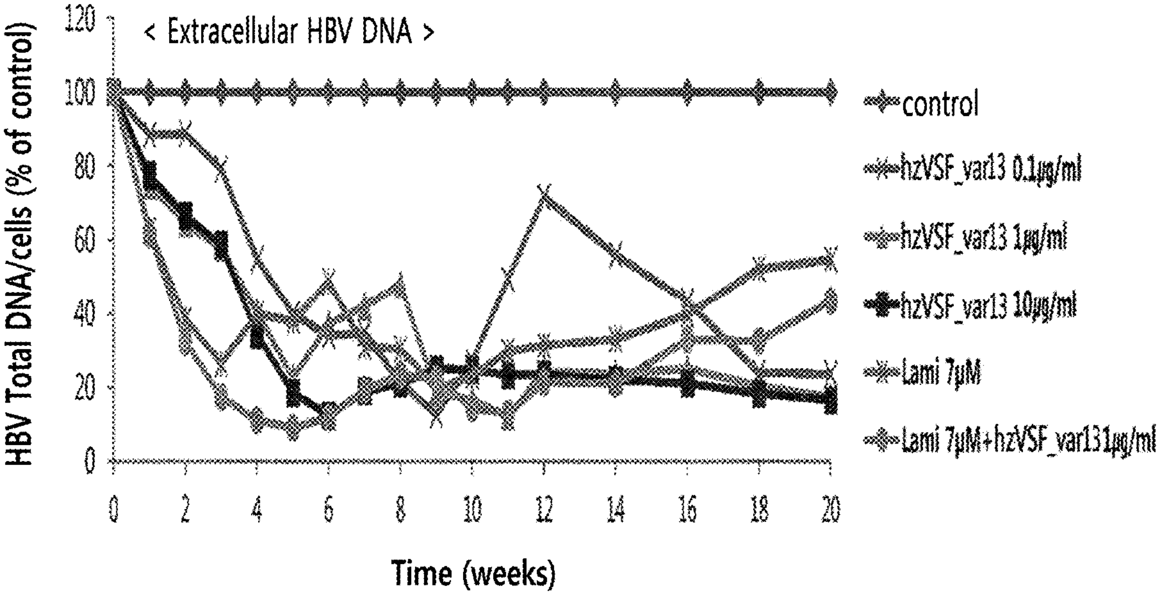

[FIG. 33]
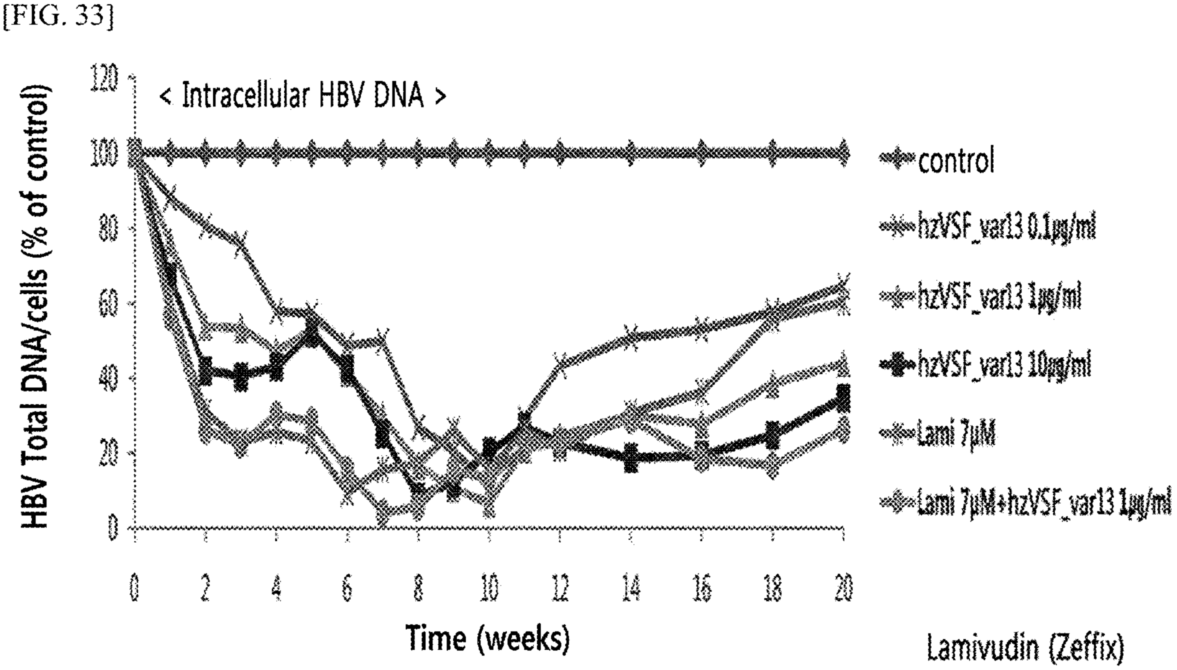
[FIG. 34]
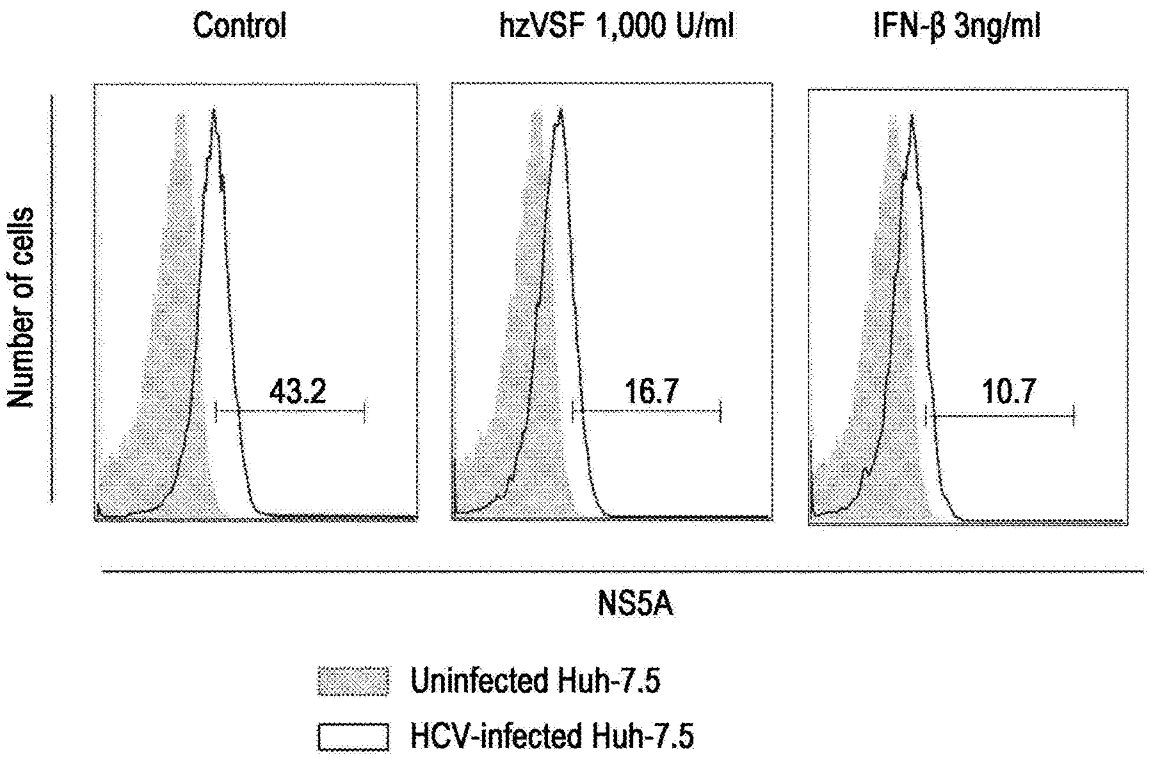

[FIG. 35]
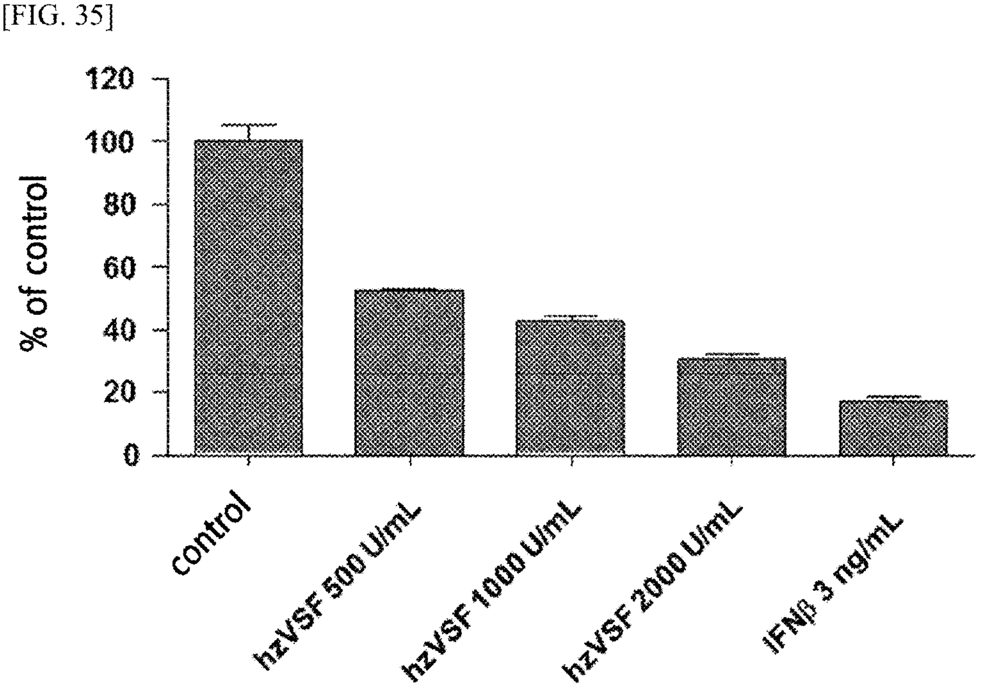

[FIG. 36]
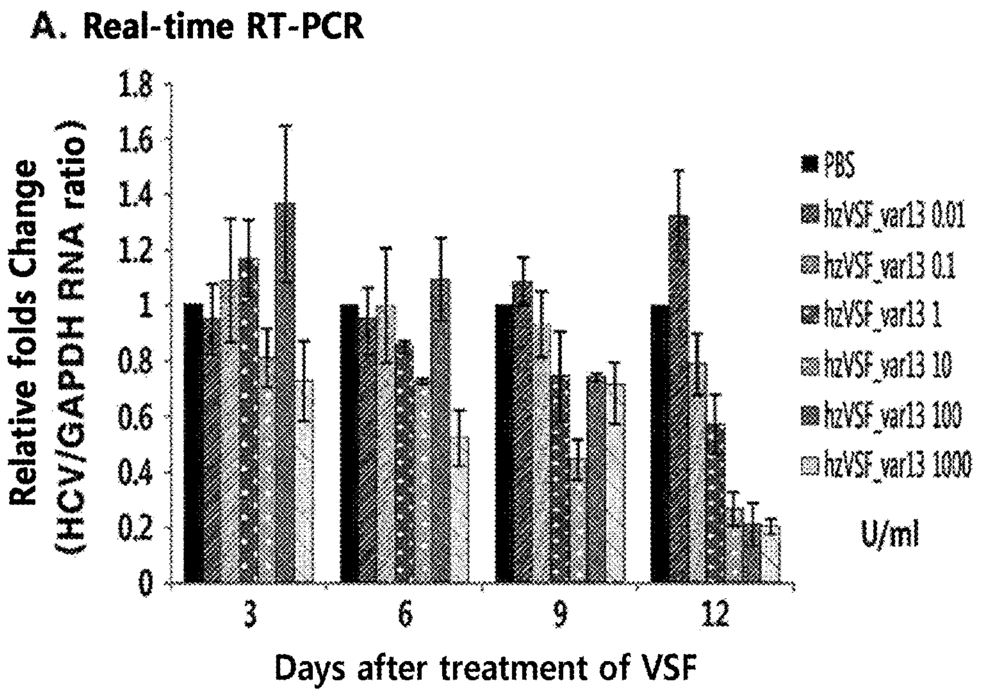
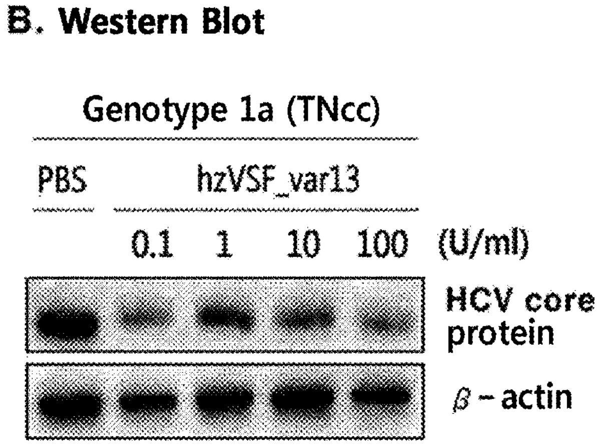
A. Real-time RT-PCR
Y-axis: Relative folds Change (HCV/GAPDH RNA ratio)
X-axis: Days after treatment of VSF (3, 6, 9, 12)
Legend (U/ml):
- PBS
- hzVSF_var13 0.01
- hzVSF_var13 0.1
- hzVSF_var13 1
- hzVSF_var13 10
- hzVSF_var13 100
- hzVSF_var13 1000
B. Western Blot
Genotype 1a (TNcc)
| PBS | hzVSF_var13 | | | |
|---|---|---|---|---|
| | 0.1 | 1 | 10 | 100 (U/ml) |
HCV core protein
β-actin

[FIG. 37]
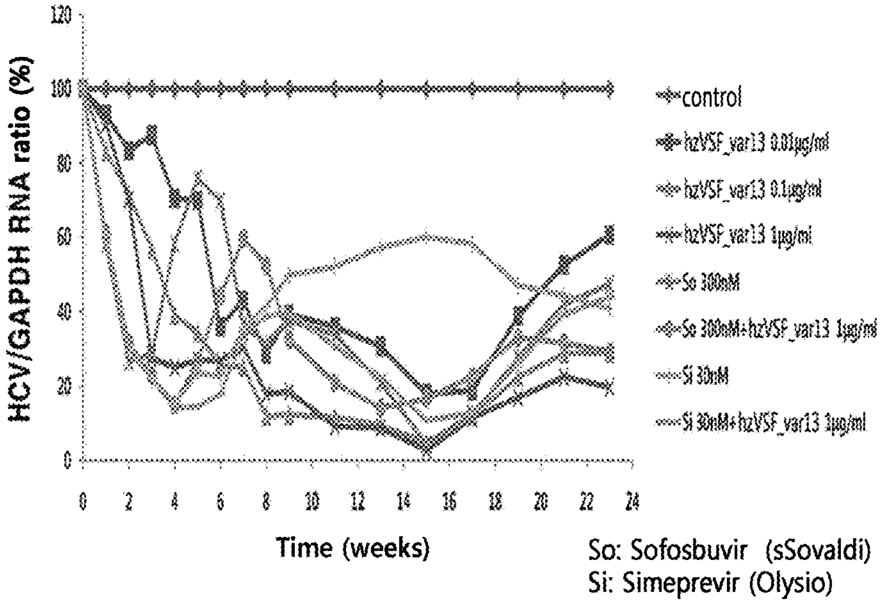
[FIG. 38]
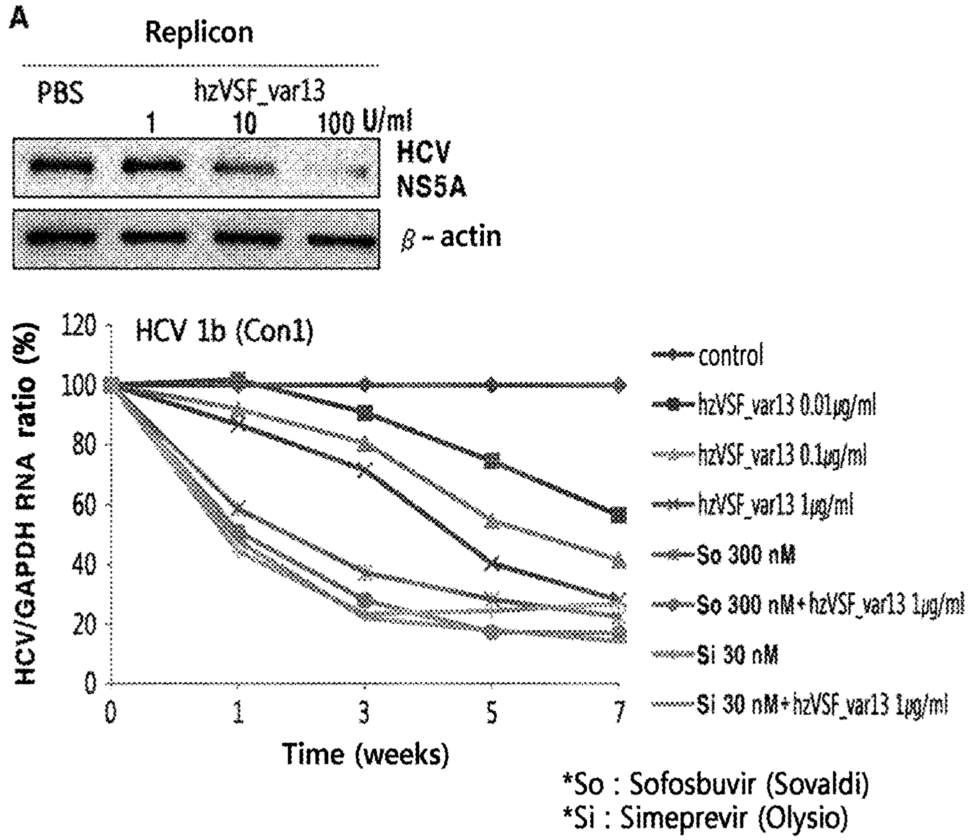

[FIG. 39]
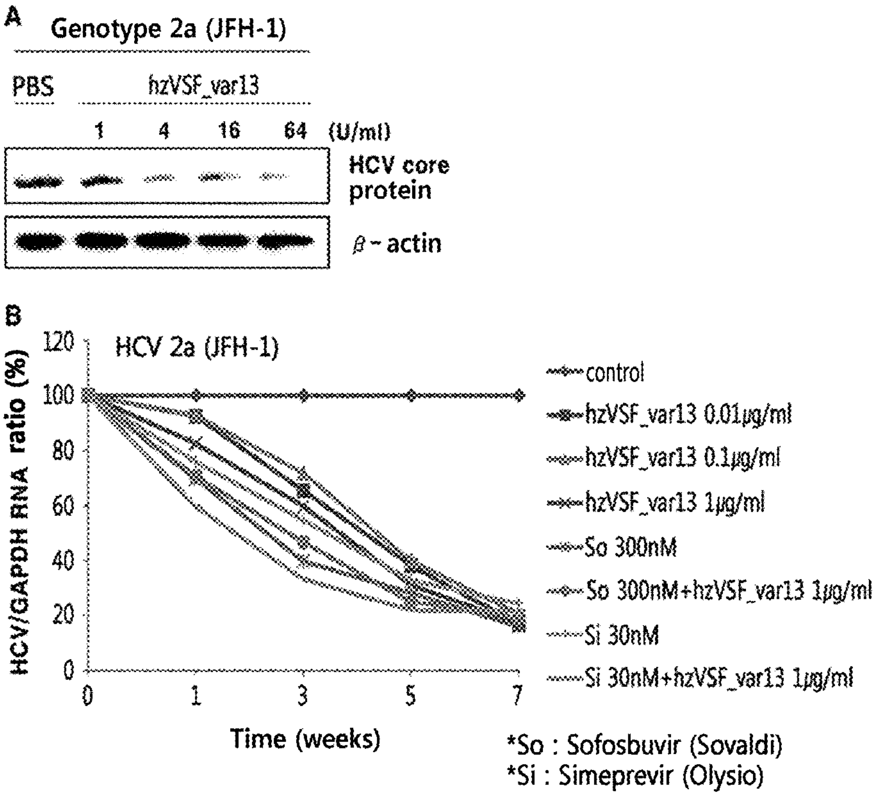
[FIG. 40]
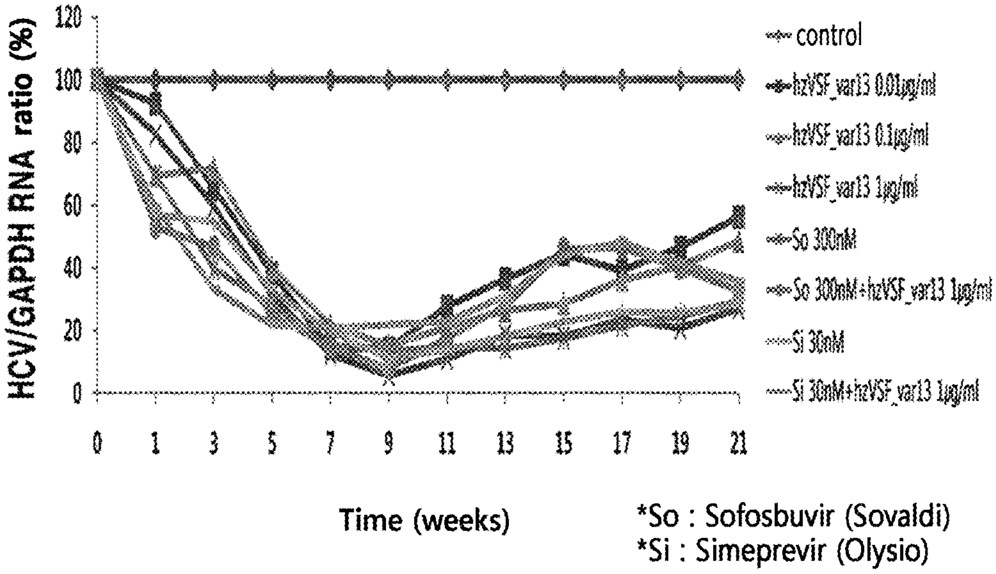

[FIG. 41]
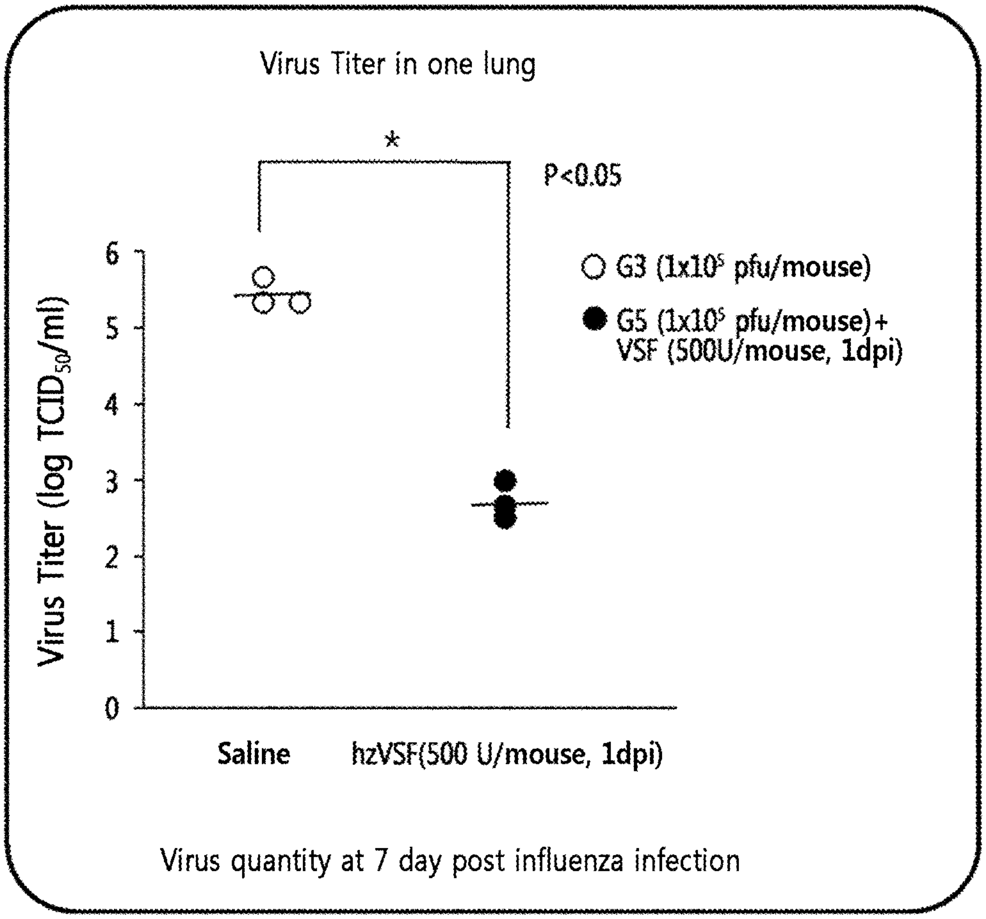

[FIG. 42]
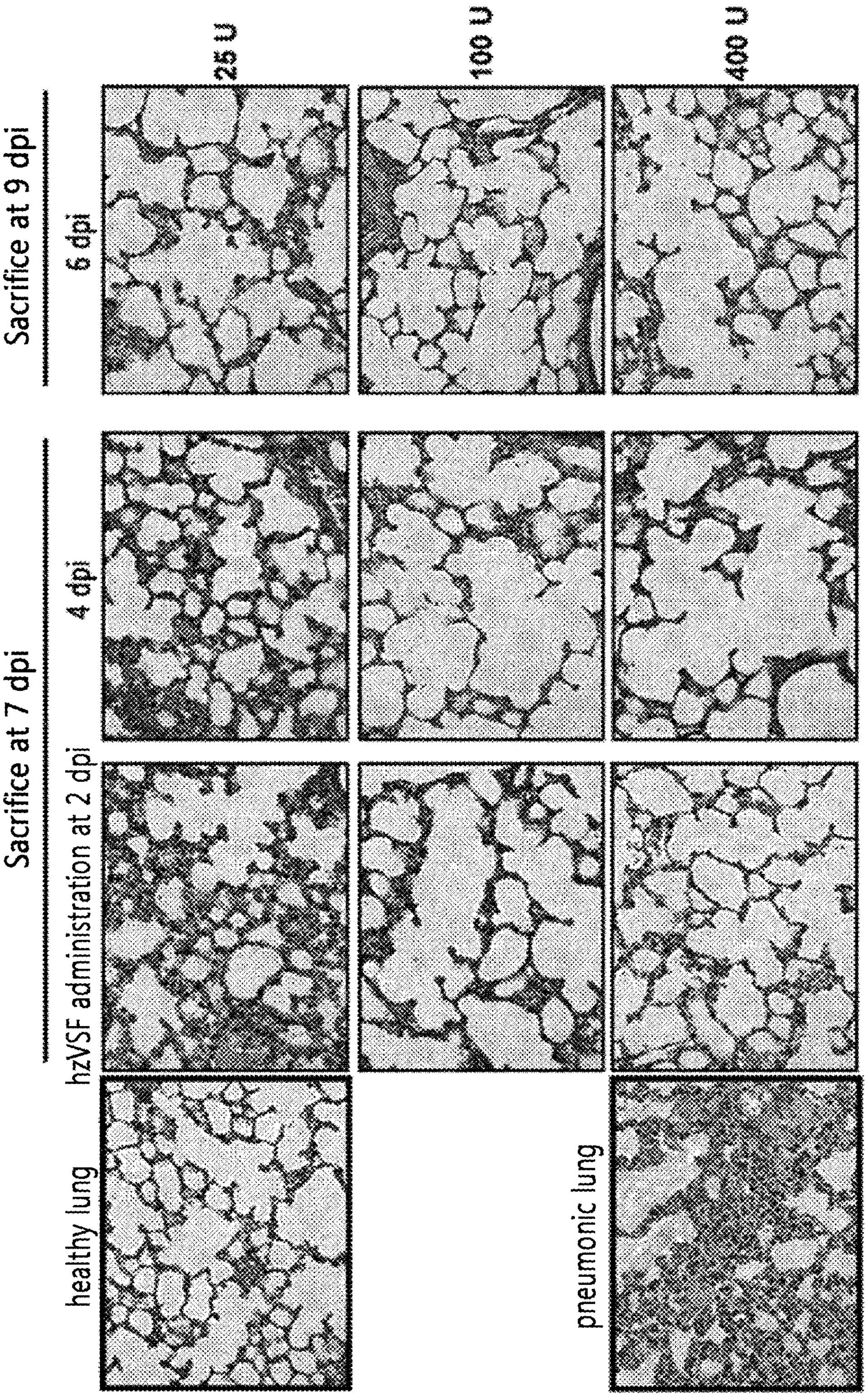

[FIG. 43]
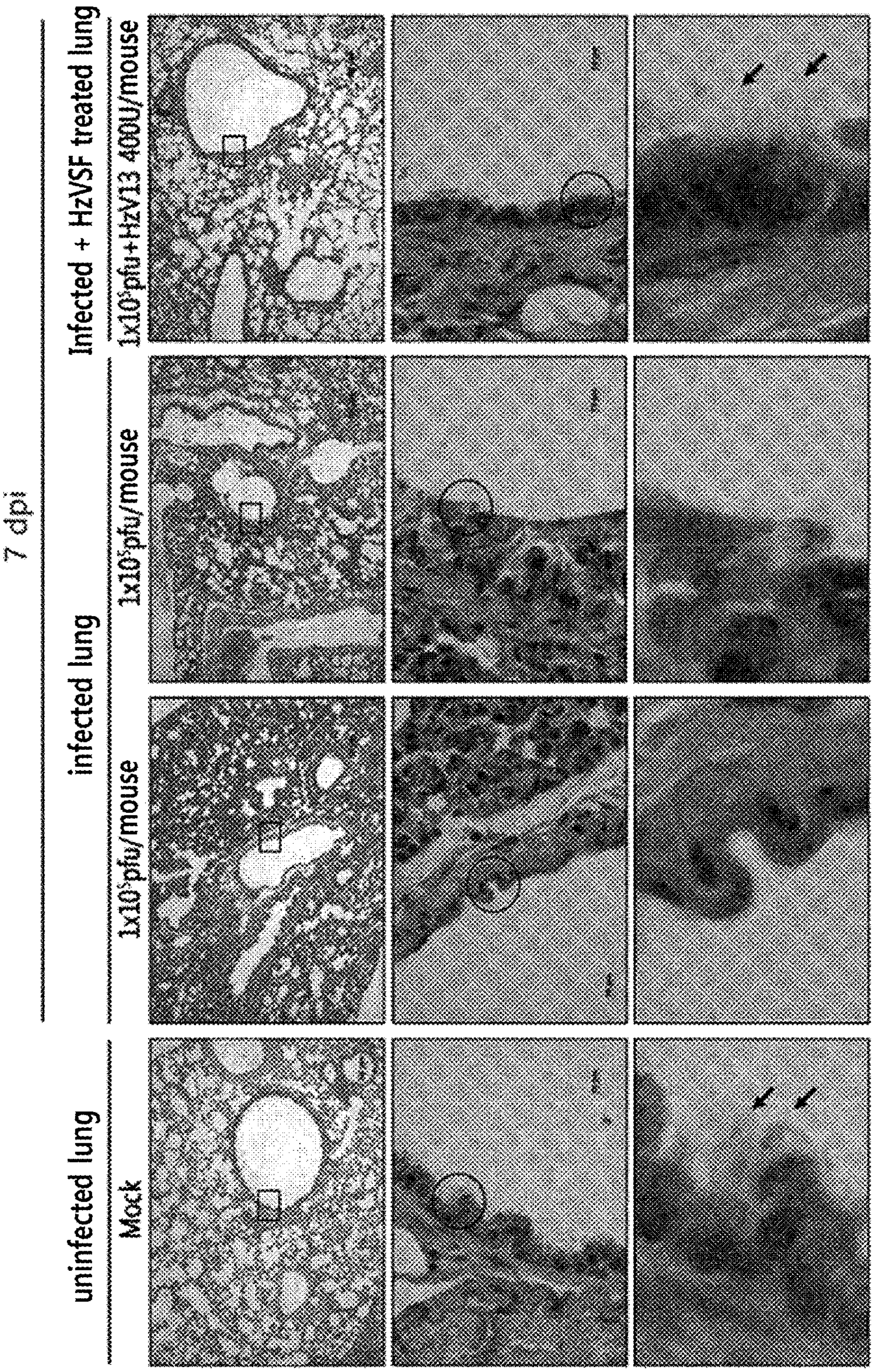

[FIG. 44]
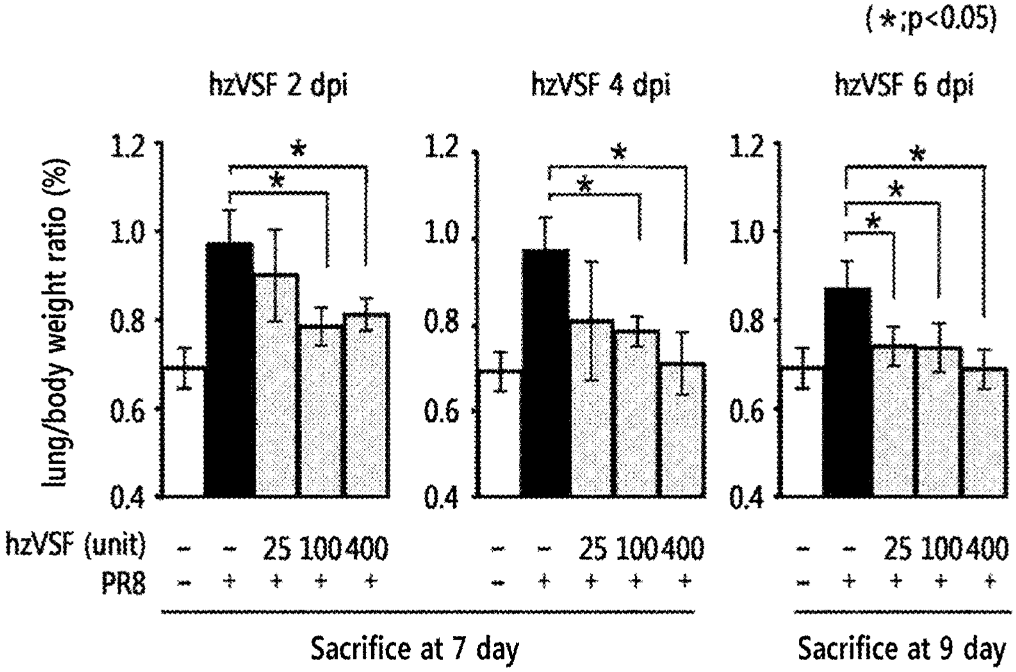
[FIG. 45]
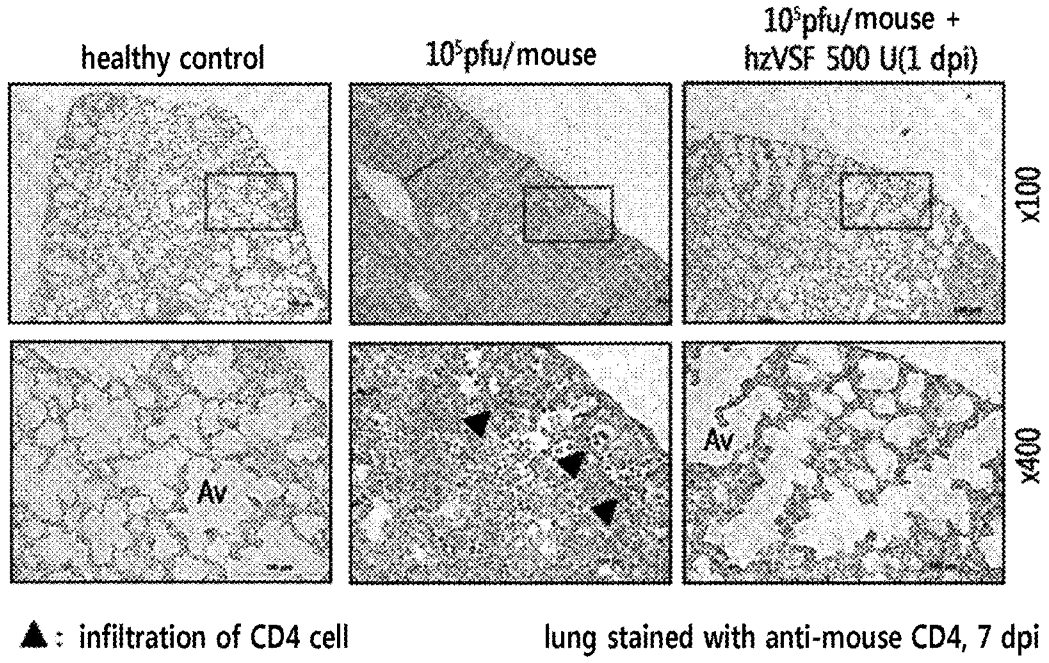

[FIG. 46]
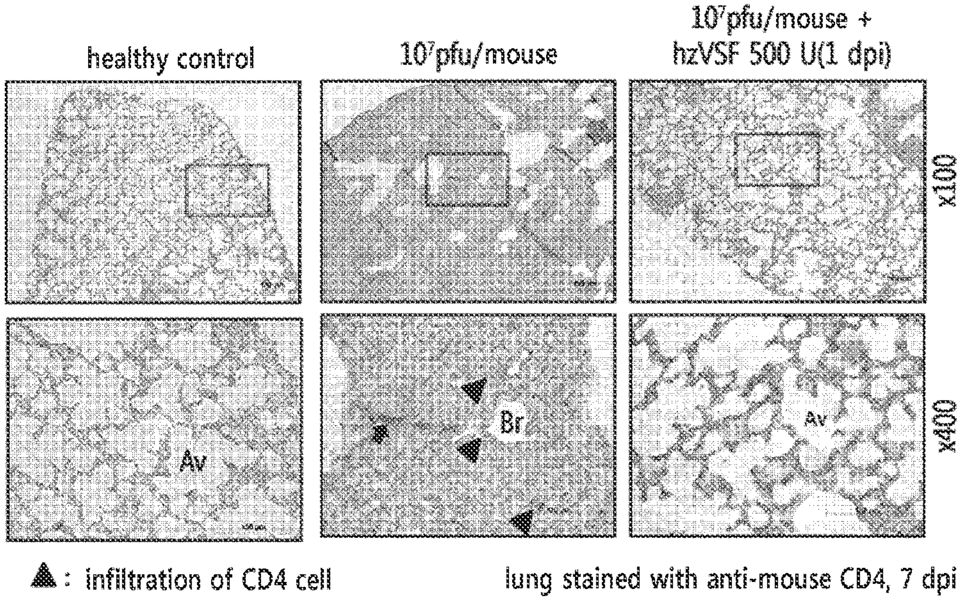

[FIG. 47]
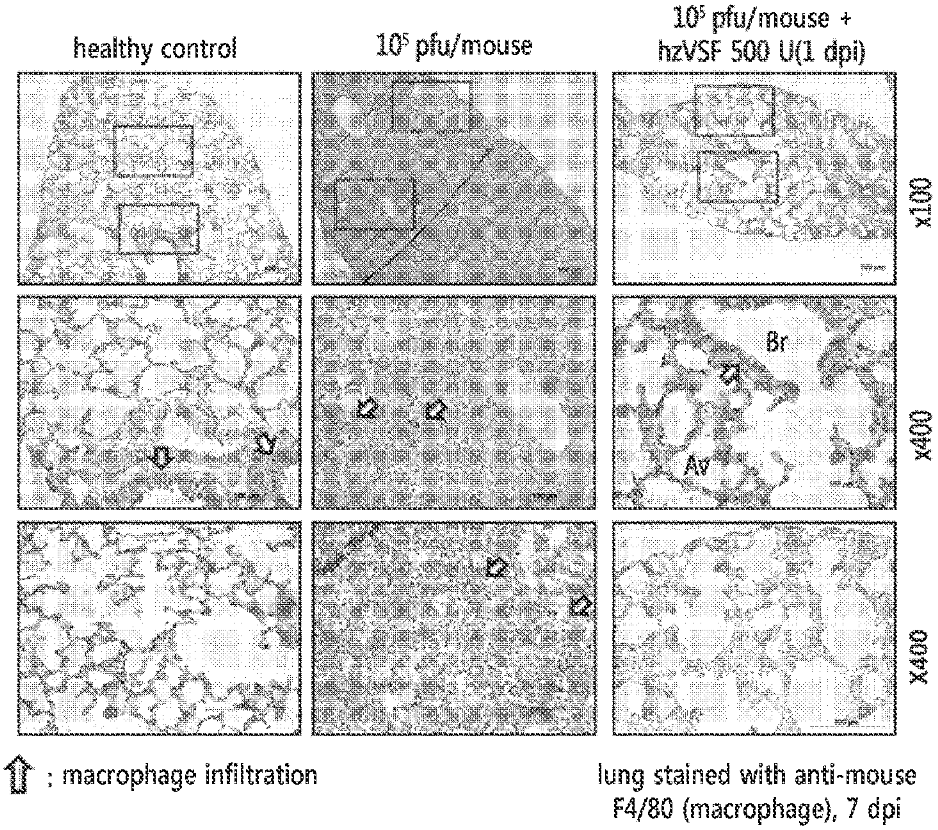

[FIG. 48]
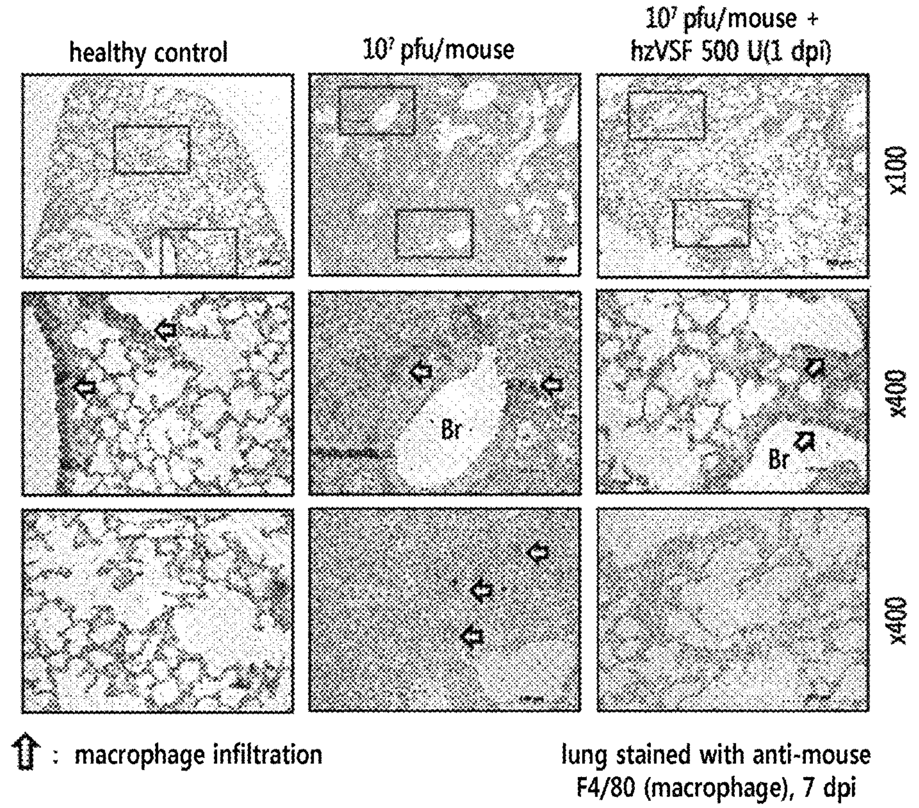

[FIG. 49]
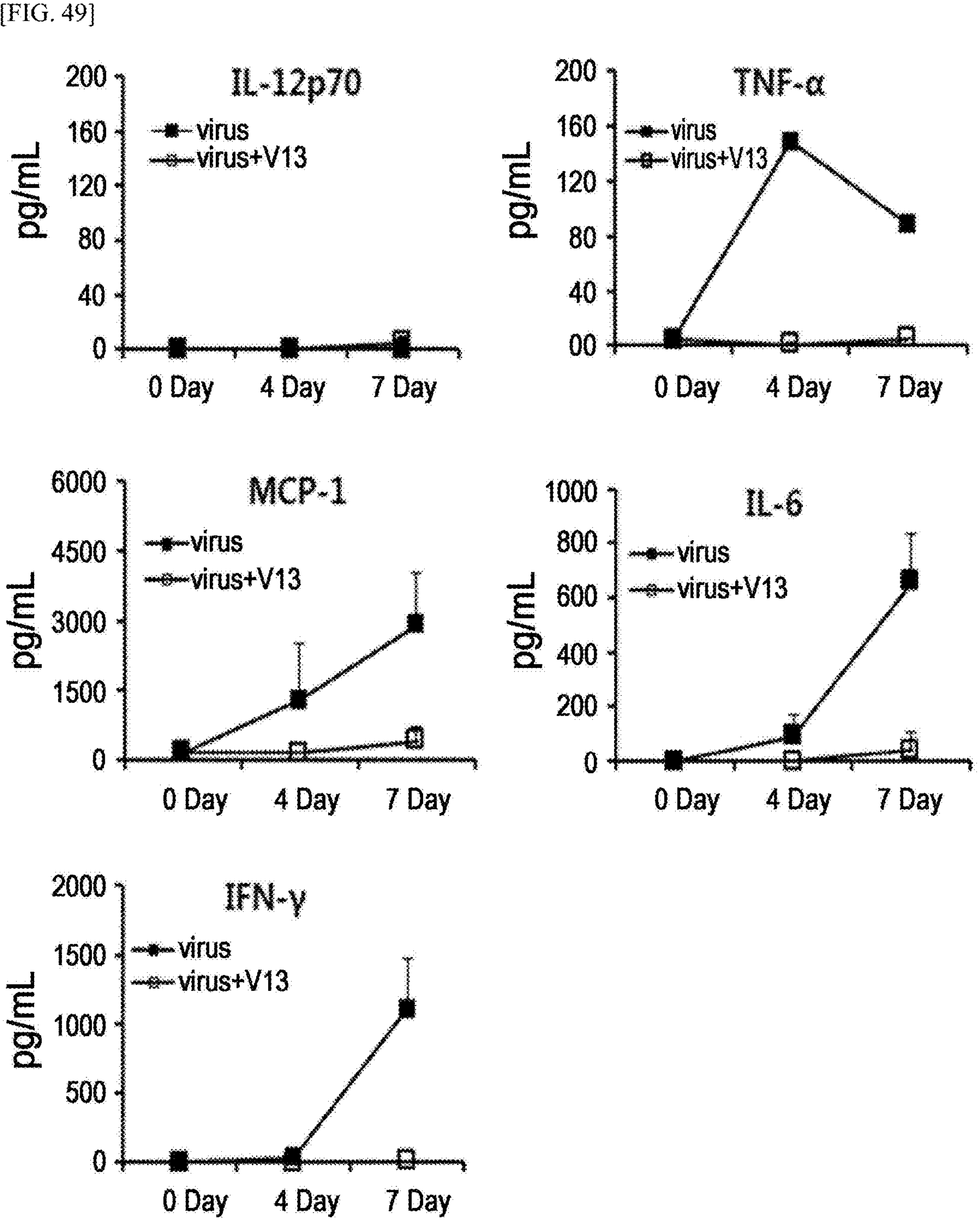

[FIG. 50]
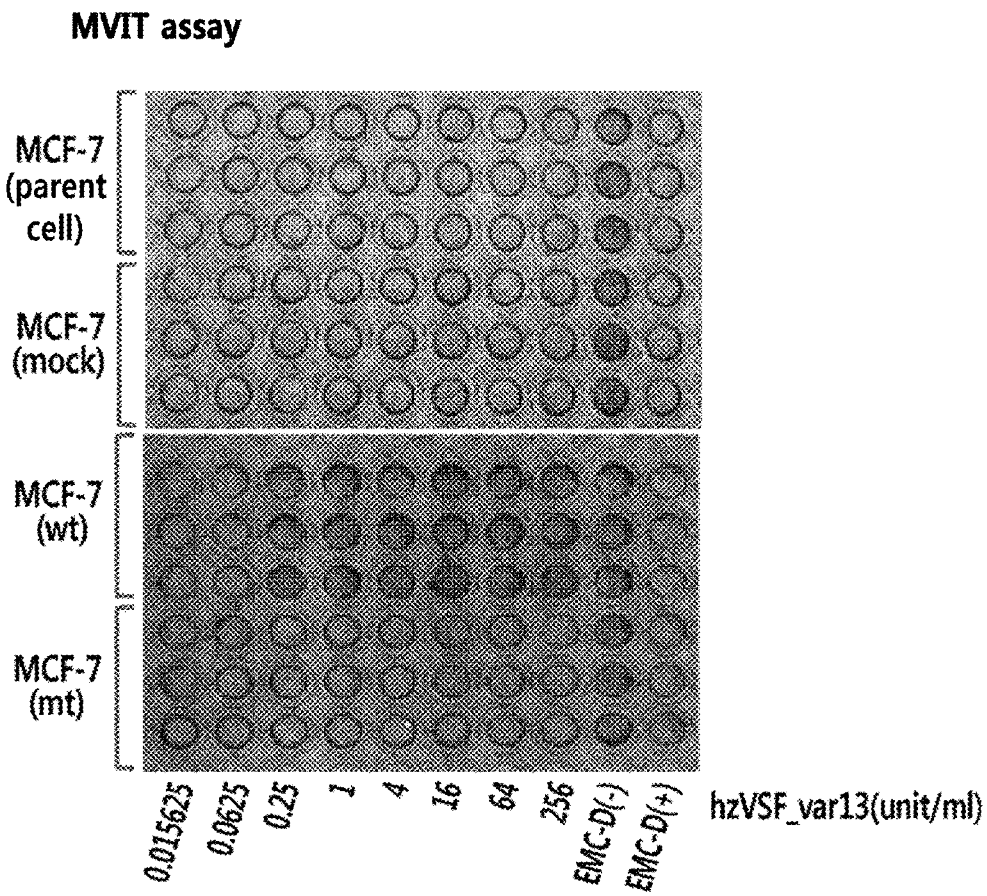

[FIG. 51]
WST assay
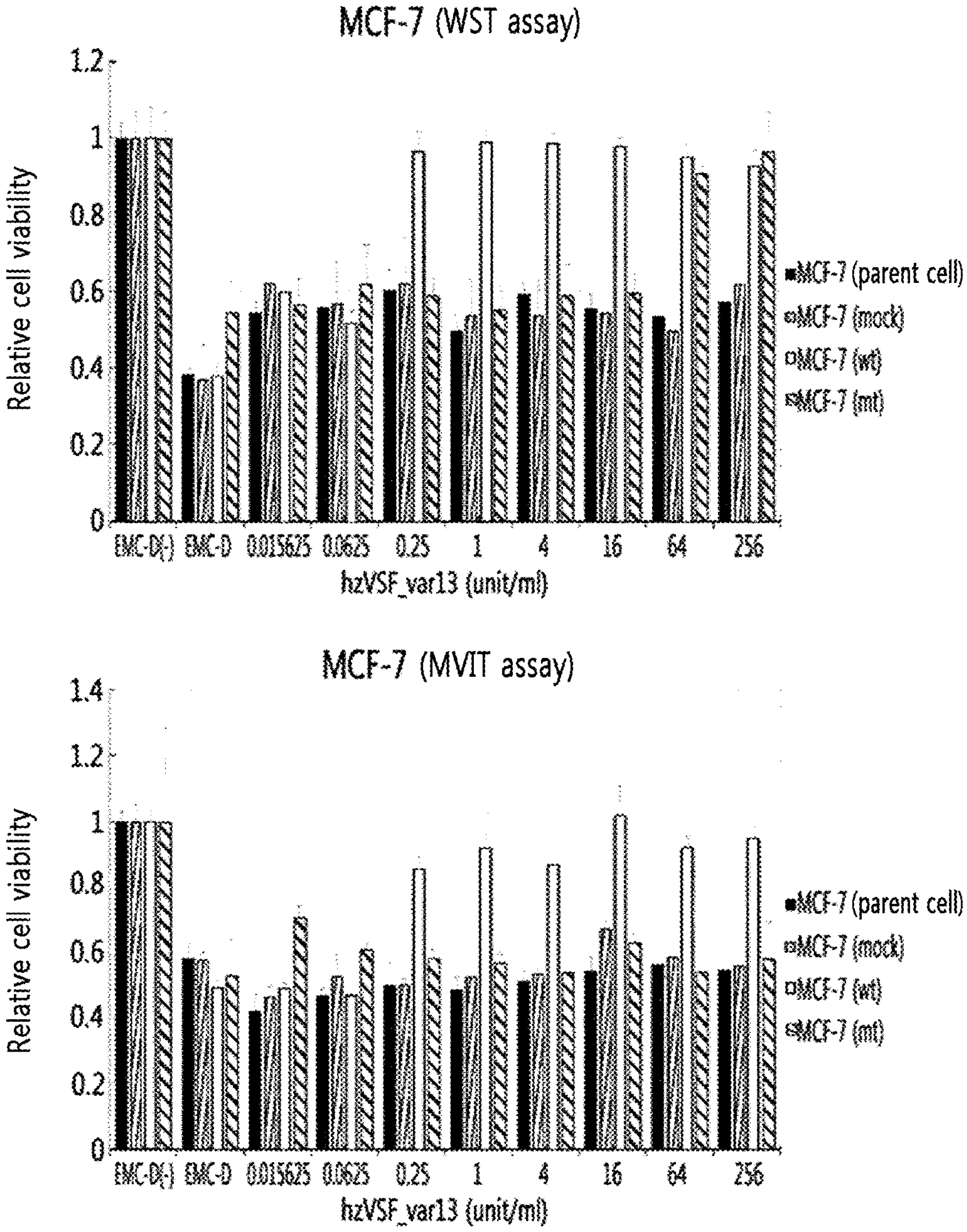

[FIG. 52]
MVIT assay
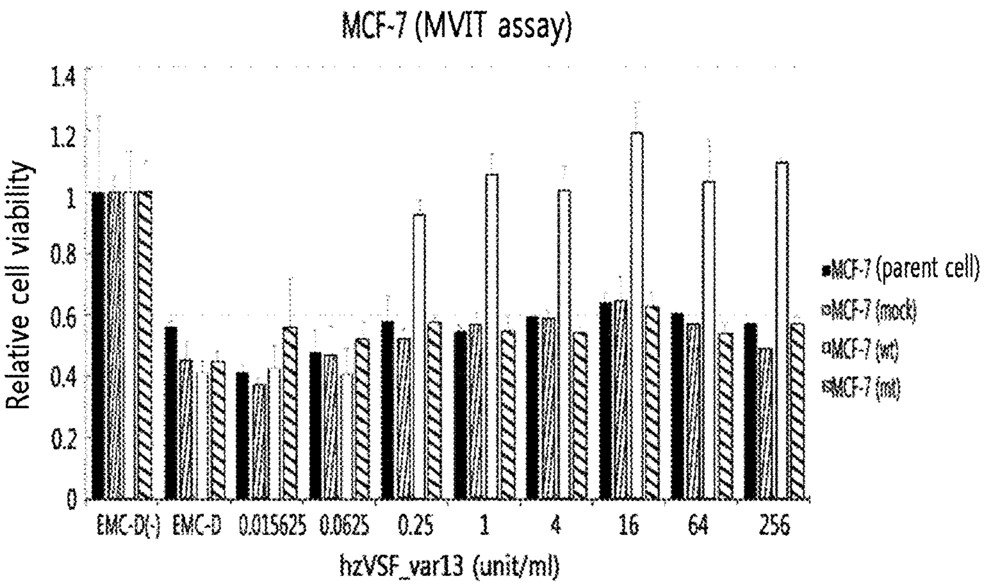

[FIG. 53]
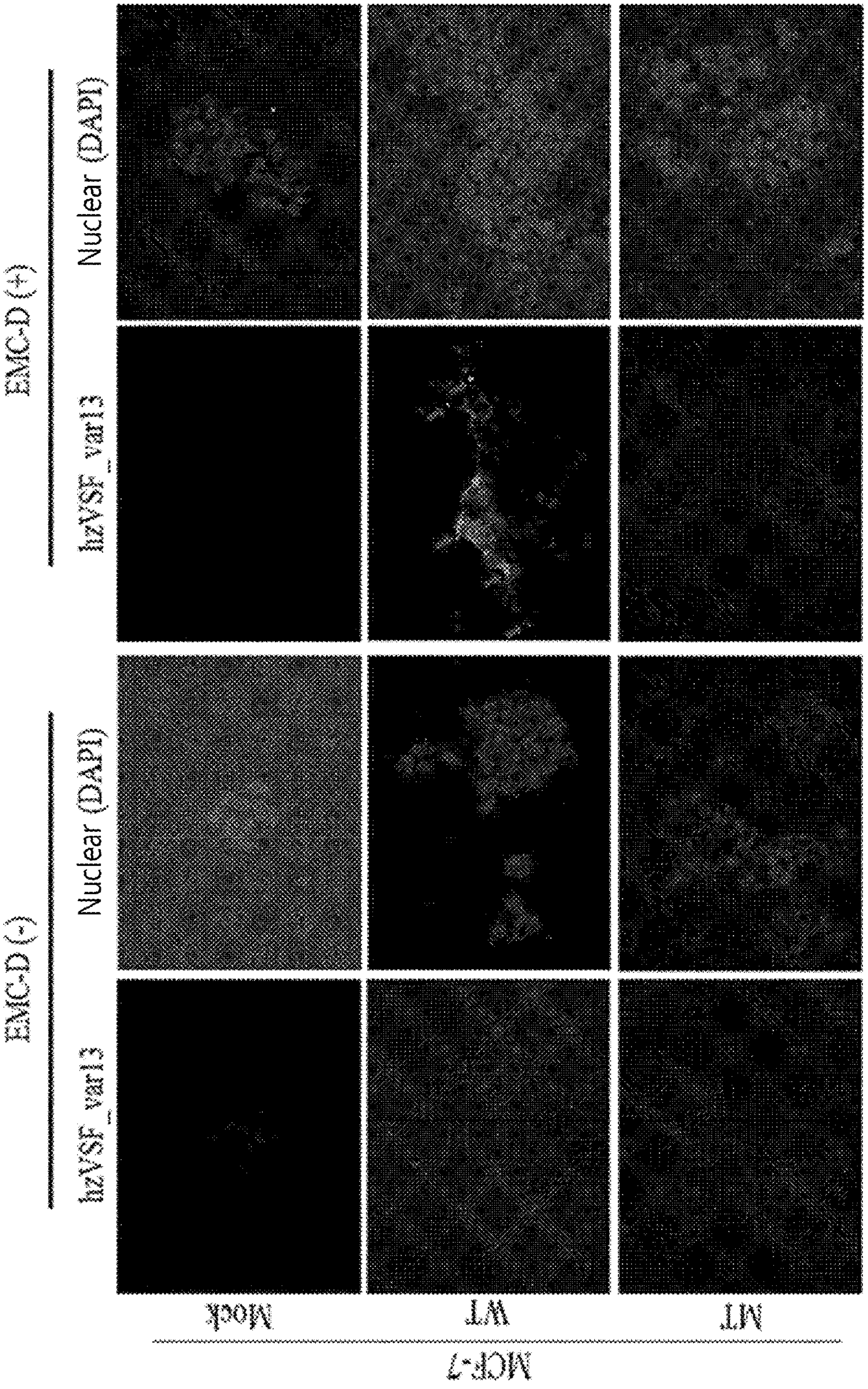

[FIG. 54]
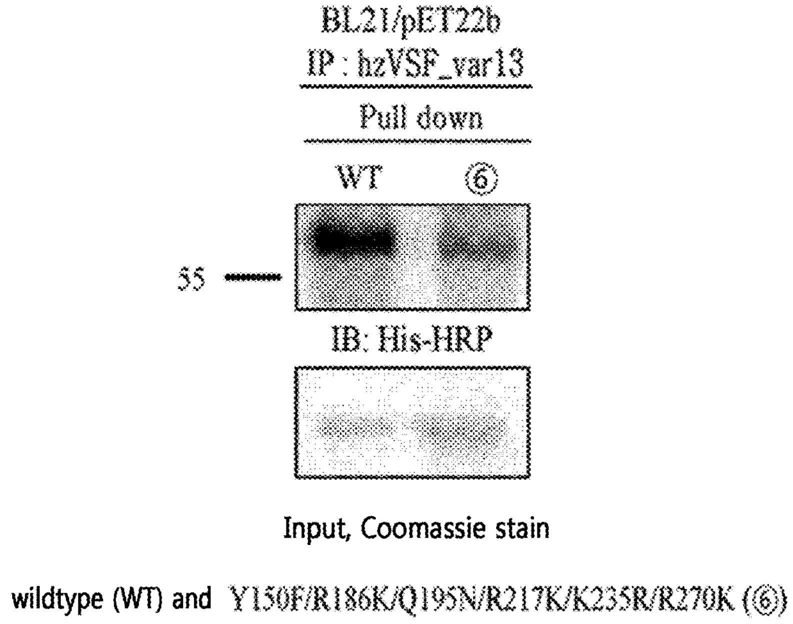
[FIG. 55]
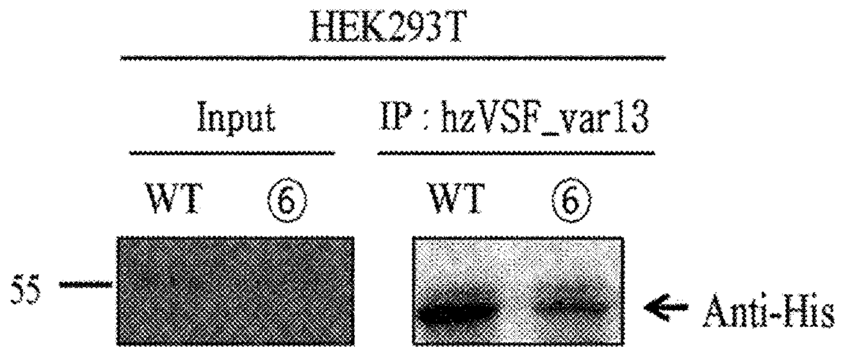

[FIG. 56]
Vimentin-VSF binding model
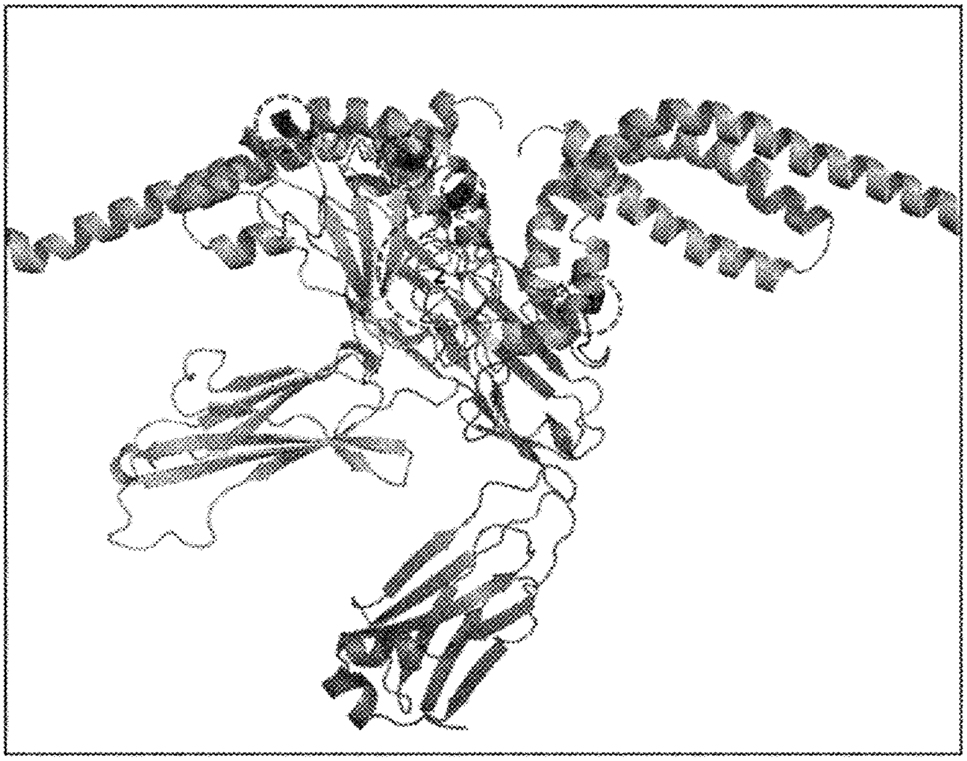
green : p60
cyan : VSF_HC
magenta : VSF_LC
red : binding residues in P60 (R186, Q195, R217, K235, R270)

[FIG. 57]
Vimentin-VSF binding model
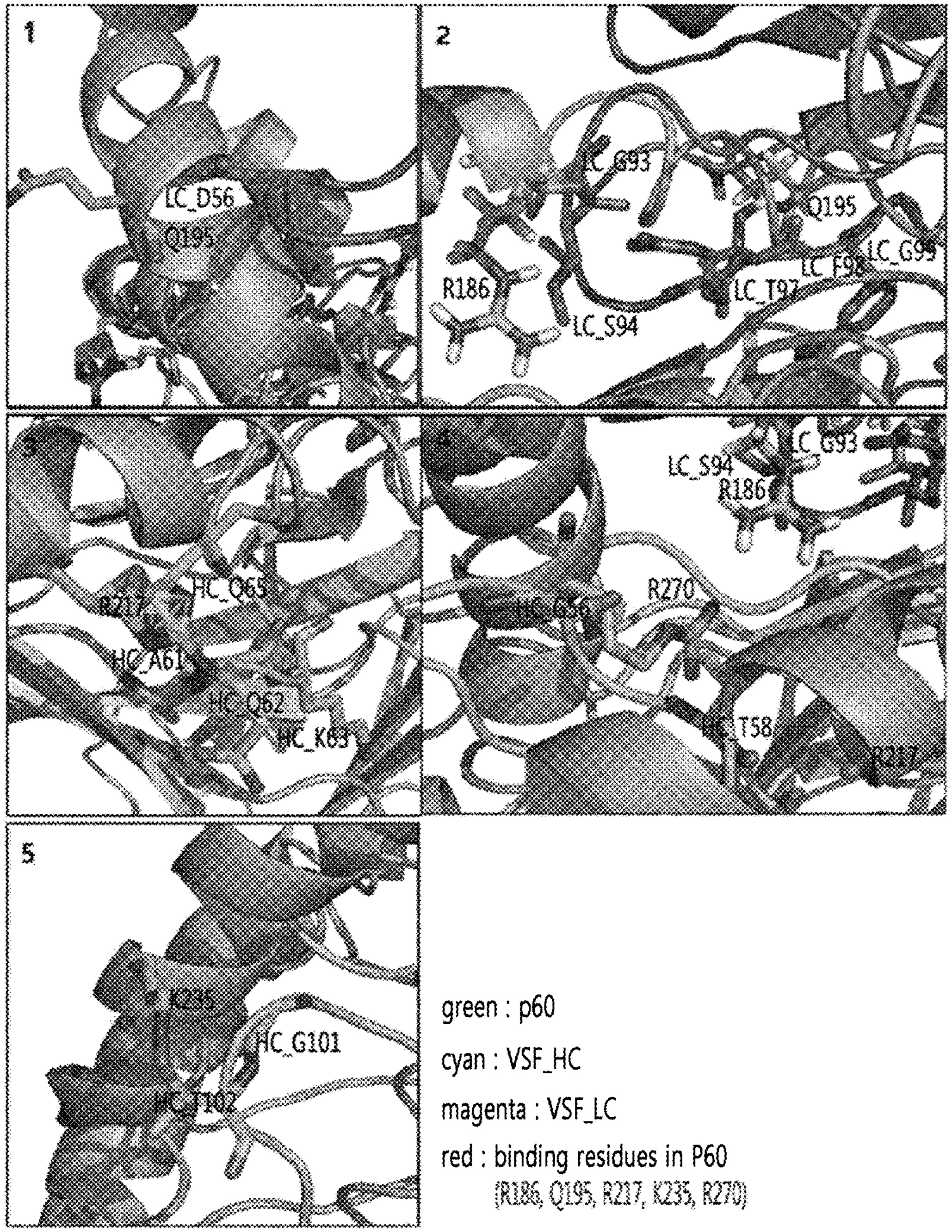

[FIG. 58]
Vimentin-VSF binding model
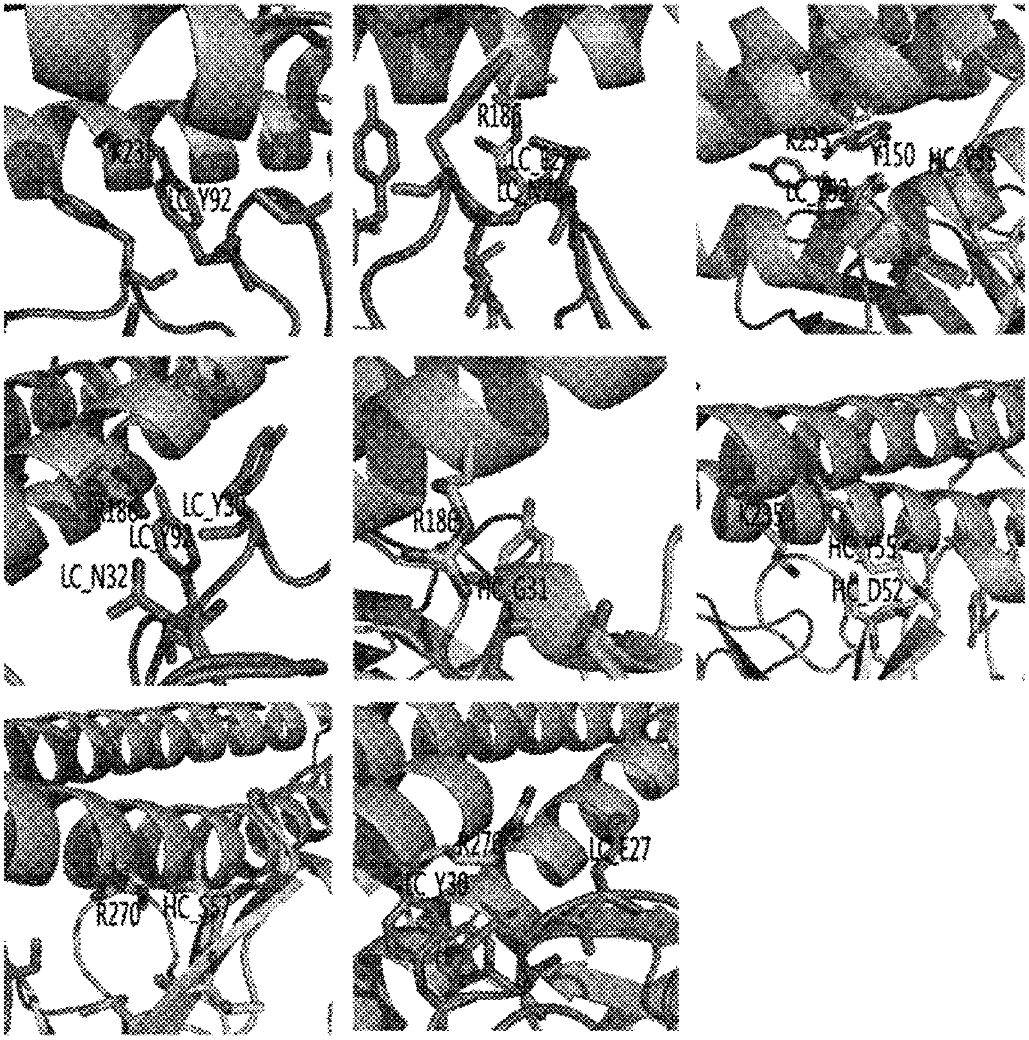
- green: p60, cyan: HC, magenta: LC
- confirmation of binding residues of tetramer VSF regarding the binding residues in P60 (Y150, R186, K235, R270)
- In the complex modeling, the binding to Q195 and R217 are not observed.

ANTIBODY SPECIFICALLY BINDING TO AN ISOLATED PEPTIDE DERIVED FROM VIMENTIN OR A FRAGMENT BINDING TO THE PEPTIDE

CROSS-REFERENCED TO RELATED APPLICATIONS

This application is a U.S. National Phase Application of PCT International Application No. PCT/KR2016/006215, filed on Jun. 10, 2016, designating the United States of America, which is an International Application of and claims the benefit of priority to Korean Patent Application No. 10-2015-0082132, filed on Jun. 10, 2015; and also claims the benefit of priority to PCT International Application No. PCT/KR2015/005917, filed on Jun. 12, 2015.

SEQUENCE LISTING STATEMENT

The present application contains a Sequence Listing, which is being submitted via EFS-Web. The Sequence Listing is submitted in a file entitled "Sequence-Listing-HAN031-001APC.txt" which was created on Mar. 2, 2018, and is approximately 204 kb in size. This Sequence Listing is hereby incorporated by reference in its entirety.

TECHNICAL FIELD

The present invention relates to an antibody specifically binding to the peptide of SEQ ID NO: 1, and specifically, to an antibody specifically binding to an isolated peptide of SEQ ID NO: 1 or a fragment binding to the peptide, a polynucleotide encoding the antibody or the fragment binding to the peptide, a vector containing the polynucleotide, a cell introduced with the vector, a method of producing the antibody or the fragment binding to the peptide using the cell, a recombinant antibody or a fragment binding to the peptide produced by the method, an antiviral composition containing the antibody or the fragment binding to the peptide, a composition for preventing or treating inflammatory diseases containing the antibody or the fragment binding to the peptide, and a method of treating infectious viral diseases or inflammatory diseases using the composition.

BACKGROUND ART

Unlike bacterial diseases, viral diseases are difficult to treat because antibiotics are not particularly effective against viruses, and viral diseases are consistently emerging as one of the main causes of diseases and deaths in humans. Additionally, infectious viral diseases induce inflammation, thereby causing various inflammatory diseases.

The therapeutic agents developed for the treatment of such infectious viral diseases may be categorized into chemical materials and bio-derived materials, and most of the chemical materials are developed to be effective only against specific viral diseases, exhibiting various adverse effects and disadvantages such as the frequent emergence of resistant viruses.

Meanwhile, well-known examples of the bio-derived materials may include cytokines such as interferon (IFN). Of these, interferon was first discovered among the cytokines produced in virus-infected cells and is known as the cytokine which has the superior antiviral activity. It has been reported that interferon can be used for treating various diseases such as chronic hepatitis B or C, blood cancer, multiple sclerosis, etc. Recently, the effect of IFN on human immunodeficiency virus (HIV) patients has been reported. As such, in an attempt to develop antiviral agents and immune booster, for the past several years, research on genetic engineering or bioengineering methods has been ongoing for the mass production of interferon, and recently, research has been actively conducted to search for compounds which can induce interferon expression from natural or synthetic materials (Alcaro S et al., *Bioorg Med Chem.* 2005, 13 (10), 3371-3378). As a result, a strong interferon inducer named Imiquimod was developed by 3M Pharmaceuticals, but its development has been discontinued due to various adverse effects observed during clinical trials.

Although interferon is known to be a strong antiviral agent, interferon has a disadvantageous in that it cannot be used for more than 6 months, because it induces inflammatory responses such as infiltration of immune cells, etc.; almost all cells express receptors for interferon at all times, showing various adverse effects such as an anti-cellular effect; and it requires large amounts to treat at clinical trials.

Accordingly, there is a need for the development of a therapeutic agent which can selectively act on virus-infected cells rather than normal cells; which is applicable in small amounts and to various types of viruses rather than specific types of viruses; and which simultaneously has both antiviral and anti-inflammatory activity by suppression of the infiltration of immune cells.

DISCLOSURE

Technical Problem

The present inventors have endeavored to develop a therapeutic agent which can specifically act on virus-infected cells and have antiviral and anti-inflammatory activity capable of inhibiting inflammation by suppressing the infiltration of immune cells. As a result, the present inventors have confirmed that not only does humanized virus-suppressing factor (hzVSF), which is a novel humanized antibody, have the ability to specifically act on various types of viruses, as well as inhibitory activity against the infiltration of immune cells and superior for antiviral activity, but also, as a humanized antibody having reduced immunogenicity, it is a safe agent without any adverse effects when administered to humans, thereby completing the present invention.

Technical Solution

An object of the present invention is to provide a novel antibody specifically binding to the peptide of SEQ ID NO: 1 or a fragment binding to the peptide.

Another object of the present invention is to provide a polynucleotide encoding the antibody or the fragment binding to the peptide, a vector containing the polynucleotide, a cell introduced with the vector, a method of producing the antibody or the fragment binding to the peptide using the cell, and an antibody or a fragment binding to the peptide produced by the method.

Still another object of the present invention is to provide an antiviral composition containing the antibody or the fragment binding to the peptide.

Still another object of the present invention is to provide a method for preventing or treating infectious viral diseases using the antiviral composition.

Still another object of the present invention is to provide a composition for preventing or treating inflammatory diseases containing the antibody or the fragment binding to the peptide.

Still another object of the present invention is to provide a method for treating inflammatory diseases using the composition for preventing or treating inflammatory diseases.

Advantageous Effects

The antibody specifically binding to the peptide of SEQ ID NO: 1 or the fragment binding to the peptide can be provided as a new humanized antibody therapeutic agent having excellent antiviral and anti-inflammatory activity because they can selectively act on virus-infected cells, thus requiring only a small amount at the time of treatment, without any adverse effects, and can also inhibit inflammation by suppressing the infiltration of immune cells.

BRIEF DESCRIPTIONS OF THE DRAWINGS

FIG. 1 shows a schematic diagram of a vector for preparing chimeric virus suppressing factor (VSF).

FIG. 2 shows a schematic diagram of chimeric VSF.

FIG. 3 shows the results confirming the expression of chimeric VSF.

FIG. 4 shows the result illustrating the DNA sequence of single-chain Fv (scFv) of VSF.

FIG. 5 shows schematic diagrams illustrating the cloning of scFv of VSF into a vector.

FIG. 6 shows the results confirming scFv of VSF after purification.

FIG. 7 shows the results confirming the antiviral activity of VSF, scFv, and anti-EMC-D virus antibodies based on the amount of viable cells remaining after viral infection.

FIG. 8 shows the result confirming the antiviral activity of chimeric VSF.

FIG. 9 shows a schematic diagram of a vector for preparing hzVSF, which is a humanized antibody.

FIG. 10 shows a schematic diagram of hzVSF, which is a humanized antibody of the present invention.

FIG. 11 shows the results confirming the expression of hzVSF, which is a humanized antibody.

FIG. 12 shows the results confirming the antiviral activity of hzVSF, which is a humanized antibody.

FIG. 13 shows the results of reducing and non-reducing SDS-PAGE confirming the physical properties of hzVSF_var13, which is a humanized antibody.

FIG. 14 shows the results of LC/MS confirming the physical properties of hzVSF_var13, which is a humanized antibody.

FIG. 15 shows the results of SEC-HPLC confirming the physical properties of hzVSF_var13, which is a humanized antibody.

FIG. 16 shows the results illustrating isoelectric focusing (IEF) confirming the physical properties of hzVSF_var13, which is a humanized antibody.

FIG. 17 shows the results illustrating the number of donors with T-cell proliferation in response to KLH, hzVSF_ var12, and hzVSF_var13 among 51 blood donors.

FIG. 18 shows the results illustrating the degree of T-cell proliferation of the 51 donors in response to hzVSF_var12 and hzVSF_var13, which are representative variants of hzVSF, a humanized antibody.

FIG. 19 shows the results illustrating the T-cell proliferation induced by KLH, hzVSF_var12, and hzVSF_var13 represented by a mean stimulation index (SI).

FIG. 20 shows the results of SDS-PAGE of hzVSF_var12 and hzVSF_var13, which are representative variants of hzVSF, a humanized antibody.

FIG. 21 shows the results of HPLC confirming the physical properties of hzVSF_var12 and hzVSF_var13, which are representative variants of hzVSF, a humanized antibody.

FIG. 22 shows the results illustrating the pharmacodynamics of hzVSF_var13, which is a representative variant of hzVSF, a humanized antibody.

FIG. 23 shows the result confirming the antiviral activity of hzVSF, and hzVSF_var12 and hzVSF_var13, which are representative variants of hzVSF, a humanized antibody.

FIG. 24 shows the results confirming the cell viability of hzVSF_var13, which is a humanized antibody, and hIFN-α in human cells.

FIG. 25 shows the images confirming the inhibitory activity of hzVSF, which is a humanized antibody, against the infiltration of inflammatory cells in viral diabetes.

FIG. 26 shows a result confirming the anti-HBV effect of mVSF.

FIG. 27 shows the images confirming the expression feature of VSF receptors in HBV-infected human liver tissue.

FIG. 28 shows the images confirming the expression feature of VSF receptors in HCV-infected human liver tissue.

FIG. 29 shows the images confirming the expression of VSF receptors in influenza virus-infected cells.

FIG. 30 shows the images confirming the expression of VSF receptors in EMC-D virus-infected cells.

FIG. 31 shows the results confirming the antiviral effect of hzVSF_var13 against hepatitis B virus represented by the amount of cccDNA using real-time quantitative PCR.

FIG. 32 shows the results confirming the antiviral effect of hzVSF_var13 against hepatitis B virus represented by the amount of extracellular HBV DNA using real-time quantitative PCR.

FIG. 33 shows the results confirming the antiviral effect of hzVSF_var13 against hepatitis B virus represented by the amount of intracellular HBV DNA using real-time quantitative PCR.

FIG. 34 shows the results confirming the antiviral effect of hzVSF against hepatitis C virus using FACS.

FIG. 35 shows the results confirming the antiviral effect of hzVSF against hepatitis C virus using real-time quantitative PCR.

FIG. 36 shows the results confirming the antiviral effect of hzVSF_var13 against hepatitis C virus genotype 1a using real-time quantitative PCR and western blot.

FIG. 37 shows the results confirming the long-term antiviral effect of hzVSF_var13 against hepatitis C virus genotype 1a using real-time quantitative PCR.

FIG. 38 shows the results confirming the antiviral effect of hzVSF_var13 against hepatitis C virus genotype 1b using real-time quantitative PCR and western blot.

FIG. 39 shows the results confirming the antiviral effect of hzVSF_var13 against hepatitis C virus genotype 2a using real-time quantitative PCR and western blot.

FIG. 40 shows the results confirming the long-term antiviral effect of hzVSF_var13 against hepatitis C virus genotype 2a using real-time quantitative PCR.

FIG. 41 shows the inhibitory effect of hzVSF_var13, which is a humanized antibody, against the proliferation of influenza virus (H1N1) confirmed in mice.

FIG. 42 shows the results confirming the therapeutic effect of hzVSF_var13, which is a representative variant of hzVSF, on lung tissue after administering to influenza virus-infected mice.

FIG. 43 shows the results confirming the protective effect of hzVSF_var13, which is a representative variant of hzVSF, on mucosal epithelial cells and cilia of influenza virus-infected mice.

FIG. 44 shows the results confirming the inhibitory effect of hzVSF_var13, which is a representative variant of hzVSF, against pneumonia in influenza virus-infected mice, according to administration time and dose.

FIG. 45 shows the inhibitory effect of hzVSF_var13, which is a representative variant of hzVSF, against the infiltration of CD4 immune cells after administering to influenza virus-infected (100,000 pfu) mice.

FIG. 46 shows the inhibitory effect of hzVSF_var13, which is a representative variant of hzVSF, against the infiltration of CD4 immune cells after administering to influenza virus-infected (10,000,000 pfu) mice.

FIG. 47 shows the inhibitory effect of hzVSF_var13, which is a representative variant of hzVSF, against the infiltration of macrophages after administering to influenza virus-infected (100,000 pfu) mice.

FIG. 48 shows the inhibitory effect of hzVSF_var13, which is a representative variant of hzVSF, against the infiltration of macrophages after administering to influenza virus-infected (10,000,000 pfu) mice.

FIG. 49 shows the results illustrating the inhibitory effect of hzVSF against the secretion of inflammatory cytokines after viral infection in mice.

FIG. 50 shows the results illustrating the antiviral activity of hzVSF_v13 confirmed by MVIT assay after infecting MCF-7 cells, which do not express VSF receptors, with virus following the overexpression of wild-type VR and mutant-type VR therein.

FIG. 51 shows the results illustrating the antiviral activity of hzVSF_v13 confirmed by WST assay after infecting MCF-7 cells, which do not express VSF receptors, with virus following the overexpression of wild-type VR and mutant-type VR therein.

FIG. 52 shows the results illustrating the antiviral activity of hzVSF_v13 confirmed by MVIT assay after infecting MCF-7 cells, which do not express VSF receptors, with virus following the overexpression of wild-type VR and mutant-type VR therein.

FIG. 53 shows the images of the binding between VSF receptors and hzVSF_v13 confirmed by immunofluorescent staining after infecting MCF-7 cells, which do not express VSF receptors, with virus following the overexpression of wild-type VR and mutant-type VR therein.

FIG. 54 shows the images of the binding between hzVSF_v13 and wild-type and mutant-type VSF receptors (vimentin) purified after overexpression in *E. coli* confirmed by pull-down assay.

FIG. 55 shows the images of the binding between hzVSF_v13 and wild-type and mutant-type VSF receptors (vimentin) purified after overexpression in HEK293T cells confirmed by immunoprecipitation.

FIG. 56 shows a schematic diagram simulating the binding region between vimentin and VSF.

FIG. 57 shows schematic diagrams simulating the binding between vimentin and VSF.

FIG. 58 shows schematic diagrams simulating the binding region between vimentin and hzVSF_v13.

BEST MODE

In order to achieve the above objects, in an aspect, the present invention provides an antibody specifically binding to the isolated peptide of SEQ ID NO: 1 or a fragment binding to the peptide.

Examples of the antibody may include mouse antibodies, chimeric antibodies, or humanized antibodies, but are not limited thereto.

The humanized antibody or the fragment binding to the peptide of the present invention has superiority in inhibiting human anti-mouse antibody (HAMA) reaction in the human body while maintaining the original affinity and specificity of mouse antibody by transplanting the complementarity-determining region (CDR) of the variable region of a mouse monoclone or monoclonal antibody, which binds directly to an antigen, to a human antibody backbone. Additionally, the humanized antibodies of the present invention have lowered immunogenicity by de-immunization, and thus can be used as a safe agent when administered to humans by significantly lowering the immunogenicity. That is, the humanized antibodies of the present invention can treat target cells more efficiently by better interacting with the human immune system while responding to and influencing the cells in which the peptide region of SEQ ID NO: 1 is exposed to the Surface of cell membrane, for example, preventing complement-dependent cytotoxicity (CDC) or antibody-dependent cell-mediated cytotoxicity (ADCC) while responding to virus-infected cells. Additionally, the humanized antibodies of the present invention have an advantage in that the human immune system does not recognize the humanized antibodies as proteins of foreign origin due to the lowered immunogenicity.

Additionally, the humanized antibodies of the present invention also have an advantage in that the half-lives of the humanized antibodies in the human circulatory system are similar to those of naturally occurring antibodies, even when the drug is administered in a smaller dose or less frequently.

In the present invention, the mouse antibodies which specifically bind to the isolated peptide of SEQ ID NO: 1 may be collectively referred to as "mouse virus suppressing factor (mVSF)"; chimeric antibodies as "chimeric virus suppressing factor (chVSF)"; and humanized antibodies as "humanized virus suppressing factor (hzVSF)". As used herein, the term "humanized antibody hzVSF" or "variants thereof" can be used interchangeably, and hzVSF can be used interchangeably with a wild-type hzVSF (hzVSF_wt) and a variant of hzVSF (e.g., indicated as hzVSF_var1, hzVSF_v1, hzVSF_1, etc.).

In the present invention, the isolated peptide of SEQ ID NO: 1 corresponds to the amino acid sequence of vimentin at amino acid positions 142 to 294, and the peptide may include not only the above amino acid sequence but also any amino acid sequences which have a homology to the above sequence of 80% or higher, preferably 90% or higher, more preferably 95% or higher, and even more preferably 97% or higher, as long as the antibody of the present invention or a peptide-binding fragment thereof can bind thereto. The isolated peptide of SEQ ID NO: 1 is an antigenic region including an epitope, and it may be an amino acid sequence of vimentin at amino acid positions 142 to 211 or at amino acid positions 211 to 294, as long as the peptide can exhibit a function similar to that of the present invention, by binding to an antibody or a peptide-binding fragment. Additionally, it is obvious that any amino acid sequences having any of the homologies described above can belong to the scope of the present invention, although the sequence may have deletion, modification, substitution, or addition in part of the sequence. Vimentin, which is a protein encoded by the VIM gene, supports and anchors intracellular organelles in place, and is known to be mainly involved in maintenance of cell shape, transport of proteins, and cell signaling. Vimentin is also known to be used as a cancer marker; however, it is not known whether antibodies capable of binding to vimentin can exhibit antiviral activity.

The antibody, which specifically binds to the isolated peptide of SEQ ID NO: 1 of the present invention, or the fragment binding to the peptide specifically responds to virus-infected cells, and the antibody and binding fragment both bind to the receptors of virus-suppressing factor (VSF) which are exposed to the cell surface in the virus-infected cells. The antibody or the fragment binding to the peptide of the present invention exhibits antiviral and anti-inflammatory activities by the specific binding to virus-infected cells, and can thus be used effectively as an antiviral composition and field of preventing or treating infectious viral diseases and inflammatory diseases.

Specifically, the antibody or the fragment binding to the peptide may be one which specifically binds to the amino acid residue at the $9^{th}$, the $45^{th}$, the $54^{th}$, the $76^{th}$, the $94^{th}$, or the $129^{th}$ position of the peptide of SEQ ID NO: 1, and more specifically, one which specifically binds to the amino acid residue at the $9^{th}$, the $45^{th}$, the $54^{th}$, the $76^{th}$, the $94^{th}$, and the $129^{th}$ positions of the peptide of SEQ ID NO: 1, but is not limited thereto as long as they can specifically bind to the isolated peptide of SEQ ID NO: 1.

As used herein, the term “antibody” immunologically refers to a protein molecule which has the role of a ligand specifically recognizing an antigen, including an immunoglobulin molecule having reactivity to a specific antigen, and it may include all of a polyclonal antibody, a monoclonal antibody, a whole antibody, and an antibody fragment. Additionally, the term “antibody” may include a chimeric antibody (e.g., a humanized murine antibody), and a bivalent or bispecific molecule (e.g., a bispecific antibody), a diabody, a triabody, and a tetrabody. Additionally, the term “antibody” may include a single-chain antibody having FcRn-binding affinity, scAb, a derivative of a constant region of an antibody, and an artificial antibody based on a protein scaffold. A whole antibody has the structure consisting of two full-length light chains and two full-length heavy chains, where each light chain is linked to a heavy chain by a disulfide bond. The whole antibody includes IgA, IgD, IgE, IgM, and IgG, and subtypes of IgG include IgG1, IgG2, IgG3, and IgG4. As used herein, the terms “fragment”, “fragment binding to a peptide”, and “antibody fragment” refer to any fragment of the antibodies or peptide-binding fragment of the present invention having antigen-binding activity and these terms may be used interchangeably. In an exemplary embodiment, the antibody fragment may include a single-chain antibody, Fd, Fab, Fab', F(ab')2, dsFv, or scFv, but is not limited thereto.

The Fd refers to a heavy chain part included in the Fab fragment. Fab has a structure consisting of variable regions of the heavy chain and the light chain, constant regions of the light chain, and the first constant region of the heavy chain (CH1 domain), and has a single antigen-binding site. Fab' differs from Fab in that Fab' has a hinge region containing at least one cysteine residue at the C-terminus of the heavy chain CH1 domain. The F(ab')2 antibody is produced when the cysteine residue in the hinge region of Fab' forms a disulfide bond. As used herein, the term “variable fragment (Fv)” refers to a minimum antibody fragment having only the variable region of a heavy chain and the variable region of a light chain. Disulfide-stabilized Fv (dsFv) is characterized in that the variable region of a heavy chain and the variable region of a light chain are linked by a disulfide bond, and single-chain Fv (scFv) is characterized in that the heavy chain variable region and the light chain variable region are generally linked by a covalent bond through a linker. These antibody fragments may be obtained using a protease (for example, papain restriction cleavage of the whole antibody can yield Fab while pepsin cleavage of the whole antibody can yield F(ab')2 fragments), and may preferably be prepared using genetic recombinant technology.

As used herein, the term “monoclonal antibody” refers to an antibody molecule consisting of a single molecule obtained from substantially the same antibody group, and the monoclonal antibody exhibits a single binding specificity and affinity to a particular epitope.

Typically, immunoglobulins have heavy chains and light chains, and each of the heavy chains and light chains includes a constant region and a variable region (also known as a domain). The variable regions of the light chain and the heavy chain include three highly variable regions, which are called complementarity-determining regions (hereinafter, “CDR”), and four framework regions (hereinafter, “FR”). The CDR mainly has a role of binding to the epitope of an antigen. The CDR in each chain is called CDR1, CDR2, and CDR3, typically starting from the N-terminus in this order, and these are identified by the chain in which a particular CDR is located.

Additionally, when the antibody of the present invention contains a constant region, a constant region derived from IgG, IgA, IgD, IgE, and IgM, or a constant region by a combination thereof or a hybrid thereof may be included.

As used herein, the term “combination” refers to the formation of a binding between a polypeptide encoding a single-chain immunoglobulin constant region of the same origin and a single-chain polypeptide of a different origin when forming a dimer or multimer. For example, a dimer or multimer may be formed from two or more constant regions selected from the group consisting of the constant regions of IgG, IgA, IgD, IgE, and IgM.

As used herein, the term “hybrid” refers to the presence of sequences corresponding to two or more immunoglobulin heavy chain constant regions of different origins within a single-chain immunoglobulin heavy chain constant region, and for example, a hybrid consisting of one to four domains selected from the group consisting of the CH1, CH2, CH3, and CH4 of IgG, IgA, IgD, IgE, and IgM may be possible.

The humanized antibody of the present invention may be humanized based on human immunoglobulin γ4, although humanization is not limited thereto, and it may have an advantage in that it does not cause CDC due to lack of complement activation.

The humanized antibody or the fragment binding to the peptide may include:

a heavy chain variable region including a heavy chain CDR1 of SEQ ID NO: 2; a heavy chain CDR2 of SEQ ID NO: 3 or SEQ ID NO: 14 (in which the $9^{th}$ amino acid of SEQ ID NO: 3, threonine, is substituted with aspartic acid); and a heavy chain CDR3 of SEQ ID NO: 4 or SEQ ID NO: 15 (in which the $4^{th}$ amino acid of SEQ ID NO: 4, threonine, is substituted with asparagine); and a light chain variable region including a light chain CDR1 of SEQ ID NO: 5; a light chain CDR2 of SEQ ID NO: 6, SEQ ID NO: 16 (in which the $3^{rd}$ amino acid of SEQ ID NO: 6, threonine, is substituted with aspartic acid), SEQ ID NO: 17 (in which the $3^{rd}$ amino acid of SEQ ID NO: 6, threonine, is substituted with aspartic acid and the $6^{th}$ amino acid of SEQ ID NO: 6, alanine, is substituted with glycine), or SEQ ID NO: 18 (in which the $3^{rd}$ amino acid of SEQ ID NO: 6, threonine, is substituted with aspartic acid; the $5^{th}$ amino acid of SEQ ID NO: 6, leucine, is substituted with arginine;

and the 6th amino acid of SEQ ID NO: 6, alanine, is substituted with glycine); and a light chain CDR3 of SEQ ID NO: 7 or SEQ ID NO: 19 (in which the 6th amino acid of SEQ ID NO: 7, serine, is substituted with threonine).

Additionally, the humanized antibody or the fragment binding to the peptide, which includes a human framework region (FR), may be human immunoglobulin gamma of SEQ ID NO: 29, SEQ ID NO: 30, and SEQ ID NO: 31, or a heavy chain variable region, which includes a heavy chain framework region 1 (FR1) of SEQ ID NO: 20, a heavy chain FR2 of SEQ ID NO: 21, a heavy chain FR3 of SEQ ID NO: 22 or SEQ ID NO: 28 (in which the 8th amino acid of SEQ ID NO: 22, lysine, is substituted with threonine; and the 10th amino acid of SEQ ID NO: 22, isoleucine, is substituted with alanine), and a heavy chain FR4 of SEQ ID NO: 23; and a light chain variable region, which includes a light chain framework region 1 (FR1) of SEQ ID NO: 24, a light chain FR2 of SEQ ID NO: 25, a light chain FR3 of SEQ ID NO: 26, and a light chain FR4 of SEQ ID NO: 27, but is not limited thereto.

Specifically, the humanized antibody or the fragment binding to the peptide may include:

(a) a heavy chain CDR1, a heavy chain CDR2, and a heavy chain CDR3 of SEQ ID NO: 2, SEQ ID NO: 3, and SEQ ID NO: 4, respectively; and a light chain CDR1, a light chain CDR2, and a light chain CDR3 of SEQ ID NO: 5, SEQ ID NO: 6, and SEQ ID NO: 7, respectively;

(b) a heavy chain CDR1, a heavy chain CDR2, and a heavy chain CDR3 of SEQ ID NO: 2, SEQ ID NO: 3, and SEQ ID NO: 4, respectively; and a light chain CDR1, a light chain CDR2, and a light chain CDR3 of SEQ ID NO: 5, SEQ ID NO: 16, and SEQ ID NO: 7, respectively;

(c) a heavy chain CDR1, a heavy chain CDR2, and a heavy chain CDR3 of SEQ ID NO: 2, SEQ ID NO: 3, and SEQ ID NO: 4, respectively; and a light chain CDR1, a light chain CDR2, and a light chain CDR3 of SEQ ID NO: 5, SEQ ID NO: 17, and SEQ ID NO: 7, respectively;

(d) a heavy chain CDR1, a heavy chain CDR2, and a heavy chain CDR3 of SEQ ID NO: 2, SEQ ID NO: 3, and SEQ ID NO: 4, respectively; and a light chain CDR1, a light chain CDR2, and a light chain CDR3 of SEQ ID NO: 5, SEQ ID NO: 18, and SEQ ID NO: 7, respectively;

(e) a heavy chain CDR1, a heavy chain CDR2, and a heavy chain CDR3 of SEQ ID NO: 2, SEQ ID NO: 3, and SEQ ID NO: 4, respectively; and a light chain CDR1, a light chain CDR2, and a light chain CDR3 of SEQ ID NO: 5, SEQ ID NO: 18, and SEQ ID NO: 19, respectively;

(f) a heavy chain CDR1, a heavy chain CDR2, and a heavy chain CDR3 of SEQ ID NO: 2, SEQ ID NO: 14, and SEQ ID NO: 4, respectively; and a light chain CDR1, a light chain CDR2, and a light chain CDR3 of SEQ ID NO: 5, SEQ ID NO: 6, and SEQ ID NO: 7, respectively;

(g) a heavy chain CDR1, a heavy chain CDR2, and a heavy chain CDR3 of SEQ ID NO: 2, SEQ ID NO: 3, and SEQ ID NO: 4, respectively; heavy chains FR1, FR2, FR3, and FR4 of SEQ ID NO: 20, SEQ ID NO: 21, SEQ ID NO: 28, and SEQ ID NO: 23, respectively; a light chain CDR1, a light chain CDR2, and a light chain CDR3 of SEQ ID NO: 5, SEQ ID NO: 6, and SEQ ID NO: 7, respectively; and light chains FR1, FR2, FR3, and FR4 of SEQ ID NO: 24, SEQ ID NO: 25, SEQ ID NO: 26, and SEQ ID NO: 27, respectively;

(h) a heavy chain CDR1, a heavy chain CDR2, and a heavy chain CDR3 of SEQ ID NO: 2, SEQ ID NO: 14, and SEQ ID NO: 4, respectively; heavy chains FR1, FR2, FR3, and FR4 of SEQ ID NO: 20, SEQ ID NO: 21, SEQ ID NO: 28, and SEQ ID NO: 23, respectively; a light chain CDR1, a light chain CDR2, and a light chain CDR3 of SEQ ID NO: 5, SEQ ID NO: 6, and SEQ ID NO: 7, respectively; and light chains FR1, FR2, FR3, and FR4 of SEQ ID NO: 24, SEQ ID NO: 25, SEQ ID NO: 26, and SEQ ID NO: 27, respectively;

(i) a heavy chain CDR1, a heavy chain CDR2, and a heavy chain CDR3 of SEQ ID NO: 2, SEQ ID NO: 14, and SEQ ID NO: 15, respectively; heavy chains FR1, FR2, FR3, and FR4 of SEQ ID NO: 20, SEQ ID NO: 21, SEQ ID NO: 28, and SEQ ID NO: 23, respectively; a light chain CDR1, a light chain CDR2, and a light chain CDR3 of SEQ ID NO: 5, SEQ ID NO: 6, and SEQ ID NO: 7, respectively; and light chains FR1, FR2, FR3, and FR4 of SEQ ID NO: 24, SEQ ID NO: 25, SEQ ID NO: 26, and SEQ ID NO: 27, respectively;

(j) a heavy chain CDR1, a heavy chain CDR2, and a heavy chain CDR3 of SEQ ID NO: 2, SEQ ID NO: 14, and SEQ ID NO: 4, respectively; heavy chains FR1, FR2, FR3, and FR4 of SEQ ID NO: 20, SEQ ID NO: 21, SEQ ID NO: 28, and SEQ ID NO: 23, respectively; a light chain CDR1, a light chain CDR2, and a light chain CDR3 of SEQ ID NO: 5, SEQ ID NO: 18, and SEQ ID NO: 7, respectively; and light chains FR1, FR2, FR3, and FR4 of SEQ ID NO: 24, SEQ ID NO: 25, SEQ ID NO: 26, and SEQ ID NO: 27, respectively;

(k) a heavy chain CDR1, a heavy chain CDR2, and a heavy chain CDR3 of SEQ ID NO: 2, SEQ ID NO: 14, and SEQ ID NO: 15, respectively; heavy chains FR1, FR2, FR3, and FR4 of SEQ ID NO: 20, SEQ ID NO: 21, SEQ ID NO: 28, and SEQ ID NO: 23, respectively; a light chain CDR1, a light chain CDR2, and a light chain CDR3 of SEQ ID NO: 5, SEQ ID NO: 18, and SEQ ID NO: 7, respectively; and light chains FR1, FR2, FR3, and FR4 of SEQ ID NO: 24, SEQ ID NO: 25, SEQ ID NO: 26, and SEQ ID NO: 27, respectively;

(l) a heavy chain CDR1, a heavy chain CDR2, and a heavy chain CDR3 of SEQ ID NO: 2, SEQ ID NO: 14, and SEQ ID NO: 4, respectively; heavy chains FR1, FR2, FR3, and FR4 of SEQ ID NO: 20, SEQ ID NO: 21, SEQ ID NO: 28, and SEQ ID NO: 23, respectively; a light chain CDR1, a light chain CDR2, and a light chain CDR3 of SEQ ID NO: 5, SEQ ID NO: 18, and SEQ ID NO: 19, respectively; and light chains FR1, FR2, FR3, and FR4 of SEQ ID NO: 24, SEQ ID NO: 25, SEQ ID NO: 26, and SEQ ID NO: 27, respectively;

(m) a heavy chain CDR1, a heavy chain CDR2, and a heavy chain CDR3 of SEQ ID NO: 2, SEQ ID NO: 14, and SEQ ID NO: 15, respectively; heavy chains FR1, FR2, FR3, and FR4 of SEQ ID NO: 20, SEQ ID NO: 21, SEQ ID NO: 28, and SEQ ID NO: 23, respectively; a light chain CDR1, a light chain CDR2, and a light chain CDR3 of SEQ ID NO: 5, SEQ ID NO: 18, and SEQ ID NO: 19, respectively; and light chains FR1, FR2, FR3, and FR4 of SEQ ID NO: 24, SEQ ID NO: 25, SEQ ID NO: 26, and SEQ ID NO: 27, respectively; and (n) a heavy chain CDR1, a heavy chain CDR2, and a heavy chain CDR3 of SEQ ID NO: 2, SEQ ID NO: 14, and SEQ ID NO: 4, respectively; and a light chain CDR1, a light chain CDR2, and a light chain CDR3 of SEQ ID NO: 5, SEQ ID NO: 16, and SEQ ID NO: 7, respectively.

The antibody (a) may include hzVSF_WT, antibody (b) may include hzVSF_var1, antibody (c) may include hzVSF_var2, antibody (d) may include hzVSF_var3, antibody (e) may include hzVSF_var4, antibody (f) may include hzVSF_var5, antibody (g) may include hzVSF_var6, antibody (h) may include hzVSF_var7, antibody (i) may include hzVSF_var8, antibody (j) may include hzVSF_var9, antibody (k) may include hzVSF_var10, antibody (l) may include hzVSF_var11, antibody (m) may include hzVSF_var12, and antibody (n) may include hzVSF_var13.

The humanized antibody or the fragment binding to the peptide may include a heavy chain variable region and a light chain variable region of SEQ ID NO: 10 and SEQ ID NO: 12; SEQ ID NO: 32 and SEQ ID NO: 34; SEQ ID NO: 36 and SEQ ID NO: 38; SEQ ID NO: 40 and SEQ ID NO: 42; SEQ ID NO: 44 and SEQ ID NO: 46; SEQ ID NO: 48 and SEQ ID NO: 50; SEQ ID NO: 52 and SEQ ID NO: 54; SEQ ID NO: 56 and SEQ ID NO: 58; SEQ ID NO: 60 and SEQ ID NO: 62; SEQ ID NO: 64 and SEQ ID NO: 66; SEQ ID NO: 68 and SEQ ID NO: 70; SEQ ID NO: 72 and SEQ ID NO: 74; SEQ ID NO: 76 and SEQ ID NO: 78; or SEQ ID NO: 80 and SEQ ID NO: 82, respectively, but is not limited thereto.

Specifically, the mouse antibody may include a heavy chain variable region including a heavy chain CDR1 of SEQ ID NO: 137; a heavy chain CDR2 of SEQ ID NO: 138; and a heavy chain CDR3 of SEQ ID NO: 139; and a light chain variable region including a light chain CDR1 of SEQ ID NO: 134; a light chain CDR2 of SEQ ID NO: 135; and a light chain CDR3 of SEQ ID NO: 136, and more specifically, include a heavy chain variable region of SEQ ID NO: 9 and a light chain variable region of SEQ ID NO: 8, but is not limited thereto.

Specifically, the chimeric antibody may include a heavy chain variable region of SEQ ID NO: 141 or SEQ ID NO: 142 and a light chain variable region of SEQ ID NO: 140, and more specifically, a heavy chain of SEQ ID NO: 146 or SEQ ID NO: 148 and a light chain of SEQ ID NO: 144, but is not limited thereto.

The scFv may also include the scFv prepared for the safety of mVSF, but is not limited thereto, and for example, the scFv may be prepared by the sequence shown in FIG. 4. Additionally, the scFv may be in a form where the heavy chain variable region of SEQ ID NO: 131 and the light chain variable region of SEQ ID NO: 133 are linked by a linker. Additionally, the scFv may be in a form where the heavy chain variable region encoding the nucleotide sequence of SEQ ID NO: 130 and the light chain variable region encoding the nucleotide sequence of SEQ ID NO: 132 are linked by a linker. These scFv may be cloned into an *E. coli* expression vector with SEQ ID NO: 150.

In an exemplary embodiment, the present inventors prepared humanized antibodies (i.e., hzVSF_wt, three alternatives, and 13 variants thereof) and confirmed their antiviral activity (Example 6). Additionally, as a result of the comparison of the antigenicity of the humanized antibodies with therapeutic antibodies which have received FDA approval and are commercially available, it was confirmed that the antigenicity of the humanized antibodies was similar to that of Humira, which has the lowest antigenicity among the above commercial therapeutic antibodies (Table 7), thus confirming that the humanized antibodies can be used as safe antivirals or drugs without any adverse effects that may occur when they are used as antivirals or anti-inflammatory agents. Additionally, it was confirmed that the above humanized antibodies do not significantly affect T cell proliferation by T cell analysis using hzVSF_variants (Table 8), and thus it was confirmed that they have a low risk of adverse reactions by acting as antigens when they are used in clinical trials. Additionally, it was confirmed that the humanized antibodies have sufficiently long duration of in vivo half-lives to be used for clinical studies by pharmacokinetic analysis (Example 8). Additionally, as a result of the comparison of cytotoxicity of the humanized antibodies with interferon, they did not exhibit any cytotoxicity at a concentration of 4 nM or higher, thus confirming that the humanized antibodies have fewer adverse effects, unlike interferon (Example 11). Additionally, it was confirmed that the hzVSF antibodies (both wild-type and variants) of the present invention have an antiviral effect against EMC-D virus infection and an inhibitory effect against infiltration of immune cells in mice, and thus the hzVSF antibodies can significantly inhibit the destruction of islets of Langerhans and treat diabetes caused by viral infection (Example 12). Additionally, it was confirmed that hzVSF antibodies can also significantly inhibit hepatitis virus (Examples 13 to 16). Additionally, it was confirmed that hzVSF antibodies also have antiviral and anti-inflammatory effects against influenza virus without the infiltration of immune cells (Example 17) and have antiviral effects against various viruses (Table 15), and thus it was confirmed that hzVSF antibodies can be used as universal antiviral agents. Additionally, it was confirmed that hzVSF antibodies can inhibit the secretion of proinflammatory cytokines in a virus-infected mouse model (Example 19), and thus hzVSF antibodies can be used as a therapeutic agent for treating various kinds of inflammatory diseases.

Another aspect of the present invention provides a polynucleotide encoding the antibody or the fragment binding to the peptide, a vector containing the polynucleotide, a cell introduced with the vector, a method of producing the antibody or the fragment binding to the peptide using the cell, and an antibody or a fragment binding to the peptide produced by the method.

The antibody and the fragment binding to the peptide are the same as described above.

The vector containing a polynucleotide encoding the antibody provided in the present invention may be a vector which can replicate and/or express the polynucleotide in eukaryotic cells or prokaryotic cells including mammalian cells (e.g., cells of humans, monkeys, rabbits, rats, hamsters, mice, etc.), plant cells, yeast cells, insect cells, or bacterial cells (e.g., *E. coli*), and preferably a vector which can be operably connected to a suitable promoter in a host cell for the expression of the nucleotide and which has at least one selective marker, but is not particularly limited thereto. For example, the vector may be in a form where the polynucleotide was introduced into a phage, a plasmid, a cosmid, a mini-chromosome, a virus, or a retroviral vector, etc.

The vector containing the polynucleotide encoding the antibody may be an expression vector which includes a polynucleotide encoding the heavy chain of the antibody or a polynucleotide encoding the light chain of the antibody, respectively, or an expression vector which includes both polynucleotides encoding the heavy chain and the light chain of the antibody.

Examples of the cells introduced with the expression vector (transformants/transfectants) provided in the present invention may include a cell of bacteria such as *E. coli, Streptomyces*, and *Salmonella typimurium*; a cell of yeasts, a cell of fungi such as *Pichia pastoris*; a cell of insects such as *Drosophila* and *Spodoptera* Sf9; a cell of animals such as Chinese hamster ovary (CHO), SP2/0 (mouse myeloma), human lymphoblastoid, COS, NSO (mouse myeloma), 293T, melanoma, HT-1080, baby hamster kidney (BHK), human embryonic kidney (HEK), and PERC.6 (human retina); or a cell of plants, introduced with the expression vector and transformed, but are not particularly limited thereto.

As used herein, the term "introduction" refers to a method of delivering a vector containing a polynucleotide encoding the above antibody to a host cell. The introduction may be performed by various methods known in the art, such as calcium phosphate-DNA co-precipitation, DEAE-dextranmediated transfection, polybrene-mediated transfection, electroporation, microinjection, liposome fusion, lipofectamine transfection, and protoplast fusion. Additionally, transduction refers to delivery of a target material into a cell via infection using a virus particle. Additionally, the vector may be introduced into a host cell by methods such as gene bombardment, etc. In the present invention, the term introduction may be used interchangeably with transformation.

In still another aspect, the present invention provides an antiviral composition containing the antibody or the fragment binding to the peptide.

The antibody and the fragment binding to the peptide are the same as explained above.

As used herein, the term "antiviral" refers to an effect of alleviating, inhibiting, or preventing viral infection by the inhibition of proliferation or replication of a pathogenic virus, but is not limited thereto. The "pathogenic virus", the proliferation or replication of which is inhibited by the antiviral activity, is characterized in that a part of vimentin in a host cell is exposed to the surface of the host cell membrane by viral infection, but is not limited thereto. Examples of the pathogenic virus, which causes a disease in animals or humans, may include a virus of the family Orthomyxoviridae, a virus of the family Picornaviridae, a virus of the family Retroviridae, a virus of the family Herpesviridae, a virus of the family Filoviridae, a virus of the family Coronaviridae, a virus of the family Hepadnaviridae, a virus of the family Flaviviridae, a virus of the family Bunyaviridae, etc. Examples of the pathogenic virus may include influenza virus, hepatitis B and C virus, encephalomyocarditis virus, Mengovirus, Ebola virus, severe acute respiratory syndrome (SARS) coronavirus, Middle East respiratory syndrome (MERS) coronavirus, reovirus, human immunodeficiency virus (HIV), human cytomegalovirus (HCMV), or hantaan virus, but are not limited thereto. Specifically, the hzVSF according to the present invention exhibited antiviral activity not only in Mengovirus of the family Picornaviridae, but also in influenza virus of the family Orthomyxoviridae, which has a genomic structure and a life cycle significantly different from those of EMC virus of the family Picornaviridae, and additionally, the hzVSF shows universal antiviral activity including the effective inhibition of HIV (belonging to the family Retroviridae) proliferation (Table 15).

The composition may be in the form of a pharmaceutical composition, a quasi-drug composition, and a functional health food composition.

The pharmaceutical composition may further include a pharmaceutically acceptable carrier.

As used herein, the term "pharmaceutically acceptable carrier" refers to a carrier or diluent which does not inhibit the biological activities or properties of a compound to be administered to an organism without causing irritation to the organism. Examples of the pharmaceutically acceptable carrier used in the composition to be formulated into a liquid solution, as ones suitable for sterilization and in vivo use, saline, sterile water, Ringer's solution, buffered saline, an albumin injection solution, a dextrose solution, a maltodextrin solution, glycerol, ethanol, and a mixture of at least one component thereof, and other conventional additive(s) such as an antioxidant, a buffer, and a bacteriostatic agent may be further added as necessary. Additionally, the composition may be formulated into injection formulations (e.g., an aqueous solution, a suspension, an emulsion, etc.), pills, capsules, granules, or tablets by additionally adding a diluent, a dispersant, a surfactant, a binder, a lubricant, etc.

The pharmaceutical composition may be prepared in various oral or parenteral formulations. For the preparation of these formulations, the pharmaceutical composition may be formulated in combination with a diluent or excipient such as a filler, an extender, a binder, a humectant, a disintegrating agent, a surfactant, etc. Solid formulations for oral administration may include tablets, pills, powders, granules, capsules, etc., and these solid formulations may be prepared by adding at least one excipient, e.g., starch, calcium carbonate, sucrose or lactose, gelatin, etc. In addition to a simple excipient, a lubricant such as magnesium stearate, talc, etc., may be used. Liquid formulations for oral administration may include suspensions, oral solutions, emulsions, syrups, etc., and in addition to a simple diluent such as water or liquid paraffin, various excipients, such as humectants, sweeteners, aromatics, preservatives, etc. may be contained in the liquid preparations. Formulations for parenteral administration may include sterile aqueous solutions, non-aqueous solvents, suspensions, emulsions, lyophilized formulations, suppositories. Examples of the non-aqueous solvents and suspensions may include propylene glycol, polyethylene glycol, vegetable oils such as olive oil, an injectable ester such as ethyl oleate, etc. Examples of the bases for suppositories may include Witepsol, macrogol, Tween 61, cacao butter, laurinum, glycerogelatin, etc.

The pharmaceutical composition may have any formulation type selected from the group consisting of tablets, pills, powders, granules, capsules, suspensions, oral solutions, emulsions, syrups, sterile aqueous solutions, non-aqueous solvents, suspensions, lyophilized formulations, and suppositories.

The composition of the present invention is administered in a pharmaceutically effective dose.

As used herein, the term "pharmaceutically effective dose" refers to an amount sufficient for the treatment of diseases at a reasonable benefit/risk ratio applicable to a medical treatment, and the level of the effective dose may be determined based on the factors including the kind of a subject, severity of illness, age, sex, kind of disease(s), drug activity, drug sensitivity, administration time, administration route and dissolution rate, duration of treatment, factors including drug(s) to be simultaneously used in combination, and other factors well-known in the medical field. The composition of the present invention may be administered as an individual therapeutic agent, in combination with other therapeutic agent(s), and sequentially or simultaneously with a conventional therapeutic agent(s), and may be administered in a single dose or multiple doses. It is important to administer an amount to obtain the maximum effect with a minimum amount without adverse effects considering the factors described above, and these factors can easily be determined by one of ordinary skill in the art. The other therapeutic agent may be interferon but is not limited thereto.

The composition may be a composition carrying out the prevention or treatment of infectious viral diseases by antiviral actions.

In the present invention, the infectious viral diseases may include diseases which cause a part of vimentin in a host cell to be exposed to the host cell membrane upon viral infection, and for example, they may include not only hepatitis, AIDS, pneumonia, and diabetes, but also all diseases that may occur by the infection of a virus of the family Orthomyxoviridae, a virus of the family Picornaviridae, a virus of the family Retroviridae, a virus of the family Filoviridae, a virus of the family Coronaviridae, a virus of the family Hepadnaviridae, a virus of the family Flaviviridae, a virus of the family Bunyaviridae, and a virus of the family Herpesviridae.

As used herein, the term "prevention" may refer to any action resulting in suppression or delay of the onset of a disease by the administration of the composition, and the term "treatment" may refer to all kinds of actions associated with the improvement or advantageous changes in symptoms of a disease by the administration of the composition.

The composition may be one that specifically acts on virus-infected cells.

The composition may be one which suppresses the infiltration of immune cells or may be one which inhibits inflammatory reactions (FIGS. 45 to 48). The composition of the present invention was confirmed to significantly inhibit proinflammatory cytokines, such as IL-6, TNF-α, IFN-γ, and CCL2 (MCP-1) (FIG. 49).

In still another aspect, the present invention provides a method for treating infectious viral diseases including administering the antiviral composition to a subject in need thereof.

The antiviral composition and infectious viral diseases are the same as explained above.

The method for treating infectious viral diseases may be a method including administering a pharmaceutical composition, which contains an antibody or additional pharmaceutically acceptable carrier, to a subject having an infectious viral disease or suspected of having the same. The pharmaceutically acceptable carrier is the same as explained above. Preferably, the method for treating the infectious viral diseases may be a method for treating infectious viral diseases including administering the composition containing an antibody to a subject infected with an infectious viral disease.

The subject may include mammals, birds, etc., such as cattle, pigs, sheep, chickens, dogs, and humans, and may include without limitation any subject in which infectious viral diseases can be treated by administering the composition of the present invention.

In particular, the composition may be administered in a pharmaceutically acceptable dose in a single or multiple administrations. The composition may be administered in the form of liquids, powders, aerosols, capsules, enteric coated tablets, capsules, or suppositories. Examples of the administration routes may include intraperitoneal, intravenous, intramuscular, subcutaneous, endothelial, oral, topical, intranasal, intrapulmonary, or intrarectal administration, etc., but is not limited thereto. However, since peptides are digested when being administered orally, the oral composition must be formulated so that the active ingredient can be coated or protected from degradation in the stomach. Additionally, the pharmaceutical composition may be administered using any device which can transport the active ingredient to the target cell.

In still another aspect, the present invention provides a composition for preventing or treating inflammatory diseases containing the antibody or the fragment binding to the peptide.

The composition for preventing or treating inflammatory diseases may be in the form of a pharmaceutical composition, a quasi-drug composition, and a functional health food composition.

The inflammatory diseases may be caused by viral infection.

In still another aspect, the present invention provides a method for treating inflammatory diseases including administering the composition for preventing or treating inflammatory diseases to a subject in need thereof.

In still another aspect, the present invention provides an antiviral use of the antibody or the fragment binding to the peptide.

Modes for Carrying Out Invention

The present invention will be described in detail with reference to accompanying examples herein below. However, the Examples disclosed herein are only for illustrative purposes and should not be construed as limiting the scope of the present invention.

Example 1: Preparation of a Novel Humanized Antibody VSF

Example 1-1: Preparation of Chimeric VSF chVSF

Based on the assumption that the major functional part of the mouse VSF (mVSF) is a monoclonal antibody, mouse/human chimeric antibody (chAb) was chimerized by genetic engineering using the mVSF and the human immunoglobulin.

Specifically, for the preparation of a chimeric antibody, the constant regions of the light and heavy chains of mVSF were replaced with the constant regions of human immunoglobulin antibody (κ, γ2 or γ4). For chVSF, an expression vector was prepared using the pCAGGS vector as a template (FIG. 1). The heavy chain variable region of mVSF (mVH) (SEQ ID NO: 9) was amplified by PCR including the SacI and KpnI restriction enzyme sites. The light chain variable region (mVL) (SEQ ID NO: 8) including ClaI and XhoI restriction enzyme sites was amplified by PCR. The primers used in PCR are described in Table 1, and the PCR was performed for a total of 35 cycles (94° C. for 45 sec, 60° C. for 45 sec, and 72° C. for 45 sec) and at 72° C. for 10 min.

TABLE 1

| Primer | Sequence | SEQ ID NO |
|---|---|---|
| mVH F | cgagctcatgggatggagctggatc | 124 |
| mVH R | cggtacctgaggagacggtgactg | 125 |
| KpnI_delR | gggcccttggtggaagctgaggagacggtgactgagg | 126 |
| mVL F | catcgatatgagtgtgcccactcag | 127 |
| mVL R | cctcgagtttgatttccagcttgg | 128 |
| Xho_modR | agatggtgcagccaccgtgcgtttgatttccagcttg gtgcc | 129 |

The human heavy chain (SEQ ID NO: 11) was cloned using KpnI and SphI restriction enzyme sites, and the light chain (SEQ ID NO: 13) was cloned using XhoI and BglI restriction enzyme sites. For the simultaneous expression of both heavy and light chains, an internal ribosome entry site (IRES) was cloned between the light chain and the heavy chain using the SphI and ClaI restriction enzyme sites. A selectable marker was inserted into the SalI restriction enzyme site. As such, chVSF was prepared as illustrated in the schematic diagram of FIG. 2.

Example 1-2: Expression of chVSF Using a Two-Vector Expression System

15 μg of pCAGGS-GFP was transfected into HEK 293T cells using 1 mg/mL of polyethylenimine (PEI) to examine the levels of transfection and expression. The chVSF prepared in Example 1-1 was transfected into HEK 293T cells in the same manner, and after 6 hours, the medium was replaced with a medium containing 2% FBS. The cell culture supernatant was collected every 3 days and impurities contained therein were removed using a filter (0.45 μm). The chVSF was purified using nProtein A Sepharose® beads. The chVSF was eluted with 0.2 M glycine/HCl buffer (pH 2.5) and 1 M Tris-Cl buffer (pH 9.0) was used as a neutralization buffer. Specifically, the VSF culture supernatant was passed through a column using homogenized resin with a 10-fold volume of 1 M Tris-Cl buffer (pH 8.0) relative to the resin volume. The resultant was washed by flowing thereinto an at least 5-fold volume of 0.1 M Tris-Cl buffer (pH 8.0) relative to the column volume. The resultant was eluted by flowing thereinto a 5-fold volume of 0.2 M glycine/HCl buffer (pH 2.5) relative to the resin volume, and purified VSFs were thereby obtained in a tube in which a neutralization buffer was added in advance. The purified VSF was confirmed by SDS-PAGE.

As a result, as illustrated in FIG. 3, it was confirmed that chVSF has a structure consisting of a heavy chain (50 kDa) and a light chain (25 kDa), which have the characteristics of immunoglobulin.

Example 2: Preparation of Single-Chain Variable Fragment (scFv) and Confirmation of Antiviral Effect Thereof The single-chain variable fragment (scFv) was prepared using the variable regions of VSF. The scFv had the DNA sequence of SEQ ID NO: 150 and the scFv was prepared by cloning the DNA into pET-22b (+), an *E. coli* expression vector (FIGS. 4 and 5).

Specifically, the scFV was prepared by linking the VH and VL of mVSF by a linker, inserted into the bacterial expression vector, pET-22b (+), treated with IPTG to induce its expression, and purified with a Ni-NTA column (FIG. 6).

The antiviral activity of the scFV was confirmed using the purified scFv. Specifically, the L929 cells, which were infected with EMC-D virus, were incubated with scFv, VSF, or anti-EMC-D virus antibodies at 37° C. for 30 hours. Then, the supernatant was removed and treated with CellTiter96 AQueous One Solution, and the absorbance was measured at $OD_{450}$. As a result, it was confirmed that all groups treated with VSF (5 ng to 500 ng), scFv (5 μg to 10 μg), and anti-EMC-D virus antigen (1:20 dilution) exhibited antiviral effects (FIG. 7).

Example 3: Confirmation of Antiviral Activity of chVSF

In order to confirm the antiviral activity of the chVSF prepared in Example 1, an MVIT assay was performed.

Specifically, the L929 cells, which are mouse fibroblasts seeded into a 96-well plate at the amount of $2\times10^4$ cells, were infected with EMC-D virus (100 pfu) for one hour using Dulbecco's Modified Eagle's Medium (DMEM) containing 2% fetal bovine serum (FBS) and then treated with VSF (4 μg/mL) by 2-fold dilutions. After 48 hours, the cells were fixed with 10% formalin for 10 minutes and stained with 1% crystal violet for 10 minutes. The stained cells were washed with PBS and the viability of the cells was evaluated based on the degree of staining. When virus proliferation was inhibited, all cells became viable and formed a uniform layer, which was also stained with crystal violet. In contrast, when the cells are lysed by viral infection, the cells were detached and thus there was almost no stained layer.

As a result, as illustrated in FIG. 8, the chVSF of the present invention exhibited antiviral activity against EMC-D virus. These results support that not only the existing mouse VSFs but also the chVSF of the present invention, which was prepared by chimerization of the existing mouse VSF with the constant region of human immunoglobulin antibody based on the assumption that the mVSF is a monoclonal antibody, can also be used as an antiviral agent.

Example 4: Preparation of Humanized Antibody VSF

A humanized antibody, hzVSF, was prepared using the chVSF based on Examples 1 and 3.

In particular, pdCMV-dhfr vector, which corresponds to a two-gene expression vector, i.e., an expression system used for expressing two different kinds of recombinant proteins using a eukaryotic cell (FIG. 9), was used. The vector consists of two different transcription units for two different kinds of genes in a single vector and thereby expresses the two different genes using the promoter and polyA signal in each transcription unit, and it is a vector system utilizing the cytomegalovirus (CMV) promoter, a strong mammalian promoter. The hzVSF was prepared using the promoter, as illustrated in FIG. 10.

In this regard, the amino acid sequence of the heavy chain variable region of the hzVSF was indicated by SEQ ID NO: 10, that of the heavy chain region by SEQ ID NO: 11, whereas the amino acid sequence of the light chain variable region was indicated by SEQ ID NO: 12 and that of the light chain was indicated by SEQ ID NO: 13.

15 μg of pCAGGS-GFP was transfected into HEK 293T cells using 1 mg/mL of polyethylenimine (PEI) to examine the levels of transfection and expression. The chVSF and hzVSF were transfected into HEK 293T cells in the same manner, and after 6 hours, the medium was replaced with media containing 2% FBS. The cell culture supernatant was collected every 3 days and impurities contained therein were removed using a filter (0.45 μm). The chVSF and hzVSF were purified using nProtein A Sepharose® beads. The chVSF and hzVSF were eluted with 0.2 M glycine/HCl buffer (pH 2.5) and 1 M Tris-Cl buffer (pH 9.0) was used as a neutralization buffer. Specifically, the VSF culture was passed through a column using homogenized resin with a 10-fold volume of 1 M Tris-Cl buffer (pH 8.0) relative to the resin volume. The resultant was washed by flowing thereinto an at least 5-fold volume of 0.1 M Tris-Cl buffer (pH 8.0) relative to the column volume. The resultant was eluted by flowing thereinto a 5-fold volume of 0.2 M glycine/HCl buffer (pH 2.5) relative to the resin volume, and purified VSFs were thereby obtained in a tube in which a neutralization buffer was added in advance. The purified VSFs were confirmed by SDS-PAGE and their activities were confirmed by MVIT assay.

The VSFs used in the experiment are shown in Table 2 below.

TABLE 2

| VSF Type | Expressed Cell | mg/L (Harvested sup.) |
|---|---|---|
| mVSF | Mouse hybridoma | 4.14 |
| *rmVSF | HEK293T | 5.71 |
| chVSFγ2 | HEK293T | 5.15 |
| chVSFγ4 | HEK293T | 7.32 |

TABLE 2-continued

| VSF Type | Expressed Cell | mg/L (Harvested sup.) |
|---|---|---|
| hzVSFγ2 | HEK293T | 5.01 |
| hzVSFγ4 | HEK293T | 9.38 |

*rmVSF: a recombinant of mouse VSF

As a result, as can be seen in FIG. 11, it was confirmed that chVSFγ2 and chVSFγ4, and hzVSFγ2 and hzVSFγ4 consist of a heavy chain (50 kDa) and a light chain (25 kDa), respectively, which have the characteristics of immunoglobulin.

Additionally, as can be seen in FIG. 12, it was confirmed that hzVSF also has an antiviral effect. These results suggest that hzVSF, as a humanized antibody, has an antiviral effect similar to that of VSF.

Example 5: Confirmation of Physical Properties of Humanized Antibody VSF

The physical properties of hzVSF prepared in Example 4 were confirmed as follows.

Example 5-1: Confirmation of Basic Molecular Weight Patterns and Purity

Molecular weight patterns and purities were confirmed by reducing and non-reducing SDS-PAGE. Specifically, hzVSF_v13 was stained by Coomassie staining in SDS-PAGE according to molecular weight, and thereby the molecular weight and purity were confirmed.

As a result, as illustrated in FIG. 13, in lane 1, being a non-reducing gel, a major band was observed in the position where IgG antibody (150 kDa) was expected to appear; and in lane 2, being a reducing gel, the bands corresponding to the positions of the heavy chain (about 50 kDa) and the light chain (about 25 kDa) of immunoglobulin G (IgG) antibody were observed, thus confirming that hzVSF_v13 shows a general IgG antibody pattern.

Example 5-2: Confirmation of Molecular Weight, Glycosylation Pattern, Size Variation, Etc In order to confirm the molecular weight, glycosylation pattern, size variation, etc., of hzVSF_v13, liquid chromatography/mass spectrometry was performed. A small amount of hzVSF_v13 was injected into HPLC and the peaks were observed.

As a result, it was confirmed that hzVSF_v13 exhibited the characteristics of IgG (FIG. 14). In Intact Mass, the total molecular weight (about 140 kDa) of hzVSF_v13 was observed, and the peak patterns corresponding to general glycosylated IgG (e.g., G0/G0, G0F/G1, G1/G1, etc.) were observed. Additionally, the heavy chain (about 49 kDa) and the light chain (about 23 kDa) after deglycosylation were observed. Summarizing the molecular weights of the heavy chain, where the glycan was removed by treating with PNGase F, and the heavy chain, which was without PNGase F treatment, a general glycan pattern of IgG could be confirmed (G0F, G1F, and G2F).

Example 5-3: Confirmation of Purity and Aggregation

In order to confirm the purity and aggregation of hzVSF_v13, SEC-HPLC was performed.

SEC-HPLC conditions are as follows:

HPLC system: Dionex Ultimate 3000

Column: Tosoh TSKgel G3000 SWx1

Mobile phase: phosphate buffer, 0.5 mL/min

Injection volume: 10 μL

As a result, 92.44% of the major peak was observed at the position corresponding to the monomers of a typical IgG antibody (at the retention time of about 16 minutes) and about 6.84% of the peaks were observed at the position corresponding to the dimers of a typical IgG antibody (at the retention time of about 13 minutes) (FIG. 15).

Example 5-4: Confirmation of pI and Charge Heterogeneity

In order to confirm the isoelectric point of hzVSF_v13, electrophoresis was performed using a gel exhibiting a gradient of pH 3 to pH 10.

As a result, as illustrated in FIG. 16, the hzVS_v13F was shown to have a pI of 7.7, and acidic/basic isoforms were also observed in addition to the major bands. This corresponds to the isomers generally observed in IgG antibodies (e.g., deamination at the C-terminal region).

The above results support that the humanized antibodies of the present invention, hzVSF_v13s, have physical properties similar to those of IgG antibodies.

Example 6: Preparation of hzVS Variants which are Humanized Antibodies with Reduced Immunogenicity while Having their Virus-Inhibitory Activity Maintained or Enhanced

Example 6-1: Preparation of hzVSF Alternatives

Three hzVSF alternatives were prepared based on the hzVSF prepared in Example 4. The activity of each alternative was similar to or lower than that of the wild-type (0.5≤≤1 U<1 mg/mL) (Tables 3 and 4). The amino acid sequences of CDR 1 to CDR 3 for each of the alternatives are shown in Table 3 and the amino acid sequences of FR1 to FR4 of each of the variants are shown in Table 4.

TABLE 3

| Antibody | | CDR1 | CDR2 | CDR3 |
|---|---|---|---|---|
| hzVSF_WT | Heavy chain | GYNMN (SEQ ID NO: 2) | NIDPYYGSTTYAQ KFQG (SEQ ID NO: 3) | ETGTRAMDY (SEQ ID NO: 4) |
| | Light chain | RASENIYSNLA (SEQ ID NO: 5) | VATNLAD (SEQ ID NO: 6) | QHFYGSPRT (SEQ ID NO: 7) |
| hzVSF_a1 | Heavy chain | GYNMN (SEQ ID NO: 2) | NIDPYYGSTTYAQ KFQG (SEQ ID NO: 3) | ETGTRAMDY (SEQ ID NO: 4) |

TABLE 3-continued

| Antibody | | CDR1 | CDR2 | CDR3 |
|---|---|---|---|---|
| | Light chain | RASENIYSNLA (SEQ ID NO: 5) | VATNLAD (SEQ ID NO: 6) | QHFYGSPRT (SEQ ID NO: 7) |
| hzVSF_a2 | Heavy chain | GYNMN (SEQ ID NO: 2) | NIDPYYGSTTYAQ KFQG (SEQ ID NO: 3) | ETGTRAMDY (SEQ ID NO: 4) |
| | Light chain | RASENIYSNLA (SEQ ID NO: 5) | VATNLAD (SEQ ID NO: 6) | QHFYGSPRT (SEQ ID NO: 7) |
| hzVSF_a3 | Heavy chain | GYNMN (SEQ ID NO: 2) | NIDPYYGSTTYAQ KFQG (SEQ ID NO: 3) | ETGTRAMDY (SEQ ID NO: 4) |
| | Light chain | RASENIYSNLA (SEQ ID NO: 5) | VATNLAD (SEQ ID NO: 6) | QHFYGSPRT (SEQ ID NO: 7) |

TABLE 4

| Antibody | | FR1 | FR2 | FR3 | FR4 |
|---|---|---|---|---|---|
| hzVSF_WT | Heavy chain | SEQ ID NO: 20 | SEQ ID NO: 21 | SEQ ID NO: 22 | SEQ ID NO: 23 |
| | Light chain | SEQ ID NO: 24 | SEQ ID NO: 25 | SEQ ID NO: 26 | SEQ ID NO: 27 |
| hzVSF_a1 | Heavy chain | SEQ ID NO: 151 | SEQ ID NO: 21 | SEQ ID NO: 22 | SEQ ID NO: 23 |
| | Light chain | SEQ ID NO: 24 | SEQ ID NO: 25 | SEQ ID NO: 26 | SEQ ID NO: 27 |
| hzVSF_a2 | Heavy chain | SEQ ID NO: 20 | SEQ ID NO: 152 | SEQ ID NO: 22 | SEQ ID NO: 23 |
| | Light chain | SEQ ID NO: 24 | SEQ ID NO: 25 | SEQ ID NO: 26 | SEQ ID NO: 27 |
| hzVSF_a3 | Heavy chain | SEQ ID NO: 151 | SEQ ID NO: 152 | SEQ ID NO: 22 | SEQ ID NO: 23 |
| | Light chain | SEQ ID NO: 24 | SEQ ID NO: 25 | SEQ ID NO: 26 | SEQ ID NO: 27 |

Example 6-2: Preparation of hzVSF Variants

Based on the hzVSF prepared in Example 4, hzVSF variants for actual use in vivo were prepared via immunogenicity reduction and affinity maturation. As a result, a total of 13 variants were prepared (Tables 5 and 6). The amino acid sequences of CDR 1 to CDR 3 for each of the variants are shown in Table 5 and the amino acid sequences of FR1 to FR4 of each of the variants are shown in Table 6.

TABLE 5

| Antibody | | CDR1 | CDR2 | CDR3 |
|---|---|---|---|---|
| hzVSF_WT | Heavy chain | GYNMN (SEQ ID NO: 2) | NIDPYYGSTTYAQKFQG (SEQ ID NO: 3) | ETGTRAMDY (SEQ ID NO: 4) |
| | Light chain | RASENIYSNLA (SEQ ID NO: 5) | VATNLAD (SEQ ID NO: 6) | QHFYGSPRT (SEQ ID NO: 7) |
| hzVSF_var1 | Heavy chain | GYNMN (SEQ ID NO: 2) | NIDPYYGSTTYAQKFQG (SEQ ID NO: 3) | ETGTRAMDY (SEQ ID NO: 4) |
| | Light chain | RASENIYSNLA (SEQ ID NO: 5) | VADNLAD (SEQ ID NO: 16) | QHFYGSPRT (SEQ ID NO: 7) |
| hzVSF_var2 | Heavy chain | GYNMN (SEQ ID NO: 2) | NIDPYYGSTTYAQKFQG (SEQ ID NO: 3) | ETGTRAMDY (SEQ ID NO: 4) |
| | Light chain | RASENIYSNLA (SEQ ID NO: 5) | VADNLGD (SEQ ID NO: 17) | QHFYGSPRT (SEQ ID NO: 7) |
| hzVSF_var3 | Heavy chain | GYNMN (SEQ ID NO: 2) | NIDPYYGSTTYAQKFQG (SEQ ID NO: 3) | ETGTRAMDY (SEQ ID NO: 4) |

TABLE 5-continued

| Antibody | | CDR1 | CDR2 | CDR3 |
|---|---|---|---|---|
| | Light chain | RASENIYSNLA (SEQ ID NO: 5) | VA**D**N**RG**D (SEQ ID NO: 18) | QHFYGSPRT (SEQ ID NO: 7) |
| hzVSF_var4 | Heavy chain | GYNMN (SEQ ID NO: 2) | NIDPYYGSTTYAQKFQG (SEQ ID NO: 3) | ETGTRAMDY (SEQ ID NO: 4) |
| | Light chain | RASENIYSNLA (SEQ ID NO: 5) | VA**D**N**RG**D (SEQ ID NO: 18) | QHFYG**T**PRT (SEQ ID NO: 19) |
| hzVSF_var5 | Heavy chain | GYNMN (SEQ ID NO: 2) | NIDPYYGS**D**TYAQKFQG (SEQ ID NO: 14) | ETGTRAMDY (SEQ ID NO: 4) |
| | Light chain | RASENIYSNLA (SEQ ID NO: 5) | VATNLAD (SEQ ID NO: 6) | QHFYGSPRT (SEQ ID NO: 7) |
| hzVSF_var6 | Heavy chain | GYNMN (SEQ ID NO: 2) | NIDPYYGSTTYAQKFQG (SEQ ID NO: 3) | ETGTRAMDY (SEQ ID NO: 4) |
| | Light chain | RASENIYSNLA (SEQ ID NO: 5) | VATNLAD (SEQ ID NO: 6) | QHFYGSPRT (SEQ ID NO: 7) |
| hzVSF_var7 | Heavy chain | GYNMN (SEQ ID NO: 2) | NIDPYYGS**D**TYAQKFQG (SEQ ID NO: 14) | ETGTRAMDY (SEQ ID NO: 4) |
| | Light chain | RASENIYSNLA (SEQ ID NO: 5) | VATNLAD (SEQ ID NO: 6) | QHFYGSPRT (SEQ ID NO: 7) |
| hzVSF_var8 | Heavy chain | GYNMN (SEQ ID NO: 2) | NIDPYYGS**D**TYAQKFQG (SEQ ID NO: 14) | ETG**N**RAMD (SEQ ID NO: 15) |
| | Light chain | RASENIYSNLA (SEQ ID NO: 5) | VATNLAD (SEQ ID NO: 6) | QHFYGSPRT (SEQ ID NO: 7) |
| hzVSF_var9 | Heavy chain | GYNMN (SEQ ID NO: 2) | NIDPYYGS**D**TYAQKFQG (SEQ ID NO: 14) | ETGTRAMDY (SEQ ID NO: 4) |
| | Light chain | RASENIYSNLA (SEQ ID NO: 5) | VA**D**N**RG**D (SEQ ID NO: 18) | QHFYGSPRT (SEQ ID NO: 7) |
| hzVSF_var10 | Heavy chain | GYNMN (SEQ ID NO: 2) | NIDPYYGS**D**TYAQKFQG (SEQ ID NO: 14) | ETG**N**RAMDY (SEQ ID NO: 15) |
| | Light chain | RASENIYSNLA (SEQ ID NO: 5) | VA**D**N**RG**D (SEQ ID NO: 18) | QHFYGSPRT (SEQ ID NO: 7) |
| hzVSF_var11 | Heavy chain | GYNMN (SEQ ID NO: 2) | NIDPYYGS**D**TYAQKFQG (SEQ ID NO: 14) | ETGTRAMDY (SEQ ID NO: 4) |
| | Light chain | RASENIYSNLA (SEQ ID NO: 5) | VA**D**N**RG**D (SEQ ID NO: 18) | QHFYG**T**PRT (SEQ ID NO: 19) |
| hzVSF_var12 | Heavy chain | GYNMN (SEQ ID NO: 2) | NIDPYYGS**D**TYAQKFQG (SEQ ID NO: 14) | ETG**N**RAMDY (SEQ ID NO: 15) |
| | Light chain | RASENIYSNLA (SEQ ID NO: 5) | VA**D**N**RG**D (SEQ ID NO: 18) | QHFYG**T**PRT (SEQ ID NO: 19) |
| hzVSF_var13 | Heavy chain | GYNMN (SEQ ID NO: 2) | NIDPYYGS**D**TYAQKFQG (SEQ ID NO: 14) | ETGTRAMDY (SEQ ID NO: 4) |
| | Light chain | RASENIYSNLA (SEQ ID NO: 5) | VA**D**NLAD (SEQ ID NO: 16) | QHFYGSPRT (SEQ ID NO: 7) |

TABLE 6

| Antibody | | FR1 | FR2 | FR3 | FR4 |
|---|---|---|---|---|---|
| hzVSF_WT | Heavy chain | SEQ ID NO: 20 | SEQ ID NO: 21 | SEQ ID NO: 22 | SEQ ID NO: 23 |
| | Light chain | SEQ ID NO: 24 | SEQ ID NO: 25 | SEQ ID NO: 26 | SEQ ID NO: 27 |
| hzVSF_var1 | Heavy chain | SEQ ID NO: 20 | SEQ ID NO: 21 | SEQ ID NO: 22 | SEQ ID NO: 23 |
| | Light chain | SEQ ID NO: 24 | SEQ ID NO: 25 | SEQ ID NO: 26 | SEQ ID NO: 27 |
| hzVSF_var2 | Heavy chain | SEQ ID NO: 20 | SEQ ID NO: 21 | SEQ ID NO: 22 | SEQ ID NO: 23 |
| | Light chain | SEQ ID NO: 24 | SEQ ID NO: 25 | SEQ ID NO: 26 | SEQ ID NO: 27 |
| hzVSF_var3 | Heavy chain | SEQ ID NO: 20 | SEQ ID NO: 21 | SEQ ID NO: 22 | SEQ ID NO: 23 |
| | Light chain | SEQ ID NO: 24 | SEQ ID NO: 25 | SEQ ID NO: 26 | SEQ ID NO: 27 |
| hzVSF_var4 | Heavy chain | SEQ ID NO: 20 | SEQ ID NO: 21 | SEQ ID NO: 22 | SEQ ID NO: 23 |
| | Light chain | SEQ ID NO: 24 | SEQ ID NO: 25 | SEQ ID NO: 26 | SEQ ID NO: 27 |
| hzVSF_var5 | Heavy chain | SEQ ID NO: 20 | SEQ ID NO: 21 | SEQ ID NO: 22 | SEQ ID NO: 23 |
| | Light chain | SEQ ID NO: 24 | SEQ ID NO: 25 | SEQ ID NO: 26 | SEQ ID NO: 27 |
| hzVSF_var6 | Heavy chain | SEQ ID NO: 20 | SEQ ID NO: 21 | SEQ ID NO: 28 (K74T, I76A) | SEQ ID NO: 23 |
| | Light chain | SEQ ID NO: 24 | SEQ ID NO: 25 | SEQ ID NO: 26 | SEQ ID NO: 27 |
| hzVSF_var7 | Heavy chain | SEQ ID NO: 20 | SEQ ID NO: 21 | SEQ ID NO: 28 (K74T, I76A) | SEQ ID NO: 23 |
| | Light chain | SEQ ID NO: 24 | SEQ ID NO: 25 | SEQ ID NO: 26 | SEQ ID NO: 27 |
| hzVSF_var8 | Heavy chain | SEQ ID NO: 20 | SEQ ID NO: 21 | SEQ ID NO: 28 (K74T, I76A) | SEQ ID NO: 23 |
| | Light chain | SEQ ID NO: 24 | SEQ ID NO: 25 | SEQ ID NO: 26 | SEQ ID NO: 27 |
| hzVSF_var9 | Heavy chain | SEQ ID NO: 20 | SEQ ID NO: 21 | SEQ ID NO: 28 (K74T, I76A) | SEQ ID NO: 23 |
| | Light chain | SEQ ID NO: 24 | SEQ ID NO: 25 | SEQ ID NO: 26 | SEQ ID NO: 27 |
| hzVSF_var10 | Heavy chain | SEQ ID NO: 20 | SEQ ID NO: 21 | SEQ ID NO: 28 (K74T, I76A) | SEQ ID NO: 23 |
| | Light chain | SEQ ID NO: 24 | SEQ ID NO: 25 | SEQ ID NO: 26 | SEQ ID NO: 27 |
| hzVSF_var11 | Heavy chain | SEQ ID NO: 20 | SEQ ID NO: 21 | SEQ ID NO: 28 (K74T, I76A) | SEQ ID NO: 23 |
| | Light chain | SEQ ID NO: 24 | SEQ ID NO: 25 | SEQ ID NO: 26 | SEQ ID NO: 27 |
| hzVSF_var12 | Heavy chain | SEQ ID NO: 20 | SEQ ID NO: 21 | SEQ ID NO: 28 (K74T, I76A) | SEQ ID NO: 23 |
| | Light chain | SEQ ID NO: 24 | SEQ ID NO: 25 | SEQ ID NO: 26 | SEQ ID NO: 27 |
| hzVSF_var13 | Heavy chain | SEQ ID NO: 20 | SEQ ID NO: 21 | SEQ ID NO: 22 | SEQ ID NO: 23 |
| | Light chain | SEQ ID NO: 24 | SEQ ID NO: 25 | SEQ ID NO: 26 | SEQ ID NO: 27 |

It was confirmed that all of the 13 variants prepared above had reduced immunogenicity while having their antiviral activity and anti-inflammatory activity maintained or enhanced compared to those of the wild-type.

hzVSF_var12, which has the lowest immunogenicity among the above variants, showed antiviral activity such that 1 unit showed antiviral activity at 500 ng/unit, the same as in hzVSF wild-type. In contrast, hzVSF_var13, which has a relatively low immunogenicity but relatively high antiviral activity, showed antiviral activity at 250 ng/unit.

Example 6-3: Confirmation of Epitope Counts of hzVSF Wild-Type and Variants Thereof The epitope counts of hzVSF wild-type; hzVSF_var12 and hzVSF_var13, which are the representative variants among the variants with reduced immunogenicity of the wild-type; and four kinds of blockbuster antibody drugs currently available in the pharmaceutical market were compared. As a result, the possibility of relative immunogenicity in each HLA class II was confirmed, as shown in Table 7.

TABLE 7

| Protein Type | DRB1 | DRB 3/4/5 | DQ | DP | Total |
|---|---|---|---|---|---|
| hzVSF w | 31 | 17 | 1 | 3 | 52 |
| hzVSF_var1 | 30 | 18 | 1 | 3 | 52 |
| hzVSF_var2 | 30 | 17 | 0 | 3 | 50 |
| hzVSF_var3 | 30 | 16 | 0 | 3 | 49 |
| hzVSF_var4 | 28 | 16 | 0 | 3 | 47 |
| hzVSF_var5 | 30 | 16 | 1 | 3 | 50 |
| hzVSF_var6 | 29 | 16 | 1 | 3 | 49 |

TABLE 7-continued

| Protein Type | DRB1 | DRB 3/4/5 | DQ | DP | Total |
|---|---|---|---|---|---|
| hzVSF_var7 | 28 | 15 | 1 | 3 | 47 |
| hzVSF_var8 | 27 | 14 | 1 | 3 | 45 |
| hzVSF_var9 | 27 | 14 | 0 | 3 | 44 |
| hzVSF var10 | 26 | 13 | 0 | 3 | 42 |
| hzVSF_var11 | 25 | 14 | 0 | 3 | 42 |
| hzVSF_var12 | 24 | 13 | 0 | 3 | 40 |
| hzVSF_var13 | 29 | 17 | 0 | 3 | 49 |
| Humira (human) | 25 | 12 | 4 | 1 | 42 |
| Remicade (chimeric) | 74 | 37 | 3 | 1 | 115 |
| Rituxan (chimeric) | 65 | 33 | 9 | 3 | 110 |
| Herceptin (humanized) | 40 | 20 | 3 | 1 | 64 |

In Table 7, a higher total value means that there is a higher likelihood of adverse effects due to the HLA class II. From the above results, it was confirmed that the epitope counts of hzVSF_var12 and hzVSF_var13 with reduced immunogenicity of the present invention were similar to that of Humira, which has the lowest epitope count of the four kinds of pharmaceutical drugs. These results suggest that the humanized antibodies of the present invention will have a very low level of serious side effects that may arise when they are used as antiviral agents, and thus support the safety of the humanized antibodies of the present invention as safe antiviral or anti-inflammatory drugs.

Additionally, the biological activity of each of the variants (from var1 to var12) was similar to that of wild-type (0.5 mg/U), but the activity of var13 was shown to be higher than that of the wild-type.

Example 6-4: Confirmation of T Cell Analysis of hzVSF Variants

In order to evaluate the immunogenicity of hzVSF_var12 and hzVSF_var13, it was confirmed whether the material examined by in vitro T cell analysis of Lonza can have an effect on T cell proliferation using the blood samples of 51 healthy donors.

The total peripheral blood mononuclear cells (PBMC) of each donor were treated with hzVSF_var12, hzVSF_var13, or Keyhole limpet hemocyanin (KLH) and cultured for 7 days. KLH is an oxygen-carrying metalloprotein that can be used as a carrier protein in the production of antibodies, and it was used as a positive control for its ability to effectively elicit immune responses. Then, the ratio of T cells stained with $CD3^+CD4^+Edu^+$ was measured. As a result, KLH showed T cell proliferation in 45 blood donors (a response rate of 88%), whereas hzVSF_var12 and hzVSF_var13 induced T cell proliferation in only 3 subjects (a response rate of 5.8%), in response to the material (FIG. 17).

Meanwhile, the stimulation index (SI) of T cell proliferation induced by KLH, hzVSF_v12, or hzVSF_v13 was calculated using the PBMC cultured as a control for 7 days. When the SI value is greater than 2, the immunogenicity is expected to be large when applied to humans. In contrast, when the SI value is less than 0.5, T cell proliferation is expected to be inhibited. As a result, it was confirmed that hzVSF_v12 and hzVSF_v13 showed low SI values of 1.12 and 1.03, respectively, and also showed SI values in the range of being equal to or greater than 0.6 and being equal to or less than 2. In contrast, KLH, which was used as a positive control, showed a high SI value of 3.91 (FIGS. 18 and 19; and Table 8).

TABLE 8

| Product (Antigen) | Mean SI | p-Value |
|---|---|---|
| hzVSF_var12 | 1.12 | 0.008 |
| hzVSF_var13 | 1.05 | 0.3229 |
| KLH | 3.91 | <0.0001 |

From the above results, it is expected that hzVSF_v12 and hzVSF_v13 will have less immunogenicity when administered to virus-infected patients and subsequently have few side effects.

Example 7: Confirmation of Binding Epitopes of hzVSF and Variants Thereof

An attempt was made to identify the peptides to which the hzVSF and variants thereof prepared in the above Examples bind.

As a result, it was confirmed that the hzVSF and variants thereof prepared in the above Examples were bound to the isolated peptide of SEQ ID NO: 1, corresponding to the amino acid sequence of vimentin at amino acid positions 142 to 294 (FIGS. 54 to 58).

Example 8: Confirmation of Physical Properties and Pharmacokinetics of hzVSF Variants In order to confirm the physical properties and pharmacokinetics of the hzVSF variants prepared in Example 6, experiments were performed regarding the representative variants hzVSF_var12 and hzVSF_var13.

Example 8-1: Confirmation of Molecular Weight Patterns and Purities of hzVSF Variants The molecular weight pattern and purity of hzVSF_var12 and hzVSF_var13 were confirmed by SDS-PAGE. The reduced sample was prepared by mixing the NuPage 4× LDS sample buffer (Invitrogen, NP0007) and NuPage 10× sample reducing agent (Invitrogen, NP0009) with hzVSF_var12 and hzVSF_var13, respectively, followed by heating at 70° C. for 10 minutes. The non-reducing sample was prepared by omitting the steps of adding a reducing agent and heating. 10 μL each of control antibodies, hzVSF_var12, and hzVSF_var13 at a concentration of 1 mg/mL, respectively, was electrophoresed on 4% to 12% SDS-PAGE, the gel was stained with InstantBlue (TripleRed, ISB01L), and the purity of hzVSF_var12 and hzVSF_var13 was confirmed.

As a result, as illustrated in FIG. 20, it was confirmed that, in lanes 2 and 4 (non-reducing samples), the major bands were observed in the position where IgG antibody (about 150 kDa) was expected to appear; and in lanes 3 and 5 (reducing samples), the bands corresponding to the positions of the heavy chain (about 50 kDa) and the light chain (about 25 kDa) of an immunoglobulin G (IgG) antibody were observed, thus confirming that the hzVSF variants also show a general IgG antibody pattern, as is the case for hzVSF. Additionally, when IgG4 was used as a control, the pattern observed was the same as those observed in lane 6 (a non-reducing sample) and lane 7 (a reducing sample). Additionally, it was confirmed that both hzVSF_var12 and hzVSF_var13 showed good purity.

Additionally, in order to confirm the purity and aggregation of hzVSF_var12 and hzVSF_var13, hzVSF_var12 and hzVSF_var13 were analyzed by size exclusion high-performance liquid chromatography (SE-HPLC) using HPLC along with a Zorbax GF-250 μm 9.2 mm ID×25 cm column (Agilent 1200 series). Before injection into HPLC, the sample at a concentration of 1 mg/mL was purified by a 0.2 μm filter to remove impurities. Each of the samples (100 μL) was injected and HPLC was operated at a rate of 1 mL/min for 15 minutes. Analysis was performed using the Chemstation software.

As a result, the major peak was observed at the position corresponding to the monomers of a typical IgG antibody (at the retention time of about 8.65 minutes) and the purity of hzVSF_var12 and hzVSF_var13 was confirmed to be 95% or higher (FIG. 21). About 3.72% and 4.43% of the peaks were observed at the position corresponding to the dimers of a typical IgG antibody (at the retention time of about 7.89 to 7.93 minutes), thus confirming that the peak shape was identical to that of the IgG antibody; this result is consistent with the SDS-PAGE result.

Example 8-2: Analysis of Pharmacokinetics of hzVSF Variants

The following experiment was carried out in order to obtain objective indices for reference during clinical tests by determining suitable in vivo dosage, administration intervals, and administration formulations of hzVSF_var13 via quantitative prediction of in vivo performance of hzVSF_var13 after its administration into mice, i.e., concentration in blood, half-life, metabolic rate, etc.

As a control, 6.25 μg (0.31 mg/kg) of human IgG (polyclonal) was used, while in the experimental groups, 6.25 μg (25 U; 0.31 mg/kg), 62.5 μg (250 U; 3.10 mg/kg), and 625 μg (2500 U; 31.0 mg/kg) of hzVSF_var13 was injected into the mouse caudal vein. After the injection, blood samples were collected from the mice at days 1, 2, 4, 8, 14, 21, 28, and 35, and the sera were separated and used for measuring the blood concentration of hzVSF_var13 using ELISA.

For ELISA assay, anti-human IgG (γ-specific) was fixed on a plate at 37° C. for 2 hours or at 4° C. overnight, and was then incubated with 3% bovine serum albumin (BSA) at 37° C. for 2 hours to block the uncoated parts. The sera obtained from the blood collected from the mice were reacted at 37° C. for 1 hour and reacted with anti-human IgG (κ-specific), to which horseradish peroxidase (HRP) was conjugated, at 37° C. for 30 minutes. The resultant was incubated in a darkroom at room temperature for 9.5 minutes using a 3,3',5,5'-tetramethylbenzidine (TMB) solution as a substrate, and the amount of hzVSF_var13 in the blood was measured according to its OD value at 450 nm. The PK parameters when a single dose of hzVSF_var13 was administered to mice at each concentration are indicated in Table 9 and in the graphs of FIG. 22.

TABLE 9

| | Sham Control (IgG 0.31 mg/kg) | hzVSF_var13 (0.31 mg/kg) | hzVSF_var13 (3.10 mg/kg) | hzVSF_var13 (31.0 mg/kg) |
|---|---|---|---|---|
| Female | | | | |
| N | 6 | 6 | 6 | 6 |
| $C_{max}$ (μg/mL) | 5.5 ± 0.1 | 5.5 ± 0.2 | 57.2 ± 1.0 | 607.2 ± 22.2 |
| AUC (μg · day/mL) | 178.1 ± 53.9 | 113.0 ± 17.8 | 948.3 ± 296.7 | 8686.9 ± 2958.8 |
| $t_{1/2}$ (days) | 20.1 ± 2.9 | 13.4 ± 2.4 | 10.8 ± 3.8 | 10.2 ± 3.0 |
| CL (mL/day/kg) | 1.8 ± 0.4 | 2.8 ± 0.4 | 3.5 ± 1.1 | 4.0 ± 1.5 |
| Male | | | | |
| N | 5 | 5 | 5 | 5 |
| $C_{max}$ (μg/mL) | 5.5 ± 0.2 | 5.2 ± 0.3 | 54.6 ± 1.4 | 563.0 ± 8.2 |
| AUC (μg · day/mL) | 121.8 ± 15.3 | 78.8 ± 20.8 | 798.1 ± 274.5 | 6939.9 ± 2311.8 |
| $t_{1/2}$ (days) | 16.6 ± 2.4 | 10.1 ± 3.1 | 9.0 ± 4.0 | 8.9 ± 3.7 |
| CL (mL/day/kg) | 2.6 ± 0.3 | 4.1 ± 0.8 | 4.2 ± 1.0 | 4.9 ± 1.2 |

As a result, when hzVSF_var13 was administered at a single dose of 25 U, the trend of hzVSF concentration in blood was decreased in the same manner as in a sham control (IgG) administered with the same dose. The maximum concentration ($C_{max}$) and the area under the concentration curve (AUC) were increased along with the increase in the administration dose and were thus confirmed to be dose-dependent. The in vivo half-life ($t_{1/2}$) of hzVSF_var13 (25 U) was 10 days for males and 13 days for females, being slightly lower than the sham control (16 days for males and 20 days for females), and the half-life was shown to be slightly decreased along with the increase in the administration dose. The $C_{max}$, AUC, in vivo half-life ($t_{1/2}$), in vivo systemic and clearance value (CLt) were all shown to be higher in females in each concentration for administration than in males. At 35 days after the administration, all mice were autopsied to conduct measurement of organ weight, histopathological examination, immunotoxicity test, and neutralizing capability to examine the presence of in vivo toxicity caused by hzVSF_var13, but no adverse effects were observed.

The above results support that hzVSF and variants thereof according to the present invention have half-lives similar to those of other humanized antibodies, and that they will have no problem for clinical applications.

Example 9: Confirmation of Virus-Inhibiting Activity of hzVSF and Variants Thereof Mouse L929 cells were infected with EMC-D virus, treated with hzVSF wild-type and hzVSF_var12 and hzVSF_var13, which are the representative variants of hzVSF variants, and their antiviral effect was confirmed by MVIT assay of Example 2.

As a result, as illustrated in FIG. 23, the hzVSF wild-type showed 100% antiviral effect at a concentration of 0.5 μg/mL; and hzVSF_var12 and hzVSF_var13 showed 100% antiviral effect at concentrations of 0.2 μg/mL and 0.1 μg/mL, respectively.

Accordingly, the minimum amount contained in 1 mL of the VSF exhibiting 100% antiviral effect when L929 cells were infected with EMC-D virus and simultaneously treated with VSF was determined as 1 unit of biological activity.

In this regard, the biological activity of each of the VSFs is shown in Table 10 below.

TABLE 10

| VSF Type | Biological Activity (1 unit) | MW (kDa) |
|---|---|---|
| mVSF | 0.09 μg | 163 |
| hzVSF_wt | 0.5 μg | 147 |
| hzVSF_var12 | 0.2 μg | 147 |
| hzVSF_var13 | 0.1 μg | 147 |

These results suggest that the hzVSF variants, which were newly prepared by performing humanization of a monoclonal antibody, reduction of immunogenicity, and affinity maturation, can exhibit excellent antiviral and anti-inflammatory effects with almost no adverse effects compared to the hzVSF_wt, although the newly prepared hzVSF variants also have a lower titer than the mVSF.

Example 10: Confirmation of Affinity of hzVSF

The affinity for the receptors of hzVSF was measured by the method described below.

L929 cells were seeded at the amount of $6\times10^5$ cells and infected with 2 MOI of EMC-D virus for 0, 2, 6, and 10 hours, respectively. Four units of ligands (mVSF, hzVSF_wt, and hzVSF_v13) were added thereto and cultured for 1 hour, and the culture supernatants were collected and their Ka values were obtained. The difference between the amount of each ligand added and the amount of the collected ligand after reaction is the amount of the ligand bound to the receptors, and based on the result, the affinity constant (Ka) and the dissociation constant (Kd) were calculated (Table 11).

TABLE 11

| VSF Type | Affinity Constant (Ka) | Dissociation Constant (Kd) |
|---|---|---|
| mVSF | $2.1 \times 10^{10}$ L/mol | $4.7 \times 10^{-11}$ M |
| hzVSF wt | $8.2 \times 10^{9}$ L/mol | $1.2 \times 10^{-10}$ M |
| hzVSF v13 | $1.7 \times 10^{10}$ L/mol | $5.9 \times 10^{-11}$ M |

As a result, hzVSF was confirmed to have an affinity constant (Ka) of $1\times10^9$ or higher, corresponding to potential biologics, and thus, as biologics, both hzVSF and their variants were also confirmed to have high binding affinity for the receptors.

Example 11: Confirmation of Anticellular Activity of hIFN-α and hzVSF_wt in Human Cells Human fibroblasts, WI-38 cells, were infected with EMC-D and treated with human interferon and hzVSF_wt at various concentrations, and the antiviral effect and viability of each cell were measured by the MTS method.

In detail, the cells were seeded into a 96-well plate and cultured while attached to the bottom for 24 hours. The cells were infected with EMC-D virus (100 pfu) and treated with interferon or hzVSF. After culturing for 48 hours, the cells were treated with [3-(4,5-dimethylthiazol-2-yl)-5-(3-carboxymethoxyphenyl)-2-(4-sulfophenyl)-2H-tetrazolium] (MTS). The cells were further incubated for 2 or 3 hours and their viability was confirmed by measuring the absorbance at 490 nm. As illustrated in FIG. 24, the cells treated with human interferon showed about 90% viability even with a lesser amount than the cells treated with hzVSF_wt; however, when the cells were treated at a high concentration (4 nM or higher) of human interferon, the cells showed cytotoxicity. In contrast, when the cells were treated with hzVSF_wt, the cells showed about 100% viability at a concentration of about 4 nM and the cells did not show any cytotoxicity at a concentration of 4 nM or higher.

From the above results, it is expected that hzVSF will have fewer adverse effects, unlike human interferon.

Example 12: Confirmation of the Inhibitory Activity of hzVSF wt Against Immune Cell Infiltration and Inflammatory Response in Viral Diabetes In order to examine the efficacy of hzVSF on diabetes in mice according to the concentration of hzVSF, 5-week-old male DBA/2N mice were infected with EMC-D virus (100 pfu) by intraperitoneal injection. Then, the hzVSF_wt at concentrations of 2, 4, and 16 units, respectively, were injected into the caudal veins and the glucose levels in the blood and urine were examined from the $3^{rd}$ day of post infection. Additionally, the mice were sacrificed on the $3^{rd}$ and the $7^{th}$ days post infection, and their pancreases were surgically removed and subjected to a biopsy followed by a histological examination.

As a result, as illustrated in FIG. 25, when the pancreases were removed from the mice after infecting them with EMC-D virus and stained with Hematoxylin & Eosin, the group infected with only virus (virus control) showed the infiltration of immune cells and a decrease in the size of islets due to destruction of the islets thereof, whereas the group administered with at least 4 units of hzVSF_wt (virus+hzVSF) showed no infiltration of immune cells, and the islets also remained normal. Accordingly, it is speculated that hzVSF_wt inhibited the proliferation of EMC-D and suppressed the infiltration of immune cells, thereby protecting the islets from being destroyed.

Additionally, as a result of the detection of blood glucose levels, diabetes was not developed in the group administered with at least 4 units of hzVSF_wt, and blood glucose levels were below 200 mg/dL, which corresponds to the range of normal mice. Regarding the urine, urine glucose was not detected in the group administered with at least 8 units of hzVSF_wt (Tables 12 to 14).

In viral diabetes, the incidence rate of diabetes according to the concentration of the hzVSF_wt is shown in Table 12, the blood glucose levels according to the concentration of the hzVSF_wt are shown in Table 13, and the urine glucose levels according to the concentration of the hzVSF_wt are shown in Table 14.

TABLE 12

| Group | Post-Infection 3 Days | 4 Days | 5 Days | 6 Days | 7 Days | Incidence Rate of Diabetes |
|---|---|---|---|---|---|---|
| Virus Control | — | 4/4 | 4/4 | 4/4 | 4/4 | 100% |
| 2 Unit/Mouse | — | — | — | 4/4 | 4/4 | 100% |
| 4 Unit/Mouse | — | — | — | — | — | 0% |
| 8 Unit/Mouse | — | — | — | — | — | 0% |
| 16 Unit/Mouse | — | — | — | — | — | 0% |

* When a mouse has a blood glucose level of 300 mg/dL or higher and the urine glucose level of "+" or higher, the mouse is considered to have diabetes.

TABLE 13

| Group | Post-Infection 3 Days | 4 Days | 5 Days | 6 Days | 7 Days |
|---|---|---|---|---|---|
| Virus Control | 157 ± 25 | 541 ± 84 | 540 ± 84 | 526 ± 91 | 529 ± 100 |
| 2 Unit/Mouse | 162 ± 24 | 157 ± 23 | 186 ± 53 | 484 ± 21 | 505 ± 26 |
| 4 Unit/Mouse | 149 ± 42 | 148 ± 6 | 135 ± 11 | 145 ± 8 | 122 ± 16 |
| 8 Unit/Mouse | 171 ± 42 | 148 ± 6 | 135 ± 11 | 145 ± 8 | 122 ± 16 |
| 16 Unit/Mouse | 163 ± 21 | 160 ± 4 | 144 ± 9 | 139 ± 8 | 157 ± 22 |

* When a mouse has a blood glucose level of 300 mg/dL or higher, the mouse is considered to have diabetes.

TABLE 14

| Group | Post-Infection 3 Day | 4 Day | 5 Day | 6 Day | 7 Day |
|---|---|---|---|---|---|
| Virus Control | – | ++++ | ++++ | ++++ | ++++ |
| 2 Unit/Mouse | – | – | – | +++ | +++ |
| 4 Unit/Mouse | – | – | – | – | – |
| 8 Unit/Mouse | – | – | – | – | – |
| 16 Unit/Mouse | – | – | – | – | – |

The above results confirmed that hzVSF and various variants thereof of the present invention, due to their antiviral effect against EMC-D virus infection and inhibitory activity against the infiltration of immune cells, significantly inhibited the destruction of the Langerhans islets and were confirmed to be capable of significantly treating diabetes induced by viral infection. That is, the above results suggest that hzVSF and various variants thereof of the present invention not only exhibit an antiviral effect without inducing the infiltration of immune cells, but also have the capability to treat viral diabetes and may thus be used as an agent for treating various kinds of inflammatory diseases.

Example 13: Confirmation of Anti-HBV Effect of mVSF

In order to confirm the antiviral effect of mVSF against human hepatitis B virus (HBV), HepG2.2.15 cells, which are human hepatocarcinoma cells expressing HBV, were used.

The HepG2.2.15 cells were seeded into a plate and treated with mVSF, and the amount of the surface antigens of HBV (HBsAg), which were proliferated in the cells and released into the culture, was quantitated every 3 days using ELISA. The result was converted into the amount of virus per cell. At the same time, the number of cells was counted and the relative amount of virus per cell was measured.

As a result, it was confirmed that the mVSF treatment distinctively reduced the amount of HBsAg, thus suggesting that mVSF has an anti-HBV effect (FIG. 26). These results support the fact that hzVSF and various variants thereof of the present invention can effectively inhibit hepatitis viruses such as HBV, and thus have an antiviral effect against various viruses. Additionally, the mVSF treatment for 9 days was shown to inhibit the viral replication in each cell by 80% or higher and is expected to further inhibit inflammation in humans, thereby suggesting that it will be particularly effective in treating clinical symptoms.

Example 14: Confirmation of Expression Patterns of VSF Receptors in Virus-Infected Cells First, in order to confirm whether VSF receptors can be expressed in virus-infected cells, a human liver tissue of a hepatitis B patient (a part of the liver tissue without cancer, although the liver progressed into cancer due to hepatitis B) and a human liver tissue of a hepatitis C patient (a part of the liver tissue without cancer, although the liver progressed into cancer due to hepatitis C) were stained with mVSF antibodies. A human liver tissue not infected with virus (without cancer) was used as control. As a result, VSF receptors were shown to be expressed in the liver tissues obtained from patients infected with HBV or HCV, but VSF receptors were not expressed in the control tissue, thus suggesting that the VSF receptors are expressed in a virus-infection specific manner. These results were shown in the same pattern when the experiment was repeatedly performed using the human liver tissues obtained from other patients (FIGS. 27 and 28).

Subsequently, in order to confirm the expression period of VSF receptors according to viral infection, H1N1 influenza virus was infected into the MDCK cell line, and the viral replication and the expression of VSF receptors were observed by fluorescent staining. As a result, it was confirmed that the virus replication occurred according to time after influenza virus infection, and the expression of VSF receptors increased following the infection (FIG. 29). Based on these results, it was confirmed that VSF receptors are induced by viral infection.

Additionally, human WI-38 fibroblasts were infected with EMC-D virus and then the expression of VSF receptors and antiviral effect of VSF were examined (FIG. 30). The images on the left of FIG. 30 show the expression of VSF receptors by the EMC-D infection, and the images on the right show the anti-EMC-D effect and the expression of VSF receptors by the hzVSF_wt treatment. Based on the above results, it was confirmed that VSF can exhibit an antiviral effect and also express its receptors in an infection-specific manner with respect to the EMC-D virus infection.

Conclusively, it was confirmed that virus-infected cells can express VSF receptors, although the expression time may vary depending on cells, and also that VSF treatment can induce an antiviral effect, although it does not affect the expression of the receptors.

Example 15: Confirmation of Antiviral Effect of hzVSF Against Hepatitis B Virus

In order to examine the effect of hzVSF against human hepatitis B virus (HBV), experiments were performed using hzVSF_var13, a representative variant of hzVSF, as described below.

Example 15-1: Analysis of Covalently Closed Circular DNA cccDNA

A HBV-infected HepG2.2.15 cell line was treated with hzVSF_var13 and an HBV drug (lamivudine; Lami) according to each dosage, the number of cells was counted every week, and the same amount of cells were harvested.

In order to obtain the cccDNA of HBV from the above cells, the HepG2.2.15 cells, upon recovery, were resuspended in a lysis buffer (25 mM EDTA, 10 mM Tris-HCl; pH 7.5, 100 mM NaCl, 1% SDS, 0.1 mg/mL proteinase K) and reacted at 55° C. for 1 hour. After purifying the total HBV DNA using the MEGA quick-spin total fragment DNA purification kit (Intron), the resultant was reacted at 37° C. with plasmid-safe ATP-dependent DNase for 1 hour, and the enzyme was inactivated at 70° C. for 30 minutes. Then, HBV relaxed circular DNA (rcDNA) was removed and only the HBV cccDNA was recovered. Subsequently, the HBV cccDNA was subjected to quantitative analysis by qPCR using the Accupower 2× greenstar qPCR Master mix (Bioneer, Korea).

The PCR primers used were a forward primer 5'-TGAATCCYGCGGACGACC-3' (SEQ ID NO: 153) and a reverse primer 5'-CAGCTTGGAGGCTTGAACAG-3' (SEQ ID NO: 154) (nucleotides 1862-1881) (Y=C/T).

As a result, it was confirmed that the cccDNA content of HBV-infected cells was decreased in a concentration-dependent manner when treated with hzVSF_var13, and in particular, there was almost no cccDNA content when treated with 10 μg/mL of hzVSF_var13 (FIG. 31).

Accordingly, it was confirmed that hzVSF administration can significantly reduce the amount of intracellular cccDNA, and thus has an excellent effect as an agent for treating HBV.

Example 15-2: Confirmation of Inhibition of HBV DNA

The HBV-infected HepG2.2.15 cell line was treated with hzVSF_var13 and an HBV drug (lamivudine; Lami) according to each dosage, the number of cells was counted every week, and the same amount of cells were harvested.

Intracellular HBV DNA was purified as follows. The HepG2.2.15 cells obtained above were resuspended in a lysis buffer (25 mM EDTA, 10 mM Tris-HCl; pH 7.5, 100 mM NaCl, 1% SDS, 0.1 mg/mL proteinase K) and reacted at 55° C. for 1 hour. Intracellular HBV DNA was purified using the MEGA quick-spin total fragment DNA purification kit (Intron).

In order to obtain extracellular HBV DNA, a certain amount of the cell culture supernatant was obtained, treated with a lysis buffer, and extracted. Then, the HBV total DNA was subjected to quantitative analysis by qPCR using the Accupower 2× greenstar qPCR Master mix (Bioneer, Korea).

The PCR primers used were a forward primer 5'-CCTCTTCATCCTGCTGCT-3' (SEQ ID NO: 155) and a reverse primer 5'-AACTGAAAGCCAAACAGTG-3' (SEQ ID NO: 156).

As a result, in the case of the extracellular HBV DNA, the amount of HBV DNA was significantly reduced when treated with hzVSF_var13 at a very low concentration (0.1 μg/mL) compared to the control, which was treated with Lamivudine (FIG. 32). In the case of the intracellular HBV DNA, HBV DNA was inhibited in a dose-dependent manner of hzVSF_var13, and the hzVSF_var13 treatment showed a significantly excellent efficacy compared to the control, which was treated with Lamivudine (FIG. 33).

Conclusively, it was confirmed that hzVSF administration can significantly reduce the amount of both intracellular and extracellular HBV DNA, and thus hzVSF has excellent activity as a therapeutic agent for HBV treatment.

Example 16: Confirmation of Antiviral Effect of hzVSF Against Hepatitis C Virus

Example 16-1: Confirmation of Antiviral Effect of hzVSF_wt Against Hepatitis C Virus In order to examine the effect of hzVSF_wt against human hepatitis C virus (HCV), experiments were performed as described below.

Hepatitis C virus JFH-1 strain was infected into human liver cells, Huh7.5 cells, at a concentration of 0.1 multiplicity of infection (MOI), and was treated with interferon-β (3 ng/mL) and hzVSF_wt (500, 1000, and 2000 units) on the $3^{rd}$ day of post infection, and the cell culture supernatants and cells were collected on the $4^{th}$ day. The cells were measured using anti-HCV NSSA antibody staining of HCV NSSA by FACS analysis, and the cell culture supernatants were measured with respect to their HCV RNA titers by real-time quantitative PCR.

As a result, the hzVSF_wt (1000 U/mL) treatment showed an anti-HCV effect similar to that of interferon-β in FACS analysis (FIG. 34). Additionally, when the virus titer was measured by real-time quantitative PCR, hzVSF_wt showed an about 50% anti-HCV effect at 1000 U/mL, but the effect was shown to be weaker compared to that of interferon-β (FIG. 35).

However, while interferon actually has adverse effects in vivo, hzVSF does not have any adverse effects and is also expected to treat symptoms due to inflammation, and thus hzVSF will show marked excellence in real applications. Therefore, at the early stages of viral infection, the combination of a chemical agent and interferon is necessary for inhibiting viral growth; and from the mid-stage of viral infection or the appearance of symptoms, the combination of a chemical agent and hzVSF is necessary for inhibiting not only immunopathological phenomena but also the virus growth. That is, the above results suggest the possibility of a combination therapy of a chemical drug having an excellent inhibitory effect against virus growth (or interferon) and hzVSF_wt and various variants thereof of the present invention having an excellent inhibitory effect against immunopathological phenomena. However, these results also suggest the application of hzVSF_wt and various variants thereof of the present invention alone as an antiviral agent without adverse effects.

Example 16-2: Confirmation of Antiviral Effect of hzVSF Variants Against Hepatitis C Virus (HCV 1a Then, to examine the effect of hzVSF variants against human hepatitis C virus (HCV), experiments were performed using hzVSF_var13, a representative variant of hzVSF, as described below.

First, in order to confirm the inhibitory effect of the hzVSF variant against the HCV 1a replication, the Huh7.5 cells infected with HCV TN cell-culture (TNcc) (genotype 1a) were treated with hzVSF_var13 according to each dosage, and the cells were collected on day 3, day 6, day 9, and day 12. Then, after collecting the HCV-infected cells, the total RNA was extracted using trizol. Subsequently, cDNA was synthesized by reverse transcription, and HCV RNA and GAPDH (a housekeeping gene) for normalization were subjected to quantitative analysis by qPCR using the Accupower 2× greenstar qPCR Master mix (Bioneer, Korea).

The HCV-targeting PCR primers used were a forward primer 5'-GGGCTATAAGGTGCTAGTGC-3' (SEQ ID NO: 157) and a reverse primer 5'-GGCTGCCAGTGGTAATTGTT-3' (SEQ ID NO: 158), and the GAPDH PCR primers used were a forward primer 5'-TCCCTGAGCTGAACGGGAAG-3' (SEQ ID NO: 159) and a reverse primer 5'-GGAGGAGTGGGTGTCGCTGT-3' (SEQ ID NO: 160).

As a result, it was confirmed that the content of HCV 1a RNA decreased with time when hzVSF_var13 was treated at a concentration of 0.1 U/mL or higher and also that the inhibitory effect against the HCV 1a replication was in a dose-dependent manner of hzVSF_var13 (FIG. 36A).

Furthermore, when hzVSF_var13 was treated, the content of HCV core protein was confirmed by western blot analysis, and as a result, it was confirmed that the protein content was decreased in a dose-dependent manner (FIG. 36B).

Then, the effect of hzVSF_var13 compared to that of HCV drugs was examined. The Huh7.5 cells infected with HCV TNcc (genotype 1a) were treated with hzVSF_var13 and HCV drugs (sofosbuvir and simeprevir) according to the dosage, and the HCV-infected cells were recovered on a weekly basis and the total RNA was extracted using trizol. Then, cDNA was synthesized by reverse transcription, and HCV total RNA (the primers of SEQ ID NOS: 157 and 158 were used) and GAPDH (a housekeeping gene) for normalization were subjected to quantitative analysis by qPCR using the Accupower 2× greenstar qPCR Master mix (Bioneer, Korea).

As a result, it was confirmed that when hzVSF_var13 was treated at a concentration of 1 μg/mL, the rate of inhibition against the HCV 1a replication was significantly higher compared to the control drugs (FIG. 37).

Accordingly, the administration of the hzVSF variant to the HCV TNcc (genotype 1a)-infected cells reduced HCV gene (RNA) and HCV core protein, and thus it was confirmed that hzVSF variants have an antiviral effect against HCV.

Example 16-3: Confirmation of Antiviral Effect of hzVSF Variants Against Hepatitis C Virus (HCV 1b Then, in order to confirm the inhibitory effect of hzVSF variants against the HCV 1b replication, the Huh7 cells, which express the subgenomic replicon of HCV genotype 1b, were treated with hzVSF_var13 and HCV drugs (sofosbuvir and simeprevir) according to the dosage, the HCV-infected cells were recovered on a weekly basis, and the total RNA was extracted using trizol. Then, cDNA was synthesized by reverse transcription, and HCV total RNA and GAPDH (a housekeeping gene) for normalization were subjected to quantitative analysis by qPCR using the Accupower 2× greenstar qPCR Master mix (Bioneer, Korea).

The HCV-targeting PCR primers used were a forward primer 5'-ATGCAGCCCAAGGGTATAAG-3' (SEQ ID NO: 161) and a reverse primer 5'-GGTTCTGATGTTAGGGTCGATAC-3' (SEQ ID NO: 162), and the GAPDH PCR primers used were the primers of SEQ ID NOS: 159 and 160.

As a result, it was confirmed that the hzVSF_var13 treatment inhibited the HCV 1b replication in a dose-dependent manner, and in particular, when hzVSF_var13 was treated at a concentration of 1 μg/mL, the inhibition was effective at a level similar to that of the control drugs (sofosbuvir and simeprevir) (FIG. 38B). Additionally, when the level of HCV NS5A was confirmed by western blot according to the concentration of hzVSF_var13 treatment, the amount of HCV NS5A was confirmed to decrease in a dose-dependent manner (FIG. 38A).

Accordingly, the administration of the hzVSF_var13 to the HCV replicon (genotype 1b)-expressing cells reduced the amount of HCV gene (RNA) and HCV NS5A protein, and thus it was confirmed that hzVSF_var13 has an antiviral activity against HCV.

Example 16-4: Confirmation of Antiviral Effect of hzVSF Variants Against Hepatitis C Virus (HCV 2a Then, in order to confirm the inhibitory effect of hzVSF variants against the HCV 2a replication, the JFH-1 cells infected with HCV genotype 2a were treated with hzVSF_var13 and HCV drugs (sofosbuvir and simeprevir) according to the dosage, the HCV-infected cells were recovered on a weekly basis, and the total RNA was extracted using trizol. Then, cDNA was synthesized by reverse transcription, and subsequently HCV total RNA and GAPDH (a housekeeping gene) for normalization were subjected to quantitative analysis by qPCR using the Accupower 2× greenstar qPCR Master mix (Bioneer, Korea). The HCV-targeting PCR primers used were the primers of SEQ ID NOS: 157 and 158, and the GAPDH PCR primers used were the primers of SEQ ID NOS: 159 and 160.

As a result, it was confirmed that when hzVSF_var13 was treated, the inhibition against the HCV 2a replication was similar to that of the control drugs without a significant difference in the concentration of treatment at the 7-week time-point (FIG. 39B). Furthermore, when the above result was examined on a long-term basis, i.e., up to the $21^{st}$ week, it was confirmed that when hzVSF_var13 was treated at a concentration of 1 μg/mL, the inhibitory effect against HCV 2a replication was maintained at a level similar to when treated with sofosbuvir and simeprevir (FIG. 40).

Summarizing the above results, it was confirmed that the administration of the hzVSF_var13 to the HCV JFH-1 (genotype 2a)-infected cells reduced the amount of HCV gene (RNA) and HCV core protein (FIG. 39A), and thus hzVSF_var13 has an antiviral activity against HCV.

Example 17: Confirmation of Therapeutic Effect of hzVSF on Influenza Virus Infection In order to confirm the antiviral and anti-inflammatory effects of hzVSF_var13, a representative variant of hzVSF, against influenza virus, experiments were performed in mice as follows.

Four-week-old female Balb/c mice were infected with H1N1 Influenza A/Puerto Rico/8/34 virus ($1\times10^5$ pfu) into nasal cavities, and 25, 100, and 400 units of hzVSF_var13 were administered into caudal veins on day 2, 4, or 6 after the infection. On the $7^{th}$ day and the $9^{th}$ day after the viral infection, the mice were sacrificed. Thereafter, weight of lung and body, mucosal epithelial cells, and cilia were examined by H&E staining, and the infiltration of the immune cells was examined by an immunohistochemical staining.

As a result, the group administered with 500 U of hzVSF_var13 showed an at least 100-fold decrease in influenza titer compared to the control group (FIG. 41).

Additionally, the group infected with H1N1 influenza virus showed the infiltration of immune cells in the alveolar sacs while the groups administered with 100 U and 400 U of hzVSF_var13 showed recovery of the symptoms by the influenza virus similar to the lung tissue of an uninfected group (healthy lung) regardless of administration period. Even the administration of 25 U of hzVSF_var13 was shown to suppress the infiltration of immune cells, although there was a difference according to the administration period, and thus the administration of 25 U of hzVSF_var13 was shown to have a therapeutic effect (FIG. 42).

Additionally, when the cilia in the respiratory epithelial cells of mouse lungs were observed, the uninfected group and the group treated with hzVSF_var13 (400 U) were shown to have epithelial cells with cilia on the trachea in the lungs while the epithelial layer was shown to be destroyed in the virus-infected lungs due to viral infection (FIG. 43).

Additionally, when the ratio between the weight of lungs and body weight of mice was measured, the virus-infected group showed an increase in the ratio of lung weight relative to the body weight due to the pneumonic symptom of the lungs filling with fluid, whereas the group treated with hzVSF_var13 showed a decrease in the ratio of the lung weight relative to the body weight of healthy mice, in proportion to the concentration of hzVSF_var13 to some extent (FIG. 44).

Lastly, the inhibitory effect of hzVSF_var13 against the infiltration of immune cells was confirmed by an immunohistochemical method using markers of CD4 T cells (FIGS. 45 and 46) and macrophage (FIGS. 47 and 48) (in particular, the infection of $10^7$ pfu in FIGS. 46 and 48). When the mouse lungs were stained on the $7^{th}$ day after the H1N1 influenza virus infection ($10^7$ pfu), the infiltration of CD4 T cells and macrophages was observed, whereas the group treated with hzVSF_var13 showed a significant decrease in the infiltration of CD4 T cells and macrophages (FIGS. 45 to 48).

These results confirmed that the hzVSF and various variants thereof of the present invention not only have an excellent antiviral effect against influenza virus but also have an anti-inflammatory effect capable of suppressing the infiltration of immune cells, thereby suggesting that they can be used as antiviral and anti-inflammatory agents without adverse effects.

Example 18: Confirmation of Antiviral Effect of hzVSF Against Various Viruses In order to confirm whether hzVSF_wt and variants thereof of the present invention have an antiviral effect against various viruses, the effects of hzVSF_wt and hzVSF_ var13, which are representative variants of hzVSF_wt, were examined in vitro and in vivo. The in vitro experiments are related to an antiviral effect, and the in vivo experiments are related to antiviral and anti-inflammatory effects.

The results are shown in Table 15.

TABLE 15

| Virus | Antiviral Effect In vitro | Antiviral Effect In vivo |
|---|---|---|
| Encephalomyocarditis virus (EMCV) | +++ | +++ |
| Mengovirus | +++ | NT |
| Reovirus | + | NT |
| Influenza virus | + | +++ |
| HIV | ++ | NT |
| HCMV | + | NT |
| Mouse Hepatitis Virus (MHV) | ++ | +++ |
| Hantaan Virus | ++ | NT |

TABLE 15-continued

| Virus | Antiviral Effect In vitro | Antiviral Effect In vivo |
|---|---|---|
| HBV | ++ | NT |
| HCV | ++ | NT |

*NT: not tested

As a result, hzVSF was shown to have excellent antiviral and anti-inflammatory effects against encephalomyocarditis virus (EMCV) both in vitro and in vivo. The hzVSF showed an excellent antiviral effect against mengovirus in vitro. The hzVSF also showed an antiviral effect against reovirus in vitro. The hzVSF also showed an antiviral effect against HIV in vitro. The hzVSF also showed antiviral and anti-inflammatory effects against HCMV. hzVSF also showed effects against Hantaan virus in vitro and showed an antiviral effect against hepatitis B and C virus in vitro. The hzVSF also showed antiviral and anti-inflammatory effects against mouse hepatitis virus (MHV), which causes hepatitis in mice by a mechanism similar to that of human hepatitis, specifically in vivo. The hzVSF also showed antiviral and anti-inflammatory effects against influenza virus both in vitro and in vivo, and the effects were more remarkable in in vivo.

Example 19: Confirmation of Inhibitory Effect of mVSF Administration Against Secretion of Inflammatory Cytokines in a Mouse Model In order to confirm the effect of mVSF on the generation of inflammatory cytokines, mice were infected with EMC-D virus and administered with mVSF, and after 3 days, the amount of inflammatory cytokines in sera was measured by ELISA. As illustrated in Table 16, the levels of inflammatory cytokines such as IL-6, TNF-α, IFN-γ, and MCP-1 increased after the viral infection; however, the mVSF administration inhibited the expression of these inflammatory cytokines.

TABLE 16

| Sample | Cytokine (pg/mL): Measured 3 Days After Viral Infection IL-12 | IL-6 | TNF-α | IFN-γ | CCL2 (MCP-1) |
|---|---|---|---|---|---|
| Normal | ND | 2.9 | 4.6 | 1.3 | 13.8 |
| EMC-B | 1.1 | 190.3 | 44.3 | 91.4 | 1752.7 |
| EMC-D | 1.6 | 21.3 | 15.8 | 29.2 | 609.3 |
| EMC-D + VSF (1000 Unit) | 1.2 | 6.5 | 8.8 | 6.2 | 124.9 |

* ND: not detected

From the above results, it was confirmed that mVSF has an anti-inflammatory effect that inhibits inflammation induced by viral infection.

Additionally, in order to confirm the effect of mVSF on the generation of inflammatory cytokines in a mouse with acute hepatitis, the mouse was infected with mouse hepatitis virus and treated with VSF, and after 1 or 3 day of post infection, the amount of inflammatory cytokines in sera was measured by ELISA. As illustrated in Table 17, the levels of inflammatory cytokines such as IL-6, TNF-α, IFN-γ, and MCP-1 increased after the viral infection; however, the VSF administration inhibited the expression of these inflammatory cytokines. Additionally, a single combined administration of IFN-α was shown to have a more significant synergistic effect.

TABLE 17

| | Sample | Cytokines (pg/mL) IL-12 | TNF-α | INF-γ | CCL2 (MCP-1) | IL-10 | IL-6 |
|---|---|---|---|---|---|---|---|
| 1 Day Post-Infection | Normal | ND | 5.4 | 1.2 | ND | ND | 1.2 |
| | Virus Infection | 14.2 | 40.0 | 166.2 | 1165.5 | ND | 205.6 |
| | Virus + VSF | ND | 8.4 | 1.9 | 16.9 | ND | 5.0 |
| | Virus + IFN-α once + VSF | ND | 9.1 | 1.6 | 13.0 | ND | 1.5 |
| 2 Day Post-Infection | Normal | ND | 2.1 | ND | ND | ND | ND |
| | Virus Infection | 8.7 | 38.0 | 724.3 | 344.5 | ND | 13.7 |
| | Virus + VSF | ND | 32.4 | 74.5 | 129.9 | ND | 9.2 |
| | Virus + IFN-α once + VSF | ND | 4.0 | 20.3 | 13.9 | ND | 1.4 |

From the above results, it was confirmed that VSF also has an anti-inflammatory effect capable of inhibiting the inflammation induced by viral infection.

Example 20: Confirmation of Inhibitory Effect of hzVSF Administration Against Secretion of Inflammatory Cytokines in a Mouse Model In order to confirm whether the hzVSF of the present invention can inhibit the secretion of inflammatory cytokines for the treatment of inflammatory diseases, experiments were performed as follows.

The lung of a mouse infected with H1N1 (Influenza A/PR8) influenza virus ($1\times10^5$ pfu) and the lung of a mouse administered with hzVSF_var13 (500 units) one day after the influenza virus infection was harvested. Greenberger lysis buffer (GLB) was homogenized with the lungs and the resultant was placed on ice for 30 minutes, and centrifuged at 3,470×g at 4° C. for 7 minutes. After collecting the supernatant, it was centrifuged at 420×g at 4° C. for 10 minutes, mixed with the supernatant from lung specimens, capture beads, and PE detection reagent in an amount of 50 μL each at a 1:1:1 ratio, and reacted at room temperature for 2 hours while blocking light. Upon reaction, the beads were resuspended in a wash buffer and the samples were measured using the FACS canto II, and the data was collected.

As a result, it was confirmed that the amount of IL-6, TNF-α, IFN-γ, and CCL2 (MCP-1), which belong to pro-inflammatory cytokines, present in the lungs of the mice was significantly increased on the 7$^{th}$ day after the influenza virus infection. However, it was confirmed that the treatment of the hzVSF_var13 of the present invention significantly inhibited the generation of cytokines in the lungs of the mice (FIG. 49).

That is, it was suggested that the hzVSF_var13 of the present invention can inhibit various kinds of inflammatory cytokines, and thus can be used as an agent for treating various inflammatory diseases caused by viral infection.

Example 21: Confirmation of the Effect of hzVSF After EMC-D Infection in a Vimentin-Overexpressing Cell Line (a Stable Cell Line MCF-7 cells, which do not express vimentin, were transfected with vimentin (wt) or vimentin (mt), in which the hzVSF-binding domain was mutated, to prepare a vimentin (wt)- or vimentin (mt)-overexpressing cell line. Then, an MVIT assay was performed using the selected cells with a similar level of vimentin expression.

Specifically, $2\times10^4$ cells were seeded per well, and the cells were infected with EMC-D virus (2 MOI), and 2 hours thereafter, treated with hzVSF_var13 at concentrations from 256 U and at 4-fold serial dilutions thereafter, and cultured for 2 days. Then, the cultured cells were fixed with methanol, stained with 0.5% crystal violet, and air-dried for observation.

As a result, it was confirmed that the effect of hzVSF against EMC-D virus infection was not observed in MCF-7 parent cells, Mock, and vimentin (mt), whereas the MCF-7 cells, which can express vimentin (wt), were induced to have a structural change of vimentin into VSF receptors (VR) by the viral infection, thus confirming the antiviral effect of hzVSF (FIGS. 50 and 51).

Then, a WST assay was performed additionally to confirm cytotoxicity by EMC-D infection.

The vimentin (wt) cells and vimentin (mt) cells were cultured for three days in the same condition as that of the MVIT assay, treated with tetrazolium salt (WST-1), cultured for an additional 4 hours, and the absorbance was measured at 450 nm. After measurement, the supernatant was removed and the cells were fixed with methanol, stained with 0.5% crystal violet for 20 minutes, and then air-dried. The stained cells were dissolved in methanol and the absorbance was measured at 540 nm.

As a result, it was confirmed that the effect of hzVSF against EMC-D virus infection was not observed in MCF-7 parent cells, Mock, and vimentin (mt), whereas the MCF-7 cells, which can express vimentin (wt), were induced to have a structural change of vimentin into VSF receptors (VR) by the viral infection, thus confirming the antiviral effect of hzVSF (FIG. 52).

Then, the expression feature of VSF receptors (VR) following EMC-D infection was examined in a vimentin-overexpressing cell line (a stable cell line). In this regard, each of the stable MCF-7 cells, i.e., vimentin (wt) and vimentin (mt) cells, was infected with EMC-D (5 MOI) for 9 hours, and then the cells were immunostained with hzVSF_ var13. The cells were then fixed and permeabilized, and the hzVSF_var13, which was diluted in a 1:250 ratio, was reacted with the cells. Then, the cells were reacted with FITC conjugated-goat human IgG as a secondary antibody, and the expression of the VSF receptors (VR) for hzVSF in the cells was examined under a fluorescence microscope (500×magnification).

As a result, as illustrated in FIG. 55, it was confirmed that hzVSF_var13 did not bind to the vimentin-expressing cells, in which the Mock- and hzVSF-binding domains were mutated, but the VR was expressed in the wild-type vimentin-expressing cells by viral infection (FIG. 53).

Example 22: Confirmation of the Binding VSF with VR WT and VR MT Purified in *E. coli*

The vimentin recombinant proteins (5 mg) purified by the Ni-NTA system and hzVSF_var13 were mixed in a 2:1 molar ratio and filled with phosphate buffered saline (PBS) to a final volume of 700 mL, and incubated in an orbital shaker at 4° C. for 3 hours. Then, protein A beads (50% slurry) were added thereto, incubated at 4° C. for 1 hour, and the protein A-hzVSF-VR complex was centrifuged at 3,000×g at 4° C. for 3 minutes. Then, the supernatant was removed and the beads were washed with PBS, and centrifuged again at 3,000×g at 4° C. for 3 minutes, and the process was repeated 3 times. Subsequently, 2× SDS-sample buffer was added thereto, and boiled for 5 minutes to perform SDS-PAGE and western blot analyses.

As a result, it was confirmed that the proteins, in which the 6 amino acid residues of vimentin, Y150, R186, Q195, R217, K235, and R270, were subjected to substitution mutation into F, K, N, K, R, and K, respectively, showed a distinct decrease in the binding with hzVSF (FIG. 54). Accordingly, it was confirmed that hzVSF can bind to Y150, R186, Q195, R217, K235, and R270 of vimentin.

Example 23: Confirmation of the Binding Between VR, which was Overexpressed in HEK293T Cells, and VSF HEK293T cells were transfected with vimentin WT or vimentin MT to examine their binding with hzVSF_v13.

Specifically, the HEK293T cells ($2\times10^6$) were seeded into 100 mm culture dishes, transfected with vimentin WT (wild-type) and MT (mutant-type) DNA (vector: pcDNA3.1mycHisC), and incubated for 48 hours. Then, the cells were harvested, treated with a 1% CHAPS lysis buffer (1 mL), and placed on ice for 20 minutes for the lysis of the cells. The lysed cells were centrifuged at 13,000 rpm at 4° C. for 15 minutes, and then the supernatant was transferred into a fresh tube.

The protein from the supernatant (700 mg) was treated with protein A beads with a 50% slurry and allowed to preclear at 4° C. for 1 hour. Then, the resultant was centrifuged at 3,000×g at 4° C. for 3 minutes and the supernatant was transferred to a fresh tube. The resultant was treated with hzVSF_var13 at a 1:100 ratio and incubated at 4° C. overnight to allow the binding between VSF and VR. Then, the protein A beads with a 50% slurry were added thereto and reacted at 4° C. for 1 hour. A protein A-VSF-VR complex was obtained as a result, and to wash the beads, it was centrifuged at 3,000×g at 4° C. for 3 minutes and the supernatant was removed. Subsequently, the precipitated complex was washed 3 times by adding a 1% CHAPS lysis buffer thereto. The resultant was treated with a 2× SDS-sample buffer, and boiled to perform SDS-PAGE and immunoblot analyses.

As a result, it was confirmed that the proteins, in which the 6 amino acids of vimentin, Y150, R186, Q195, R217, K235, and R270, were subjected to substitution mutation into F, K, N, K, R, and K, respectively, showed a distinct decrease in the binding with hzVSF (FIG. 55). Accordingly, it was confirmed that hzVSF can bind to Y150, R186, Q195, R217, K235, and R270 of vimentin.

The weak binding with VSF in the lane, in which the 6 amino acid residues were substituted by mutation, is presumed to be ascribed to the dimerization and tetramerization with wild-type vimentin, which is endogenous to the HEK293T cells, and the overexpressed, mutant vimentin.

Further to the above results, the vimentin-VSF binding model was examined using computer programs (FIGS. 56 to 58). The specific programs used for the analysis are shown below.

VR dimer modeling: Protein Homology/analogY Recognition Engine V 2.0

(Component software Template detection: HHpred 1.51
Secondary structure prediction: Psi-pred 2.5
Disorder prediction: Disopred 2.4
Transmembrane prediction: Memsat_SVM
Multi-template modeling and ab initio: Poing 1.0
Re-orientation of structures for easy viewing: OVOP)
Complex modeling of VR_dimer and VSF: Pymol
Complex modeling of VR_dimer and chemical: autodock vina The structure in which VR and hzVSF were bound together was deduced by the VR dimer modeling, and conclusively, it was confirmed that hzVSF binds to the residues of Y150, R186, Q195, R217, K235, and R270.

The above results suggest that the antibody of the present invention, which specifically binds to the peptide of SEQ ID NO: 1, or a fragment binding to the peptide which specifically binds to the peptide, can exhibit antiviral and anti-inflammatory effects against a broad range of viral diseases. Unlike the existing antiviral agents such as interferon or chemotherapeutic agents, they can be selectively applied to virus-infected cells without any adverse effects, require a small amount for treatment, and have anti-inflammatory activity by suppressing the infiltration of immune cells, thereby suggesting that they can be used as agents for treating various viral diseases.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A humanized antibody specifically binding to the peptide of SEQ ID NO: 1 or a fragment specifically binding to the peptide, wherein the humanized antibody or fragment comprises:

a heavy chain variable region comprising a heavy chain CDR1 of SEQ ID NO: 2; a heavy chain CDR2 of SEQ ID NO: 3 or SEQ ID NO: 14; and a heavy chain CDR3 of SEQ ID NO: 4 or SEQ ID NO: 15; and a light chain variable region comprising a light chain CDR1 of SEQ ID NO: 5; a light chain CDR2 of SEQ ID NO: 6, SEQ ID NO: 16, SEQ ID NO: 17, or SEQ ID NO: 18; and a light chain CDR3 of SEQ ID NO: 7 or SEQ ID NO: 19.

2. The humanized antibody or fragment of claim 1, wherein the humanized antibody or fragment further comprises:

a heavy chain variable region comprising a heavy chain Framework region 1 (FR1) of SEQ ID NO: 20; a heavy chain FR2 of SEQ ID NO: 21; a heavy chain FR3 of SEQ ID NO: 22 or SEQ ID NO: 28; and a heavy chain FR4 of SEQ ID NO: 23; and a light chain variable region comprising a light chain FR1 of SEQ ID NO: 24; a light chain FR2 of SEQ ID NO: 25; a light chain FR3 of SEQ ID NO: 26; and a light chain FR4 of SEQ ID NO: 27.

3. The humanized antibody or fragment of claim 1, wherein the humanized antibody or fragment comprises:

(a) a heavy chain CDR1 of SEQ ID NO: 2, a heavy chain CDR2 of SEQ ID NO: 3, and a heavy chain CDR3 of SEQ ID NO: 4; and a light chain CDR1 of SEQ ID NO: 5, a light chain CDR2 of SEQ ID NO: 6, and a light chain CDR3 of SEQ ID NO: 7;

(b) a heavy chain CDR1 of SEQ ID NO: 2, a heavy chain CDR2 of SEQ ID NO: 3, and a heavy chain CDR3 of SEQ ID NO: 4; and a light chain CDR1 of SEQ ID NO: 5, a light chain CDR2 of SEQ ID NO: 16, and a light chain CDR3 of SEQ ID NO: 7;

(c) a heavy chain CDR1 of SEQ ID NO: 2, a heavy chain CDR2 of SEQ ID NO: 3, and a heavy chain CDR3 of SEQ ID NO: 4; and a light chain CDR1 of SEQ ID NO: 5, a light chain CDR2 of SEQ ID NO: 17, and a light chain CDR3 of SEQ ID NO: 7;

(d) a heavy chain CDR1 of SEQ ID NO: 2, a heavy chain CDR2 of SEQ ID NO: 3, and a heavy chain CDR3 of SEQ ID NO: 4; and a light chain CDR1 of SEQ ID NO: 5, a light chain CDR2 of SEQ ID NO: 18, and a light chain CDR3 of SEQ ID NO: 7;

(e) a heavy chain CDR1 of SEQ ID NO: 2, a heavy chain CDR2 of SEQ ID NO: 3, and a heavy chain CDR3 of SEQ ID NO: 4; and a light chain CDR1 of SEQ ID NO: 5, a light chain CDR2 of SEQ ID NO: 18, and a light chain CDR3 of SEQ ID NO: 19;

(f) a heavy chain CDR1 of SEQ ID NO: 2, a heavy chain CDR2 of SEQ ID NO: 14, and a heavy chain CDR3 of SEQ ID NO: 4; and a light chain CDR1 of SEQ ID NO: 5, a light chain CDR2 of SEQ ID NO: 6, and a light chain CDR3 of SEQ ID NO: 7;

(g) a heavy chain CDR1 of SEQ ID NO: 2, a heavy chain CDR2 of SEQ ID NO: 3, and a heavy chain CDR3 of SEQ ID NO: 4; a heavy chain FR1 of SEQ ID NO: 20, a heavy chain FR2 of SEQ ID NO: 21, a heavy chain FR3 of SEQ ID NO: 28, and a heavy chain FR4 of SEQ ID NO: 23; a light chain CDR1 of SEQ ID NO: 5, a light chain CDR2 of SEQ ID NO: 6, and a light chain CDR3 of SEQ ID NO: 7; and a light chain FR1 of SEQ ID NO 24, a light chain FR2 of SEQ ID NO: 25, a light chain FR3 of SEQ ID NO: 26, and a light chain FR4 of SEQ ID NO: 27;

(h) a heavy chain CDR1 of SEQ ID NO: 2, a heavy chain CDR2 of SEQ ID NO: 14, and a heavy chain CDR3 of SEQ ID NO: 4; a heavy chain FR1 of SEQ ID NO: 20, a heavy chain FR2 of SEQ ID NO: 21, a heavy chain FR3 of SEQ ID NO: 28, and a heavy chain FR4 of SEQ ID NO: 23; a light chain CDR1 of SEQ ID NO: 5, a light chain CDR2 of SEQ ID NO: 6, and a light chain CDR3 of SEQ ID NO: 7; and a light chain FR1 of SEQ ID NO: 24, a light chain FR2 of SEQ ID NO: 25, a light chain FR3 of SEQ ID NO: 26, and a light chain FR4 SEQ ID NO: 27;

(i) a heavy chain CDR1 of SEQ ID NO: 2, a heavy chain CDR2 of SEQ ID NO: 14, and a heavy chain CDR3 of SEQ ID NO: 15; a heavy chain FR1 of SEQ ID NO: 20, a heavy chain FR2 of SEQ ID NO: 21, a heavy chain FR3 of SEQ ID NO: 28, and a heavy chain FR4 of SEQ ID NO: 23; a light chain CDR1 of SEQ ID NO: 5, a light chain CDR2 of SEQ ID NO: 6, and a light chain CDR3 of SEQ ID NO: 7; and a light chain FR1 of SEQ ID NO: 24, a light chain FR2 of SEQ ID NO: 25, a light chain FR3 of SEQ ID NO: 26, and a light chain FR4 of SEQ ID NO: 27;

(j) a heavy chain CDR1 of SEQ ID NO: 2, a heavy chain CDR2 of SEQ ID NO: 14, and a heavy chain CDR3 of SEQ ID NO: 4; a heavy chain FR1 of SEQ ID NO: 20, a heavy chain FR2 of SEQ ID NO: 21, a heavy chain FR3 of SEQ ID NO: 28, and a heavy chain FR4 of SEQ ID NO: 23; a light chain CDR1 of SEQ ID NO: 5, a light chain CDR2 of SEQ ID NO: 18, and a light chain CDR3 of SEQ ID NO: 7; and a light chain FR1 of SEQ ID NO: 24, a light chain FR2 of SEQ ID NO: 25, a light chain FR3 of SEQ ID NO: 26, and a light chain FR4 of SEQ ID NO: 27;

(k) a heavy chain CDR1 of SEQ ID NO: 2, a heavy chain CDR2 of SEQ ID NO: 14, and a heavy chain CDR3 of SEQ ID NO: 15; a heavy chain FR1 of SEQ ID NO: 20, a heavy chain FR2 of SEQ ID NO: 21, a heavy chain FR3 of SEQ ID NO: 28, and a heavy chain FR4 of SEQ ID NO: 23; a light chain CDR1 of SEQ ID NO: 5, a light chain CDR2 of SEQ ID NO: 18, and a light chain CDR3 of SEQ ID NO: 7; and a light chain FR1 of SEQ ID NO: 24, a light chain FR2 of SEQ ID NO: 25, a light chain FR3 of SEQ ID NO: 26, and a light chain FR4 of SEQ ID NO: 27;

(l) a heavy chain CDR1 of SEQ ID NO: 2, a heavy chain CDR2 of SEQ ID NO: 14, and a heavy chain CDR3 of SEQ ID NO: 4; a heavy chain FR1 of SEQ ID NO: 20, a heavy chain FR2 of SEQ ID NO: 21, a heavy chain FR3 of SEQ ID NO: 28, and a heavy chain FR4 of SEQ ID NO: 23; a light chain CDR1 of SEQ ID NO: 5, a light chain CDR2 of SEQ ID NO: 18, and a light chain CDR3 of SEQ ID NO: 19; and a light chain FR1 of SEQ ID NO: 24, a light chain FR2 of SEQ ID NO: 25, a light chain FR3 of SEQ ID NO: 26, and a light chain FR4 of SEQ ID NO: 27;

(m) a heavy chain CDR1 of SEQ ID NO: 2, a heavy chain CDR2 of SEQ ID NO: 14, and a heavy chain CDR3 of SEQ ID NO: 15; a heavy chain FR1 of SEQ ID NO: 20, a heavy chain FR2 of SEQ ID NO: 21, a heavy chain FR3 of SEQ ID NO: 28, and a heavy chain FR4 of SEQ ID NO: 23; a light chain CDR1 of SEQ ID NO: 5, a light chain CDR2 of SEQ ID NO: 18, and a light chain CDR3 of SEQ ID NO: 19; and a light chain FR1 of SEQ ID NO: 24, a light chain FR2 of SEQ ID NO: 25, a light chain FR3 of SEQ ID NO: 26, and a light chain FR4 of SEQ ID NO: 27, or (n) a heavy chain CDR1 of SEQ ID NO: 2, a heavy chain CDR2 of SEQ ID NO: 14, and a heavy chain CDR3 of SEQ ID NO: 4; and a light chain CDR1 of SEQ ID NO: 5, a light chain CDR2 of SEQ ID NO: 16, and a light chain CDR3 of SEQ ID NO: 7.

4. The humanized antibody or fragment of claim 1, wherein the humanized antibody or fragment comprises a heavy chain variable region and a light chain variable region of SEQ ID NO: 10 and SEQ ID NO: 12; SEQ ID NO: 32 and SEQ ID NO: 34; SEQ ID NO: 36 and SEQ ID NO: 38; SEQ ID NO: 40 and SEQ ID NO: 42; SEQ ID NO: 44 and SEQ ID NO: 46; SEQ ID NO: 48 and SEQ ID NO: 50; SEQ ID NO: 52 and SEQ ID NO: 54; SEQ ID NO: 56 and SEQ ID NO: 58; SEQ ID NO: 60 and SEQ ID NO: 62; SEQ ID NO: 64 and SEQ ID NO: 66; SEQ ID NO: 68 and SEQ ID NO: 70; SEQ ID NO: 72 and SEQ ID NO: 74; SEQ ID NO: 76 and SEQ ID NO: 78; or SEQ ID NO: 80 and SEQ ID NO: 82, respectively.

5. A scFv that specifically binds to the peptide of SEQ ID NO: 1, wherein the scFv consists of a heavy chain variable region of SEQ ID NO: 131 and a light chain variable region of SEQ ID NO: 133, which are linked by a linker.

6. The scFv of claim 5, wherein the scFv consists of a heavy chain variable region encoded by the nucleotide sequence of SEQ ID NO: 130 and a light chain variable region encoded by the nucleotide sequence of SEQ ID NO: 132, which are linked by a linker.

7. The scFv of claim 5, wherein the scFv specifically binds to the $9^{th}$, the $45^{th}$, the $54^{th}$, the $76^{th}$, the $94^{th}$, or the $129^{th}$ amino acid residue of the peptide of SEQ ID NO: 1.

8. A polynucleotide encoding the humanized antibody specifically binding to the peptide of SEQ ID NO: 1 or a fragment specifically binding to the peptide according to claim 1.

9. A vector comprising the polynucleotide of claim 8.

10. An isolated host cell introduced with the vector of claim 9.

11. A method of producing the humanized antibody specifically binding to the peptide of SEQ ID NO: 1 or a fragment specifically binding to the peptide using the isolated host cell of claim 10.

12. The humanized antibody specifically binding to the peptide of SEQ ID NO: 1 or a fragment specifically binding to the peptide produced by the production method of claim 11.

13. An antiviral composition comprising the humanized antibody specifically binding to the peptide of SEQ ID NO: 1 or a fragment specifically binding to the peptide according to claim 1.

14. The humanized antibody or fragment of claim 1, wherein the humanized antibody or fragment specifically binds to the $9^{th}$, the $45^{th}$, the $54^{th}$, the $76^{th}$, the $94^{th}$, or the $129^{th}$ amino acid residue of the peptide of SEQ ID NO: 1.

15. A method for treating an infectious or inflammatory viral disease comprising administering an antiviral composition comprising the humanized antibody specifically binding to the peptide of SEQ ID NO: 1 or a fragment specifically binding to the peptide according to claim 1 to an individual in need thereof.

16. The method of claim 15, wherein the composition acts specifically on virus-infected cells.

17. The method of claim 15, wherein the composition suppresses immune cell infiltration.

18. The method of claim 15, wherein the composition inhibits inflammatory responses.

19. The method of claim 16, wherein the virus is selected from the group consisting of the family Orthomyxoviridae, the family Picornaviridae, the family Retroviridae, the family Herpesviridae, the family Hepadnaviridae, the family Flaviviridae, and the family Bunyaviridae.

20. The method of claim 16, wherein the virus is selected from the group consisting of influenza virus, hepatitis virus, encephalomyocarditis virus, mengovirus, reovirus, human immunodeficiency virus (HIV), human cytomegalovirus (HCMV), and Hantaan virus.

21. The method of claim 15, wherein the inflammatory viral disease is caused by a viral infection.

* * * * *

SEQUENCE LISTING

```
<160> NUMBER OF SEQ ID NOS: 162

<210> SEQ ID NO 1
<211> LENGTH: 153
<212> TYPE: PRT
<213> ORGANISM: Artificial Sequence
<220> FEATURE:
<223> OTHER INFORMATION: Isolated Vimentin fragment (142-294)

<400> SEQUENCE: 1

Gly Lys Ser Arg Leu Gly Asp Leu Tyr Glu Glu Glu Met Arg Glu Leu
1               5                   10                  15

Arg Arg Gln Val Asp Gln Leu Thr Asn Asp Lys Ala Arg Val Glu Val
```

-continued

```
            20                  25                  30

Glu Arg Asp Asn Leu Ala Glu Asp Ile Met Arg Leu Arg Glu Lys Leu
        35                  40                  45

Gln Glu Glu Met Leu Gln Arg Glu Glu Ala Glu Asn Thr Leu Gln Ser
    50                  55                  60

Phe Arg Gln Asp Val Asp Asn Ala Ser Leu Ala Arg Leu Asp Leu Glu
65                  70                  75                  80

Arg Lys Val Glu Ser Leu Gln Glu Glu Ile Ala Phe Leu Lys Lys Leu
                85                  90                  95

His Glu Glu Glu Ile Gln Glu Leu Gln Ala Gln Ile Gln Glu Gln His
            100                 105                 110

Val Gln Ile Asp Val Asp Val Ser Lys Pro Asp Leu Thr Ala Ala Leu
        115                 120                 125

Arg Asp Val Arg Gln Gln Tyr Glu Ser Val Ala Ala Lys Asn Leu Gln
    130                 135                 140

Glu Ala Glu Glu Trp Tyr Lys Ser Lys
145                 150


<210> SEQ ID NO 2
<211> LENGTH: 5
<212> TYPE: PRT
<213> ORGANISM: Artificial Sequence
<220> FEATURE:
<223> OTHER INFORMATION: CDR1 of heavy chain

<400> SEQUENCE: 2

Gly Tyr Asn Met Asn
1               5


<210> SEQ ID NO 3
<211> LENGTH: 17
<212> TYPE: PRT
<213> ORGANISM: Artificial Sequence
<220> FEATURE:
<223> OTHER INFORMATION: CDR2 of heavy chain

<400> SEQUENCE: 3

Asn Ile Asp Pro Tyr Tyr Gly Ser Thr Thr Tyr Ala Gln Lys Phe Gln
1               5                   10                  15

Gly


<210> SEQ ID NO 4
<211> LENGTH: 9
<212> TYPE: PRT
<213> ORGANISM: Artificial Sequence
<220> FEATURE:
<223> OTHER INFORMATION: CDR3 of heavy chain

<400> SEQUENCE: 4

Glu Thr Gly Thr Arg Ala Met Asp Tyr
1               5


<210> SEQ ID NO 5
<211> LENGTH: 11
<212> TYPE: PRT
<213> ORGANISM: Artificial Sequence
<220> FEATURE:
<223> OTHER INFORMATION: CDR1 of light chain

<400> SEQUENCE: 5

Arg Ala Ser Glu Asn Ile Tyr Ser Asn Leu Ala
1               5                   10
```

<210> SEQ ID NO 6
<211> LENGTH: 7
<212> TYPE: PRT
<213> ORGANISM: Artificial Sequence
<220> FEATURE:
<223> OTHER INFORMATION: CDR2 of light chain

<400> SEQUENCE: 6

```
Val Ala Thr Asn Leu Ala Asp
1               5
```

<210> SEQ ID NO 7
<211> LENGTH: 9
<212> TYPE: PRT
<213> ORGANISM: Artificial Sequence
<220> FEATURE:
<223> OTHER INFORMATION: CDR3 of light chain

<400> SEQUENCE: 7

```
Gln His Phe Tyr Gly Ser Pro Arg Thr
1               5
```

<210> SEQ ID NO 8
<211> LENGTH: 169
<212> TYPE: PRT
<213> ORGANISM: Artificial Sequence
<220> FEATURE:
<223> OTHER INFORMATION: mVSF_VL

<400> SEQUENCE: 8

```
Met Ser Val Pro Thr Gln Val Leu Gly Leu Leu Leu Leu Trp Leu Thr
1               5                   10                  15

Gly Asn Glu Asp Ser Thr Arg Asn Leu Leu Ser Phe Leu His Ser Val
            20                  25                  30

Leu Leu Gly Leu Asn Glu Asn Ser Leu Val Arg Glu Leu Ile Met Trp
        35                  40                  45

Val Ser Val Phe Asn Phe Pro Ile Val Gly Ala Arg Cys Asp Ile Gln
    50                  55                  60

Met Thr Gln Ser Pro Ala Ser Leu Ser Ala Ser Val Gly Glu Thr Val
65                  70                  75                  80

Thr Met Thr Cys Arg Ala Ser Glu Asn Ile Tyr Ser Asn Leu Ala Trp
                85                  90                  95

Tyr Gln Gln Lys Gln Gly Lys Ser Pro Gln Leu Leu Val Tyr Val Ala
            100                 105                 110

Thr Asn Leu Ala Asp Gly Val Pro Ser Arg Phe Ser Gly Ser Gly Ser
        115                 120                 125

Gly Thr Gln Phe Ser Leu Lys Ile Asn Ser Leu Gln Pro Glu Asp Phe
    130                 135                 140

Gly Ser Tyr Tyr Cys Gln His Phe Tyr Gly Ser Pro Arg Thr Phe Gly
145                 150                 155                 160

Gly Gly Thr Lys Leu Glu Ile Lys Arg
                165
```

<210> SEQ ID NO 9
<211> LENGTH: 118
<212> TYPE: PRT
<213> ORGANISM: Artificial Sequence
<220> FEATURE:
<223> OTHER INFORMATION: mVSF_VH

<400> SEQUENCE: 9

```
Glu Ile Gln Leu Gln Gln Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser His Gly Lys Ser Leu Glu Trp Ile
        35                  40                  45

Gly Asn Ile Asp Pro Tyr Tyr Gly Ser Thr Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Glu Thr Gly Thr Arg Ala Met Asp Tyr Trp Gly Gln Gly Thr
            100                 105                 110

Ser Val Thr Val Ser Ser
        115


<210> SEQ ID NO 10
<211> LENGTH: 118
<212> TYPE: PRT
<213> ORGANISM: Artificial Sequence
<220> FEATURE:
<223> OTHER INFORMATION: HzVSF_VH_WT

<400> SEQUENCE: 10

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Thr Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser
        115


<210> SEQ ID NO 11
<211> LENGTH: 445
<212> TYPE: PRT
<213> ORGANISM: Artificial Sequence
<220> FEATURE:
<223> OTHER INFORMATION: HzVSF_HC_WT - HzVSF hVH.hCgamma4_WT

<400> SEQUENCE: 11

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Thr Thr Tyr Ala Gln Lys Phe
```

-continued

```
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445
```

<210> SEQ ID NO 12
<211> LENGTH: 107
<212> TYPE: PRT
<213> ORGANISM: Artificial Sequence

```
<220> FEATURE:
<223> OTHER INFORMATION: HzVSF_VL_WT

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys
            100                 105


<210> SEQ ID NO 13
<211> LENGTH: 214
<212> TYPE: PRT
<213> ORGANISM: Artificial Sequence
<220> FEATURE:
<223> OTHER INFORMATION: HzVSF_LC_WT

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 14
<211> LENGTH: 17
<212> TYPE: PRT
<213> ORGANISM: Artificial Sequence
<220> FEATURE:
<223> OTHER INFORMATION: CDR2 of heavy chain

<400> SEQUENCE: 14

```
Asn Ile Asp Pro Tyr Tyr Gly Ser Asp Thr Tyr Ala Gln Lys Phe Gln
1               5                   10                  15

Gly
```

<210> SEQ ID NO 15
<211> LENGTH: 9
<212> TYPE: PRT
<213> ORGANISM: Artificial Sequence
<220> FEATURE:
<223> OTHER INFORMATION: CDR3 of heavy chain

<400> SEQUENCE: 15

```
Glu Thr Gly Asn Arg Ala Met Asp Tyr
1               5
```

<210> SEQ ID NO 16
<211> LENGTH: 7
<212> TYPE: PRT
<213> ORGANISM: Artificial Sequence
<220> FEATURE:
<223> OTHER INFORMATION: CDR2 of light chain

<400> SEQUENCE: 16

```
Val Ala Asp Asn Leu Ala Asp
1               5
```

<210> SEQ ID NO 17
<211> LENGTH: 7
<212> TYPE: PRT
<213> ORGANISM: Artificial Sequence
<220> FEATURE:
<223> OTHER INFORMATION: CDR2 of light chain

<400> SEQUENCE: 17

```
Val Ala Asp Asn Leu Gly Asp
1               5
```

<210> SEQ ID NO 18
<211> LENGTH: 7
<212> TYPE: PRT
<213> ORGANISM: Artificial Sequence
<220> FEATURE:
<223> OTHER INFORMATION: CDR2 of light chain

<400> SEQUENCE: 18

```
Val Ala Asp Asn Arg Gly Asp
1               5
```

<210> SEQ ID NO 19
<211> LENGTH: 9
<212> TYPE: PRT
<213> ORGANISM: Artificial Sequence
<220> FEATURE:
<223> OTHER INFORMATION: CDR3of light chain

<400> SEQUENCE: 19

```
Gln His Phe Tyr Gly Thr Pro Arg Thr
1               5
```

<210> SEQ ID NO 20
<211> LENGTH: 30
<212> TYPE: PRT
<213> ORGANISM: Artificial Sequence
<220> FEATURE:
<223> OTHER INFORMATION: FR1 of heavy chain

<400> SEQUENCE: 20

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 21
<211> LENGTH: 14
<212> TYPE: PRT
<213> ORGANISM: Artificial Sequence
<220> FEATURE:
<223> OTHER INFORMATION: FR2 of heavy chain

<400> SEQUENCE: 21

Trp Val Arg Gln Ala Pro Gly Lys Gly Leu Glu Trp Met Gly
1               5                   10

<210> SEQ ID NO 22
<211> LENGTH: 32
<212> TYPE: PRT
<213> ORGANISM: Artificial Sequence
<220> FEATURE:
<223> OTHER INFORMATION: FR3 of heavy chain

<400> SEQUENCE: 22

Arg Val Thr Met Thr Val Asp Lys Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 23
<211> LENGTH: 11
<212> TYPE: PRT
<213> ORGANISM: Artificial Sequence
<220> FEATURE:
<223> OTHER INFORMATION: FR4 of heavy chain

<400> SEQUENCE: 23

Trp Gly Gln Gly Thr Leu Val Thr Val Ser Ser
1               5                   10

<210> SEQ ID NO 24
<211> LENGTH: 23
<212> TYPE: PRT
<213> ORGANISM: Artificial Sequence
<220> FEATURE:
<223> OTHER INFORMATION: FR1 of light chain

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 25
<211> LENGTH: 15
<212> TYPE: PRT
<213> ORGANISM: Artificial Sequence
<220> FEATURE:
<223> OTHER INFORMATION: FR2 of light chain

<400> SEQUENCE: 25

Trp Tyr Gln Gln Lys Pro Gly Lys Ala Pro Lys Leu Leu Ile Tyr
1               5                   10                  15

<210> SEQ ID NO 26
<211> LENGTH: 32
<212> TYPE: PRT
<213> ORGANISM: Artificial Sequence
<220> FEATURE:
<223> OTHER INFORMATION: FR3 of light chain

<400> SEQUENCE: 26

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 27
<211> LENGTH: 10
<212> TYPE: PRT
<213> ORGANISM: Artificial Sequence
<220> FEATURE:
<223> OTHER INFORMATION: FR4 of light chain

<400> SEQUENCE: 27

Phe Gly Gly Gly Thr Lys Val Glu Ile Lys
1               5                   10

<210> SEQ ID NO 28
<211> LENGTH: 32
<212> TYPE: PRT
<213> ORGANISM: Artificial Sequence
<220> FEATURE:
<223> OTHER INFORMATION: FR3 of heavy chain

<400> SEQUENCE: 28

Arg Val Thr Met Thr Val Asp Thr Ser Ala Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 29
<211> LENGTH: 445
<212> TYPE: PRT
<213> ORGANISM: Artificial Sequence
<220> FEATURE:
<223> OTHER INFORMATION: HzVSF_a1_gamma4

<400> SEQUENCE: 29

Glu Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Thr Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys

```
                85                  90                  95

Ala Arg Glu Thr Gly Thr Arg Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445


<210> SEQ ID NO 30
<211> LENGTH: 445
<212> TYPE: PRT
<213> ORGANISM: Artificial Sequence
<220> FEATURE:
<223> OTHER INFORMATION: HzVSF_a2_gamma4

<400> SEQUENCE: 30

Glu Val Gln Leu Val Gln Ser Gly Ala Glu Val Lys Lys Pro Gly Ala
```

-continued

```
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Ile
        35                  40                  45

Gly Asn Ile Asp Pro Tyr Tyr Gly Ser Thr Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430
```

```
His Tyr Thr Gln Lys Ser Leu Ser Leu Ser Leu Gly Lys
        435                 440                 445


<210> SEQ ID NO 31
<211> LENGTH: 445
<212> TYPE: PRT
<213> ORGANISM: Artificial Sequence
<220> FEATURE:
<223> OTHER INFORMATION: HzVSF_a3_gamma4

<400> SEQUENCE: 31

Glu Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Ile
        35                  40                  45

Gly Asn Ile Asp Pro Tyr Tyr Gly Ser Thr Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350
```

```
Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445


<210> SEQ ID NO 32
<211> LENGTH: 118
<212> TYPE: PRT
<213> ORGANISM: Artificial Sequence
<220> FEATURE:
<223> OTHER INFORMATION: HzVSF_VH_V1

<400> SEQUENCE: 32

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Thr Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser
        115


<210> SEQ ID NO 33
<211> LENGTH: 445
<212> TYPE: PRT
<213> ORGANISM: Artificial Sequence
<220> FEATURE:
<223> OTHER INFORMATION: HzVSF_HC_V1

<400> SEQUENCE: 33

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Thr Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
```

-continued

```
                85                  90                  95

Ala Arg Glu Thr Gly Thr Arg Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445


<210> SEQ ID NO 34
<211> LENGTH: 107
<212> TYPE: PRT
<213> ORGANISM: Artificial Sequence
<220> FEATURE:
<223> OTHER INFORMATION: HzVSF_VL_V1

<400> SEQUENCE: 34

Asp Ile Gln Met Thr Gln Ser Pro Ser Ser Leu Ser Ala Ser Val Gly
```

-continued

```
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys
            100                 105


<210> SEQ ID NO 35
<211> LENGTH: 214
<212> TYPE: PRT
<213> ORGANISM: Artificial Sequence
<220> FEATURE:
<223> OTHER INFORMATION: HzVSF_LC_V1

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 36
<211> LENGTH: 118
<212> TYPE: PRT
<213> ORGANISM: Artificial Sequence
<220> FEATURE:
<223> OTHER INFORMATION: HzVSF_VH_V2
```

<400> SEQUENCE: 36

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Thr Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser
        115

<210> SEQ ID NO 37
<211> LENGTH: 445
<212> TYPE: PRT
<213> ORGANISM: Artificial Sequence
<220> FEATURE:
<223> OTHER INFORMATION: HzVSF_HC_V2

<400> SEQUENCE: 37

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Thr Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225 230 235 240

Phe Pro Pro Lys Pro Lys Asp Thr Leu Met Ile Ser Arg Thr Pro Glu
245 250 255

Val Thr Cys Val Val Val Asp Val Ser Gln Glu Asp Pro Glu Val Gln
260 265 270

Phe Asn Trp Tyr Val Asp Gly Val Glu Val His Asn Ala Lys Thr Lys
275 280 285

Pro Arg Glu Glu Gln Phe Asn Ser Thr Tyr Arg Val Val Ser Val Leu
290 295 300

Thr Val Leu His Gln Asp Trp Leu Asn Gly Lys Glu Tyr Lys Cys Lys
305 310 315 320

Val Ser Asn Lys Gly Leu Pro Ser Ser Ile Glu Lys Thr Ile Ser Lys
325 330 335

Ala Lys Gly Gln Pro Arg Glu Pro Gln Val Tyr Thr Leu Pro Pro Ser
340 345 350

Gln Glu Glu Met Thr Lys Asn Gln Val Ser Leu Thr Cys Leu Val Lys
355 360 365

Gly Phe Tyr Pro Ser Asp Ile Ala Val Glu Trp Glu Ser Asn Gly Gln
370 375 380

Pro Glu Asn Asn Tyr Lys Thr Thr Pro Pro Val Leu Asp Ser Asp Gly
385 390 395 400

Ser Phe Phe Leu Tyr Ser Arg Leu Thr Val Asp Lys Ser Arg Trp Gln
405 410 415

Glu Gly Asn Val Phe Ser Cys Ser Val Met His Glu Ala Leu His Asn
420 425 430

His Tyr Thr Gln Lys Ser Leu Ser Leu Ser Leu Gly Lys
435 440 445

<210> SEQ ID NO 38
<211> LENGTH: 107
<212> TYPE: PRT
<213> ORGANISM: Artificial Sequence
<220> FEATURE:
<223> OTHER INFORMATION: HzVSF_VL_V2

<400> SEQUENCE: 38

Asp Ile Gln Met Thr Gln Ser Pro Ser Ser Leu Ser Ala Ser Val Gly
1 5 10 15

Asp Arg Val Thr Ile Thr Cys Arg Ala Ser Glu Asn Ile Tyr Ser Asn
20 25 30

Leu Ala Trp Tyr Gln Gln Lys Pro Gly Lys Ala Pro Lys Leu Leu Ile
35 40 45

Tyr Val Ala Asp Asn Leu Gly Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln His Phe Tyr Gly Ser Pro Arg
85 90 95

Thr Phe Gly Gly Gly Thr Lys Val Glu Ile Lys
100 105

<210> SEQ ID NO 39
<211> LENGTH: 214
<212> TYPE: PRT
<213> ORGANISM: Artificial Sequence
<220> FEATURE:

<223> OTHER INFORMATION: HzVSF_LC_V2

<400> SEQUENCE: 39

Asp Ile Gln Met Thr Gln Ser Pro Ser Ser Leu Ser Ala Ser Val Gly
1 5 10 15

Asp Arg Val Thr Ile Thr Cys Arg Ala Ser Glu Asn Ile Tyr Ser Asn
20 25 30

Leu Ala Trp Tyr Gln Gln Lys Pro Gly Lys Ala Pro Lys Leu Leu Ile
35 40 45

Tyr Val Ala Asp Asn Leu Gly Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln His Phe Tyr Gly Ser Pro Arg
85 90 95

Thr Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 40
<211> LENGTH: 118
<212> TYPE: PRT
<213> ORGANISM: Artificial Sequence
<220> FEATURE:
<223> OTHER INFORMATION: HzVSF_VH_V3

<400> SEQUENCE: 40

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Asn Met Asn Trp Val Arg Gln Ala Pro Gly Lys Gly Leu Glu Trp Met
35 40 45

Gly Asn Ile Asp Pro Tyr Tyr Gly Ser Thr Thr Tyr Ala Gln Lys Phe
50 55 60

Gln Gly Arg Val Thr Met Thr Val Asp Lys Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Glu Thr Gly Thr Arg Ala Met Asp Tyr Trp Gly Gln Gly Thr
100 105 110

Leu Val Thr Val Ser Ser
115

<210> SEQ ID NO 41
<211> LENGTH: 445
<212> TYPE: PRT
<213> ORGANISM: Artificial Sequence
<220> FEATURE:
<223> OTHER INFORMATION: HzVSF_HC_V3

<400> SEQUENCE: 41

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Thr Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365
```

```
Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445


<210> SEQ ID NO 42
<211> LENGTH: 107
<212> TYPE: PRT
<213> ORGANISM: Artificial Sequence
<220> FEATURE:
<223> OTHER INFORMATION: HzVSF_VL_V3

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Arg Gly Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys
            100                 105


<210> SEQ ID NO 43
<211> LENGTH: 214
<212> TYPE: PRT
<213> ORGANISM: Artificial Sequence
<220> FEATURE:
<223> OTHER INFORMATION: HzVSF_LC_V3

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Arg Gly Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
```

```
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 44
<211> LENGTH: 118
<212> TYPE: PRT
<213> ORGANISM: Artificial Sequence
<220> FEATURE:
<223> OTHER INFORMATION: HzVSF_VH_V4

<400> SEQUENCE: 44

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Thr Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser
        115


<210> SEQ ID NO 45
<211> LENGTH: 445
<212> TYPE: PRT
<213> ORGANISM: Artificial Sequence
<220> FEATURE:
<223> OTHER INFORMATION: HzVSF_HC_V4

<400> SEQUENCE: 45

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Thr Thr Tyr Ala Gln Lys Phe
    50                  55                  60

Gln Gly Arg Val Thr Met Thr Val Asp Lys Ser Ile Ser Thr Ala Tyr
65                  70                  75                  80
```

-continued

```
Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445
```

<210> SEQ ID NO 46
<211> LENGTH: 107
<212> TYPE: PRT
<213> ORGANISM: Artificial Sequence
<220> FEATURE:
<223> OTHER INFORMATION: HzVSF_VL_V4

<400> SEQUENCE: 46

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Arg Gly Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Thr Pro Arg
                85                  90                  95

Thr Phe Gly Gly Gly Thr Lys Val Glu Ile Lys
            100                 105


<210> SEQ ID NO 47
<211> LENGTH: 214
<212> TYPE: PRT
<213> ORGANISM: Artificial Sequence
<220> FEATURE:
<223> OTHER INFORMATION: HzVSF_LC_V4

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Arg Gly Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Thr Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 48
<211> LENGTH: 118
<212> TYPE: PRT
<213> ORGANISM: Artificial Sequence
<220> FEATURE:
```

<223> OTHER INFORMATION: HzVSF_VH_V5

<400> SEQUENCE: 48

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Asp Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser
        115
```

<210> SEQ ID NO 49
<211> LENGTH: 445
<212> TYPE: PRT
<213> ORGANISM: Artificial Sequence
<220> FEATURE:
<223> OTHER INFORMATION: HzVSF_HC_V5

<400> SEQUENCE: 49

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Asp Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220
```

Pro Ser Cys Pro Ala Pro Glu Phe Leu Gly Gly Pro Ser Val Phe Leu
225 230 235 240

Phe Pro Pro Lys Pro Lys Asp Thr Leu Met Ile Ser Arg Thr Pro Glu
245 250 255

Val Thr Cys Val Val Val Asp Val Ser Gln Glu Asp Pro Glu Val Gln
260 265 270

Phe Asn Trp Tyr Val Asp Gly Val Glu Val His Asn Ala Lys Thr Lys
275 280 285

Pro Arg Glu Glu Gln Phe Asn Ser Thr Tyr Arg Val Val Ser Val Leu
290 295 300

Thr Val Leu His Gln Asp Trp Leu Asn Gly Lys Glu Tyr Lys Cys Lys
305 310 315 320

Val Ser Asn Lys Gly Leu Pro Ser Ser Ile Glu Lys Thr Ile Ser Lys
325 330 335

Ala Lys Gly Gln Pro Arg Glu Pro Gln Val Tyr Thr Leu Pro Pro Ser
340 345 350

Gln Glu Glu Met Thr Lys Asn Gln Val Ser Leu Thr Cys Leu Val Lys
355 360 365

Gly Phe Tyr Pro Ser Asp Ile Ala Val Glu Trp Glu Ser Asn Gly Gln
370 375 380

Pro Glu Asn Asn Tyr Lys Thr Thr Pro Pro Val Leu Asp Ser Asp Gly
385 390 395 400

Ser Phe Phe Leu Tyr Ser Arg Leu Thr Val Asp Lys Ser Arg Trp Gln
405 410 415

Glu Gly Asn Val Phe Ser Cys Ser Val Met His Glu Ala Leu His Asn
420 425 430

His Tyr Thr Gln Lys Ser Leu Ser Leu Ser Leu Gly Lys
435 440 445

<210> SEQ ID NO 50
<211> LENGTH: 107
<212> TYPE: PRT
<213> ORGANISM: Artificial Sequence
<220> FEATURE:
<223> OTHER INFORMATION: HzVSF_VL_V5

<400> SEQUENCE: 50

Asp Ile Gln Met Thr Gln Ser Pro Ser Ser Leu Ser Ala Ser Val Gly
1 5 10 15

Asp Arg Val Thr Ile Thr Cys Arg Ala Ser Glu Asn Ile Tyr Ser Asn
20 25 30

Leu Ala Trp Tyr Gln Gln Lys Pro Gly Lys Ala Pro Lys Leu Leu Ile
35 40 45

Tyr Val Ala Thr Asn Leu Ala Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln His Phe Tyr Gly Ser Pro Arg
85 90 95

Thr Phe Gly Gly Gly Thr Lys Val Glu Ile Lys
100 105

<210> SEQ ID NO 51
<211> LENGTH: 214
<212> TYPE: PRT
<213> ORGANISM: Artificial Sequence
<220> FEATURE:
<223> OTHER INFORMATION: HzVSF_LC_V5

<400> SEQUENCE: 51

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 52
<211> LENGTH: 118
<212> TYPE: PRT
<213> ORGANISM: Artificial Sequence
<220> FEATURE:
<223> OTHER INFORMATION: HzVSF_VH_V6

<400> SEQUENCE: 52

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Thr Thr Tyr Ala Gln Lys Phe
    50                  55                  60

Gln Gly Arg Val Thr Met Thr Val Asp Thr Ser Ala Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser
```

115

<210> SEQ ID NO 53
<211> LENGTH: 445
<212> TYPE: PRT
<213> ORGANISM: Artificial Sequence
<220> FEATURE:
<223> OTHER INFORMATION: HzVSF_HC_V6

<400> SEQUENCE: 53

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Asn Met Asn Trp Val Arg Gln Ala Pro Gly Lys Gly Leu Glu Trp Met
35 40 45

Gly Asn Ile Asp Pro Tyr Tyr Gly Ser Thr Thr Tyr Ala Gln Lys Phe
50 55 60

Gln Gly Arg Val Thr Met Thr Val Asp Thr Ser Ala Ser Thr Ala Tyr
65 70 75 80

Met Glu Leu Ser Arg Leu Arg Ser Asp Asp Thr Ala Val Tyr Tyr Cys
85 90 95

Ala Arg Glu Thr Gly Thr Arg Ala Met Asp Tyr Trp Gly Gln Gly Thr
100 105 110

Leu Val Thr Val Ser Ser Ala Ser Thr Lys Gly Pro Ser Val Phe Pro
115 120 125

Leu Ala Pro Cys Ser Arg Ser Thr Ser Glu Ser Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Lys Thr Tyr Thr Cys Asn Val Asp His Lys Pro Ser
195 200 205

Asn Thr Lys Val Asp Lys Arg Val Glu Ser Lys Tyr Gly Pro Pro Cys
210 215 220

Pro Ser Cys Pro Ala Pro Glu Phe Leu Gly Gly Pro Ser Val Phe Leu
225 230 235 240

Phe Pro Pro Lys Pro Lys Asp Thr Leu Met Ile Ser Arg Thr Pro Glu
245 250 255

Val Thr Cys Val Val Val Asp Val Ser Gln Glu Asp Pro Glu Val Gln
260 265 270

Phe Asn Trp Tyr Val Asp Gly Val Glu Val His Asn Ala Lys Thr Lys
275 280 285

Pro Arg Glu Glu Gln Phe Asn Ser Thr Tyr Arg Val Val Ser Val Leu
290 295 300

Thr Val Leu His Gln Asp Trp Leu Asn Gly Lys Glu Tyr Lys Cys Lys
305 310 315 320

Val Ser Asn Lys Gly Leu Pro Ser Ser Ile Glu Lys Thr Ile Ser Lys
325 330 335

Ala Lys Gly Gln Pro Arg Glu Pro Gln Val Tyr Thr Leu Pro Pro Ser
340 345 350

Gln Glu Glu Met Thr Lys Asn Gln Val Ser Leu Thr Cys Leu Val Lys

```
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445


<210> SEQ ID NO 54
<211> LENGTH: 107
<212> TYPE: PRT
<213> ORGANISM: Artificial Sequence
<220> FEATURE:
<223> OTHER INFORMATION: HzVSF_VL_V6

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys
            100                 105


<210> SEQ ID NO 55
<211> LENGTH: 214
<212> TYPE: PRT
<213> ORGANISM: Artificial Sequence
<220> FEATURE:
<223> OTHER INFORMATION: HzVSF_LC_V6

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys Arg Thr Val Ala Ala
            100                 105                 110
```

-continued

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 56
<211> LENGTH: 118
<212> TYPE: PRT
<213> ORGANISM: Artificial Sequence
<220> FEATURE:
<223> OTHER INFORMATION: HzVSF_VH_V7

<400> SEQUENCE: 56

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Asp Thr Tyr Ala Gln Lys Phe
    50                  55                  60

Gln Gly Arg Val Thr Met Thr Val Asp Thr Ser Ala Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser
        115


<210> SEQ ID NO 57
<211> LENGTH: 445
<212> TYPE: PRT
<213> ORGANISM: Artificial Sequence
<220> FEATURE:
<223> OTHER INFORMATION: HzVSF_HC_V7

<400> SEQUENCE: 57

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Asp Thr Tyr Ala Gln Lys Phe
    50                  55                  60

Gln Gly Arg Val Thr Met Thr Val Asp Thr Ser Ala Ser Thr Ala Tyr
65                  70                  75                  80
```

-continued

```
Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445
```

<210> SEQ ID NO 58
<211> LENGTH: 107
<212> TYPE: PRT
<213> ORGANISM: Artificial Sequence
<220> FEATURE:
<223> OTHER INFORMATION: HzVSF_VL_V7

<400> SEQUENCE: 58

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys
            100                 105


<210> SEQ ID NO 59
<211> LENGTH: 214
<212> TYPE: PRT
<213> ORGANISM: Artificial Sequence
<220> FEATURE:
<223> OTHER INFORMATION: HzVSF_LC_V7

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 60
<211> LENGTH: 118
<212> TYPE: PRT
<213> ORGANISM: Artificial Sequence
```

<220> FEATURE:
<223> OTHER INFORMATION: HzVSF_VH_V8

<400> SEQUENCE: 60

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Asn Met Asn Trp Val Arg Gln Ala Pro Gly Lys Gly Leu Glu Trp Met
35 40 45

Gly Asn Ile Asp Pro Tyr Tyr Gly Ser Asp Thr Tyr Ala Gln Lys Phe
50 55 60

Gln Gly Arg Val Thr Met Thr Val Asp Thr Ser Ala Ser Thr Ala Tyr
65 70 75 80

Met Glu Leu Ser Arg Leu Arg Ser Asp Asp Thr Ala Val Tyr Tyr Cys
85 90 95

Ala Arg Glu Thr Gly Asn Arg Ala Met Asp Tyr Trp Gly Gln Gly Thr
100 105 110

Leu Val Thr Val Ser Ser
115

<210> SEQ ID NO 61
<211> LENGTH: 445
<212> TYPE: PRT
<213> ORGANISM: Artificial Sequence
<220> FEATURE:
<223> OTHER INFORMATION: HzVSF_HC_V8

<400> SEQUENCE: 61

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Asn Met Asn Trp Val Arg Gln Ala Pro Gly Lys Gly Leu Glu Trp Met
35 40 45

Gly Asn Ile Asp Pro Tyr Tyr Gly Ser Asp Thr Tyr Ala Gln Lys Phe
50 55 60

Gln Gly Arg Val Thr Met Thr Val Asp Thr Ser Ala Ser Thr Ala Tyr
65 70 75 80

Met Glu Leu Ser Arg Leu Arg Ser Asp Asp Thr Ala Val Tyr Tyr Cys
85 90 95

Ala Arg Glu Thr Gly Asn Arg Ala Met Asp Tyr Trp Gly Gln Gly Thr
100 105 110

Leu Val Thr Val Ser Ser Ala Ser Thr Lys Gly Pro Ser Val Phe Pro
115 120 125

Leu Ala Pro Cys Ser Arg Ser Thr Ser Glu Ser Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Lys Thr Tyr Thr Cys Asn Val Asp His Lys Pro Ser
195 200 205

Asn Thr Lys Val Asp Lys Arg Val Glu Ser Lys Tyr Gly Pro Pro Cys

```
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445
```

<210> SEQ ID NO 62
<211> LENGTH: 107
<212> TYPE: PRT
<213> ORGANISM: Artificial Sequence
<220> FEATURE:
<223> OTHER INFORMATION: HzVSF_VL_V8

<400> SEQUENCE: 62

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys
            100                 105
```

<210> SEQ ID NO 63
<211> LENGTH: 214
<212> TYPE: PRT

<213> ORGANISM: Artificial Sequence
<220> FEATURE:
<223> OTHER INFORMATION: HzVSF_LC_V8

<400> SEQUENCE: 63

Asp Ile Gln Met Thr Gln Ser Pro Ser Ser Leu Ser Ala Ser Val Gly
1 5 10 15

Asp Arg Val Thr Ile Thr Cys Arg Ala Ser Glu Asn Ile Tyr Ser Asn
20 25 30

Leu Ala Trp Tyr Gln Gln Lys Pro Gly Lys Ala Pro Lys Leu Leu Ile
35 40 45

Tyr Val Ala Thr Asn Leu Ala Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln His Phe Tyr Gly Ser Pro Arg
85 90 95

Thr Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 64
<211> LENGTH: 118
<212> TYPE: PRT
<213> ORGANISM: Artificial Sequence
<220> FEATURE:
<223> OTHER INFORMATION: HzVSF_VH_V9

<400> SEQUENCE: 64

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Asn Met Asn Trp Val Arg Gln Ala Pro Gly Lys Gly Leu Glu Trp Met
35 40 45

Gly Asn Ile Asp Pro Tyr Tyr Gly Ser Asp Thr Tyr Ala Gln Lys Phe
50 55 60

Gln Gly Arg Val Thr Met Thr Val Asp Thr Ser Ala Ser Thr Ala Tyr
65 70 75 80

Met Glu Leu Ser Arg Leu Arg Ser Asp Asp Thr Ala Val Tyr Tyr Cys
85 90 95

Ala Arg Glu Thr Gly Thr Arg Ala Met Asp Tyr Trp Gly Gln Gly Thr
100 105 110

```
Leu Val Thr Val Ser Ser
        115


<210> SEQ ID NO 65
<211> LENGTH: 445
<212> TYPE: PRT
<213> ORGANISM: Artificial Sequence
<220> FEATURE:
<223> OTHER INFORMATION: HzVSF_HC_V9

<400> SEQUENCE: 65

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Asp Thr Tyr Ala Gln Lys Phe
    50                  55                  60

Gln Gly Arg Val Thr Met Thr Val Asp Thr Ser Ala Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350
```

-continued

Gln Glu Glu Met Thr Lys Asn Gln Val Ser Leu Thr Cys Leu Val Lys
355 360 365

Gly Phe Tyr Pro Ser Asp Ile Ala Val Glu Trp Glu Ser Asn Gly Gln
370 375 380

Pro Glu Asn Asn Tyr Lys Thr Thr Pro Pro Val Leu Asp Ser Asp Gly
385 390 395 400

Ser Phe Phe Leu Tyr Ser Arg Leu Thr Val Asp Lys Ser Arg Trp Gln
405 410 415

Glu Gly Asn Val Phe Ser Cys Ser Val Met His Glu Ala Leu His Asn
420 425 430

His Tyr Thr Gln Lys Ser Leu Ser Leu Ser Leu Gly Lys
435 440 445

<210> SEQ ID NO 66
<211> LENGTH: 107
<212> TYPE: PRT
<213> ORGANISM: Artificial Sequence
<220> FEATURE:
<223> OTHER INFORMATION: HzVSF_VL_V9

<400> SEQUENCE: 66

Asp Ile Gln Met Thr Gln Ser Pro Ser Ser Leu Ser Ala Ser Val Gly
1 5 10 15

Asp Arg Val Thr Ile Thr Cys Arg Ala Ser Glu Asn Ile Tyr Ser Asn
20 25 30

Leu Ala Trp Tyr Gln Gln Lys Pro Gly Lys Ala Pro Lys Leu Leu Ile
35 40 45

Tyr Val Ala Asp Asn Arg Gly Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln His Phe Tyr Gly Ser Pro Arg
85 90 95

Thr Phe Gly Gly Gly Thr Lys Val Glu Ile Lys
100 105

<210> SEQ ID NO 67
<211> LENGTH: 214
<212> TYPE: PRT
<213> ORGANISM: Artificial Sequence
<220> FEATURE:
<223> OTHER INFORMATION: HzVSF_LC_V9

<400> SEQUENCE: 67

Asp Ile Gln Met Thr Gln Ser Pro Ser Ser Leu Ser Ala Ser Val Gly
1 5 10 15

Asp Arg Val Thr Ile Thr Cys Arg Ala Ser Glu Asn Ile Tyr Ser Asn
20 25 30

Leu Ala Trp Tyr Gln Gln Lys Pro Gly Lys Ala Pro Lys Leu Leu Ile
35 40 45

Tyr Val Ala Asp Asn Arg Gly Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln His Phe Tyr Gly Ser Pro Arg
85 90 95

Thr Phe Gly Gly Gly Thr Lys Val Glu Ile Lys Arg Thr Val Ala Ala
100 105 110

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 68
<211> LENGTH: 118
<212> TYPE: PRT
<213> ORGANISM: Artificial Sequence
<220> FEATURE:
<223> OTHER INFORMATION: HzVSF_VH_V10

<400> SEQUENCE: 68

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Asp Thr Tyr Ala Gln Lys Phe
    50                  55                  60

Gln Gly Arg Val Thr Met Thr Val Asp Thr Ser Ala Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Asn Arg Ala Met Asp Tyr Trp Gly Gln Gly Thr
            100                 105                 110

Leu Val Thr Val Ser Ser
        115


<210> SEQ ID NO 69
<211> LENGTH: 445
<212> TYPE: PRT
<213> ORGANISM: Artificial Sequence
<220> FEATURE:
<223> OTHER INFORMATION: HzVSF_HC_V10

<400> SEQUENCE: 69

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Asp Thr Tyr Ala Gln Lys Phe
    50                  55                  60

Gln Gly Arg Val Thr Met Thr Val Asp Thr Ser Ala Ser Thr Ala Tyr
```

-continued

```
65                  70                  75                  80

Met Glu Leu Ser Arg Leu Arg Ser Asp Asp Thr Ala Val Tyr Tyr Cys
                85                  90                  95

Ala Arg Glu Thr Gly Asn Arg Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445
```

<210> SEQ ID NO 70
<211> LENGTH: 107
<212> TYPE: PRT
<213> ORGANISM: Artificial Sequence
<220> FEATURE:
<223> OTHER INFORMATION: HzVSF_VL_V10

<400> SEQUENCE: 70

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Arg Gly Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys
            100                 105
```

<210> SEQ ID NO 71
<211> LENGTH: 214
<212> TYPE: PRT
<213> ORGANISM: Artificial Sequence
<220> FEATURE:
<223> OTHER INFORMATION: HzVSF_LC_V10

<400> SEQUENCE: 71

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Arg Gly Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 72
<211> LENGTH: 118
<212> TYPE: PRT

```
<213> ORGANISM: Artificial Sequence
<220> FEATURE:
<223> OTHER INFORMATION: HzVSF_VH_V11

<400> SEQUENCE: 72

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Asp Thr Tyr Ala Gln Lys Phe
    50                  55                  60

Gln Gly Arg Val Thr Met Thr Val Asp Thr Ser Ala Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser
        115


<210> SEQ ID NO 73
<211> LENGTH: 445
<212> TYPE: PRT
<213> ORGANISM: Artificial Sequence
<220> FEATURE:
<223> OTHER INFORMATION: HzVSF_HC_V11

<400> SEQUENCE: 73

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Asp Thr Tyr Ala Gln Lys Phe
    50                  55                  60

Gln Gly Arg Val Thr Met Thr Val Asp Thr Ser Ala Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205
```

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 74
<211> LENGTH: 107
<212> TYPE: PRT
<213> ORGANISM: Artificial Sequence
<220> FEATURE:
<223> OTHER INFORMATION: HzVSF_VL_V11

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Arg Gly Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Thr Pro Arg
                85                  90                  95

Thr Phe Gly Gly Gly Thr Lys Val Glu Ile Lys
            100                 105

<210> SEQ ID NO 75
<211> LENGTH: 214

<212> TYPE: PRT
<213> ORGANISM: Artificial Sequence
<220> FEATURE:
<223> OTHER INFORMATION: HzVSF_LC_V11

<400> SEQUENCE: 75

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Arg Gly Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Thr Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 76
<211> LENGTH: 118
<212> TYPE: PRT
<213> ORGANISM: Artificial Sequence
<220> FEATURE:
<223> OTHER INFORMATION: HzVSF_VH_V12

<400> SEQUENCE: 76

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Asp Thr Tyr Ala Gln Lys Phe
    50                  55                  60

Gln Gly Arg Val Thr Met Thr Val Asp Thr Ser Ala Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Asn Arg Ala Met Asp Tyr Trp Gly Gln Gly Thr
            100                 105                 110
```

```
Leu Val Thr Val Ser Ser
        115


<210> SEQ ID NO 77
<211> LENGTH: 445
<212> TYPE: PRT
<213> ORGANISM: Artificial Sequence
<220> FEATURE:
<223> OTHER INFORMATION: HzVSF_HC_V12

<400> SEQUENCE: 77

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Asp Thr Tyr Ala Gln Lys Phe
    50                  55                  60

Gln Gly Arg Val Thr Met Thr Val Asp Thr Ser Ala Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Asn Arg Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350
```

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 78
<211> LENGTH: 107
<212> TYPE: PRT
<213> ORGANISM: Artificial Sequence
<220> FEATURE:
<223> OTHER INFORMATION: HzVSF_VL_V12

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Arg Gly Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Thr Pro Arg
                85                  90                  95

Thr Phe Gly Gly Gly Thr Lys Val Glu Ile Lys
            100                 105

<210> SEQ ID NO 79
<211> LENGTH: 214
<212> TYPE: PRT
<213> ORGANISM: Artificial Sequence
<220> FEATURE:
<223> OTHER INFORMATION: zVSF_LC_V12

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Arg Gly Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Thr Pro Arg
                85                  90                  95

Thr Phe Gly Gly Gly Thr Lys Val Glu Ile Lys Arg Thr Val Ala Ala

```
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 80
<211> LENGTH: 118
<212> TYPE: PRT
<213> ORGANISM: Artificial Sequence
<220> FEATURE:
<223> OTHER INFORMATION: HzVSF_VH_V13

<400> SEQUENCE: 80

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Asp Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser
        115


<210> SEQ ID NO 81
<211> LENGTH: 445
<212> TYPE: PRT
<213> ORGANISM: Artificial Sequence
<220> FEATURE:
<223> OTHER INFORMATION: HzVSF_HC_V13

<400> SEQUENCE: 81

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Asp Thr Tyr Ala Gln Lys Phe
    50                  55                  60
```

-continued

```
Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445
```

<210> SEQ ID NO 82
<211> LENGTH: 107
<212> TYPE: PRT
<213> ORGANISM: Artificial Sequence
<220> FEATURE:
<223> OTHER INFORMATION: HzVSF_VL_V13

<400> SEQUENCE: 82

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys
            100                 105
```

<210> SEQ ID NO 83
<211> LENGTH: 214
<212> TYPE: PRT
<213> ORGANISM: Artificial Sequence
<220> FEATURE:
<223> OTHER INFORMATION: HzVSF_LC_V13

<400> SEQUENCE: 83

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 84
<211> LENGTH: 645

<212> TYPE: DNA
<213> ORGANISM: Artificial Sequence
<220> FEATURE:
<223> OTHER INFORMATION: HzVSF hVL.hCkappa

<400> SEQUENCE: 84
gacatccaga tgacccagtc tccatcctcc ctgtctgcat ctgtaggaga cagagtcacc 60
atcacttgcc gagcaagtga gaatatttac agtaatttag catggtatca gcagaaacca 120
gggaaagctc ctaagctcct gatctatgtt gcaacaaact tagcagatgg ggtcccatca 180
aggttcagcg gcagtggatc tgggacagat ttcactctca ccatcagcag cctgcagcct 240
gaagattttg caacttatta ctgtcaacat ttttatggtt ctcctcggac gttcggcgga 300
gggaccaagg tggagatcaa acgcacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gttag 645

<210> SEQ ID NO 85
<211> LENGTH: 1335
<212> TYPE: DNA
<213> ORGANISM: Artificial Sequence
<220> FEATURE:
<223> OTHER INFORMATION: hVH.hCgamma2

<400> SEQUENCE: 85
gaggtgcagc tggtgcagtc tggggctgag gtgaagaagc ctggggcctc agtgaaggtc 60
tcctgcaagg cttctggata caccttcacc ggctacaaca tgaactgggt gcgacaggct 120
cctggaaaag ggcttgagtg gatgggaaat attgatcctt actatggtag tactacctat 180
gcacagaagt ttcagggcag ggtcaccatg accgtagaca aatccatcag cacagcctac 240
atggagctga gcaggctgag atctgacgac acggccgtgt attactgtgc gagagagact 300
gggacgaggg ctatggacta ctggggtcaa ggaaccctgg tcaccgtctc ctcagcctcc 360
accaagggcc catcggtctt ccccctggcg ccctgctcca ggagcacctc cgagagcaca 420
gcggccctgg gctgcctggt caaggactac ttccccgaac cggtgacggt gtcgtggaac 480
tcaggcgctc tgaccagcgg cgtgcacacc ttcccggctg tcctacagtc ctcaggactc 540
tactccctca gcagcgtggt gaccgtgccc tccagcaact tcggcaccca gacctacacc 600
tgcaacgtag atcacaagcc cagcaacacc aaggtggaca agacagttga gcgcaaatgt 660
tgtgtcgagt gcccaccgtg cccagcacca cctgtggcag gaccgtcagt cttcctcttc 720
cccccaaaac ccaaggacac cctcatgatc tcccggaccc ctgaggtcac gtgcgtggtg 780
gtggacgtga gccacgaaga ccccgaggtc cagttcaact ggtacgtgga cggcgtggag 840
gtgcataatg ccaagacaaa gccacgggag gagcagttca acagcacgtt ccgtgtggtc 900
agcgtcctca ccgtcgtgca ccaggactgg ctgaacggca aggagtacaa gtgcaaggtc 960
tccaacaaag gcctcccagc ccccatcgag aaaaccatct ccaaaaccaa agggcagccc 1020
cgagaaccac aggtgtacac cctgccccca tcccgggagg agatgaccaa gaaccaggtc 1080
agcctgacct gcctggtcaa aggcttctac cccagcgaca tcgccgtgga gtgggagagc 1140
aatgggcagc cggagaacaa ctacaacacc acacctccca tgctggactc cgacggctcc 1200

```
ttcttcctct acagcaagct caccgtggac aagagcaggt ggcagcaggg gaacgtcttc   1260

tcatgctccg tgatgcatga ggctctgcac aaccactaca cgcagaagag cctctccctg   1320

tctccgggta aatga                                                    1335
```

<210> SEQ ID NO 86
<211> LENGTH: 1338
<212> TYPE: DNA
<213> ORGANISM: Artificial Sequence
<220> FEATURE:
<223> OTHER INFORMATION: hVH.hCgamma4

<400> SEQUENCE: 86

```
gaggtgcagc tggtgcagtc tggggctgag gtgaagaagc ctggggcctc agtgaaggtc     60

tcctgcaagg cttctggata caccttcacc ggctacaaca tgaactgggt gcgacaggct    120

cctggaaaag ggcttgagtg gatgggaaat attgatcctt actatggtag tactacctat    180

gcacagaagt ttcagggcag ggtcaccatg accgtagaca aatccatcag cacagcctac    240

atggagctga gcaggctgag atctgacgac acggccgtgt attactgtgc gagagagact    300

gggacgaggg ctatggacta ctggggtcaa ggaaccctgg tcaccgtctc ctcagcttcc    360

accaagggcc catccgtctt cccctggcg ccctgctcca ggagcacctc cgagagcaca    420

gccgccctgg gctgcctggt caaggactac ttccccgaac cggtgacggt gtcgtggaac    480

tcaggcgccc tgaccagcgg cgtgcacacc ttcccggctg tcctacagtc ctcaggactc    540

tactccctca gcagcgtggt gaccgtgccc tccagcagct tgggcacgaa gacctacacc    600

tgcaacgtag atcacaagcc cagcaacacc aaggtggaca agagagttga gtccaaatat    660

ggtcccccat gcccatcatg cccagcacct gagttcctgg ggggaccatc agtcttcctg    720

ttccccccaa aacccaagga cactctcatg atctcccgga cccctgaggt cacgtgcgtg    780

gtggtggacg tgagccagga agaccccgag gtccagttca actggtacgt ggatggcgtg    840

gaggtgcata atgccaagac aaagccgcgg gaggagcagt tcaacagcac gtaccgtgtg    900

gtcagcgtcc tcaccgtcct gcaccaggac tggctgaacg gcaaggagta caagtgcaag    960

gtctccaaca aaggcctccc gtcctccatc gagaaaacca tctccaaagc caaagggcag   1020

ccccgagagc cacaggtgta caccctgccc ccatcccagg aggagatgac caagaaccag   1080

gtcagcctga cctgcctggt caaaggcttc taccccagcg acatcgccgt ggagtgggag   1140

agcaatgggc agccggagaa caactacaag accacgcctc ccgtgctgga ctccgacggc   1200

tccttcttcc tctacagcag gctaaccgtg gacaagagca ggtggcagga ggggaatgtc   1260

ttctcatgct ccgtgatgca tgaggctctg cacaaccact acacacagaa gagcctctcc   1320

ctgtctctgg gtaaatga                                                 1338
```

<210> SEQ ID NO 87
<211> LENGTH: 1338
<212> TYPE: DNA
<213> ORGANISM: Artificial Sequence
<220> FEATURE:
<223> OTHER INFORMATION: HzVSF a1 gamma4

<400> SEQUENCE: 87

```
gagatccagc tggtgcagtc tggggctgag gtgaagaagc ctggggcctc agtgaaggtc     60

tcctgcaagg cttctggata caccttcacc ggctacaaca tgaactgggt gcgacaggct    120

cctggaaaag ggcttgagtg gatgggaaat attgatcctt actatggtag tactacctat    180

gcacagaagt ttcagggcag ggtcaccatg accgtagaca aatccatcag cacagcctac    240
```

-continued

```
atggagctga gcaggctgag atctgacgac acggccgtgt attactgtgc gagagagact    300

gggacgaggg ctatggacta ctggggtcaa ggaaccctgg tcaccgtctc ctcagcctcc    360

accaagggcc catccgtctt cccccctggcg ccctgctcca ggagcacctc cgagagcaca    420

gccgccctgg gctgcctggt caaggactac ttccccgaac cggtgacggt gtcgtggaac    480

tcaggcgccc tgaccagcgg cgtgcacacc ttcccggctg tcctacagtc ctcaggactc    540

tactccctca gcagcgtggt gaccgtgccc tccagcagct tgggcacgaa gacctacacc    600

tgcaacgtag atcacaagcc cagcaacacc aaggtggaca agagagttga gtccaaatat    660

ggtcccccat gcccatcatg cccagcacct gagttcctgg ggggaccatc agtcttcctg    720

ttccccccaa aacccaagga cactctcatg atctcccgga cccctgaggt cacgtgcgtg    780

gtggtggacg tgagccagga agaccccgag gtccagttca actggtacgt ggatggcgtg    840

gaggtgcata atgccaagac aaagccgcgg gaggagcagt tcaacagcac gtaccgtgtg    900

gtcagcgtcc tcaccgtcct gcaccaggac tggctgaacg gcaaggagta caagtgcaag    960

gtctccaaca aaggcctccc gtcctccatc gagaaaacca tctccaaagc caaagggcag   1020

ccccgagagc cacaggtgta caccctgccc ccatcccagg aggagatgac caagaaccag   1080

gtcagcctga cctgcctggt caaaggcttc taccccagcg acatcgccgt ggagtgggag   1140

agcaatgggc agccggagaa caactacaag accacgcctc ccgtgctgga ctccgacggc   1200

tccttcttcc tctacagcag gctaaccgtg gacaagagca ggtggcagga ggggaatgtc   1260

ttctcatgct ccgtgatgca tgaggctctg cacaaccact acacacagaa gagcctctcc   1320

ctgtctctgg gtaaatga                                                  1338
```

```
<210> SEQ ID NO 88
<211> LENGTH: 1338
<212> TYPE: DNA
<213> ORGANISM: Artificial Sequence
<220> FEATURE:
<223> OTHER INFORMATION: HzVSF a2 gamma4

<400> SEQUENCE: 88
```

```
gaggtgcagc tggtgcagtc tggggctgag gtgaagaagc ctggggcctc agtgaaggtc     60

tcctgcaagg cttctggata caccttcacc ggctacaaca tgaactgggt gcgacaggct    120

cctggaaaag ggcttgagtg gattggaaat attgatcctt actatggtag tactacctat    180

gcacagaagt ttcagggcag ggtcaccatg accgtagaca aatccatcag cacagcctac    240

atggagctga gcaggctgag atctgacgac acggccgtgt attactgtgc gagagagact    300

gggacgaggg ctatggacta ctggggtcaa ggaaccctgg tcaccgtctc ctcagcctcc    360

accaagggcc catccgtctt cccccctggcg ccctgctcca ggagcacctc cgagagcaca    420

gccgccctgg gctgcctggt caaggactac ttccccgaac cggtgacggt gtcgtggaac    480

tcaggcgccc tgaccagcgg cgtgcacacc ttcccggctg tcctacagtc ctcaggactc    540

tactccctca gcagcgtggt gaccgtgccc tccagcagct tgggcacgaa gacctacacc    600

tgcaacgtag atcacaagcc cagcaacacc aaggtggaca agagagttga gtccaaatat    660

ggtcccccat gcccatcatg cccagcacct gagttcctgg ggggaccatc agtcttcctg    720

ttccccccaa aacccaagga cactctcatg atctcccgga cccctgaggt cacgtgcgtg    780

gtggtggacg tgagccagga agaccccgag gtccagttca actggtacgt ggatggcgtg    840

gaggtgcata atgccaagac aaagccgcgg gaggagcagt tcaacagcac gtaccgtgtg    900
```

gtcagcgtcc tcaccgtcct gcaccaggac tggctgaacg gcaaggagta caagtgcaag 960
gtctccaaca aaggcctccc gtcctccatc gagaaaacca tctccaaagc caaagggcag 1020
ccccgagagc cacaggtgta caccctgccc ccatcccagg aggagatgac caagaaccag 1080
gtcagcctga cctgcctggt caaaggcttc taccccagcg acatcgccgt ggagtgggag 1140
agcaatgggc agccggagaa caactacaag accacgcctc ccgtgctgga ctccgacggc 1200
tccttcttcc tctacagcag gctaaccgtg gacaagagca ggtggcagga ggggaatgtc 1260
ttctcatgct ccgtgatgca tgaggctctg cacaaccact acacacagaa gagcctctcc 1320
ctgtctctgg gtaaatga 1338

<210> SEQ ID NO 89
<211> LENGTH: 1338
<212> TYPE: DNA
<213> ORGANISM: Artificial Sequence
<220> FEATURE:
<223> OTHER INFORMATION: HzVSF a3 gamma4

<400> SEQUENCE: 89
gagatccagc tggtgcagtc tggggctgag gtgaagaagc ctggggcctc agtgaaggtc 60
tcctgcaagg cttctggata caccttcacc ggctacaaca tgaactgggt gcgacaggct 120
cctggaaaag ggcttgagtg gattggaaat attgatcctt actatggtag tactacctat 180
gcacagaagt ttcagggcag ggtcaccatg accgtagaca aatccatcag cacagcctac 240
atggagctga gcaggctgag atctgacgac acggccgtgt attactgtgc gagagagact 300
gggacgaggg ctatggacta ctggggtcaa ggaaccctgg tcaccgtctc ctcagcctcc 360
accaagggcc catccgtctt ccccctggcg ccctgctcca ggagcacctc cgagagcaca 420
gccgccctgg gctgcctggt caaggactac ttccccgaac cggtgacggt gtcgtggaac 480
tcaggcgccc tgaccagcgg cgtgcacacc ttcccggctg tcctacagtc ctcaggactc 540
tactccctca gcagcgtggt gaccgtgccc tccagcagct tgggcacgaa gacctacacc 600
tgcaacgtag atcacaagcc cagcaacacc aaggtggaca agagagttga gtccaaatat 660
ggtcccccat gcccatcatg cccagcacct gagttcctgg ggggaccatc agtcttcctg 720
ttccccccaa aacccaagga cactctcatg atctcccgga cccctgaggt cacgtgcgtg 780
gtggtggacg tgagccagga agaccccgag gtccagttca actggtacgt ggatggcgtg 840
gaggtgcata atgccaagac aaagccgcgg gaggagcagt tcaacagcac gtaccgtgtg 900
gtcagcgtcc tcaccgtcct gcaccaggac tggctgaacg gcaaggagta caagtgcaag 960
gtctccaaca aaggcctccc gtcctccatc gagaaaacca tctccaaagc caaagggcag 1020
ccccgagagc cacaggtgta caccctgccc ccatcccagg aggagatgac caagaaccag 1080
gtcagcctga cctgcctggt caaaggcttc taccccagcg acatcgccgt ggagtgggag 1140
agcaatgggc agccggagaa caactacaag accacgcctc ccgtgctgga ctccgacggc 1200
tccttcttcc tctacagcag gctaaccgtg gacaagagca ggtggcagga ggggaatgtc 1260
ttctcatgct ccgtgatgca tgaggctctg cacaaccact acacacagaa gagcctctcc 1320
ctgtctctgg gtaaatga 1338

<210> SEQ ID NO 90
<211> LENGTH: 645
<212> TYPE: DNA
<213> ORGANISM: Artificial Sequence
<220> FEATURE:
<223> OTHER INFORMATION: LC1

<400> SEQUENCE: 90
gacatccaga tgacccagtc tccatcctcc ctgtctgcat ctgtaggaga cagagtcacc 60
atcacttgcc gagcaagtga gaatatttac agtaatttag catggtatca gcagaaacca 120
gggaaagctc ctaagctcct gatctatgtt gcagacaact tagcagatgg ggtcccatca 180
aggttcagcg gcagtggatc tgggacagat ttcactctca ccatcagcag cctgcagcct 240
gaagattttg caacttatta ctgtcaacat ttttatggtt ctcctcggac gttcggcgga 300
gggaccaagg tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gttag 645

<210> SEQ ID NO 91
<211> LENGTH: 645
<212> TYPE: DNA
<213> ORGANISM: Artificial Sequence
<220> FEATURE:
<223> OTHER INFORMATION: LC4

<400> SEQUENCE: 91
gacatccaga tgacccagtc tccatcctcc ctgtctgcat ctgtaggaga cagagtcacc 60
atcacttgcc gagcaagtga gaatatttac agtaatttag catggtatca gcagaaacca 120
gggaaagctc ctaagctcct gatctatgtt gcagacaacc gcggagatgg ggtcccatca 180
aggttcagcg gcagtggatc tgggacagat ttcactctca ccatcagcag cctgcagcct 240
gaagattttg caacttatta ctgtcaacat ttttatggta cccctcggac gttcggcgga 300
gggaccaagg tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gttag 645

<210> SEQ ID NO 92
<211> LENGTH: 354
<212> TYPE: DNA
<213> ORGANISM: Artificial Sequence
<220> FEATURE:
<223> OTHER INFORMATION: VH1

<400> SEQUENCE: 92
gaggtgcagc tggtgcagtc tggggctgag gtgaagaagc ctggggcctc agtgaaggtc 60
tcctgcaagg cttctggata caccttcacc ggctacaaca tgaactgggt gcgacaggct 120
cctggaaaag ggcttgagtg gatgggaaat attgatcctt actatggtag tgatacctat 180
gcacagaagt ttcagggcag ggtcaccatg accgtagaca aatccatcag cacagcctac 240
atggagctga gcaggctgag atctgacgac acggccgtgt attactgtgc gagagagact 300
gggacgaggg ctatggacta ctggggtcaa ggaaccctgg tcaccgtctc ctca 354

<210> SEQ ID NO 93
<211> LENGTH: 354
<212> TYPE: DNA
<213> ORGANISM: Artificial Sequence
<220> FEATURE:
<223> OTHER INFORMATION: VH4

<400> SEQUENCE: 93

```
gaggtgcagc tggtgcagtc tggggctgag gtgaagaagc ctggggcctc agtgaaggtc     60

tcctgcaagg cttctggata caccttcacc ggctacaaca tgaactgggt gcgacaggct    120

cctggaaaag ggcttgagtg gatgggaaat attgatcctt actatggtag tgatacctat    180

gcacagaagt ttcagggcag ggtcaccatg accgtagaca cttccgcaag cacagcctac    240

atggagctga gcaggctgag atctgacgac acggccgtgt attactgtgc gagagagact    300

gggaataggg ctatggacta ctggggtcaa ggaaccctgg tcaccgtctc ctca          354
```

<210> SEQ ID NO 94
<211> LENGTH: 1338
<212> TYPE: DNA
<213> ORGANISM: Artificial Sequence
<220> FEATURE:
<223> OTHER INFORMATION: HzVSF_V1_HC

<400> SEQUENCE: 94

```
gaggtgcagc tggtgcagtc tggggctgag gtgaagaagc ctggggcctc agtgaaggtc     60

tcctgcaagg cttctggata caccttcacc ggctacaaca tgaactgggt gcgacaggct    120

cctggaaaag ggcttgagtg gatgggaaat attgatcctt actatggtag tactacctat    180

gcacagaagt ttcagggcag ggtcaccatg accgtagaca aatccatcag cacagcctac    240

atggagctga gcaggctgag atctgacgac acggccgtgt attactgtgc gagagagact    300

gggacgaggg ctatggacta ctggggtcaa ggaaccctgg tcaccgtctc ctcagcttcc    360

accaagggcc catccgtctt ccccctggcg ccctgctcca ggagcacctc cgagagcaca    420

gccgccctgg gctgcctggt caaggactac ttccccgaac cggtgacggt gtcgtggaac    480

tcaggcgccc tgaccagcgg cgtgcacacc ttcccggctg tcctacagtc ctcaggactc    540

tactccctca gcagcgtggt gaccgtgccc tccagcagct tgggcacgaa gacctacacc    600

tgcaacgtag atcacaagcc cagcaacacc aaggtggaca agagagttga gtccaaatat    660

ggtcccccat gcccatcatg cccagcacct gagttcctgg ggggaccatc agtcttcctg    720

ttccccccaa aacccaagga cactctcatg atctcccgga cccctgaggt cacgtgcgtg    780

gtggtggacg tgagccagga agaccccgag gtccagttca actggtacgt ggatggcgtg    840

gaggtgcata atgccaagac aaagccgcgg gaggagcagt tcaacagcac gtaccgtgtg    900

gtcagcgtcc tcaccgtcct gcaccaggac tggctgaacg gcaaggagta caagtgcaag    960

gtctccaaca aaggcctccc gtcctccatc gagaaaacca tctccaaagc caaagggcag   1020

ccccgagagc cacaggtgta caccctgccc ccatcccagg aggagatgac caagaaccag   1080

gtcagcctga cctgcctggt caaaggcttc taccccagcg acatcgccgt ggagtgggag   1140

agcaatgggc agccggagaa caactacaag accacgcctc ccgtgctgga ctccgacggc   1200

tccttcttcc tctacagcag gctaaccgtg gacaagagca ggtggcagga ggggaatgtc   1260

ttctcatgct ccgtgatgca tgaggctctg cacaaccact acacacagaa gagcctctcc   1320

ctgtctctgg gtaaatga                                                 1338
```

-continued

<210> SEQ ID NO 95
<211> LENGTH: 645
<212> TYPE: DNA
<213> ORGANISM: Artificial Sequence
<220> FEATURE:
<223> OTHER INFORMATION: HzVSF_V1_LC

<400> SEQUENCE: 95
gacatccaga tgacccagtc tccatcctcc ctgtctgcat ctgtaggaga cagagtcacc 60
atcacttgcc gagcaagtga gaatatttac agtaatttag catggtatca gcagaaacca 120
gggaaagctc ctaagctcct gatctatgtt gcagacaact tagcagatgg ggtcccatca 180
aggttcagcg gcagtggatc tgggacagat ttcactctca ccatcagcag cctgcagcct 240
gaagattttg caacttatta ctgtcaacat ttttatggtt ctcctcggac gttcggcgga 300
gggaccaagg tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gttag 645

<210> SEQ ID NO 96
<211> LENGTH: 1338
<212> TYPE: DNA
<213> ORGANISM: Artificial Sequence
<220> FEATURE:
<223> OTHER INFORMATION: HzVSF_V2_HC

<400> SEQUENCE: 96
gaggtgcagc tggtgcagtc tggggctgag gtgaagaagc ctggggcctc agtgaaggtc 60
tcctgcaagg cttctggata caccttcacc ggctacaaca tgaactgggt gcgacaggct 120
cctggaaaag ggcttgagtg gatgggaaat attgatcctt actatggtag tactacctat 180
gcacagaagt ttcagggcag ggtcaccatg accgtagaca aatccatcag cacagcctac 240
atggagctga gcaggctgag atctgacgac acggccgtgt attactgtgc gagagagact 300
gggacgaggg ctatggacta ctggggtcaa ggaaccctgg tcaccgtctc ctcagcttcc 360
accaagggcc catccgtctt cccccctggcg ccctgctcca ggagcacctc cgagagcaca 420
gccgccctgg gctgcctggt caaggactac ttccccgaac cggtgacggt gtcgtggaac 480
tcaggcgccc tgaccagcgg cgtgcacacc ttcccggctg tcctacagtc ctcaggactc 540
tactccctca gcagcgtggt gaccgtgccc tccagcagct tgggcacgaa gacctacacc 600
tgcaacgtag atcacaagcc cagcaacacc aaggtggaca agagagttga gtccaaatat 660
ggtcccccat gcccatcatg cccagcacct gagttcctgg ggggaccatc agtcttcctg 720
ttccccccaa aacccaagga cactctcatg atctcccgga cccctgaggt cacgtgcgtg 780
gtggtggacg tgagccagga agaccccgag gtccagttca actggtacgt ggatggcgtg 840
gaggtgcata atgccaagac aaagccgcgg gaggagcagt tcaacagcac gtaccgtgtg 900
gtcagcgtcc tcaccgtcct gcaccaggac tggctgaacg gcaaggagta caagtgcaag 960
gtctccaaca aaggcctccc gtcctccatc gagaaaacca tctccaaagc caaagggcag 1020
ccccgagagc cacaggtgta caccctgccc ccatcccagg aggagatgac caagaaccag 1080
gtcagcctga cctgcctggt caaaggcttc taccccagcg acatcgccgt ggagtgggag 1140
agcaatgggc agccggagaa caactacaag accacgcctc ccgtgctgga ctccgacggc 1200
tccttcttcc tctacagcag gctaaccgtg gacaagagca ggtggcagga ggggaatgtc 1260
ttctcatgct ccgtgatgca tgaggctctg cacaaccact acacacagaa gagcctctcc 1320
ctgtctctgg gtaaatga 1338

<210> SEQ ID NO 97
<211> LENGTH: 645
<212> TYPE: DNA
<213> ORGANISM: Artificial Sequence
<220> FEATURE:
<223> OTHER INFORMATION: HzVSF_V2_LC

<400> SEQUENCE: 97
gacatccaga tgacccagtc tccatcctcc ctgtctgcat ctgtaggaga cagagtcacc 60
atcacttgcc gagcaagtga gaatatttac agtaatttag catggtatca gcagaaacca 120
gggaaagctc ctaagctcct gatctatgtt gcagacaact taggagatgg ggtcccatca 180
aggttcagcg gcagtggatc tgggacagat ttcactctca ccatcagcag cctgcagcct 240
gaagattttg caacttatta ctgtcaacat ttttatggtt ctcctcggac gttcggcgga 300
gggaccaagg tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gttag 645

<210> SEQ ID NO 98
<211> LENGTH: 1338
<212> TYPE: DNA
<213> ORGANISM: Artificial Sequence
<220> FEATURE:
<223> OTHER INFORMATION: HzVSF_V3_HC

<400> SEQUENCE: 98
gaggtgcagc tggtgcagtc tggggctgag gtgaagaagc ctggggcctc agtgaaggtc 60
tcctgcaagg cttctggata caccttcacc ggctacaaca tgaactgggt gcgacaggct 120
cctggaaaag ggcttgagtg gatgggaaat attgatcctt actatggtag tactacctat 180
gcacagaagt ttcagggcag ggtcaccatg accgtagaca aatccatcag cacagcctac 240
atggagctga gcaggctgag atctgacgac acggccgtgt attactgtgc gagagagact 300
gggacgaggg ctatggacta ctggggtcaa ggaaccctgg tcaccgtctc ctcagcttcc 360
accaagggcc catccgtctt ccccctggcg ccctgctcca ggagcacctc cgagagcaca 420
gccgccctgg gctgcctggt caaggactac ttccccgaac cggtgacggt gtcgtggaac 480
tcaggcgccc tgaccagcgg cgtgcacacc ttcccggctg tcctacagtc ctcaggactc 540
tactccctca gcagcgtggt gaccgtgccc tccagcagct tgggcacgaa gacctacacc 600
tgcaacgtag atcacaagcc cagcaacacc aaggtggaca agagagttga gtccaaatat 660
ggtcccccat gcccatcatg cccagcacct gagttcctgg ggggaccatc agtcttcctg 720
ttccccccaa aacccaagga cactctcatg atctcccgga cccctgaggt cacgtgcgtg 780
gtggtggacg tgagccagga agaccccgag gtccagttca actggtacgt ggatggcgtg 840
gaggtgcata atgccaagac aaagccgcgg gaggagcagt tcaacagcac gtaccgtgtg 900

```
gtcagcgtcc tcaccgtcct gcaccaggac tggctgaacg gcaaggagta caagtgcaag    960

gtctccaaca aaggcctccc gtcctccatc gagaaaacca tctccaaagc caaagggcag   1020

ccccgagagc cacaggtgta caccctgccc ccatcccagg aggagatgac caagaaccag   1080

gtcagcctga cctgcctggt caaaggcttc taccccagcg acatcgccgt ggagtgggag   1140

agcaatgggc agccggagaa caactacaag accacgcctc ccgtgctgga ctccgacggc   1200

tccttcttcc tctacagcag gctaaccgtg gacaagagca ggtggcagga ggggaatgtc   1260

ttctcatgct ccgtgatgca tgaggctctg cacaaccact acacacagaa gagcctctcc   1320

ctgtctctgg gtaaatga                                                 1338
```

<210> SEQ ID NO 99
<211> LENGTH: 645
<212> TYPE: DNA
<213> ORGANISM: Artificial Sequence
<220> FEATURE:
<223> OTHER INFORMATION: HzVSF_V3_LC

<400> SEQUENCE: 99

```
gacatccaga tgacccagtc tccatcctcc ctgtctgcat ctgtaggaga cagagtcacc     60

atcacttgcc gagcaagtga gaatatttac agtaatttag catggtatca gcagaaacca    120

gggaaagctc ctaagctcct gatctatgtt gcagacaacc gcggagatgg ggtcccatca    180

aggttcagcg gcagtggatc tgggacagat ttcactctca ccatcagcag cctgcagcct    240

gaagattttg caacttatta ctgtcaacat ttttatggtt ctcctcggac gttcggcgga    300

gggaccaagg tggagatcaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gttag                    645
```

<210> SEQ ID NO 100
<211> LENGTH: 1338
<212> TYPE: DNA
<213> ORGANISM: Artificial Sequence
<220> FEATURE:
<223> OTHER INFORMATION: HzVSF_V4_HC

<400> SEQUENCE: 100

```
gaggtgcagc tggtgcagtc tggggctgag gtgaagaagc ctggggcctc agtgaaggtc     60

tcctgcaagg cttctggata caccttcacc ggctacaaca tgaactgggt gcgacaggct    120

cctggaaaag ggcttgagtg gatgggaaat attgatcctt actatggtag tactacctat    180

gcacagaagt ttcagggcag ggtcaccatg accgtagaca aatccatcag cacagcctac    240

atggagctga gcaggctgag atctgacgac acggccgtgt attactgtgc gagagagact    300

gggacgaggg ctatggacta ctggggtcaa ggaaccctgg tcaccgtctc ctcagcttcc    360

accaagggcc catccgtctt ccccctggcg ccctgctcca ggagcacctc cgagagcaca    420

gccgccctgg gctgcctggt caaggactac ttccccgaac cggtgacggt gtcgtggaac    480

tcaggcgccc tgaccagcgg cgtgcacacc ttcccggctg tcctacagtc ctcaggactc    540

tactccctca gcagcgtggt gaccgtgccc tccagcagct tgggcacgaa gacctacacc    600
```

-continued

```
tgcaacgtag atcacaagcc cagcaacacc aaggtggaca agagagttga gtccaaatat    660

ggtcccccat gcccatcatg cccagcacct gagttcctgg ggggaccatc agtcttcctg    720

ttccccccaa aacccaagga cactctcatg atctcccgga cccctgaggt cacgtgcgtg    780

gtggtggacg tgagccagga agaccccgag gtccagttca actggtacgt ggatggcgtg    840

gaggtgcata atgccaagac aaagccgcgg gaggagcagt tcaacagcac gtaccgtgtg    900

gtcagcgtcc tcaccgtcct gcaccaggac tggctgaacg gcaaggagta caagtgcaag    960

gtctccaaca aaggcctccc gtcctccatc gagaaaacca tctccaaagc caaagggcag   1020

ccccgagagc cacaggtgta caccctgccc ccatcccagg aggagatgac caagaaccag   1080

gtcagcctga cctgcctggt caaaggcttc taccccagcg acatcgccgt ggagtgggag   1140

agcaatgggc agccggagaa caactacaag accacgcctc ccgtgctgga ctccgacggc   1200

tccttcttcc tctacagcag gctaaccgtg gacaagagca ggtggcagga ggggaatgtc   1260

ttctcatgct ccgtgatgca tgaggctctg cacaaccact acacacagaa gagcctctcc   1320

ctgtctctgg gtaaatga                                                 1338
```

```
<210> SEQ ID NO 101
<211> LENGTH: 645
<212> TYPE: DNA
<213> ORGANISM: Artificial Sequence
<220> FEATURE:
<223> OTHER INFORMATION: HzVSF_V4_LC

<400> SEQUENCE: 101

gacatccaga tgacccagtc tccatcctcc ctgtctgcat ctgtaggaga cagagtcacc     60

atcacttgcc gagcaagtga gaatatttac agtaatttag catggtatca gcagaaacca    120

gggaaagctc ctaagctcct gatctatgtt gcagacaacc gcggagatgg ggtcccatca    180

aggttcagcg gcagtggatc tgggacagat ttcactctca ccatcagcag cctgcagcct    240

gaagattttg caacttatta ctgtcaacat ttttatggta cccctcggac gttcggcgga    300

gggaccaagg tggagatcaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gttag                   645
```

```
<210> SEQ ID NO 102
<211> LENGTH: 1338
<212> TYPE: DNA
<213> ORGANISM: Artificial Sequence
<220> FEATURE:
<223> OTHER INFORMATION: HzVSF_V5_HC

<400> SEQUENCE: 102

gaggtgcagc tggtgcagtc tggggctgag gtgaagaagc ctggggcctc agtgaaggtc     60

tcctgcaagg cttctggata caccttcacc ggctacaaca tgaactgggt gcgacaggct    120

cctggaaaag ggcttgagtg gatgggaaat attgatcctt actatggtag tgatacctat    180

gcacagaagt ttcagggcag ggtcaccatg accgtagaca aatccatcag cacagcctac    240

atggagctga gcaggctgag atctgacgac acggccgtgt attactgtgc gagagagact    300

gggacgaggg ctatggacta ctggggtcaa ggaaccctgg tcaccgtctc ctcagcttcc    360
```

-continued accaagggcc catccgtctt ccccctggcg ccctgctcca ggagcacctc cgagagcaca 420
gccgccctgg gctgcctggt caaggactac ttccccgaac cggtgacggt gtcgtggaac 480
tcaggcgccc tgaccagcgg cgtgcacacc ttcccggctg tcctacagtc ctcaggactc 540
tactccctca gcagcgtggt gaccgtgccc tccagcagct tgggcacgaa gacctacacc 600
tgcaacgtag atcacaagcc cagcaacacc aaggtggaca agagagttga gtccaaatat 660
ggtcccccat gcccatcatg cccagcacct gagttcctgg ggggaccatc agtcttcctg 720
ttccccccaa aacccaagga cactctcatg atctcccgga cccctgaggt cacgtgcgtg 780
gtggtggacg tgagccagga agaccccgag gtccagttca actggtacgt ggatggcgtg 840
gaggtgcata atgccaagac aaagccgcgg gaggagcagt tcaacagcac gtaccgtgtg 900
gtcagcgtcc tcaccgtcct gcaccaggac tggctgaacg gcaaggagta caagtgcaag 960
gtctccaaca aaggcctccc gtcctccatc gagaaaacca tctccaaagc caaagggcag 1020
ccccgagagc cacaggtgta caccctgccc ccatcccagg aggagatgac caagaaccag 1080
gtcagcctga cctgcctggt caaaggcttc taccccagcg acatcgccgt ggagtgggag 1140
agcaatgggc agccggagaa caactacaag accacgcctc ccgtgctgga ctccgacggc 1200
tccttcttcc tctacagcag gctaaccgtg gacaagagca ggtggcagga ggggaatgtc 1260
ttctcatgct ccgtgatgca tgaggctctg cacaaccact acacacagaa gagcctctcc 1320
ctgtctctgg gtaaatga 1338

<210> SEQ ID NO 103
<211> LENGTH: 645
<212> TYPE: DNA
<213> ORGANISM: Artificial Sequence
<220> FEATURE:
<223> OTHER INFORMATION: HzVSF_V5_LC

<400> SEQUENCE: 103
gacatccaga tgacccagtc tccatcctcc ctgtctgcat ctgtaggaga cagagtcacc 60
atcacttgcc gagcaagtga gaatatttac agtaatttag catggtatca gcagaaacca 120
gggaaagctc ctaagctcct gatctatgtt gcaacaaact tagcagatgg ggtcccatca 180
aggttcagcg gcagtggatc tgggacagat ttcactctca ccatcagcag cctgcagcct 240
gaagattttg caacttatta ctgtcaacat ttttatggtt ctcctcggac gttcggcgga 300
gggaccaagg tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gttag 645

<210> SEQ ID NO 104
<211> LENGTH: 1338
<212> TYPE: DNA
<213> ORGANISM: Artificial Sequence
<220> FEATURE:
<223> OTHER INFORMATION: HzVSF_V6_HC

<400> SEQUENCE: 104
gaggtgcagc tggtgcagtc tggggctgag gtgaagaagc ctggggcctc agtgaaggtc 60

-continued

```
tcctgcaagg cttctggata caccttcacc ggctacaaca tgaactgggt gcgacaggct    120

cctggaaaag ggcttgagtg gatgggaaat attgatcctt actatggtag tactacctat    180

gcacagaagt ttcagggcag ggtcaccatg accgtagaca cttccgcaag cacagcctac    240

atggagctga gcaggctgag atctgacgac acggccgtgt attactgtgc gagagagact    300

gggacgaggg ctatggacta ctggggtcaa ggaaccctgg tcaccgtctc ctcagcttcc    360

accaagggcc catccgtctt ccccctggcg ccctgctcca ggagcacctc cgagagcaca    420

gccgccctgg gctgcctggt caaggactac ttccccgaac cggtgacggt gtcgtggaac    480

tcaggcgccc tgaccagcgg cgtgcacacc ttcccggctg tcctacagtc ctcaggactc    540

tactccctca gcagcgtggt gaccgtgccc tccagcagct tgggcacgaa gacctacacc    600

tgcaacgtag atcacaagcc cagcaacacc aaggtggaca agagagttga gtccaaatat    660

ggtcccccat gcccatcatg cccagcacct gagttcctgg ggggaccatc agtcttcctg    720

ttccccccaa aacccaagga cactctcatg atctcccgga cccctgaggt cacgtgcgtg    780

gtggtggacg tgagccagga agaccccgag gtccagttca actggtacgt ggatggcgtg    840

gaggtgcata atgccaagac aaagccgcgg gaggagcagt tcaacagcac gtaccgtgtg    900

gtcagcgtcc tcaccgtcct gcaccaggac tggctgaacg gcaaggagta caagtgcaag    960

gtctccaaca aaggcctccc gtcctccatc gagaaaacca tctccaaagc caaagggcag   1020

ccccgagagc cacaggtgta caccctgccc ccatcccagg aggagatgac caagaaccag   1080

gtcagcctga cctgcctggt caaaggcttc taccccagcg acatcgccgt ggagtgggag   1140

agcaatgggc agccggagaa caactacaag accacgcctc ccgtgctgga ctccgacggc   1200

tccttcttcc tctacagcag gctaaccgtg gacaagagca ggtggcagga ggggaatgtc   1260

ttctcatgct ccgtgatgca tgaggctctg cacaaccact acacacagaa gagcctctcc   1320

ctgtctctgg gtaaatga                                                 1338
```

<210> SEQ ID NO 105
<211> LENGTH: 645
<212> TYPE: DNA
<213> ORGANISM: Artificial Sequence
<220> FEATURE:
<223> OTHER INFORMATION: HzVSF_V6_LC

<400> SEQUENCE: 105

```
gacatccaga tgacccagtc tccatcctcc ctgtctgcat ctgtaggaga cagagtcacc     60

atcacttgcc gagcaagtga gaatatttac agtaatttag catggtatca gcagaaacca    120

gggaaagctc ctaagctcct gatctatgtt gcaacaaact tagcagatgg ggtcccatca    180

aggttcagcg gcagtggatc tgggacagat ttcactctca ccatcagcag cctgcagcct    240

gaagattttg caacttatta ctgtcaacat ttttatggtt ctcctcggac gttcggcgga    300

gggaccaagg tggagatcaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gttag                    645
```

<210> SEQ ID NO 106
<211> LENGTH: 1338

<212> TYPE: DNA
<213> ORGANISM: Artificial Sequence
<220> FEATURE:
<223> OTHER INFORMATION: HzVSF_V7_HC

<400> SEQUENCE: 106
gaggtgcagc tggtgcagtc tggggctgag gtgaagaagc ctggggcctc agtgaaggtc 60
tcctgcaagg cttctggata caccttcacc ggctacaaca tgaactgggt gcgacaggct 120
cctggaaaag ggcttgagtg gatgggaaat attgatcctt actatggtag tgatacctat 180
gcacagaagt ttcagggcag ggtcaccatg accgtagaca cwtccgsmag cacagcctac 240
atggagctga gcaggctgag atctgacgac acggccgtgt attactgtgc gagagagact 300
gggacgaggg ctatggacta ctggggtcaa ggaaccctgg tcaccgtctc ctcagcttcc 360
accaagggcc catccgtctt cccccctggcg ccctgctcca ggagcacctc cgagagcaca 420
gccgccctgg gctgcctggt caaggactac ttccccgaac cggtgacggt gtcgtggaac 480
tcaggcgccc tgaccagcgg cgtgcacacc ttcccggctg tcctacagtc ctcaggactc 540
tactccctca gcagcgtggt gaccgtgccc tccagcagct tgggcacgaa gacctacacc 600
tgcaacgtag atcacaagcc cagcaacacc aaggtggaca agagagttga gtccaaatat 660
ggtcccccat gcccatcatg cccagcacct gagttcctgg ggggaccatc agtcttcctg 720
ttccccccaa aacccaagga cactctcatg atctcccgga cccctgaggt cacgtgcgtg 780
gtggtggacg tgagccagga agaccccgag gtccagttca actggtacgt ggatggcgtg 840
gaggtgcata atgccaagac aaagccgcgg gaggagcagt tcaacagcac gtaccgtgtg 900
gtcagcgtcc tcaccgtcct gcaccaggac tggctgaacg gcaaggagta caagtgcaag 960
gtctccaaca aaggcctccc gtcctccatc gagaaaacca tctccaaagc caaagggcag 1020
ccccgagagc cacaggtgta caccctgccc ccatcccagg aggagatgac caagaaccag 1080
gtcagcctga cctgcctggt caaaggcttc taccccagcg acatcgccgt ggagtgggag 1140
agcaatgggc agccggagaa caactacaag accacgcctc ccgtgctgga ctccgacggc 1200
tccttcttcc tctacagcag gctaaccgtg gacaagagca ggtggcagga ggggaatgtc 1260
ttctcatgct ccgtgatgca tgaggctctg cacaaccact acacacagaa gagcctctcc 1320
ctgtctctgg gtaaatga 1338

<210> SEQ ID NO 107
<211> LENGTH: 645
<212> TYPE: DNA
<213> ORGANISM: Artificial Sequence
<220> FEATURE:
<223> OTHER INFORMATION: HzVSF_V7_LC

<400> SEQUENCE: 107
gacatccaga tgacccagtc tccatcctcc ctgtctgcat ctgtaggaga cagagtcacc 60
atcacttgcc gagcaagtga gaatatttac agtaatttag catggtatca gcagaaacca 120
gggaaagctc ctaagctcct gatctatgtt gcaacaaact tagcagatgg ggtcccatca 180
aggttcagcg gcagtggatc tgggacagat ttcactctca ccatcagcag cctgcagcct 240
gaagattttg caacttatta ctgtcaacat tttatggtt ctcctcggac gttcggcgga 300
gggaccaagg tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gttag 645

<210> SEQ ID NO 108
<211> LENGTH: 1338
<212> TYPE: DNA
<213> ORGANISM: Artificial Sequence
<220> FEATURE:
<223> OTHER INFORMATION: HzVSF_V8_HC

<400> SEQUENCE: 108
gaggtgcagc tggtgcagtc tggggctgag gtgaagaagc ctggggcctc agtgaaggtc 60
tcctgcaagg cttctggata caccttcacc ggctacaaca tgaactgggt gcgacaggct 120
cctggaaaag ggcttgagtg gatgggaaat attgatcctt actatggtag tgatacctat 180
gcacagaagt ttcagggcag ggtcaccatg accgtagaca cttccgcaag cacagcctac 240
atggagctga gcaggctgag atctgacgac acggccgtgt attactgtgc gagagagact 300
gggaataggg ctatggacta ctggggtcaa ggaaccctgg tcaccgtctc ctcagcttcc 360
accaagggcc catccgtctt ccccctggcg ccctgctcca ggagcacctc cgagagcaca 420
gccgccctgg gctgcctggt caaggactac ttccccgaac cggtgacggt gtcgtggaac 480
tcaggcgccc tgaccagcgg cgtgcacacc ttcccggctg tcctacagtc ctcaggactc 540
tactccctca gcagcgtggt gaccgtgccc tccagcagct tgggcacgaa gacctacacc 600
tgcaacgtag atcacaagcc cagcaacacc aaggtggaca agagagttga gtccaaatat 660
ggtcccccat gcccatcatg cccagcacct gagttcctgg ggggaccatc agtcttcctg 720
ttccccccaa aacccaagga cactctcatg atctcccgga cccctgaggt cacgtgcgtg 780
gtggtggacg tgagccagga agaccccgag gtccagttca actggtacgt ggatggcgtg 840
gaggtgcata atgccaagac aaagccgcgg gaggagcagt tcaacagcac gtaccgtgtg 900
gtcagcgtcc tcaccgtcct gcaccaggac tggctgaacg gcaaggagta caagtgcaag 960
gtctccaaca aaggcctccc gtcctccatc gagaaaacca tctccaaagc caaagggcag 1020
ccccgagagc cacaggtgta caccctgccc ccatcccagg aggagatgac caagaaccag 1080
gtcagcctga cctgcctggt caaaggcttc taccccagcg acatcgccgt ggagtgggag 1140
agcaatgggc agccggagaa caactacaag accacgcctc ccgtgctgga ctccgacggc 1200
tccttcttcc tctacagcag gctaaccgtg gacaagagca ggtggcagga ggggaatgtc 1260
ttctcatgct ccgtgatgca tgaggctctg cacaaccact acacacagaa gagcctctcc 1320
ctgtctctgg gtaaatga 1338

<210> SEQ ID NO 109
<211> LENGTH: 645
<212> TYPE: DNA
<213> ORGANISM: Artificial Sequence
<220> FEATURE:
<223> OTHER INFORMATION: HzVSF_V8_LC

<400> SEQUENCE: 109
gacatccaga tgacccagtc tccatcctcc ctgtctgcat ctgtaggaga cagagtcacc 60
atcacttgcc gagcaagtga gaatatttac agtaatttag catggtatca gcagaaacca 120
gggaaagctc ctaagctcct gatctatgtt gcaacaaact tagcagatgg ggtcccatca 180
aggttcagcg gcagtggatc tgggacagat ttcactctca ccatcagcag cctgcagcct 240
gaagattttg caacttatta ctgtcaacat ttttatggtt ctcctcggac gttcggcgga 300
gggaccaagg tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gttag 645

<210> SEQ ID NO 110
<211> LENGTH: 1338
<212> TYPE: DNA
<213> ORGANISM: Artificial Sequence
<220> FEATURE:
<223> OTHER INFORMATION: HzVSF_V9_HC

<400> SEQUENCE: 110
gaggtgcagc tggtgcagtc tggggctgag gtgaagaagc ctggggcctc agtgaaggtc 60
tcctgcaagg cttctggata caccttcacc ggctacaaca tgaactgggt gcgacaggct 120
cctggaaaag ggcttgagtg gatgggaaat attgatcctt actatggtag tgatacctat 180
gcacagaagt ttcagggcag ggtcaccatg accgtagaca cttccgcaag cacagcctac 240
atggagctga gcaggctgag atctgacgac acggccgtgt attactgtgc gagagagact 300
gggacgaggg ctatggacta ctggggtcaa ggaaccctgg tcaccgtctc ctcagcttcc 360
accaagggcc catccgtctt cccccctggcg ccctgctcca ggagcacctc cgagagcaca 420
gccgccctgg gctgcctggt caaggactac ttccccgaac cggtgacggt gtcgtggaac 480
tcaggcgccc tgaccagcgg cgtgcacacc ttcccggctg tcctacagtc ctcaggactc 540
tactccctca gcagcgtggt gaccgtgccc tccagcagct tgggcacgaa gacctacacc 600
tgcaacgtag atcacaagcc cagcaacacc aaggtggaca agagagttga gtccaaatat 660
ggtcccccat gcccatcatg cccagcacct gagttcctgg ggggaccatc agtcttcctg 720
ttccccccaa aacccaagga cactctcatg atctcccgga cccctgaggt cacgtgcgtg 780
gtggtggacg tgagccagga agaccccgag gtccagttca actggtacgt ggatggcgtg 840
gaggtgcata atgccaagac aaagccgcgg gaggagcagt tcaacagcac gtaccgtgtg 900
gtcagcgtcc tcaccgtcct gcaccaggac tggctgaacg gcaaggagta caagtgcaag 960
gtctccaaca aaggcctccc gtcctccatc gagaaaacca tctccaaagc caaagggcag 1020
ccccgagagc cacaggtgta caccctgccc ccatcccagg aggagatgac caagaaccag 1080
gtcagcctga cctgcctggt caaaggcttc taccccagcg acatcgccgt ggagtgggag 1140
agcaatgggc agccggagaa caactacaag accacgcctc ccgtgctgga ctccgacggc 1200
tccttcttcc tctacagcag gctaaccgtg gacaagagca ggtggcagga ggggaatgtc 1260
ttctcatgct ccgtgatgca tgaggctctg cacaaccact acacacagaa gagcctctcc 1320
ctgtctctgg gtaaatga 1338

<210> SEQ ID NO 111
<211> LENGTH: 645
<212> TYPE: DNA
<213> ORGANISM: Artificial Sequence
<220> FEATURE:
<223> OTHER INFORMATION: HzVSF_V9_LC

<400> SEQUENCE: 111
gacatccaga tgacccagtc tccatcctcc ctgtctgcat ctgtaggaga cagagtcacc 60
atcacttgcc gagcaagtga gaatatttac agtaatttag catggtatca gcagaaacca 120
gggaaagctc ctaagctcct gatctatgtt gcagacaacc gcggagatgg ggtcccatca 180
aggttcagcg gcagtggatc tgggacagat ttcactctca ccatcagcag cctgcagcct 240
gaagattttg caacttatta ctgtcaacat ttttatggtt ctcctcggac gttcggcgga 300
gggaccaagg tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gttag 645

<210> SEQ ID NO 112
<211> LENGTH: 1338
<212> TYPE: DNA
<213> ORGANISM: Artificial Sequence
<220> FEATURE:
<223> OTHER INFORMATION: HzVSF_V10_HC

<400> SEQUENCE: 112
gaggtgcagc tggtgcagtc tggggctgag gtgaagaagc ctggggcctc agtgaaggtc 60
tcctgcaagg cttctggata caccttcacc ggctacaaca tgaactgggt gcgacaggct 120
cctggaaaag ggcttgagtg gatgggaaat attgatcctt actatggtag tgatacctat 180
gcacagaagt ttcagggcag ggtcaccatg accgtagaca cttccgcaag cacagcctac 240
atggagctga gcaggctgag atctgacgac acggccgtgt attactgtgc gagagagact 300
gggaataggg ctatggacta ctggggtcaa ggaaccctgg tcaccgtctc ctcagcttcc 360
accaagggcc catccgtctt cccccctggcg ccctgctcca ggagcacctc cgagagcaca 420
gccgccctgg gctgcctggt caaggactac ttccccgaac cggtgacggt gtcgtggaac 480
tcaggcgccc tgaccagcgg cgtgcacacc ttcccggctg tcctacagtc ctcaggactc 540
tactccctca gcagcgtggt gaccgtgccc tccagcagct tgggcacgaa gacctacacc 600
tgcaacgtag atcacaagcc cagcaacacc aaggtggaca agagagttga gtccaaatat 660
ggtcccccat gcccatcatg cccagcacct gagttcctgg ggggaccatc agtcttcctg 720
ttccccccaa aacccaagga cactctcatg atctcccgga cccctgaggt cacgtgcgtg 780
gtggtggacg tgagccagga agaccccgag gtccagttca actggtacgt ggatggcgtg 840
gaggtgcata atgccaagac aaagccgcgg gaggagcagt tcaacagcac gtaccgtgtg 900
gtcagcgtcc tcaccgtcct gcaccaggac tggctgaacg gcaaggagta caagtgcaag 960
gtctccaaca aaggcctccc gtcctccatc gagaaaacca tctccaaagc caaagggcag 1020
ccccgagagc cacaggtgta caccctgccc ccatcccagg aggagatgac caagaaccag 1080
gtcagcctga cctgcctggt caaaggcttc taccccagcg acatcgccgt ggagtgggag 1140
agcaatgggc agccggagaa caactacaag accacgcctc ccgtgctgga ctccgacggc 1200
tccttcttcc tctacagcag gctaaccgtg gacaagagca ggtggcagga ggggaatgtc 1260
ttctcatgct ccgtgatgca tgaggctctg cacaaccact acacacagaa gagcctctcc 1320
ctgtctctgg gtaaatga 1338

<210> SEQ ID NO 113
<211> LENGTH: 645
<212> TYPE: DNA
<213> ORGANISM: Artificial Sequence
<220> FEATURE:
<223> OTHER INFORMATION: HzVSF_V10_LC

<400> SEQUENCE: 113
gacatccaga tgacccagtc tccatcctcc ctgtctgcat ctgtaggaga cagagtcacc 60
atcacttgcc gagcaagtga gaatatttac agtaatttag catggtatca gcagaaacca 120
gggaaagctc ctaagctcct gatctatgtt gcagacaacc gcggagatgg ggtcccatca 180
aggttcagcg gcagtggatc tgggacagat ttcactctca ccatcagcag cctgcagcct 240
gaagattttg caacttatta ctgtcaacat ttttatggtt ctcctcggac gttcggcgga 300
gggaccaagg tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gttag 645

<210> SEQ ID NO 114
<211> LENGTH: 1338
<212> TYPE: DNA
<213> ORGANISM: Artificial Sequence
<220> FEATURE:
<223> OTHER INFORMATION: HzVSF_V11_HC

<400> SEQUENCE: 114
gaggtgcagc tggtgcagtc tggggctgag gtgaagaagc ctggggcctc agtgaaggtc 60
tcctgcaagg cttctggata caccttcacc ggctacaaca tgaactgggt gcgacaggct 120
cctggaaaag ggcttgagtg gatgggaaat attgatcctt actatggtag tgatacctat 180
gcacagaagt ttcagggcag ggtcaccatg accgtagaca cttccgcaag cacagcctac 240
atggagctga gcaggctgag atctgacgac acggccgtgt attactgtgc gagagagact 300
gggacgaggg ctatggacta ctggggtcaa ggaaccctgg tcaccgtctc ctcagcttcc 360
accaagggcc catccgtctt cccctggcg ccctgctcca ggagcacctc cgagagcaca 420
gccgccctgg gctgcctggt caaggactac ttccccgaac cggtgacggt gtcgtggaac 480
tcaggcgccc tgaccagcgg cgtgcacacc ttcccggctg tcctacagtc ctcaggactc 540
tactccctca gcagcgtggt gaccgtgccc tccagcagct tgggcacgaa gacctacacc 600
tgcaacgtag atcacaagcc cagcaacacc aaggtggaca agagagttga gtccaaatat 660
ggtcccccat gcccatcatg cccagcacct gagttcctgg ggggaccatc agtcttcctg 720
ttccccccaa aacccaagga cactctcatg atctcccgga cccctgaggt cacgtgcgtg 780
gtggtggacg tgagccagga agaccccgag gtccagttca actggtacgt ggatggcgtg 840
gaggtgcata atgccaagac aaagccgcgg gaggagcagt tcaacagcac gtaccgtgtg 900
gtcagcgtcc tcaccgtcct gcaccaggac tggctgaacg gcaaggagta caagtgcaag 960
gtctccaaca aaggcctccc gtcctccatc gagaaaacca tctccaaagc caaagggcag 1020
ccccgagagc cacaggtgta caccctgccc ccatcccagg aggagatgac caagaaccag 1080
gtcagcctga cctgcctggt caaaggcttc taccccagcg acatcgccgt ggagtgggag 1140
agcaatgggc agccggagaa caactacaag accacgcctc ccgtgctgga ctccgacggc 1200
tccttcttcc tctacagcag gctaaccgtg gacaagagca ggtggcagga ggggaatgtc 1260
ttctcatgct ccgtgatgca tgaggctctg cacaaccact acacacagaa gagcctctcc 1320
ctgtctctgg gtaaatga 1338

<210> SEQ ID NO 115
<211> LENGTH: 645
<212> TYPE: DNA
<213> ORGANISM: Artificial Sequence
<220> FEATURE:
<223> OTHER INFORMATION: HzVSF_V11_LC

<400> SEQUENCE: 115
gacatccaga tgacccagtc tccatcctcc ctgtctgcat ctgtaggaga cagagtcacc 60
atcacttgcc gagcaagtga gaatatttac agtaatttag catggtatca gcagaaacca 120
gggaaagctc ctaagctcct gatctatgtt gcagacaacc gcggagatgg ggtcccatca 180
aggttcagcg gcagtggatc tgggacagat ttcactctca ccatcagcag cctgcagcct 240
gaagattttg caacttatta ctgtcaacat ttttatggta cccctcggac gttcggcgga 300
gggaccaagg tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gttag 645

<210> SEQ ID NO 116
<211> LENGTH: 1338
<212> TYPE: DNA
<213> ORGANISM: Artificial Sequence
<220> FEATURE:
<223> OTHER INFORMATION: HzVSF_V12_HC

<400> SEQUENCE: 116
gaggtgcagc tggtgcagtc tggggctgag gtgaagaagc ctggggcctc agtgaaggtc 60
tcctgcaagg cttctggata caccttcacc ggctacaaca tgaactgggt gcgacaggct 120
cctggaaaag ggcttgagtg gatgggaaat attgatcctt actatggtag tgatacctat 180
gcacagaagt ttcagggcag ggtcaccatg accgtagaca cttccgcaag cacagcctac 240
atggagctga gcaggctgag atctgacgac acggccgtgt attactgtgc gagagagact 300
gggaataggg ctatggacta ctggggtcaa ggaaccctgg tcaccgtctc ctcagcttcc 360
accaagggcc catccgtctt ccccctggcg ccctgctcca ggagcacctc cgagagcaca 420
gccgccctgg gctgcctggt caaggactac ttccccgaac cggtgacggt gtcgtggaac 480
tcaggcgccc tgaccagcgg cgtgcacacc ttcccggctg tcctacagtc ctcaggactc 540
tactccctca gcagcgtggt gaccgtgccc tccagcagct tgggcacgaa gacctacacc 600
tgcaacgtag atcacaagcc cagcaacacc aaggtggaca agagagttga gtccaaatat 660
ggtcccccat gcccatcatg cccagcacct gagttcctgg ggggaccatc agtcttcctg 720
ttccccccaa aacccaagga cactctcatg atctcccgga cccctgaggt cacgtgcgtg 780
gtggtggacg tgagccagga agaccccgag gtccagttca actggtacgt ggatggcgtg 840

```
gaggtgcata atgccaagac aaagccgcgg gaggagcagt tcaacagcac gtaccgtgtg    900

gtcagcgtcc tcaccgtcct gcaccaggac tggctgaacg gcaaggagta caagtgcaag    960

gtctccaaca aaggcctccc gtcctccatc gagaaaacca tctccaaagc caaagggcag   1020

ccccgagagc cacaggtgta caccctgccc ccatcccagg aggagatgac caagaaccag   1080

gtcagcctga cctgcctggt caaaggcttc taccccagcg acatcgccgt ggagtgggag   1140

agcaatgggc agccggagaa caactacaag accacgcctc ccgtgctgga ctccgacggc   1200

tccttcttcc tctacagcag gctaaccgtg gacaagagca ggtggcagga ggggaatgtc   1260

ttctcatgct ccgtgatgca tgaggctctg cacaaccact acacacagaa gagcctctcc   1320

ctgtctctgg gtaaatga                                                 1338
```

<210> SEQ ID NO 117
<211> LENGTH: 645
<212> TYPE: DNA
<213> ORGANISM: Artificial Sequence
<220> FEATURE:
<223> OTHER INFORMATION: HzVSF_V12_LC

<400> SEQUENCE: 117

```
gacatccaga tgacccagtc tccatcctcc ctgtctgcat ctgtaggaga cagagtcacc     60

atcacttgcc gagcaagtga gaatatttac agtaatttag catggtatca gcagaaacca    120

gggaaagctc ctaagctcct gatctatgtt gcagacaacc gcggagatgg ggtcccatca    180

aggttcagcg gcagtggatc tgggacagat ttcactctca ccatcagcag cctgcagcct    240

gaagattttg caacttatta ctgtcaacat tttatggta  cccctcggac gttcggcgga    300

gggaccaagg tggagatcaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gttag                    645
```

<210> SEQ ID NO 118
<211> LENGTH: 1338
<212> TYPE: DNA
<213> ORGANISM: Artificial Sequence
<220> FEATURE:
<223> OTHER INFORMATION: HzVSF_V13_HC

<400> SEQUENCE: 118

```
gaggtgcagc tggtgcagtc tggggctgag gtgaagaagc ctggggcctc agtgaaggtc     60

tcctgcaagg cttctggata caccttcacc ggctacaaca tgaactgggt gcgacaggct    120

cctggaaaag ggcttgagtg gatgggaaat attgatcctt actatggtag tgatacctat    180

gcacagaagt ttcagggcag ggtcaccatg accgtagaca aatccatcag cacagcctac    240

atggagctga gcaggctgag atctgacgac acggccgtgt attactgtgc gagagagact    300

gggacgaggg ctatggacta ctggggtcaa ggaaccctgg tcaccgtctc ctcagcttcc    360

accaagggcc catccgtctt ccccctggcg ccctgctcca ggagcacctc cgagagcaca    420

gccgccctgg gctgcctggt caaggactac ttccccgaac cggtgacggt gtcgtggaac    480

tcaggcgccc tgaccagcgg cgtgcacacc ttcccggctg tcctacagtc ctcaggactc    540
```

```
tactccctca gcagcgtggt gaccgtgccc tccagcagct tgggcacgaa gacctacacc    600

tgcaacgtag atcacaagcc cagcaacacc aaggtggaca agagagttga gtccaaatat    660

ggtcccccat gcccatcatg cccagcacct gagttcctgg ggggaccatc agtcttcctg    720

ttccccccaa aacccaagga cactctcatg atctcccgga cccctgaggt cacgtgcgtg    780

gtggtggacg tgagccagga agaccccgag gtccagttca actggtacgt ggatggcgtg    840

gaggtgcata atgccaagac aaagccgcgg gaggagcagt tcaacagcac gtaccgtgtg    900

gtcagcgtcc tcaccgtcct gcaccaggac tggctgaacg gcaaggagta caagtgcaag    960

gtctccaaca aaggcctccc gtcctccatc gagaaaacca tctccaaagc caaagggcag   1020

ccccgagagc cacaggtgta caccctgccc ccatcccagg aggagatgac caagaaccag   1080

gtcagcctga cctgcctggt caaaggcttc taccccagcg acatcgccgt ggagtgggag   1140

agcaatgggc agccggagaa caactacaag accacgcctc ccgtgctgga ctccgacggc   1200

tccttcttcc tctacagcag gctaaccgtg gacaagagca ggtggcagga ggggaatgtc   1260

ttctcatgct ccgtgatgca tgaggctctg cacaaccact acacacagaa gagcctctcc   1320

ctgtctctgg gtaaatga                                                  1338
```

<210> SEQ ID NO 119
<211> LENGTH: 645
<212> TYPE: DNA
<213> ORGANISM: Artificial Sequence
<220> FEATURE:
<223> OTHER INFORMATION: HzVSF_V13_LC

<400> SEQUENCE: 119

```
gacatccaga tgacccagtc tccatcctcc ctgtctgcat ctgtaggaga cagagtcacc     60

atcacttgcc gagcaagtga gaatatttac agtaatttag catggtatca gcagaaacca    120

gggaaagctc ctaagctcct gatctatgtt gcagacaact tagcagatgg ggtcccatca    180

aggttcagcg gcagtggatc tgggacagat ttcactctca ccatcagcag cctgcagcct    240

gaagattttg caacttatta ctgtcaacat ttttatggtt ctcctcggac gttcggcgga    300

gggaccaagg tggagatcaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gttag                    645
```

<210> SEQ ID NO 120
<211> LENGTH: 1417
<212> TYPE: DNA
<213> ORGANISM: Artificial Sequence
<220> FEATURE:
<223> OTHER INFORMATION: HzVSF V12_HC_optimization

<400> SEQUENCE: 120

```
aagcttgccg ccaccatgga atggtcctgg gtgttcctgt tcttcctgtc cgtgaccacc     60

ggcgtgcact ccgaagtgca gctggtgcag tctggcgccg aagtgaagaa acctggcgcc    120

tccgtgaagg tgtcctgcaa ggcttccggc tacaccttta ccggctacaa catgaactgg    180

gtgcgacagg cccctggcaa gggcctggaa tggatgggca acatcgaccc ctactacggc    240

tccgacacct acgcccagaa attccagggc agagtgacca tgaccgtgga cacctctgcc    300
```

```
tccaccgcct acatggaact gtcccggctg agatccgacg acaccgccgt gtactactgc    360
gccagagaga caggcaaccg ggccatggat tattggggcc agggcaccct cgtgaccgtg    420
tctagcgctt ctaccaaggg cccctccgtg ttccctctgg ccccttgctc cagatccacc    480
tccgagtcta ccgccgctct gggctgcctc gtgaaggact acttccccga gcccgtgaca    540
gtgtcctgga actctggcgc tctgacctct ggcgtgcaca ccttccctgc tgtgctgcag    600
tcctccggcc tgtactccct gtcctccgtc gtgactgtgc cctccagctc tctgggcacc    660
aagacctaca cctgtaacgt ggaccacaag ccctccaaca ccaaggtgga caagcgggtg    720
gaatctaagt acggccctcc ctgccctagc tgccctgccc ctgagtttct gggaggccct    780
tctgtgtttc tgttcccccc aaagcccaag gacaccctga tgatctcccg gacccccgaa    840
gtgacctgcg tggtggtgga tgtgtcccag gaagatcccg aggtgcagtt caattggtac    900
gtggacggcg tggaagtgca caacgccaag accaagccta gagaggaaca gttcaactcc    960
acctaccggg tggtgtccgt gctgaccgtg ctgcaccagg attggctgaa cggcaaagag   1020
tacaagtgca aggtgtccaa caagggactg cccagctcca tcgaaaagac catctccaag   1080
gccaagggcc agccccggga accccaggtg tacacactgc ctccaagcca ggaagagatg   1140
accaagaacc aggtgtccct gacctgtctc gtgaaaggct tctacccctc cgatatcgcc   1200
gtggaatggg agtccaacgg ccagcctgag aacaactaca agaccacccc ccctgtgctg   1260
gactccgacg gctccttctt tctgtactct cggctgacag tggacaagtc ccggtggcag   1320
gaaggcaacg tgttctcctg cagcgtgatg cacgaggccc tgcacaacca ctacacccag   1380
aagtccctgt ccctgtctct gggaaagtga tgaattc                            1417

<210> SEQ ID NO 121
<211> LENGTH: 727
<212> TYPE: DNA
<213> ORGANISM: Artificial Sequence
<220> FEATURE:
<223> OTHER INFORMATION: HzVSF V12_LC_optimization

<400> SEQUENCE: 121

aagcttgccg ccaccatgtc cgtgcctacc caggtgctgg gactgctgct gctgtggctg     60
accgacgcca gatgcgacat ccagatgacc cagtccccct ccagcctgtc tgcttccgtg    120
ggcgacagag tgaccatcac ctgtcgggcc tccgagaaca tctactccaa cctggcctgg    180
tatcagcaga agcccggcaa ggcccccaag ctgctgatct acgtggccga caatagaggc    240
gacggcgtgc cctccagatt ctccggctct ggctctggca ccgactttac cctgaccatc    300
agctccctgc agcccgagga cttcgccacc tactactgcc agcacttcta cggcaccccc    360
cggacatttg gcggaggcac caaggtggaa atcaagcgga ccgtggccgc tccctccgtg    420
ttcatcttcc caccttccga cgagcagctg aagtccggca ccgcttctgt cgtgtgcctg    480
ctgaacaact tctacccccg cgaggccaag gtgcagtgga aggtggacaa cgccctgcag    540
tccggcaact cccaggaatc cgtgaccgag caggactcca aggacagcac ctactccctg    600
tcctccaccc tgaccctgtc caaggccgac tacgagaagc acaaggtgta cgcctgcgaa    660
gtgacccacc agggcctgtc tagccccgtg accaagtctt tcaaccgggg cgagtgctga    720
tgaattc                                                              727

<210> SEQ ID NO 122
<211> LENGTH: 1417
<212> TYPE: DNA
```

<213> ORGANISM: Artificial Sequence
<220> FEATURE:
<223> OTHER INFORMATION: HzVSF V13_HC_optimization
<400> SEQUENCE: 122
aagcttgccg ccaccatgga atggtcctgg gtgttcctgt tcttcctgtc cgtgaccacc 60
ggcgtgcact ccgaagtgca gctggtgcag tctggcgccg aagtgaagaa acctggcgcc 120
tccgtgaagg tgtcctgcaa ggcttccggc tacaccttta ccggctacaa catgaactgg 180
gtgcgacagg cccctggcaa gggcctggaa tggatgggca acatcgaccc ctactacggc 240
tccgacacct acgcccagaa attccagggc agagtgacca tgaccgtgga caagtccatc 300
tccaccgcct acatggaact gtcccggctg agatccgacg acaccgccgt gtactactgc 360
gccagagaga caggcacccg ggccatggat tattggggcc agggcaccct cgtgaccgtg 420
tcctctgctt ctaccaaggg cccctccgtg ttccctctgg ccccttgctc cagatccacc 480
tccgagtcta ccgccgctct gggctgcctc gtgaaggact acttccccga gcccgtgaca 540
gtgtcttgga actctggcgc cctgacctct ggcgtgcaca cctttccagc tgtgctgcag 600
tcctccggcc tgtactccct gtcctccgtc gtgactgtgc cctccagctc tctgggcacc 660
aagacctaca cctgtaacgt ggaccacaag ccctccaaca ccaaggtgga caagcgggtg 720
gaatctaagt acggccctcc ctgccctagc tgccctgccc ctgagtttct gggaggccct 780
tctgtgtttc tgttcccccc aaagcccaag gacaccctga tgatctcccg gacccccgaa 840
gtgacctgcg tggtggtgga tgtgtcccag gaagatcccg aggtgcagtt caattggtac 900
gtggacggcg tggaagtgca caacgccaag accaagccta gagaggaaca gttcaactcc 960
acctaccggg tggtgtccgt gctgaccgtg ctgcaccagg attggctgaa cggcaaagag 1020
tacaagtgca aggtgtccaa caagggactg cccagctcca tcgaaaagac catctccaag 1080
gccaagggcc agccccggga accccaggtg tacacactgc ctccaagcca ggaagagatg 1140
accaagaacc aggtgtccct gacctgtctc gtgaaaggct tctacccctc cgatatcgcc 1200
gtggaatggg agtccaacgg ccagcctgag aacaactaca agaccacccc ccctgtgctg 1260
gactccgacg gctccttctt tctgtactct cggctgacag tggataagtc ccggtggcag 1320
gaaggcaacg tgttctcctg cagcgtgatg cacgaggccc tgcacaacca ctacacccag 1380
aagtccctgt ccctgtctct gggaaagtga tgaattc 1417

<210> SEQ ID NO 123
<211> LENGTH: 727
<212> TYPE: DNA
<213> ORGANISM: Artificial Sequence
<220> FEATURE:
<223> OTHER INFORMATION: HzVSF V13_LC_optimization
<400> SEQUENCE: 123
aagcttgccg ccaccatgtc cgtgcctacc caggtgctgg gactgctgct gctgtggctg 60
accgacgcca gatgcgacat ccagatgacc cagtccccct ccagcctgtc tgcttccgtg 120
ggcgacagag tgaccatcac ctgtcgggcc tccgagaaca tctactccaa cctggcctgg 180
tatcagcaga agcccggcaa ggcccccaag ctgctgatct acgtggccga taacctggcc 240
gacggcgtgc cctctagatt ctccggctct ggctctggca ccgactttac cctgaccatc 300
agctccctgc agcccgagga cttcgccacc tactactgcc agcacttcta cggctccccc 360
cggacatttg gcggaggcac caaggtggaa atcaagcgga ccgtggccgc tccctccgtg 420
ttcatcttcc caccttccga cgagcagctg aagtccggca ccgcttctgt cgtgtgcctg 480
ctgaacaact tctacccccg cgaggccaag gtgcagtgga aggtggacaa cgccctgcag 540
tccggcaact cccaggaatc cgtgaccgag caggactcca aggacagcac ctactccctg 600
tcctccaccc tgaccctgtc caaggccgac tacgagaagc acaaggtgta cgcctgcgaa 660
gtgacccacc agggcctgtc tagccccgtg accaagtctt tcaaccgggg cgagtgctga 720
tgaattc 727

<210> SEQ ID NO 124
<211> LENGTH: 25
<212> TYPE: DNA
<213> ORGANISM: Artificial Sequence
<220> FEATURE:
<223> OTHER INFORMATION: mVH F primer

<400> SEQUENCE: 124
cgagctcatg ggatggagct ggatc 25

<210> SEQ ID NO 125
<211> LENGTH: 24
<212> TYPE: DNA
<213> ORGANISM: Artificial Sequence
<220> FEATURE:
<223> OTHER INFORMATION: mVH R primer

<400> SEQUENCE: 125
cggtacctga ggagacggtg actg 24

<210> SEQ ID NO 126
<211> LENGTH: 37
<212> TYPE: DNA
<213> ORGANISM: Artificial Sequence
<220> FEATURE:
<223> OTHER INFORMATION: KpnI_delR primer

<400> SEQUENCE: 126
gggcccttgg tggaagctga ggagacggtg actgagg 37

<210> SEQ ID NO 127
<211> LENGTH: 25
<212> TYPE: DNA
<213> ORGANISM: Artificial Sequence
<220> FEATURE:
<223> OTHER INFORMATION: mVL F primer

<400> SEQUENCE: 127
catcgatatg agtgtgccca ctcag 25

<210> SEQ ID NO 128
<211> LENGTH: 24
<212> TYPE: DNA
<213> ORGANISM: Artificial Sequence
<220> FEATURE:
<223> OTHER INFORMATION: mVL R primer

<400> SEQUENCE: 128
cctcgagttt gatttccagc ttgg 24

<210> SEQ ID NO 129
<211> LENGTH: 42
<212> TYPE: DNA
<213> ORGANISM: Artificial Sequence
<220> FEATURE:
<223> OTHER INFORMATION: Xho_modR primer

<400> SEQUENCE: 129
agatggtgca gccaccgtgc gtttgatttc cagcttggtg cc 42

<210> SEQ ID NO 130
<211> LENGTH: 354
<212> TYPE: DNA
<213> ORGANISM: Artificial Sequence
<220> FEATURE:
<223> OTHER INFORMATION: ScFv VSF H

<400> SEQUENCE: 130
gagatccagc tgcagcagtc tggagctgag ctggtgaagc ctggggcttc agtgaagata 60
tcctgcaagg cttctggtta ctcattcact ggctacaaca tgaactgggt gaagcagagc 120
catggaaaga gccttgagtg gattggaaat attgatcctt actatggtag tactacctac 180
aatcagaagt tcaagggcaa ggccacattg actgtagaca aatcttccag cacagcctac 240
atgcagctca acagcctgac atctgaggac tctgcagtct attactgtgc aagagagact 300
gggacgaggg ctatggacta ctggggtcaa ggaacctcag tcaccgtctc ctca 354

<210> SEQ ID NO 131
<211> LENGTH: 118
<212> TYPE: PRT
<213> ORGANISM: Artificial Sequence
<220> FEATURE:
<223> OTHER INFORMATION: scFv VSF H

<400> SEQUENCE: 131

Glu Ile Gln Leu Gln Gln Ser Gly Ala Glu Leu Val Lys Pro Gly Ala
1 5 10 15

Ser Val Lys Ile Ser Cys Lys Ala Ser Gly Tyr Ser Phe Thr Gly Tyr
20 25 30

Asn Met Asn Trp Val Lys Gln Ser His Gly Lys Ser Leu Glu Trp Ile
35 40 45

Gly Asn Ile Asp Pro Tyr Tyr Gly Ser Thr Thr Tyr Asn Gln Lys Phe
50 55 60

Lys Gly Lys Ala Thr Leu Thr Val Asp Lys Ser Ser Ser Thr Ala Tyr
65 70 75 80

Met Gln Leu Asn Ser Leu Thr Ser Glu Asp Ser Ala Val Tyr Tyr Cys
85 90 95

Ala Arg Glu Thr Gly Thr Arg Ala Met Asp Tyr Trp Gly Gln Gly Thr
100 105 110

Ser Val Thr Val Ser Ser
115

<210> SEQ ID NO 132
<211> LENGTH: 321
<212> TYPE: DNA
<213> ORGANISM: Artificial Sequence
<220> FEATURE:
<223> OTHER INFORMATION: scFv VSF L3

<400> SEQUENCE: 132
gacatccaga tgactcagtc tccagcctcc ctatctgcat ctgtgggaga aactgtcacc 60
atgacatgtc gagcaagtga gaatatttac agtaatttag catggtatca gcagaaacag 120
ggaaaatctc ctcagctcct ggtctatgtt gcaacaaact tagcagatgg tgtgccatca 180
aggttcagtg gcagtggatc aggcacacag ttttctctga agatcaacag cctgcagcct 240
gaagattttg ggagttatta ctgtcaacat ttttatggtt ctcctcggac gttcggtgga 300
ggcaccaagc tggaaatcaa a 321

<210> SEQ ID NO 133
<211> LENGTH: 107
<212> TYPE: PRT
<213> ORGANISM: Artificial Sequence
<220> FEATURE:
<223> OTHER INFORMATION: scFv VSF L3

<400> SEQUENCE: 133

Asp Ile Gln Met Thr Gln Ser Pro Ala Ser Leu Ser Ala Ser Val Gly
1 5 10 15

Glu Thr Val Thr Met Thr Cys Arg Ala Ser Glu Asn Ile Tyr Ser Asn
20 25 30

Leu Ala Trp Tyr Gln Gln Lys Gln Gly Lys Ser Pro Gln Leu Leu Val
35 40 45

Tyr Val Ala Thr Asn Leu Ala Asp Gly Val Pro Ser Arg Phe Ser Gly
50 55 60

Ser Gly Ser Gly Thr Gln Phe Ser Leu Lys Ile Asn Ser Leu Gln Pro
65 70 75 80

Glu Asp Phe Gly Ser Tyr Tyr Cys Gln His Phe Tyr Gly Ser Pro Arg
85 90 95

Thr Phe Gly Gly Gly Thr Lys Leu Glu Ile Lys
100 105

<210> SEQ ID NO 134
<211> LENGTH: 13
<212> TYPE: PRT
<213> ORGANISM: Artificial Sequence
<220> FEATURE:
<223> OTHER INFORMATION: mVSF CDR-L1

<400> SEQUENCE: 134

Arg Ala Ser Glu Asn Ile Tyr Ser Asn Leu Ala Trp Tyr
1 5 10

<210> SEQ ID NO 135
<211> LENGTH: 11
<212> TYPE: PRT
<213> ORGANISM: Artificial Sequence
<220> FEATURE:
<223> OTHER INFORMATION: mVSF CDR-L2

<400> SEQUENCE: 135

Leu Leu Val Tyr Val Ala Thr Asn Leu Ala Asp
1 5 10

<210> SEQ ID NO 136
<211> LENGTH: 9
<212> TYPE: PRT
<213> ORGANISM: Artificial Sequence
<220> FEATURE:
<223> OTHER INFORMATION: mVSF CDR-L3

<400> SEQUENCE: 136

Gln His Phe Tyr Gly Ser Pro Arg Thr
1 5

<210> SEQ ID NO 137
<211> LENGTH: 10
<212> TYPE: PRT
<213> ORGANISM: Artificial Sequence
<220> FEATURE:

<223> OTHER INFORMATION: mVSF CDR-H1

<400> SEQUENCE: 137

Gly Tyr Ser Phe Thr Gly Tyr Asn Met Asn
1               5                   10

<210> SEQ ID NO 138
<211> LENGTH: 16
<212> TYPE: PRT
<213> ORGANISM: Artificial Sequence
<220> FEATURE:
<223> OTHER INFORMATION: mVSF CDR-H2

<400> SEQUENCE: 138

Trp Ile Gly Asn Ile Asp Pro Tyr Tyr Gly Ser Thr Thr Tyr Asn Gln
1               5                   10                  15

<210> SEQ ID NO 139
<211> LENGTH: 11
<212> TYPE: PRT
<213> ORGANISM: Artificial Sequence
<220> FEATURE:
<223> OTHER INFORMATION: mVSF CDR-H3

<400> SEQUENCE: 139

Ala Arg Glu Thr Gly Thr Arg Ala Met Asp Tyr
1               5                   10

<210> SEQ ID NO 140
<211> LENGTH: 154
<212> TYPE: PRT
<213> ORGANISM: Artificial Sequence
<220> FEATURE:
<223> OTHER INFORMATION: chVSFk

<400> SEQUENCE: 140

Met Ser Val Pro Thr Gln Val Leu Gly Leu Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Met Thr Cys Arg Ala Ser Glu Asn
        35                  40                  45

Ile Tyr Ser Asn Leu Ala Trp Tyr Gln Gln Lys Gln Gly Lys Ser Pro
    50                  55                  60

Gln Leu Leu Val Tyr Val Ala Thr Asn Leu Ala Asp Gly Val Pro Ser
65                  70                  75                  80

Arg Phe Ser Gly Ser Gly Ser Gly Thr Gln Phe Ser Leu Lys Ile Asn
                85                  90                  95

Ser Leu Gln Pro Glu Asp Phe Gly Ser Tyr Tyr Cys Gln His Phe Tyr
            100                 105                 110

Gly Ser Pro Arg Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys
145                 150

<210> SEQ ID NO 141
<211> LENGTH: 142
<212> TYPE: PRT
<213> ORGANISM: Artificial Sequence
<220> FEATURE:

<223> OTHER INFORMATION: hVSFg4

<400> SEQUENCE: 141

Met Gly Trp Ser Trp Ile Phe Leu Phe Leu Leu Ser Val Thr Ala Gly
1               5                   10                  15

Val His Ser Glu Ile Gln Leu Gln Gln Ser Gly Ala Glu Leu Val Lys
            20                  25                  30

Pro Gly Ala Ser Val Lys Ile Ser Cys Lys Ala Ser Gly Tyr Ser Phe
        35                  40                  45

Thr Gly Tyr Asn Met Asn Trp Val Lys Gln Ser His Gly Lys Ser Leu
    50                  55                  60

Glu Trp Ile Gly Asn Ile Asp Pro Tyr Tyr Gly Ser Thr Thr Tyr Asn
65                  70                  75                  80

Gln Lys Phe Lys Gly Lys Ala Thr Leu Thr Val Asp Lys Ser Ser Ser
                85                  90                  95

Thr Ala Tyr Met Gln Leu Asn Ser Leu Thr Ser Glu Asp Ser Ala Val
            100                 105                 110

Tyr Tyr Cys Ala Arg Glu Thr Gly Thr Arg Ala Met Asp Tyr Asn Gly
        115                 120                 125

Gln Gly Thr Ser Val Thr Val Ser Ser Gly Thr Ala Ser Thr
    130                 135                 140

<210> SEQ ID NO 142
<211> LENGTH: 131
<212> TYPE: PRT
<213> ORGANISM: Artificial Sequence
<220> FEATURE:
<223> OTHER INFORMATION: chVSFg2

<400> SEQUENCE: 142

Glu Ile Gln Leu Gln Gln Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser His Gly Lys Ser Leu Glu Trp Ile
        35                  40                  45

Gly Asn Ile Asp Pro Tyr Tyr Gly Ser Thr Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Glu Thr Gly Thr Arg Ala Met Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro
    130

<210> SEQ ID NO 143
<211> LENGTH: 234
<212> TYPE: PRT
<213> ORGANISM: Artificial Sequence
<220> FEATURE:
<223> OTHER INFORMATION: chVSF light chain

<400> SEQUENCE: 143

Met Ser Val Pro Thr Gln Val Leu Gly Leu Leu Leu Leu Trp Leu Thr 1 5 10 15

Gly Ala Arg Cys Asp Ile Gln Met Thr Gln Ser Pro Ala Ser Leu Ser
20 25 30

Ala Ser Val Gly Glu Thr Val Thr Met Thr Cys Arg Ala Ser Glu Asn
35 40 45

Ile Tyr Ser Asn Leu Ala Trp Tyr Gln Gln Lys Gln Gly Lys Ser Pro
50 55 60

Gln Leu Leu Val Tyr Val Ala Thr Asn Leu Ala Asp Gly Val Pro Ser
65 70 75 80

Arg Phe Ser Gly Ser Gly Ser Gly Thr Gln Phe Ser Leu Lys Ile Asn
85 90 95

Ser Leu Gln Pro Glu Asp Phe Gly Ser Tyr Tyr Cys Gln His Phe Tyr
100 105 110

Gly Ser Pro Arg Thr Phe Gly Gly Gly Thr Lys Leu Glu Ile Lys Arg
115 120 125

Thr Val Ala Ala Pro Ser Val Phe Ile Phe Pro Pro Ser Asp Glu Gln
130 135 140

Leu Lys Ser Gly Thr Ala Ser Val Val Cys Leu Leu Asn Asn Phe Tyr
145 150 155 160

Pro Arg Glu Ala Lys Val Gln Trp Lys Val Asp Asn Ala Leu Gln Ser
165 170 175

Gly Asn Ser Gln Glu Ser Val Thr Glu Gln Asp Ser Lys Asp Ser Thr
180 185 190

Tyr Ser Leu Ser Ser Thr Leu Thr Leu Ser Lys Ala Asp Tyr Glu Lys
195 200 205

His Lys Val Tyr Ala Cys Glu Val Thr His Gln Gly Leu Ser Ser Pro
210 215 220

Val Thr Lys Ser Phe Asn Arg Gly Glu Cys
225 230

<210> SEQ ID NO 144
<211> LENGTH: 234
<212> TYPE: PRT
<213> ORGANISM: Artificial Sequence
<220> FEATURE:
<223> OTHER INFORMATION: hCk - mVL

<400> SEQUENCE: 144

Met Ser Val Pro Thr Gln Val Arg Gly Leu Leu Leu Leu Trp Leu Thr
1 5 10 15

Gly Ala Arg Cys Asp Ile Gln Met Thr Gln Ser Pro Ala Ser Leu Ser
20 25 30

Ala Ser Val Gly Glu Thr Val Thr Met Thr Cys Arg Ala Ser Glu Asn
35 40 45

Ile Tyr Ser Asn Leu Ala Trp Tyr Gln Gln Lys Gln Gly Lys Ser Pro
50 55 60

Gln Leu Leu Val Tyr Val Ala Thr Asn Leu Ala Asp Gly Val Pro Ser
65 70 75 80

Arg Phe Ser Gly Ser Gly Ser Gly Thr Gln Phe Ser Leu Met Ile Asn
85 90 95

Ser Leu Gln Pro Glu Asp Phe Gly Ser Tyr Tyr Cys Gln His Phe Tyr
100 105 110

Gly Pro Pro Arg Thr Phe Gly Gly Gly Thr Lys Leu Glu Ile Lys Leu
115 120 125

Glu Val Ala Ala Pro Ser Val Phe Ile Phe Pro Pro Ser Asp Glu Gln

```
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230


<210> SEQ ID NO 145
<211> LENGTH: 705
<212> TYPE: DNA
<213> ORGANISM: Artificial Sequence
<220> FEATURE:
<223> OTHER INFORMATION: hCk - mVL

<400> SEQUENCE: 145

atgagtgtgc ccactcaggt ccgggggttg ctgctgctgt ggcttacagg tgccagatgt      60

gacatccaga tgactcagtc tccagcctcc ctatctgcat ctgtgggaga aactgtcacc     120

atgacatgtc gagcaagtga gaatatttac agtaatttag catggtatca gcagaaacag     180

ggaaaatctc ctcagctcct ggtctatgtt gcaacaaact tagcagatgg tgtgccatca     240

aggttcagtg gcagtggatc aggcacacag ttttctctga tgatcaacag cctgcagcct     300

gaagattttg ggagttatta ctgtcaacat ttttatggtc ctcctcggac gttcggtgga     360

ggcaccaagc tggaaatcaa actcgaggtg gctgcaccat ctgtcttcat cttcccgcca     420

tctgatgagc agttgaaatc tggaactgcc tctgttgtgt gcctgctgaa taacttctat     480

cccagagagg ccaaagtaca gtggaaggtg gataacgccc tccaatcggg taactcccag     540

gagagtgtca cagagcagga cagcaaggac agcacctaca gcctcagcag caccctgacg     600

ctgagcaaag cagactacga gaaacacaaa gtctacgcct gcgaagtcac ccatcagggc     660

ctgagctcgc ccgtcacaaa gagcttcaac aggggagagt gttag                     705


<210> SEQ ID NO 146
<211> LENGTH: 465
<212> TYPE: PRT
<213> ORGANISM: Artificial Sequence
<220> FEATURE:
<223> OTHER INFORMATION: hCr2 - mVH

<400> SEQUENCE: 146

Met Gly Trp Ser Trp Ile Phe Leu Phe Leu Leu Ser Val Thr Ala Gly
1               5                   10                  15

Val His Ser Glu Ile Gln Leu Gln Gln Ser Gly Ala Glu Leu Val Lys
            20                  25                  30

Pro Gly Ala Ser Val Lys Ile Ser Cys Lys Ala Ser Gly Tyr Ser Phe
        35                  40                  45

Thr Gly Tyr Asn Met Asn Trp Val Lys Gln Ser His Gly Lys Ser Leu
    50                  55                  60

Glu Trp Ile Gly Asn Ile Asp Pro Tyr Tyr Gly Ser Thr Thr Tyr Asn
65                  70                  75                  80
```

```
Gln Lys Phe Lys Gly Lys Ala Thr Leu Thr Val Asp Lys Ser Ser Ser
                85                  90                  95

Thr Ala Tyr Met Gln Leu Asn Ser Leu Thr Ser Glu Asp Ser Ala Val
            100                 105                 110

Tyr Tyr Cys Ala Arg Glu Thr Gly Thr Arg Ala Met Asp Tyr Trp Gly
        115                 120                 125

Gln Gly Thr Ser Val Thr Val Ser Ser Gly Thr Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Phe Arg Val
305                 310                 315                 320

Val Ser Val Leu Thr Val Val His Gln Asp Trp Leu Asn Gly Lys Glu
                325                 330                 335

Tyr Lys Cys Lys Val Ser Asn Lys Gly Leu Pro Ala Pro Ile Glu Lys
            340                 345                 350

Thr Ile Ser Lys Thr Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Asn Thr Thr Pro Pro Met Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465
```

<210> SEQ ID NO 147
<211> LENGTH: 1398
<212> TYPE: DNA

<213> ORGANISM: Artificial Sequence
<220> FEATURE:
<223> OTHER INFORMATION: hCr2 - mVH

<400> SEQUENCE: 147
atgggatgga gctggatctt tctcttcctt ctgtcagtaa ctgcaggtgt ccactctgag 60
atccagctgc agcagtctgg agctgagctg gtgaagcctg gggcttcagt gaagatatcc 120
tgcaaggctt ctggttactc attcactggc tacaacatga actgggtgaa gcagagccat 180
ggaaagagcc ttgagtggat tggaaatatt gatccttact atggtagtac tacctacaat 240
cagaagttca agggcaaggc cacattgact gtagacaaat cttccagcac agcctacatg 300
cagctcaaca gcctgacatc tgaggactct gcagtctatt actgtgcaag agagactggg 360
acgagggcta tggactactg gggtcaagga acctcagtca ccgtctcctc aggtaccgcc 420
tccaccaagg gcccatcggt cttcccccctg gcgccctgct ccaggagcac ctccgagagc 480
acagcggccc tgggctgcct ggtcaaggac tacttccccg aaccggtgac ggtgtcgtgg 540
aactcaggcg ctctgaccag cggcgtgcac accttcccgg ctgtcctaca gtcctcagga 600
ctctactccc tcagcagcgt ggtgaccgtg ccctccagca acttcggcac ccagacctac 660
acctgcaacg tagatcacaa gcccagcaac accaaggtgg acaagacagt tgagcgcaaa 720
tgttgtgtcg agtgcccacc gtgcccagca ccacctgtgg caggaccgtc agtcttcctc 780
ttccccccaa aacccaagga caccctcatg atctcccgga cccctgaggt cacgtgcgtg 840
gtggtggacg tgagccacga agaccccgag gtccagttca actggtacgt ggacggcgtg 900
gaggtgcata atgccaagac aaagccacgg gaggagcagt tcaacagcac gttccgtgtg 960
gtcagcgtcc tcaccgtcgt gcaccaggac tggctgaacg gcaaggagta caagtgcaag 1020
gtctccaaca aaggcctccc agcccccatc gagaaaacca tctccaaaac caaagggcag 1080
ccccgagaac cacaggtgta caccctgccc ccatcccggg aggagatgac caagaaccag 1140
gtcagcctga cctgcctggt caaaggcttc taccccagcg acatcgccgt ggagtgggag 1200
agcaatgggc agccggagaa caactacaac accacacctc ccatgctgga ctccgacggc 1260
tccttcttcc tctacagcaa gctcaccgtg gacaagagca ggtggcagca ggggaacgtc 1320
ttctcatgct ccgtgatgca tgaggctctg cacaaccact acacgcagaa gagcctctcc 1380
ctgtctccgg gtaaatga 1398

<210> SEQ ID NO 148
<211> LENGTH: 466
<212> TYPE: PRT
<213> ORGANISM: Artificial Sequence
<220> FEATURE:
<223> OTHER INFORMATION: hCr4 - mVH

<400> SEQUENCE: 148

Met Gly Trp Ser Trp Ile Phe Leu Phe Leu Leu Ser Val Thr Ala Gly
1 5 10 15

Val His Ser Glu Ile Gln Leu Gln Gln Ser Gly Ala Glu Leu Val Lys
20 25 30

Pro Gly Ala Ser Val Lys Ile Ser Cys Lys Ala Ser Gly Tyr Ser Phe
35 40 45

Thr Gly Tyr Asn Met Asn Trp Val Lys Gln Ser His Gly Lys Ser Leu
50 55 60

Glu Trp Ile Gly Asn Ile Asp Pro Tyr Tyr Gly Ser Thr Thr Tyr Asn
65 70 75 80

```
Gln Lys Phe Lys Gly Lys Ala Thr Leu Thr Val Asp Lys Ser Ser Ser
                85                  90                  95

Thr Ala Tyr Met Gln Leu Asn Ser Leu Thr Ser Glu Asp Ser Ala Val
            100                 105                 110

Tyr Tyr Cys Ala Arg Glu Thr Gly Thr Arg Ala Met Asp Tyr Trp Gly
        115                 120                 125

Gln Gly Thr Ser Val Thr Val Ser Ser Gly Thr Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Ser Cys Pro Ala Pro Glu Phe Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Gln Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
            420                 425                 430

Lys Ser Arg Trp Gln Glu Gly Asn Val Phe Ser Cys Ser Val Met His
        435                 440                 445

Glu Ala Leu His Asn His Tyr Thr Gln Lys Ser Leu Ser Leu Ser Leu
    450                 455                 460

Gly Lys
465
```

<210> SEQ ID NO 149
<211> LENGTH: 1401
<212> TYPE: DNA

<213> ORGANISM: Artificial Sequence
<220> FEATURE:
<223> OTHER INFORMATION: hCr4 - mVH

<400> SEQUENCE: 149
atgggatgga gctggatctt tctcttcctt ctgtcagtaa ctgcaggtgt ccactctgag 60
atccagctgc agcagtctgg agctgagctg gtgaagcctg gggcttcagt gaagatatcc 120
tgcaaggctt ctggttactc attcactggc tacaacatga actgggtgaa gcagagccat 180
ggaaagagcc ttgagtggat tggaaatatt gatccttact atggtagtac tacctacaat 240
cagaagttca agggcaaggc cacattgact gtagacaaat cttccagcac agcctacatg 300
cagctcaaca gcctgacatc tgaggactct gcagtctatt actgtgcaag agagactggg 360
acgagggcta tggactactg gggtcaagga acctcagtca ccgtctcctc aggtaccgct 420
tccaccaagg gcccatccgt cttcccctg gcgccctgct ccaggagcac ctccgagagc 480
acagccgccc tgggctgcct ggtcaaggac tacttccccg aaccggtgac ggtgtcgtgg 540
aactcaggcg ccctgaccag cggcgtgcac accttcccgg ctgtcctaca gtcctcagga 600
ctctactccc tcagcagcgt ggtgaccgtg ccctccagca gcttgggcac gaagacctac 660
acctgcaacg tagatcacaa gcccagcaac accaaggtgg acaagagagt tgagtccaaa 720
tatggtcccc catgcccatc atgcccagca cctgagttcc tggggggacc atcagtcttc 780
ctgttccccc caaaacccaa ggacactctc atgatctccc ggacccctga ggtcacgtgc 840
gtggtggtgg acgtgagcca ggaagacccc gaggtccagt tcaactggta cgtggatggc 900
gtggaggtgc ataatgccaa gacaaagccg cgggaggagc agttcaacag cacgtaccgt 960
gtggtcagcg tcctcaccgt cctgcaccag gactggctga acggcaagga gtacaagtgc 1020
aaggtctcca acaaaggcct cccgtcctcc atcgagaaaa ccatctccaa agccaaaggg 1080
cagccccgag agccacaggt gtacaccctg cccccatccc aggaggagat gaccaagaac 1140
caggtcagcc tgacctgcct ggtcaaaggc ttctacccca gcgacatcgc cgtggagtgg 1200
gagagcaatg ggcagccgga gaacaactac aagaccacgc ctcccgtgct ggactccgac 1260
ggctccttct tcctctacag caggctaacc gtggacaaga gcaggtggca ggaggggaat 1320
gtcttctcat gctccgtgat gcatgaggct ctgcacaacc actacacaca gaagagcctc 1380
tccctgtctc tgggtaaatg a 1401

<210> SEQ ID NO 150
<211> LENGTH: 851
<212> TYPE: DNA
<213> ORGANISM: Artificial Sequence
<220> FEATURE:
<223> OTHER INFORMATION: scFv VSF DNA

<400> SEQUENCE: 150
cgtcgacgag atccagctgc agcagtctga gatccagctg cagcagtctg gagctgagct 60
ggtgaagcct ggggcttcag tgaagatatc ctgcaaggct tctggttact cattcactgg 120
ctacaacatg aactgggtga agcagagcca tggaaagagc cttgagtgga ttggaaatat 180
tgatccttac tatggtagta ctacctacaa tcagaagttc aagggcaagg ccacattgac 240
tgtagacaaa tcttccagca cagcctacat gcagctcaac agcctgacat ctgaggactc 300
tgcagtctat tactgtgcaa gagagactgg gacgagggct atggactact ggggtcaagg 360
aacctcagtc accgtctcct caccttggag tcagtggcag aggagtccac ctcacgagac 420
cacccctcct aggccacctc aggaggatcc ggtggaggtg gctctggtgg aggtggctct 480

```
gacatccaga tgactcagtc gacatccaga tgactcagtc tccagcctcc ctatctgcat    540

ctgtgggaga aactgtcacc atgacatgtc gagcaagtga gaatatttac agtaatttag    600

catggtatca gcagaaacag ggaaaatctc ctcagctcct ggtctatgtt gcaacaaact    660

tagcagatgg tgtgccatca aggttcagtg gcagtggatc aggcacacag ttttctctga    720

agatcaacag cctgcagcct gaagattttg ggagttatta ctgtcaacat ttttatggtt    780

ctcctcggac gttcggtgga ggcaccaagc tggaaatcaa acccgtggtt cgacctttag    840

tttggagctc c                                                         851


<210> SEQ ID NO 151
<211> LENGTH: 30
<212> TYPE: PRT
<213> ORGANISM: Artificial Sequence
<220> FEATURE:
<223> OTHER INFORMATION: FR1 of heavy chain

<400> SEQUENCE: 151

Glu Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30


<210> SEQ ID NO 152
<211> LENGTH: 14
<212> TYPE: PRT
<213> ORGANISM: Artificial Sequence
<220> FEATURE:
<223> OTHER INFORMATION: FR2 of heavy chain

<400> SEQUENCE: 152

Trp Val Arg Gln Ala Pro Gly Lys Gly Leu Glu Trp Ile Gly
1               5                   10


<210> SEQ ID NO 153
<211> LENGTH: 18
<212> TYPE: DNA
<213> ORGANISM: Artificial Sequence
<220> FEATURE:
<223> OTHER INFORMATION: HBV cccDNA primer

<400> SEQUENCE: 153

tgaatccygc ggacgacc                                                   18


<210> SEQ ID NO 154
<211> LENGTH: 20
<212> TYPE: DNA
<213> ORGANISM: Artificial Sequence
<220> FEATURE:
<223> OTHER INFORMATION: HBV cccDNA primer R

<400> SEQUENCE: 154

cagcttggag gcttgaacag                                                 20


<210> SEQ ID NO 155
<211> LENGTH: 18
<212> TYPE: DNA
<213> ORGANISM: Artificial Sequence
<220> FEATURE:
<223> OTHER INFORMATION: HBV total DNA primer F

<400> SEQUENCE: 155

cctcttcatc ctgctgct                                                   18
```

<210> SEQ ID NO 156
<211> LENGTH: 19
<212> TYPE: DNA
<213> ORGANISM: Artificial Sequence
<220> FEATURE:
<223> OTHER INFORMATION: HBV total DNA primer R

<400> SEQUENCE: 156
aactgaaagc caaacagtg 19

<210> SEQ ID NO 157
<211> LENGTH: 20
<212> TYPE: DNA
<213> ORGANISM: Artificial Sequence
<220> FEATURE:
<223> OTHER INFORMATION: HCV target primer F

<400> SEQUENCE: 157
gggctataag gtgctagtgc 20

<210> SEQ ID NO 158
<211> LENGTH: 20
<212> TYPE: DNA
<213> ORGANISM: Artificial Sequence
<220> FEATURE:
<223> OTHER INFORMATION: HCV target primer R

<400> SEQUENCE: 158
ggctgccagt ggtaattgtt 20

<210> SEQ ID NO 159
<211> LENGTH: 20
<212> TYPE: DNA
<213> ORGANISM: Artificial Sequence
<220> FEATURE:
<223> OTHER INFORMATION: GAPDH primer F

<400> SEQUENCE: 159
tccctgagct gaacgggaag 20

<210> SEQ ID NO 160
<211> LENGTH: 20
<212> TYPE: DNA
<213> ORGANISM: Artificial Sequence
<220> FEATURE:
<223> OTHER INFORMATION: GAPDH primer R

<400> SEQUENCE: 160
ggaggagtgg gtgtcgctgt 20

<210> SEQ ID NO 161
<211> LENGTH: 20
<212> TYPE: DNA
<213> ORGANISM: Artificial Sequence
<220> FEATURE:
<223> OTHER INFORMATION: HCV target primer F-2

<400> SEQUENCE: 161
atgcagccca agggtataag 20

<210> SEQ ID NO 162
<211> LENGTH: 23
<212> TYPE: DNA
<213> ORGANISM: Artificial Sequence
<220> FEATURE:

-continued

```
<223> OTHER INFORMATION: HCV target primer R-2

<400> SEQUENCE: 162

ggttctgatg ttagggtcga tac                                              23
```